(12) United States Patent
Zhao et al.

(10) Patent No.: US 12,365,892 B2
(45) Date of Patent: *Jul. 22, 2025

(54) DOUBLE-STRANDED SPLINT ADAPTORS WITH UNIVERSAL LONG SPLINT STRANDS AND METHODS OF USE

(71) Applicant: Element Biosciences, Inc., San Diego, CA (US)

(72) Inventors: Junhua Zhao, San Diego, CA (US); Xiaodong Qi, San Diego, CA (US); Kelly Wiseman, San Diego, CA (US); Hua Yu, San Diego, CA (US); Matthew Kellinger, San Diego, CA (US)

(73) Assignee: Element Biosciences, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/465,687

(22) Filed: Sep. 12, 2023

(65) Prior Publication Data

US 2024/0191225 A1  Jun. 13, 2024

Related U.S. Application Data

(60) Provisional application No. 63/405,733, filed on Sep. 12, 2022.

(51) Int. Cl.
*C12N 15/10* (2006.01)

(52) U.S. Cl.
CPC .............................. *C12N 15/1093* (2013.01)

(58) Field of Classification Search
CPC ................................................ C12N 15/1093
See application file for complete search history.

(56) References Cited

U.S. PATENT DOCUMENTS

| | | | |
|---|---|---|---|
| 5,558,991 A | 9/1996 | Trainor | |
| 5,576,448 A | 11/1996 | Van Daele et al. | |
| 5,700,642 A | 12/1997 | Monforte et al. | |
| 5,750,341 A | 5/1998 | Macevicz | |
| 5,854,033 A | 12/1998 | Lizardi | |
| 5,871,921 A | 2/1999 | Landegren et al. | |
| 6,284,497 B1 | 9/2001 | Sabanayagam et al. | |
| 6,576,448 B2 | 6/2003 | Weissman et al. | |
| 6,977,153 B2 | 12/2005 | Kumar et al. | |
| 7,170,050 B2 | 1/2007 | Turner et al. | |
| 7,195,872 B2 | 3/2007 | Agrawal et al. | |
| 7,302,146 B2 | 11/2007 | Turner et al. | |
| 7,405,281 B2 | 7/2008 | Xu et al. | |
| 7,432,048 B2 | 10/2008 | Neri et al. | |
| 7,709,197 B2 | 5/2010 | Drmanac | |
| 7,741,463 B2 | 6/2010 | Gormley et al. | |
| 7,820,387 B2 | 10/2010 | Neri et al. | |
| 7,862,999 B2 | 1/2011 | Zheng et al. | |
| 7,910,302 B2 | 3/2011 | Drmanac et al. | |
| 7,910,354 B2 | 3/2011 | Drmanac et al. | |
| 7,968,702 B2 | 6/2011 | Wegener et al. | |
| 7,989,166 B2 | 8/2011 | Koch et al. | |
| 8,053,192 B2 | 11/2011 | Bignell et al. | |
| 8,182,989 B2 | 5/2012 | Bignell et al. | |
| 8,252,910 B2 | 8/2012 | Korlach et al. | |
| 8,445,196 B2 | 5/2013 | Drmanac et al. | |
| 8,476,022 B2 | 7/2013 | Ronaghi et al. | |
| 8,563,477 B2 | 10/2013 | Smith et al. | |
| 8,563,478 B2 | 10/2013 | Gormley et al. | |
| 8,637,650 B2 | 1/2014 | Cherkasov et al. | |
| 8,715,966 B2 | 5/2014 | Xiaohai et al. | |
| 8,716,190 B2 | 5/2014 | Fu et al. | |
| 8,822,150 B2 | 9/2014 | Bignell et al. | |
| 8,906,612 B2 | 12/2014 | Shen et al. | |
| 8,927,212 B2 | 1/2015 | Kong et al. | |
| 8,932,994 B2 | 1/2015 | Gormley et al. | |

(Continued)

FOREIGN PATENT DOCUMENTS

| | | |
|---|---|---|
| CN | 108203847 B | 1/2022 |
| EP | 2423325 B1 | 4/2019 |

(Continued)

OTHER PUBLICATIONS

Obi, P., et al., "The design and synthesis of circular RNAs," Methods. (2021); 196:85-103.
Wang, F. et al., "Tequila-seq: a versatile and low-cost method for targeted long-read RNA sequencing," Nat Commun., (2023); 14(1):4760, pp. 1-15.
Diegelman, A. M. & Tool, E.T., "Chemical and Enzymatic Methods for Preparing Circular Single-Stranded DNAs" Curr Protoc Nucleic Acid Chem, May 2001, Chapter 5:Unit 5.2, 27 pages.
Eschenmoser, A., "Chemical Etiology of Nucleic Acid Structure," Science, Jun. 25, 1999, 284:2118-2124.
Ferraro, M. & Gotor, V., "Biocatalytic Selective Modifications of Conventional Nucleosides, Carbocyclic Nucleosides, and C-Nucleosides," Chem. Rev., 2000, 100:4319-4347.

(Continued)

*Primary Examiner* — Sahana S Kaup
(74) *Attorney, Agent, or Firm* — FENWICK & WEST; Heidi A. Erlacher; Jessica D. Cande

(57) ABSTRACT

The present disclosure provides compositions comprising nucleic acid double-stranded splint adaptors, including kits, and methods that employ the double-stranded splint adaptors. The double-stranded splint adaptors (200) can be used in a one-pot, multi-enzyme reaction to introduce one or more new adaptor sequences into a library molecule. The double-stranded splint adaptor (200) comprises a first splint strand (long splint strand (300)) and a second splint strand (short splint strand (400)), where the first and second splint strands are hybridized together to form the double-stranded splint adaptor (200) having a double-stranded region and two flanking single-stranded regions. The second splint strand (400) carries the new adaptor sequence(s) to be introduced, such as for example a universal binding sequence, an index sequence and/or a random sequence.

26 Claims, 48 Drawing Sheets
(13 of 48 Drawing Sheet(s) Filed in Color)
Specification includes a Sequence Listing.

(56) References Cited

U.S. PATENT DOCUMENTS

| | | | |
|---|---|---|---|
| 8,969,258 B2 | 3/2015 | Smith et al. |
| 8,980,563 B2 | 3/2015 | Zheng et al. |
| 9,029,103 B2 | 5/2015 | Rigatti et al. |
| 9,085,802 B2 | 7/2015 | Liu et al. |
| 9,228,228 B2 | 1/2016 | Drmanac et al. |
| 9,328,378 B2 | 5/2016 | Earnshaw et al. |
| 9,388,457 B2 | 7/2016 | Fu et al. |
| 9,416,415 B2 | 8/2016 | Ronaghi et al. |
| 9,493,818 B2 | 11/2016 | Kazakov et al. |
| 9,498,763 B2 | 11/2016 | Liu et al. |
| 9,512,478 B2 | 12/2016 | Bignell et al. |
| 9,650,673 B2 | 5/2017 | Drmanac et al. |
| 9,777,326 B2 | 10/2017 | Ronaghi et al. |
| 9,822,408 B2 | 11/2017 | Amorese et al. |
| 9,879,312 B2 | 1/2018 | Steemers et al. |
| 9,889,422 B2 | 2/2018 | Smith et al. |
| 9,896,709 B2 | 2/2018 | Makarov et al. |
| 9,902,994 B2 | 2/2018 | Gormley et al. |
| 9,944,984 B2 | 4/2018 | Drmanac et al. |
| 9,957,291 B2 | 5/2018 | Sebo et al. |
| 9,982,293 B2 | 5/2018 | Fu et al. |
| 9,999,866 B2 | 6/2018 | Liu et al. |
| 10,072,260 B2 | 9/2018 | Happe et al. |
| 10,155,980 B2 | 12/2018 | Weng et al. |
| 10,184,122 B2 | 1/2019 | Grunenwald et al. |
| 10,246,744 B2 | 4/2019 | Vijayan et al. |
| 10,287,574 B2 | 5/2019 | Goryshin et al. |
| 10,329,600 B2 | 6/2019 | Fu et al. |
| 10,351,909 B2 | 7/2019 | Drmanac et al. |
| 10,407,722 B2 | 9/2019 | Barany et al. |
| 10,525,437 B2 | 1/2020 | Smith et al. |
| 10,590,464 B2 | 3/2020 | Boutell et al. |
| 10,669,299 B2 | 6/2020 | Sebo et al. |
| 10,710,046 B2 | 7/2020 | Liu et al. |
| 10,731,141 B2 | 8/2020 | Iyidogan |
| 10,731,194 B2 | 8/2020 | Makarov et al. |
| 10,768,173 B1 | 9/2020 | Arslan et al. |
| 10,781,483 B2 | 9/2020 | Sebo et al. |
| 10,920,269 B2 | 2/2021 | Fu et al. |
| 10,953,379 B2 | 3/2021 | Smith et al. |
| 11,028,435 B2 | 6/2021 | Kelley et al. |
| 11,028,436 B2 | 6/2021 | Singer et al. |
| 11,028,438 B2 | 6/2021 | Rearick et al. |
| 11,118,207 B2 | 9/2021 | Makarov et al. |
| 11,124,829 B2 | 9/2021 | Fisher et al. |
| 11,168,360 B2 | 11/2021 | George et al. |
| 11,180,749 B2 | 11/2021 | Dambacher et al. |
| 11,220,707 B1 * | 1/2022 | Arslan | G01N 21/6428 |
| 11,230,731 B2 | 1/2022 | Sekedat et al. |
| 11,236,388 B1 | 2/2022 | Arslan et al. |
| 11,255,847 B2 | 2/2022 | Schnall-Levin |
| 11,279,975 B2 | 3/2022 | Rigatti et al. |
| 11,408,094 B2 | 8/2022 | Fu et al. |
| 11,427,855 B1 | 8/2022 | Arslan et al. |
| 11,434,538 B2 | 9/2022 | Babic et al. |
| 11,535,892 B1 | 12/2022 | Arslan et al. |
| 11,578,320 B2 | 2/2023 | Glezer et al. |
| 11,634,765 B2 | 4/2023 | Boutell et al. |
| 11,649,452 B2 | 5/2023 | Glezer et al. |
| 11,654,411 B2 | 5/2023 | Smith et al. |
| 11,781,185 B2 | 10/2023 | Arslan et al. |
| 11,821,030 B2 | 11/2023 | Zheng et al. |
| 11,859,241 B2 | 1/2024 | Arslan et al. |
| 11,891,651 B2 | 2/2024 | Arslan et al. |
| 11,905,553 B2 | 2/2024 | Gawad et al. |
| 12,104,194 B2 | 10/2024 | Makarov et al. |
| 2002/0076716 A1 | 6/2002 | Sabanayagam et al. |
| 2004/0110153 A1 | 6/2004 | Dong et al. |
| 2009/0018024 A1 | 1/2009 | Church et al. |
| 2009/0186343 A1 | 7/2009 | Wang et al. |
| 2010/0035252 A1 | 2/2010 | Rothberg et al. |
| 2010/0035454 A1 | 2/2010 | Morgan et al. |
| 2010/0121582 A1 | 5/2010 | Pan et al. |
| 2012/0196279 A1 | 8/2012 | Underwood et al. |
| 2017/0022553 A1 | 1/2017 | Vijayan et al. |
| 2018/0044668 A1 | 2/2018 | Jiang et al. |
| 2019/0119742 A1 | 4/2019 | Zhang et al. |
| 2019/0194737 A1 | 6/2019 | Ach et al. |
| 2020/0149095 A1 | 5/2020 | Arslan et al. |
| 2020/0216891 A1 | 7/2020 | Francais et al. |
| 2020/0308576 A1 | 10/2020 | Badenhorst et al. |
| 2020/0347443 A1 | 11/2020 | Arslan et al. |
| 2022/0042082 A1 | 2/2022 | Fu et al. |
| 2022/0356519 A1 | 11/2022 | Shen et al. |
| 2022/0403351 A1 | 12/2022 | Ambroso et al. |
| 2022/0403352 A1 | 12/2022 | Ambroso et al. |
| 2022/0403353 A1 | 12/2022 | Ambroso et al. |
| 2022/0403445 A1 | 12/2022 | Arslan et al. |
| 2022/0403463 A1 | 12/2022 | Arslan et al. |
| 2023/0193354 A1 | 6/2023 | Arslan et al. |
| 2023/0203564 A1 | 6/2023 | Arslan et al. |
| 2023/0265400 A1 | 8/2023 | Hentshcel et al. |
| 2023/0265401 A1 | 8/2023 | Hentshcel et al. |
| 2023/0265402 A1 | 8/2023 | Hentshcel et al. |
| 2023/0279382 A1 | 9/2023 | Light et al. |
| 2023/0279483 A1 * | 9/2023 | Light | C12Q 1/6869 506/4 |
| 2023/0392144 A1 | 12/2023 | Price et al. |
| 2023/0392201 A1 | 12/2023 | Stapleton et al. |
| 2024/0011022 A1 | 1/2024 | Zhao et al. |
| 2024/0052398 A1 | 2/2024 | Previte et al. |
| 2024/0084380 A1 | 3/2024 | Arslan et al. |
| 2024/0191278 A1 | 6/2024 | Arslan et al. |

FOREIGN PATENT DOCUMENTS

| | | | |
|---|---|---|---|
| EP | 1954818 B2 | 1/2021 |
| WO | WO-2005111236 A1 | 11/2005 |
| WO | WO-2005111240 A2 | 11/2005 |
| WO | WO-2009006907 A1 | 1/2009 |
| WO | WO-2012003374 A2 | 1/2012 |
| WO | WO-2014196863 A1 | 12/2014 |
| WO | WO-2015154028 A1 | 10/2015 |
| WO | WO-2016058517 A1 | 4/2016 |
| WO | WO-2018175258 A1 | 9/2018 |
| WO | WO-2019068797 A1 | 4/2019 |
| WO | WO-2019149958 A1 | 8/2019 |
| WO | WO-2020102594 A1 | 5/2020 |
| WO | WO-2021061841 A1 * | 4/2021 | C12Q 1/6834 |
| WO | WO-2021178467 A1 | 9/2021 |
| WO | WO-2021236792 A1 | 11/2021 |
| WO | WO-2022026891 A1 | 2/2022 |
| WO | WO-2022266462 A2 | 12/2022 |
| WO | WO-2022266470 A1 | 12/2022 |
| WO | WO-2023114392 A1 | 6/2023 |
| WO | WO-2023168443 A1 | 9/2023 |
| WO | WO-2023168444 A1 | 9/2023 |
| WO | WO-2023235865 A1 | 12/2023 |
| WO | WO-2023240093 A1 | 12/2023 |
| WO | WO-2024011145 A1 | 1/2024 |
| WO | WO-2024040058 A1 | 2/2024 |
| WO | WO-2024040068 A1 | 2/2024 |
| WO | WO-2024059550 A1 | 3/2024 |
| WO | WO-2025024465 A1 | 1/2025 |

OTHER PUBLICATIONS

Fire, A. & Xu, S.-Q., "Rolling replication of short DNA circles" Proc Natl Acad Sci USA, May 1995; 92(10):4641-4645.

Floyd, D.L. et, al., "Single-particle kinetics of influenza virus membrane fusion" Proc Natl Acad Sci USA, Oct. 7, 2008; 105(40):15382-15387.

Harris T.D., et al., "Single-Molecule DNA Sequencing of a Viral Genome," Science, Apr. 4, 2008, vol. 320 (5872): 106-109.

Jeong, L.S. et al., "Structure-Activity Relationships of β-D-(2S,5R)- and α-D-(2S,5S)-1,3-Oxathiolanyl Nucleosides as Potential Anti-HIV Agents," J. Med. Chem., 1993, 36: 2627-2638.

Joneja, A. & Huang, X., "Linear nicking endonuclease-mediated strand-displacement DNA amplification," Anal Biochem. (Jul. 2011); 414(1):58-69.

Kim, H. O. et al., "1,3-Dioxolanylpurine Nucleosides (2R,4R) and (2R,4S) with Selective Anti-HIV-1 Activity in Human Lymphocytes," J. Med. Chem., 1993, 36:30-37.

(56) References Cited

OTHER PUBLICATIONS

Korostin D., et al., "Comparative analysis of novel MGISEQ-2000 sequencing platform vs Illumina HiSeq 2500 for whole-genome sequencing", PLoS One (Mar. 16, 2020); 15(3):e0230301, 13 pages.
Lindahl, T. Nyberg, B., "Heat-induced deamination of cytosine residues in deoxyribonucleic acid," Biochemistry (Jul. 1974); 13(16):3405-3410.
Lizardi, P. M. et al., "Mutation detection and single-molecule counting using isothermal rolling-circle amplification" Nat Genet. Jul. 1998;19(3):225-232.
Martinez, C. I. et al., "Acyclic Nucleoside Triphosphate Analogs as Terminators in Biocatalytic DNA Replication," Bioorganic & Medicinal Chemistry Letters, 1997, 7(23):3013-3016.
Martinez, C. I. et al., "An allylic/acyclic adenosine nucleoside triphosphate for termination of DNA synthesis by DNA template-dependent polymerases," Nucleic Acids Research, 1999, 27(5):1271-1274.
McNaughton, A. L. et al. "Illumina and Nanopore methods for whole genome sequencing of hepatitis B virus (HBV)," Scientific Reports, 2019, 9:7081, pp. 1-14.
Ruparel, H. et al., "Design and synthesis of a 3' -O-allyl photocleavable fluorescent nucleotide as a reversible terminator for DNA sequencing by synthesis," Proceedings of the National Academy of Sciences of the United States of America, 2005, 102(17): 5932-5937.
Wang, R.Y.-H. et al., "Heat- and alkali-induced deamination of 5-methylcytosine and cytosine residues in DNA," Biochim Biophys Acta, (Jun. 1982); 697(3):371-377.
Co-pending U.S. Appl. No. 18/347,440, inventors Junhua Zhao et al., filed Jul. 5, 2023.
Anderson, J.P. et al.; Fluorescent Structural DNA Nanoballs Functionalized with Phosphate-Linked Nucleotide Triphosphates. Nano Letters 10(3):788-792 (2010).
Balakrishnan, L., et al.; "Flap Endonuclease 1," Annual Review Biochemistry 82:119-138 (2013).
Chen, X., et al.; "Efficient in situ barcode sequencing using padlock probe-based BaristaSeq," Nucleic Acids Research; 46(4):e22 pp. 1-10 (2018).
Ericsson, O., et al.; "A dual-tag microarray platform for high-performance nucleic acid and protein analyses," Nucleic Acids Research, 36(8):e45, pp. 1-9 (2008).
Friedrich-Heineken, E., et al.; "The Fen1 extrahelical 3'-flap pocket is conserved from archaea to human and regulates DNA substrate specificity," Nucleic Acids Research, 32(8):2520-2528 (2004).
GenBank Accession AAB52611.1; "DNA polymerase I [Geobacillus stearothermophilus]," Apr. 21, 1997; [retrieved online Sep. 23, 2024] URL: www.ncbi.nlm.nih.gov/protein/AAB52611.1, 2 pages.
GenBank Accession KUO42443.1; "MAG: hypothetical protein APZ16_03045 [Candidatus Hadarchaeum yellowstonense]," Jan. 14, 2016; [retrieved online Sep. 23, 2024], URL: www.ncbi.nlm.nih.gov/protein/KUO42443.1, 2 pages.
GenBank Accession MBC7218772.1; "MAG: DNA polymerase [Hadesarchaea archaeon]," Sep. 1, 2020; [retrieved online Sep. 23, 2024] URL: www.ncbi.nlm.nih.gov/protein/mbc7218772.1, 2 pages.
GenBank Accession NOZ58130.1; "MAG: DNA polymerase [Euryarchaeota archaeon]," Mar. 17, 2023 [retrieved online Sep. 23, 2024] URL: www.ncbi.nlm.nih.gov/protein/NOZ58130, 2 pages.
GenBank Accession NOZ77387.1; "MAG: DNA polymerase, partial [Euryarchaeota archaeon]," Mar. 17, 2023 [retrieved online Sep. 23, 2024] URL: www.ncbi.nlm.nih.gov/protein/NOZ77387.1, 2 pages.
GenBank Accession RLF78286.1; "MAG: DNA polymerase [Thermococci archaeon]," Oct. 15, 2018; URL: www.ncbi.nlm.nih.gov/protein/RLF78286.1, 2 pages.
GenBank Accession RLF89458.1; "MAG: DNA polymerase [Thermococci archaeon]," Oct. 15, 2018; [retrieved online Sep. 23, 2024] URL: www.ncbi.nlm.nih.gov/protein/RLF89458.1, 2 pages.
GenBank Accession RLI89578.1; "MAG: DNA polymerase [Candidatus Altiarchaeales archaeon]," Oct. 15, 2018; [retrieved online Sep. 23, 2024] URL: www.ncbi.nlm.nih.gov/protein/RLI89578.1, 2 pages.
GenBank Accession RMF90817.1; "MAG: DNA polymerase [Euryarchaeota archaeon]," Oct. 29, 2018; [retrieved online Sep. 23, 2024] URL: www.ncbi.nlm.nih.gov/protein/RMF90817.1, 2 pages.
Greenough, L., et al.; "Adapting capillary gel electrophoresis as a sensitive, high-throughput method to accelerate characterization of nucleic acid metabolic enzymes," Nucleic Acids Research, 44(2):e15, pp. 1-11 (2016).
Hatch, A., et al.; "Rolling circle amplification of DNA immobilized on solid surfaces and its application to multiplex mutation detection," Genetic Analysis: Biomolecular Engineering, 15(2):35-40 (1999).
Illumina: Illumina Adapter Sequences guide (Oct. 2015), 34 pages.
Kao, H-I, et al.; "Cleavage specificity of *Saccharomyces cerevisiae* flap endonuclease 1 suggests a double-flap structure as the cellular substrate," Journal of Biological Chemistry, 277(17):14379-14389 (2002).
Konry, T., et al.; "Microsphere-based rolling circle amplification microarray for the detection of DNA and proteins in a single assay," Analytical Chemistry, 81(14):5777-5782 (2009).
Lee, B-I., et al.; "The RAD2 domain of human exonuclease 1 exhibits 5' to 3' exonuclease and flap structure-specific endonuclease activities," Journal of Biological Chemistry, 274(53):37763-37769 (1999).
Lee, J., et al.; "Diffractometric detection of proteins using microbead-based rolling circle amplification," Analytical Chemistry, 82(1):197-202 (2010).
Lin, T., et al.; "Biochemical characterization and mutational analysis of a novel flap endonuclease 1 from Thermococcus barophilus Ch5," International Journal of Biochemistry and Cell Biology, 143:106154, pp. 1-11 (2022).
Lu, M., et al.; "A surface invasive cleavage assay for highly parallel SNP analysis," Human Mutation, 19(4):416-422 (2002).
Mignardi, M., et al.; "Fourth-generation sequencing in the cell and the clinic," Genome Med.; 6(4):31; pp. 1-4 (2014).
NCBI Reference Sequence: NP_041963.1; Accession NC_001604.1; "DNA ligase [*Escherichia* phage T7]," Jan. 7, 2023; [retrieved online Sep. 23, 2024] URL: www.ncbi.nlm.nih.gov/protein/9627435, 3 pages.
NCBI Reference Sequence: NP_049813.1; Accession NC_000866.4; "DNA ligase [*Escherichia* phage T4]," Jan. 11, 2023; [retrieved online Sep. 23, 2024] URL: www.ncbi.nlm.nih.gov/protein/9632609, 2 pages.
NCBI Reference Sequence: NP_523305.1; Accession NC_003298.1; "DNA ligase [Enterobacteria phage T3]," Jan. 7, 2023; [retrieved online Sep. 23, 2024] URL: www.ncbi.nlm.nih.gov/protein/17570796, 2 pages.
NCBI Reference Sequence: WP_042693257.1; Accession WP_042693257; "ATP-dependent DNA ligase [Thermococcus nautili]," Jun. 2, 2024; [retrieved online Sep. 23, 2024] URL: www.ncbi.nlm.nih.gov/protein/757139009, 1 page.
NCBI Reference Sequence: WP_175059460.1; Accession WP_175059460; "DNA-directed DNA polymerase [*Thermococcus* sp. 2319x1]," May 21, 2021; [retrieved online Sep. 23, 2024] URL: www.ncbi.nlm.nih.gov/protein/WP_175059460.1, 1 page.
Russell, C., et al.; "Gold nanowire based electrical DNA detection using rolling circle amplification," ACS Nano, 8(2):1147-1153 (2014).
Stougaard, M., et al.; "In situ detection of non-polyadenylated RNA molecules using Turtle Probes and target primed rolling circle PRINS," BMC Biotechnology, 7:69, pp. 1-10 (2007).
Tsutakawa, S.E., et al.; "Human flap endonuclease structures, DNA double-base flipping, and a unified understanding of the FEN1 superfamily," Cell., 145(2):198-211, with supplemental pp. S1-S7, 21 pages (2011).
Tsutakawa, S.E., et al.; "Phosphate steering by Flap Endonuclease 1 promotes 5'-flap specificity and incision to prevent genome instability," Nature Communications, 8:15855, pp. 1-15 (2017).
UniProtKB: POCL77—DPOL_PYRAB; "DNA polymerase 1," Last Updated: Apr. 5, 2011; [retrieved online Sep. 23, 2024] URL: www.uniprot.org/uniprotkb/P0CL77/entry, 5 pages.
UniProtKB: P30317—DPOL_THELI; "DNA polymerase," Last Updated: Apr. 1, 1993 [retrieved online Sep. 23, 2024] URL: www.uniprot.org/uniprotkb/P30317/entry, 6 pages.

(56) References Cited

OTHER PUBLICATIONS

UniProtKB: P61875—DPOL_PYRFU; "DNA polymerase," Last Updated: Jun. 7, 2004 [retrieved online Sep. 23, 2024] URL: www.uniprot.org/uniprotkb/P61875/entry, 6 pages.

UniProtKB: Q38087—DPOL_BPR69; "DNA-directed DNA polymerase," Last Updated: Nov. 1, 1996 [retrieved online Sep. 23, 2024] URL: www.uniprot.org/uniprotkb/Q38087/entry, 6 pages.

UniProtKB: Q51334—DPOL_PYRSD; "DNA polymerase," Last Updated: Nov. 1, 1996 [retrieved online Sep. 23, 2024] URL: www.uniprot.org/uniprotkb/Q51334/entry, 6 pages.

UniProtKB: Q56366—DPOL_THES9; "DNA polymerase," Last Updated: Nov. 1, 1996 [retrieved online Sep. 23, 2024] URL: www.uniprot.org/uniprotkb/Q56366/entry, 7 pages.

UniProtKB/Swiss-Prot: P03680.1—DPOL_BPPH2; "DNA polymerase," Last Updated: Jul. 21, 1986; [retrieved online Sep. 23, 2024] URL: www.uniprot.org/uniprotkb/P03680/entry, 7 pages.

UniProtKB/Swiss-Prot: Q9HH07.1; "RecName: Full=DNA ligase; AltName: Full=Polydeoxyribonucleotide synthase [ATP/NAD (+)]," Date updated: Mar. 1, 2001; [retrieved online Sep. 20, 2024] URL: www.ncbi.nlm.nih.gov/protein/Q9HH07, 2 pages.

U.S. Appl. No. 18/824,527, filed Sep. 4, 2024, by Sinan Arslan, et al.

Gao, H., et al.; "Rolling circle amplification for single cell analysis and in situ sequencing," TrAC Trends in Analytical Chemistry; 121:115700; pp. 1-13 (2019).

Hu, T., et al.; "Next-generation sequencing technologies: An overview," Hum Immunol.; 82(11):801-811 (2021).

Illumina "Overview of Illumina Sequencing by Synthesis Workflow," Oct. 5, 2016 (Oct. 5, 2016) [retrieved online Oct. 9, 2024] https://www.youtube.com/watch?v=fCd6B5HRaZ8, 2 pages.

Pettersson, E., et al.; "Generations of sequencing technologies," Genomics 93(2):105-111 (2009).

Schlecht, U., et al.; "ConcatSeq: A method for increasing throughput of single molecule sequencing by concatenating short DNA fragments," Sci Rep; 7(1):5252; pp. 1-10 (2017).

Ulahannan, N., et al.; "Nanopore sequencing of DNA concatemers reveals higher-order features of chromatin structure," bioRxiv, Nov. 7, 2019 [retrieved on Oct. 9, 2024] https://www.biorxiv.org/content/10.1101/833590v1.full.pdf, 19 pages.

Ohtsubo, Y., et al.; "Efficient N-tailing of blunt DNA ends by Moloney murine leukemia virus reverse transcriptase," Sci Rep.; 7:41769; pp. 1-10; doi: 10.1038/srep41769 (2017).

Ohtsubo, Y., et al.; "Optimization of single strand DNA incorporation reaction by Moloney murine leukaemia virus reverse transcriptase," DNA Res.; 25(5):477-487 (2018).

\* cited by examiner

Spacer: 
Linkers:
11 atom Linker: 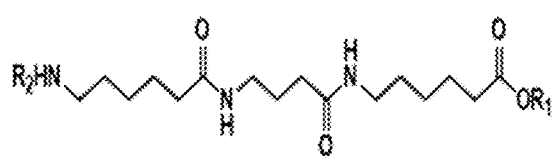
16 atom Linker: 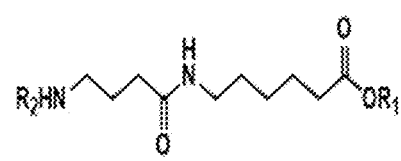
23 atom Linker:
N3 Linker: 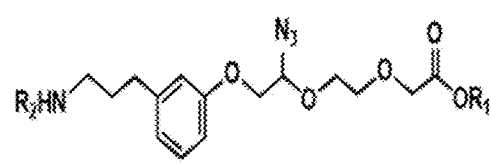
FIG. 25 dNTP-PA-NH₂:
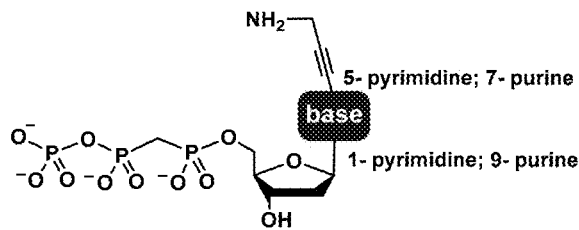
dNTP-PA-11 Atom Linker-NH₂:
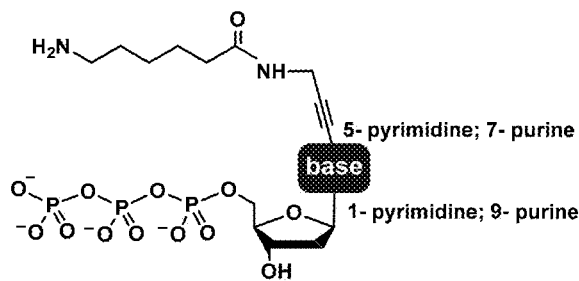
dNTP-PA-16 Atom Linker-NH₂:
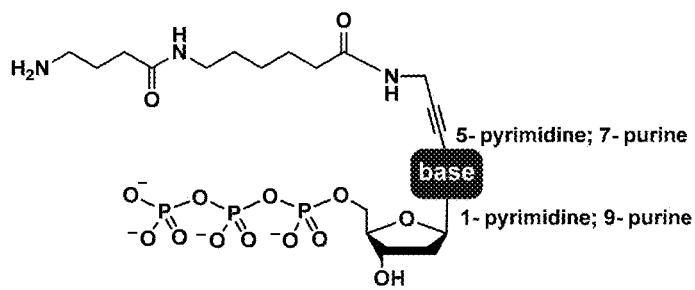
dNTP-PA-23 Atom Linker-NH₂:
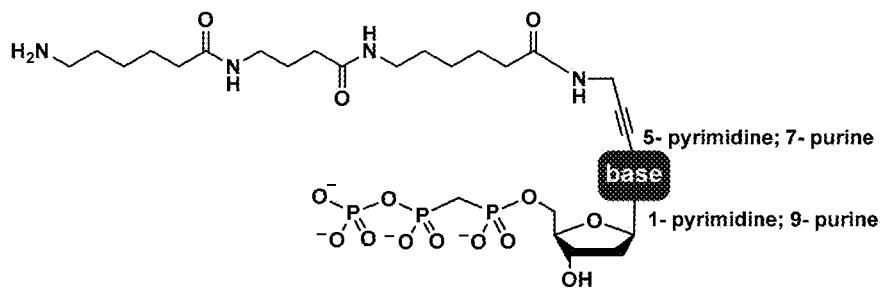
FIG. 27 dNTP-PA-N3 Linker-NH₂:
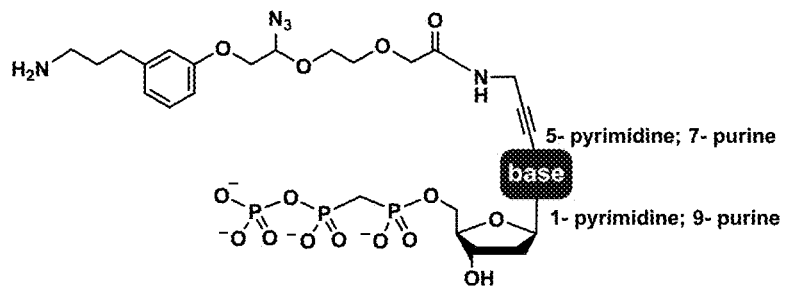
dNTP-PA-Linker 1-NH₂:
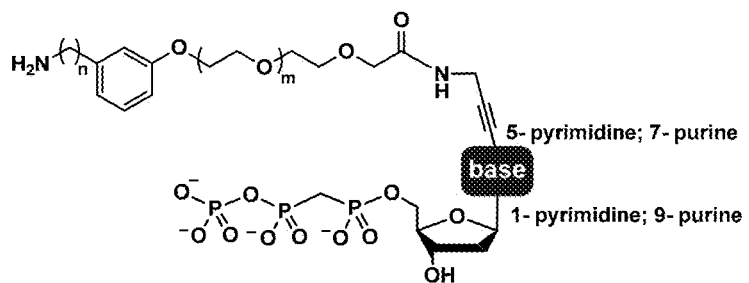
dNTP-PA-Linker 2-NH₂:
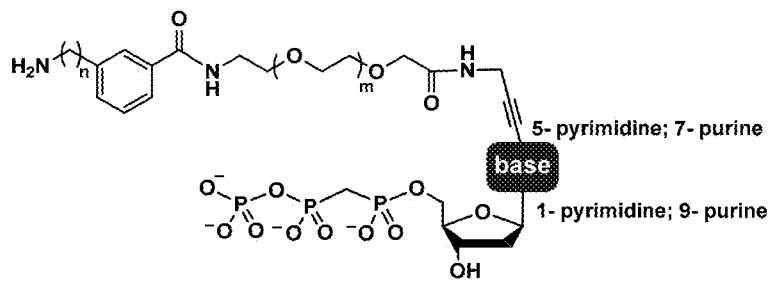
FIG. 28 dNTP-PA-Linker 3-NH₂:
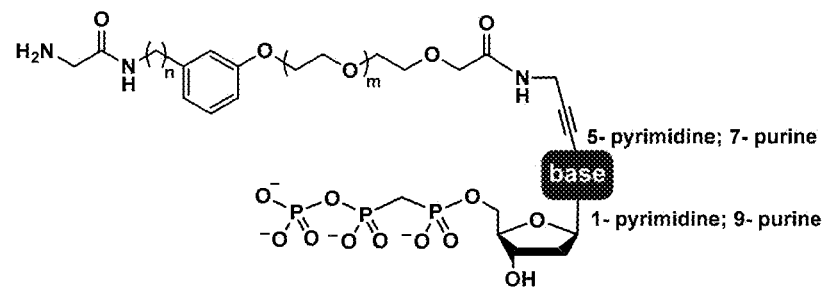
dNTP-PA-Linker 4-NH₂:
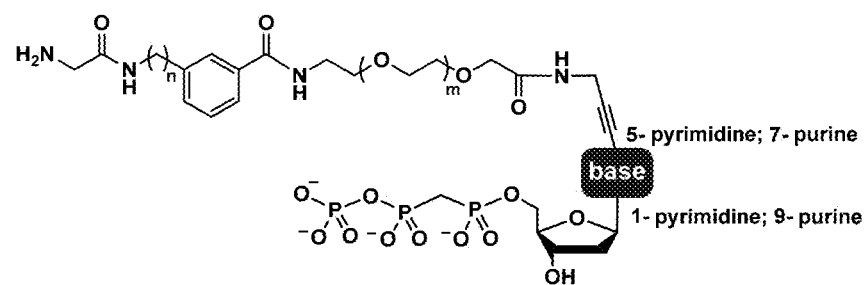
dNTP-PA-N3 Linker-NH₂:
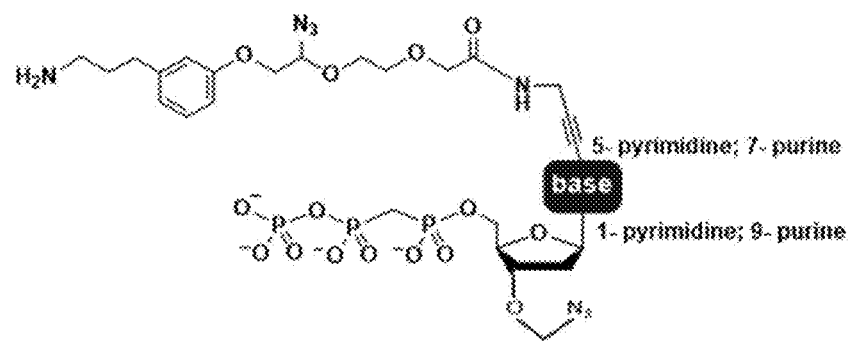
FIG. 29

G-tetrad

Table 1:

| First left index sequences (160) | | |
|---|---|---|
| Index Name | Sequence (orientation: 5' to 3') | SEQ ID NO: |
| 007 | CCACTCATT | 1 |
| 008 | AACTAACAC | 2 |
| 037 | TTATGGAGA | 3 |
| 022 | GAGTTCGCT | 4 |
| 002 | TTGTTGTTC | 5 |
| 035 | CCATATTCT | 6 |
| 001 | AATCATGCG | 7 |
| 014 | GGACAGCTC | 8 |
| 004 | CCAACACGA | 9 |
| 034 | TGTAAGCGG | 10 |
| 012 | ATAACTACC | 11 |
| 019 | CGCACTGTG | 12 |
| 020 | TTACACTCA | 13 |
| 045 | ATTGACCTG | 14 |
| 011 | CACCAGTGT | 15 |
| 038 | GGTGCTCCT | 16 |
| 033 | ATCCGCGTC | 17 |
| 026 | CGGTCCTAA | 18 |
| 046 | TGGTATGCC | 19 |
| 036 | AAGATAGAG | 20 |
| 015 | CCGGTATCG | 21 |
| 042 | GGTCCGAGA | 22 |
| 023 | CGTGATAGC | 23 |
| 081 | TATGTGGCC | 24 |
| 024 | GTACCAGAG | 25 |
| 016 | TACATCAGA | 26 |
| 028 | AGGCGACCT | 27 |
| 039 | CAGCACAAG | 28 |
| 031 | CTCTGTCCA | 29 |
| 013 | TCTTGTGAT | 30 |
| 043 | CCAGGAGTC | 31 |
| 025 | ACCGTTCGT | 32 |
| 044 | GACACTTAT | 33 |

FIG. 33-1

Table 1 (continued):

| First left index sequences (160) | | |
|---|---|---|
| Index Name | Sequence (orientation: 5' to 3') | SEQ ID NO: |
| 005 | TTGGCTGGA | 34 |
| 017 | ATTGCGTAT | 35 |
| 080 | CTCGAAGAT | 36 |
| 094 | TGAACGGAT | 37 |
| 049 | AATACCGGT | 38 |
| 058 | GGCCTTCAA | 39 |
| 067 | TGAGAACAA | 40 |
| 079 | AGATCTCTA | 41 |
| 054 | GGCAACGCA | 42 |
| 086 | CGAATGACA | 43 |
| 051 | CAAGTGCAG | 44 |
| 059 | CAAGCAACT | 45 |
| 065 | TTCAGGTCT | 46 |
| 064 | CAGTAGGTA | 47 |
| 060 | ACGAAGGCT | 48 |
| 053 | TTCTATTGG | 49 |
| 062 | GTGTCTCAC | 50 |
| 077 | GCTGAATGT | 51 |
| 071 | GAAGATGTT | 52 |
| 088 | ATTCGTTGA | 53 |
| 095 | TCGCATAGT | 54 |
| 057 | TCATGCTTG | 55 |
| 050 | TGGAGTATA | 56 |
| 055 | AAGGTGATT | 57 |
| 063 | AGAGGAAGG | 58 |
| 069 | GATCGCGAA | 59 |
| 056 | CTTCGACAC | 60 |
| 066 | GCTATTATG | 61 |
| 082 | GACTGATTA | 62 |
| 085 | ACGGCCAAC | 63 |
| 075 | CTTATCGCG | 64 |
| 061 | TCTCTCTGC | 65 |
| 073 | CAGCGTTCC | 66 |

FIG. 33-2

Table 1 (continued):

| First left index sequences (160) | | |
|---|---|---|
| Index Name | Sequence (orientation: 5' to 3') | SEQ ID NO: |
| 092 | GATTCACGG | 67 |
| 074 | TCCTCGCAA | 68 |
| 072 | ACCACAATT | 69 |
| 097 | CGTTGAATT | 70 |
| 106 | CAGTTGACC | 71 |
| 111 | CCACGAACG | 72 |
| 112 | AGCACCTAG | 73 |
| 113 | TAGGCCGTC | 74 |
| 114 | GTTCTGTAA | 75 |
| 115 | CACTGACGT | 76 |
| 116 | TCCAATACC | 77 |
| 117 | ATATTGGTG | 78 |
| 119 | CCGACCACT | 79 |
| 120 | GAACAACGA | 80 |
| 121 | ATTGTAACC | 81 |
| 123 | TCCACCTGT | 82 |
| 124 | CTACATGAA | 83 |
| 127 | CCAATGTTG | 84 |
| 132 | GTTACCAAC | 85 |
| 133 | CAATTGTGA | 86 |
| 134 | AGGCGTAAG | 87 |
| 135 | ACAGCCGTT | 88 |
| 136 | CACCAACCG | 89 |
| 137 | TCTAGCCTC | 90 |
| 138 | GTGTTAGGA | 91 |
| 139 | CGCGAGACT | 92 |
| 140 | TCAACTTAG | 93 |
| 141 | AAGAGCGCC | 94 |
| 143 | CGACCTTGA | 95 |
| 144 | TACGTACTC | 96 |

FIG. 33-3

Table 1 (continued):

| First right index sequences (170) | | |
|---|---|---|
| Index Name | Sequence (orientation: 5' to 3') | SEQ ID NO: |
| 001 | NNNGTAGGAGCC | 97 |
| 003 | NNNCCGCTGCTA | 98 |
| 004 | NNNAACAACAAG | 99 |
| 006 | NNNGGTGGTCTA | 100 |
| 008 | NNNTTGGCCAAC | 101 |
| 011 | NNNTCCATCGTT | 102 |
| 013 | NNNATTCTAGAG | 103 |
| 014 | NNNGGATGCAAT | 104 |
| 015 | NNNCAGGAGTGC | 105 |
| 016 | NNNATCACACTA | 106 |
| 018 | NNNGCGGATGAT | 107 |
| 019 | NNNCGAATCTGG | 108 |
| 021 | NNNATGCGTCCT | 109 |
| 022 | NNNGGTCTGAGC | 110 |
| 023 | NNNGCCTCATAG | 111 |
| 024 | NNNCTATACCTC | 112 |
| 025 | NNNAAGATTGGA | 113 |
| 026 | NNNTGCCAGCAT | 114 |
| 027 | NNNACTAGCTCA | 115 |
| 028 | NNNTAAGTACTG | 116 |
| 029 | NNNCGTGCAACG | 117 |
| 030 | NNNGTCCACGGA | 118 |
| 034 | NNNAGGTCCGTG | 119 |
| 035 | NNNCTCGTTAGT | 120 |
| 036 | NNNACACAATCC | 121 |
| 037 | NNNTCTTCGCAA | 122 |
| 038 | NNNGGTCACTTG | 123 |
| 039 | NNNCCGATATAT | 124 |
| 040 | NNNACAGGTCGC | 125 |
| 042 | NNNGTGCGGTTC | 126 |
| 043 | NNNCACGCACAT | 127 |
| 044 | NNNTGGATCACA | 128 |
| 045 | NNNATATTCGGT | 129 |

FIG. 33-4

Table 1 (continued):

| First right index sequences (170) | | |
|---|---|---|
| Index Name | Sequence (orientation: 5' to 3') | SEQ ID NO: |
| 047 | NNNCCAGAGATG | 130 |
| 048 | NNNTACCGTTGA | 131 |
| 049 | NNNATTGATACC | 132 |
| 051 | NNNCCAAGACCG | 133 |
| 052 | NNNAAGCCGGAC | 134 |
| 054 | NNNGGATCTCCG | 135 |
| 055 | NNNCCTGGAGAA | 136 |
| 056 | NNNATCCTCATC | 137 |
| 057 | NNNTATGTCTCT | 138 |
| 059 | NNNACGTAGAGT | 139 |
| 060 | NNNGTACTTCAA | 140 |
| 061 | NNNCATTCCAGC | 141 |
| 062 | NNNTGGCGTGAG | 142 |
| 063 | NNNTCAACGTCT | 143 |
| 064 | NNNAACGAAGTC | 144 |
| 065 | NNNCTTAATCGA | 145 |
| 066 | NNNGCGGCCTTA | 146 |
| 068 | NNNTTCCGAACG | 147 |
| 071 | NNNCGCACCGAA | 148 |
| 073 | NNNTAGTGACCA | 149 |
| 074 | NNNGTTATGCTG | 150 |
| 075 | NNNCTCCGCTAT | 151 |
| 076 | NNNTGAGATGGA | 152 |
| 078 | NNNGATAGATGT | 153 |
| 079 | NNNCCTCATGTC | 154 |
| 081 | NNNGACTTAACC | 155 |
| 082 | NNNCAAGGCGTT | 156 |
| 083 | NNNAGGAAGCCG | 157 |
| 084 | NNNTCACTCAAG | 158 |
| 085 | NNNTCCACTAGC | 159 |
| 087 | NNNCTGTCATGA | 160 |
| 088 | NNNAGCGTTCAG | 161 |
| 089 | NNNGCATAGGCA | 162 |

FIG. 33-5

Table 1 (continued):

| First right index sequences (170) | | |
|---|---|---|
| Index Name | Sequence (orientation: 5' to 3') | SEQ ID NO: |
| 091 | NNNTATCAACGC | 163 |
| 092 | NNNACAGTGTAA | 164 |
| 096 | NNNTGCGGATAC | 165 |
| 097 | NNNGCTATTACT | 166 |
| 106 | NNNGCTCAATAA | 167 |
| 111 | NNNCAGAGCTCC | 168 |
| 112 | NNNACGGACGA | 169 |
| 113 | NNNTTCCTTGGC | 170 |
| 114 | NNNGGTTGGATG | 171 |
| 115 | NNNCCACACCAT | 172 |
| 116 | NNNTACATATCG | 173 |
| 117 | NNNATTGCCATA | 174 |
| 119 | NNNCCATCTTGC | 175 |
| 120 | NNNTGGAATGCT | 176 |
| 121 | NNNAATTCGTCT | 177 |
| 123 | NNNCACCGACTC | 178 |
| 124 | NNNACAATCAGC | 179 |
| 127 | NNNCCGCGAACA | 180 |
| 132 | NNNGAGCATCTA | 181 |
| 133 | NNNCTATTAGAC | 182 |
| 134 | NNNTGTGGCAGT | 183 |
| 135 | NNNCAACCGCAG | 184 |
| 136 | NNNACCTATTCT | 185 |
| 137 | NNNTGTAGGCCA | 186 |
| 138 | NNNGTGGTTATC | 187 |
| 139 | NNNCACCAATGG | 188 |
| 140 | NNNACAACCGAT | 189 |
| 141 | NNNTGTCTGTAA | 190 |
| 143 | NNNTCCGCACTC | 191 |
| 144 | NNNGAGAGCAGA | 192 |

FIG. 33-6

DOUBLE-STRANDED SPLINT ADAPTORS WITH UNIVERSAL LONG SPLINT STRANDS AND METHODS OF USE

CROSS REFERENCE TO RELATED APPLICATIONS

This application claims priority to, and benefit of, U.S. Provisional Application No. 63/405,733, filed on Sep. 12, 2022, the contents of which are incorporated by reference in their entirety herein.

REFERENCE TO AN ELECTRONIC SEQUENCE LISTING

The contents of the electronic sequence listing (ELEM-015_001 US_SeqList_ST26.xml; Size: 88,981 bytes; and Date of Creation: Sep. 8, 2023) are herein incorporated by reference in their entirety.

TECHNICAL FIELD

The present disclosure is directed to methods of DNA sequencing, and library preparation, including compositions comprising nucleic acid double-stranded splint adaptors, and methods for using the double-stranded splint adaptors. The double-stranded splint adaptors can hybridize to portions of library molecules to form library-splint complexes having nicks, where the nicks can be ligated to form covalently closed circular molecules which can be subjected to downstream amplification and sequencing workflows.

BACKGROUND

The present disclosure relates to preparing libraries of covalently closed circular molecules using double stranded splint adaptors, and methods of sequencing the libraries prepared using the compositions and methods described herein. Improvements in next generation sequencing technology have greatly increased sequencing speed and data output, resulting in the high sample throughput of current sequencing platforms. Efficient preparation of closed circular library molecules having target sequences is important for downstream amplification and sequencing workflows. Another aspect of increasing sequencing throughput is the addition of unique index sequences to DNA fragments during library preparation, which allows large number of libraries to be pooled and sequenced simultaneously during each sequencing run. Accordingly, there is a need for alternative methods for producing and sequencing circular library molecules containing target sequences and unique index sequences, which are compatible with downstream next generation sequencing technologies. Provided herein are compositions, methods and kits addressing this need.

SUMMARY

The disclosure provides library-splint complexes (500) comprising: (i) a single-stranded nucleic acid library molecule (100) comprising a sequence of interest (110) flanked on one side by at least a first left universal adaptor sequence (120), and flanked on the other side by at least a first right universal adaptor sequence (130); and (ii) a double-stranded splint adaptor (200) comprising a first splint strand (300) and a second splint strand (400), wherein the double-stranded splint adaptor (200) comprises a double-stranded region and two single-stranded regions, one on either side of the double-stranded region, wherein the first splint strand comprises a first region (320), an internal region (310), and a second region (330); wherein the internal region of the first splint strand (310) is hybridized to the second splint strand (400), wherein the first region of the first splint strand (320) is hybridized to the at least first left universal adaptor sequence (120) of the library molecule, and wherein a second region of the first splint strand (330) is hybridized to the at least first right universal sequence (130) of the library molecule, thereby circularizing the library molecule to generate a library-splint complex (500).

In some embodiments of the library-splint complexes (500) of the disclosure, the nucleic acid library molecule (100) further comprises: a second left universal adaptor sequence (140). In some embodiments, the second left universal adaptor sequence (140) is between the at least first left universal adaptor sequence (120) and the sequence of interest (110). In some embodiments, the nucleic acid library molecule (100) further comprises: a second right universal adaptor sequence (150). In some embodiments, the second right universal adaptor sequence (150) is between the sequence of interest (110) and the at least first right universal adaptor sequence (130). In some embodiments, the nucleic acid library molecule (100) further comprises: a first left index sequence (160). In some embodiments, the first left index sequence (160) is between the at least first left universal adaptor sequence (120) and the sequence of interest (110). In some embodiments, the nucleic acid library molecule (100) further comprises: a first right index sequence (170). In some embodiments, the first right index sequence (170) is between the second right universal adaptor sequence (150) and the at least first right universal adaptor sequence (130). In some embodiments, the nucleic acid library molecule (100) further comprises: a first left unique identification sequence (180). In some embodiments, the first left unique identification sequence (180) is between the at least first left universal adaptor sequence (120) and the first left index sequence (160). In some embodiments, the nucleic acid library molecule (100) further comprises: a first right unique identification sequence (190). In some embodiments, first right unique identification sequence (190) is between the first right index sequence (170) and the at least first right universal adaptor sequence (130).

In some embodiments of the library-splint complexes (500) of the disclosure, the nucleic acid library molecule (100) further comprises any one or any combination of two or more of: (i) a second left universal adaptor sequence (140); (ii) a second right universal adaptor sequence (150); (iii) a first left index sequence (160); (iv) a first right index sequence (170); (v) a first left unique identification sequence (180); and/or (vi) a first right unique identification sequence (190).

In some embodiments of the library-splint complexes (500) of the disclosure, the first left universal adaptor sequence (120) and/or the second left universal adaptor sequence (140), comprises: (i) a universal binding sequence for a forward sequencing primer; (ii) a universal binding sequence for a reverse sequencing primer; (iii) a universal binding sequence for an first surface primer; (iv) a universal binding sequence for an second surface primer; (v) a universal binding sequence for a forward amplification primer; (vi) a universal binding sequence for a reverse amplification primer; and/or (vii) a universal binding sequence for a compaction oligonucleotide. In some embodiments, the first right universal adaptor sequence (130) and/or the second right universal adaptor sequence (150), comprises: (i) a universal binding sequence for a forward sequencing primer;

(ii) a universal binding sequence for a reverse sequencing primer; (iii) a universal binding sequence for an first surface primer; (iv) a universal binding sequence for an second surface primer; (v) a universal binding sequence for a forward amplification primer; (vi) a universal binding sequence for a reverse amplification primer; and/or (vii) a universal binding sequence for a compaction oligonucleotide.

In some embodiments of the library-splint complexes (500) of the disclosure, the second splint strand (400) includes at least two sub-regions, the first sub-region comprising a universal binding sequence for a third surface primer, and the second sub-region comprising a universal binding sequence for a fourth surface primer, wherein the first and second sub-regions do not hybridize or exhibit very little hybridization to the first and second surface primers. In some embodiments, the second splint strand (400) comprises an optional third sub-region, wherein the third sub-region comprises a sample index sequence having 5-20 bases and/or a unique identification sequence having 2-10 or more bases. In some embodiments, the unique identification sequence comprises a random sequence.

In some embodiments of the library-splint complexes (500) of the disclosure, the first splint strand (300) includes an internal region (310) comprising at least two sub-regions, the fourth sub-region comprising a universal binding sequence for a third surface primer and the fourth sub-region hybridizes to the first sub-region of the second splint strand (400), and the fifth sub-region comprising a universal binding sequence for a fourth surface primer and the fifth sub-region hybridizes to the second sub-region of the second splint strand (400), wherein the fourth and fifth sub-regions do not hybridize or exhibit very little hybridization to the first and second surface primers. In some embodiments, the first splint strand (300) includes an internal region (310) which further comprises a sixth sub-region which comprises a sample index sequence having 5-20 bases and/or a unique identification sequence having 2-10 or more bases, wherein the sixth sub-region hybridizes to the third sub-region of the second splint strand (400). In some embodiments, the unique identification sequence comprises a random sequence.

The disclosure provides library-splint complexes (500) comprising: (a) a single-stranded nucleic acid library molecule (100) comprising components arranged in a 5' to 3' order: (i) a first left universal adaptor sequence (120) having a binding sequence for a first surface primer (120); (ii) a second left universal adaptor sequence (140) having a binding sequence for a first sequencing primer; (iii) a sequence of interest (110); (iv) a second right universal adaptor sequence (150) having a binding sequence for a second sequencing primer; and (v) a first right universal adaptor sequence (130) having a binding sequence for a second surface primer (130); (b) first splint strand (300) comprising components arranged in a 5' to 3' order: a first region (320); an internal region (310); and a second region (330); and (c) a second splint strand (400) comprising sub-regions arranged in a 3' to 5' order: a first sub-region having a universal binding sequence for a third surface primer; and a second sub-region having a universal binding sequence for a fourth surface primer; wherein the first splint strand (300) is hybridized to portions of the library molecule (100) thereby circularizing the library molecule to generate a library-splint complex (500), such that the first region (320) of the first splint strand is hybridized to the binding sequence for the first surface primer (120), and the third region (330) of the first splint strand is hybridized to the binding sequence for the second surface primer (130), wherein the second splint strand (400) is hybridized to the internal region (310) of the first splint strand (300), wherein the library-splint complex (500) comprises a first nick between the 5' end of the library molecule and the 3' end of the second splint strand, wherein the library-splint complex (500) comprises a second nick between the 5' end of the second splint strand and the 3' end of the library molecule.

In some embodiments of the library-splint complexes (500) of the disclosure, the first and second nicks are enzymatically ligatable.

The disclosure provides a plurality of library-splint complexes comprising the library-splint complexes (500) of the disclosure, wherein the sequence of interest (110) of individual library-splint complexes in the plurality comprise the same sequence of interest or different sequences of interest.

The disclosure provides methods of generating the library-splint complexes of the disclosure, comprising: (a) providing a plurality of single-stranded nucleic acid library molecules (100); (b) providing a plurality of double-stranded splint adaptors (200) a first splint strand (300) and a second splint strand (400); and (c) contacting the plurality of single-stranded nucleic acid library molecules with the plurality of double-stranded splint adaptors under conditions sufficient for the ends of the first splint strands to hybridize to the ends of the library molecules, thereby generating a plurality of library-splint complexes.

The disclosure provides methods of generating the library-splint complexes of the disclosure, comprising: (a) providing a plurality of single-stranded nucleic acid library molecules, a plurality of first splint strands, and a plurality of second splint strands; and (b) contacting the plurality of single-stranded nucleic acid library molecules with the pluralities of first splint strands and second splint strands under conditions sufficient for the second splint strands to hybridize to the first splint stands, and the ends of the first splint strands to hybridize to the ends of the library molecules, thereby generating a plurality of library-splint complexes.

The disclosure provides methods of sequencing a plurality concatemer template molecules comprising: (a) providing a plurality of the library-splint complexes of the disclosure; (b) performing rolling circle amplification on the plurality of the library-splint complexes to generate a plurality of concatemer template molecules; and (c) sequencing the plurality of concatemer template molecules.

The disclosure provides kits comprising a plurality of the double-stranded splint adaptors of the disclosure.

DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 11A, the second splint strand (top strand, 400) has a sequence of SEQ ID NO:202, and the first splint strand (bottom strand, 300) has a sequence of SEQ ID NO:199.

FIG. 25 shows the chemical structure of an exemplary spacer (top), and the chemical structures of various exemplary linkers, including an 11-atom Linker, 16-atom Linker, 23-atom Linker and an N3 Linker (bottom).

FIG. 27 shows the chemical structures of various exemplary linkers joined/attached to nucleotide units.

FIG. 28 shows the chemical structures of various exemplary linkers joined/attached to nucleotide units.

FIG. 29 shows the chemical structures of various exemplary linkers joined/attached to nucleotide units.

FIGS. 33-1, 33-2, 33-3, 33-4, 33-5, and 33-6 is Table 1 (6 sheets) which lists the sequences of exemplary first left index sequences (160) and first right index sequences (170).

DETAILED DESCRIPTION

Definitions

Figure 1:
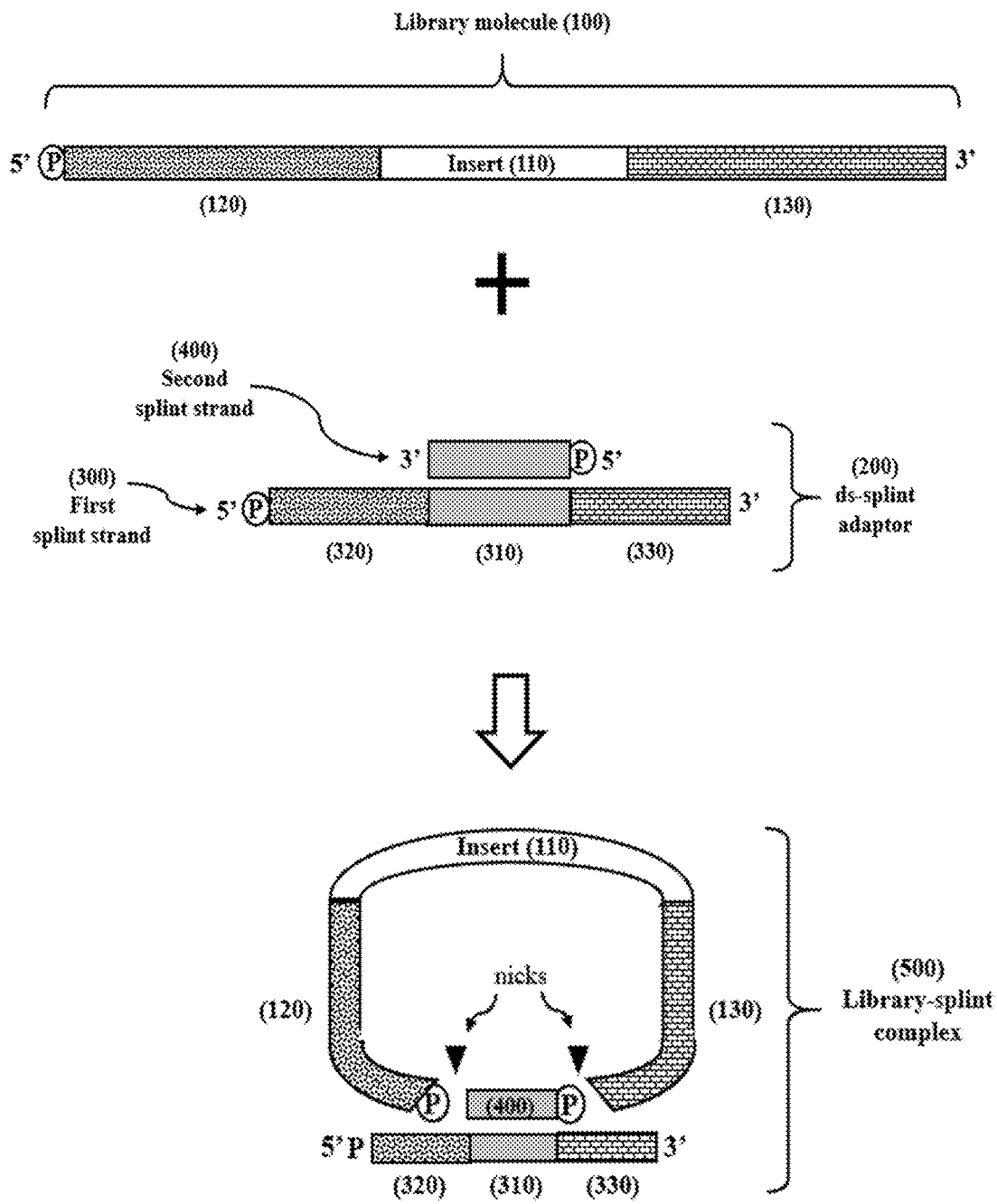
FIG. 1 is a schematic showing an exemplary linear single stranded library molecule (100) hybridizing with a double-stranded splint molecule (200, also termed "ds-splint adaptor"), thereby circularizing the library molecule to form a library-splint complex (500) with two nicks. The library molecule (100) comprises a sequence of interest (Insert (110)) flanked on one side by a first left universal adaptor sequence (120) and flanked on the other side by a first right universal adaptor sequence (130). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400). "P"s indicate 5' terminal phosphate groups.

Throughout this application various publications, patents, and/or patent applications are referenced. The disclosures of the publications, patents and/or patent applications are hereby incorporated by reference in their entireties into this application in order to more fully describe the state of the art to which this disclosure pertains.

The headings provided herein are not limitations of the various aspects of the disclosure, which aspects can be understood by reference to the specification as a whole.

Unless defined otherwise, technical and scientific terms used herein have meanings that are commonly understood by those of ordinary skill in the art unless defined otherwise. Generally, terminologies pertaining to techniques of molecular biology, nucleic acid chemistry, protein chemistry, genetics, microbiology, transgenic cell production, and hybridization described herein are those well-known and commonly used in the art. Techniques and procedures described herein are generally performed according to conventional methods well known in the art and as described in various general and more specific references that are cited and discussed throughout the instant specification. For example, see Sambrook et al., Molecular Cloning: A Laboratory Manual (Third ed., Cold Spring Harbor Laboratory Press, Cold Spring Harbor, N.Y. 2000). See also Ausubel et al., Current Protocols in Molecular Biology, Greene Publishing Associates (1992). The nomenclatures utilized in connection with, and the laboratory procedures and techniques described herein are those well-known and commonly used in the art.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative term (e.g., "or") is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include: "A and B"; "A or B"; "A" (A alone); and "B" (B alone). In a similar manner, the term "and/or" as used in a phrase such as "A, B, and/or C" is intended to encompass each of the following aspects: "A, B, and C"; "A, B, or C"; "A or C"; "A or B"; "B or C"; "A and B"; "B and C"; "A and C"; "A" (A alone); "B" (B alone); and "C" (C alone).

As used herein and in the appended claims, the terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the terms "about" and "approximately" refer to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition. Also, where ranges and/or subranges of values are provided, the ranges and/or subranges can include the endpoints of the ranges and/or subranges.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to post-translation modification such as proteolytic cleavage, cleavage due to ribosomal skipping, hydroxylation, methylation, lipidation, acetylation, SUMOylation, ubiquitination, glycosylation, phosphorylation and/or disulfide bond formation. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins.

The term "cellular biological sample" refers to a single cell, a plurality of cells, a tissue, an organ, an organism, or section of any of these cellular biological samples. The cellular biological sample can be extracted (e.g., biopsied) from an organism, or obtained from a cell culture grown in liquid or in a culture dish. The cellular biological sample comprises a sample that is fresh, frozen, fresh frozen, or archived (e.g., formalin-fixed paraffin-embedded; FFPE). The cellular biological sample can be embedded in a wax, resin, epoxy or agar. The cellular biological sample can be fixed, for example in any one or any combination of two or more of acetone, ethanol, methanol, formaldehyde, paraformaldehyde-Triton or glutaraldehyde. The cellular biological sample can be sectioned or non-sectioned. The cellular biological sample can be stained, de-stained or non-stained.

The nucleic acids of interest, sometimes referred to herein as sequences of interest, can be extracted from cells or cellular biological samples using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis. A variety of suitable commercial nucleic acid extraction and purification kits are consistent with the disclosure herein. Examples include, but are not limited to, the QIAamp kits (for isolation of genomic DNA from human samples) and DNAeasy kits (for isolation of genomic DNA from animal or plant samples) from Qiagen (Germantown, MD), or the Maxwell® and ReliaPrep™ series of kits from Promega (Madison, WI). Nucleic acids of interest can be ribonucleic acids (RNA), or deoxyribonucleic acids (DNA), such as genomic DNA or complementary DNA (cDNA) reverse transcribed from RNA.

The term "polymerase" and its variants, as used herein, comprises an enzyme comprising a domain that binds a nucleotide (or nucleoside) where the polymerase can form a complex having a template nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. A polymerase can be any enzyme that can catalyze polymerization of nucleotides (including analogs thereof) into a nucleic acid strand. Typically but not necessarily such nucleotide polymerization can occur in a template-dependent fashion. Typically, a polymerase comprises one or more active sites at which nucleotide binding and/or catalysis of nucleotide polymerization can occur. In some embodiments, a polymerase includes other enzymatic activities, such as for example, 3' to 5' exonuclease activity or 5' to 3' exonuclease activity. In some embodiments, a polymerase has strand displacing activity. A polymerase can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze nucleotide polymerization (e.g., catalytically active fragment). The term polymerase includes catalytically inactive polymerases, catalytically active polymerases, reverse transcriptases, and other enzymes comprising a nucleotide binding domain. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof. A polymerase can be derived from a prokaryote, eukaryote, virus or phage. A polymerase comprises DNA-directed DNA polymerase and RNA-directed DNA polymerase.

The term "strand displacing" refers to the ability of a polymerase to locally separate strands of double-stranded nucleic acids and synthesize a new strand in a template-based manner. Strand displacing polymerases displace a complementary strand from a template strand and catalyze new strand synthesis. Strand displacing polymerases include mesophilic and thermophilic polymerases. Strand displacing polymerases include wild type enzymes, and variants including exonuclease minus mutants, mutant versions, chimeric enzymes and truncated enzymes. Examples of strand displacing polymerases include phi29 DNA polymerase, large fragment of Bst DNA polymerase, large fragment of Bsu DNA polymerase (exo-), Bca DNA polymerase (exo-), Klenow fragment of E. coli DNA polymerase, T5 polymerase, M-MuLV reverse transcriptase, HIV viral reverse transcriptase, Deep Vent® DNA polymerase and KOD DNA polymerase. The phi29 DNA polymerase can be wild type phi29 DNA polymerase (e.g., MagniPhi™ from Expedeon), or variant EquiPhi29™ DNA polymerase (e.g., from Thermo Fisher Scientific), or chimeric QualiPhi™ DNA polymerase (e.g., from 4basebio).

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids can be isolated. Nucleic acids include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and chimeric forms containing DNA and RNA. Nucleic acids can be single-stranded or double-stranded. Nucleic acids comprise polymers of nucleotides, where the nucleotides include natural or non-natural bases and/or sugars. Nucleic acids comprise naturally-occurring internucleosidic linkages, for example phosphodiester linkages. Nucleic acids comprise non-natural internucleoside linkages, including phosphorothioate, phosphorothiolate, or peptide nucleic acid (PNA) linkages. Nucleic acids can comprise a one type of polynucleotides, or a mixture of two or more different types of polynucleotides.

The term "operably linked" and "operably joined" or related terms as used herein refers to juxtaposition of components. The juxtaposed components can be linked together covalently. For example, two nucleic acid components can be enzymatically ligated together where the linkage that joins together the two components comprises phosphodiester linkage. A first and second nucleic acid component can be linked together, where the first nucleic acid component can confer a function on a second nucleic acid component. For example, linkage between a primer binding sequence and a sequence of interest forms a nucleic acid library molecule having a portion that can bind to a primer. In another example, a transgene (e.g., a nucleic acid encoding a polypeptide or a nucleic acid sequence of interest) can be ligated to a vector where the linkage permits expression or functioning of the transgene sequence contained in the vector. In a still further example, a transgene is operably linked to a host cell regulatory sequence (e.g., a promoter sequence) that affects expression of the transgene. In an exemplary vector, the vector comprises at least one host cell regulatory sequence, including a promoter sequence, enhancer, transcription and/or translation initiation sequence, transcription and/or translation termination sequence, polypeptide secretion signal sequences, and the like, which are said to be operably linked. In the foregoing example, the host cell regulatory sequence controls expression of the level, timing and/or location of the transgene.

The terms "linked", "joined", "attached", "appended" and variants thereof comprise any type of fusion, bond, adherence or association between any combination of compounds or molecules that is of sufficient stability to withstand use in the particular procedure. The procedure can include but are not limited to: nucleotide binding; nucleotide incorporation; de-blocking (e.g., removal of chain-terminating moiety); washing; removing; flowing; detecting; imaging and/or identifying. Such linkage can comprise, for example, covalent, ionic, hydrogen, dipole-dipole, hydrophilic, hydrophobic, or affinity bonding, bonds or associations involving van der Waals forces, mechanical bonding, and the like. Such linkages can occur intramolecularly, for example linking together the ends of a single-stranded or double-stranded linear nucleic acid molecule to form a circular molecule. Alternatively, such linkages can occur between a combination of different molecules, or between a molecule and a non-molecule, including but not limited to: linkage between a nucleic acid molecule and a solid surface; linkage between a protein and a detectable reporter moiety; linkage between a nucleotide and detectable reporter moiety; and the like. Some examples of linkages can be found, for example, in Hermanson, G., "Bioconjugate Techniques", Second Edition (2008); Aslam, M., Dent, A., "Bioconjugation: Protein Coupling Techniques for the Biomedical Sciences", London: Macmillan (1998); Aslam, M., Dent, A., "Bioconjugation: Protein Coupling Techniques for the Biomedical Sciences", London: Macmillan (1998).

The term "primer" and related terms used herein refer to an oligonucleotide that is capable of hybridizing with a DNA and/or RNA polynucleotide template to form a duplex molecule. Primers can be single-stranded along their entire length or have single-stranded and double-stranded portions. Primers can comprise natural nucleotides and/or nucleotide analogs. Primers can be recombinant nucleic acid molecules. Primers may have any length, but typically range from 4-50 nucleotides. A typical primer comprises a 5' end and 3' end. The 3' end of the primer can include a 3' OH moiety which serves as a nucleotide polymerization initiation site in a polymerase-catalyzed primer extension reaction. Alternatively, the 3' end of the primer can lack a 3' OH moiety, or can include a terminal 3' blocking group that inhibits nucleotide polymerization in a polymerase-catalyzed reaction. Any one nucleotide, or more than one nucleotide, along the length of the primer can be labeled with a detectable reporter moiety. A primer can be in solution (e.g., a soluble primer) or can be immobilized to a support (e.g., a capture primer).

The term "template nucleic acid", "template polynucleotide", "target nucleic acid" "target polynucleotide", "template strand" and other variations refer to a nucleic acid strand that serves as the basis nucleic acid molecule for any of the amplification and/or sequencing methods describe herein. The template nucleic acid can be single-stranded or double-stranded, or the template nucleic acid can have single-stranded or double-stranded portions. The template nucleic acid can be obtained from a naturally-occurring source, recombinant form, or chemically synthesized to include any type of nucleic acid analog. The template nucleic acid can be linear, concatemeric, circular, or other forms. The template nucleic acid can encode the sequence of interest.

The term "adaptor" and related terms refers to oligonucleotides that can be operably linked (appended) to a target polynucleotide, where the adaptor confers a function to the co-joined adaptor-target molecule. Adaptors comprise DNA, RNA, chimeric DNA/RNA, or analogs thereof. Adaptors can include at least one ribonucleoside residue. Adaptors can be single-stranded, double-stranded, or have single-stranded and/or double-stranded portions. Adaptors can be configured to be linear, stem-looped, hairpin, or Y-shaped forms. Adaptors can be any length, including 4-100 nucleotides or longer. Adaptors can have blunt ends, overhang ends, or a combination of both. Overhang ends include 5' overhang and 3' overhang ends. The 5' end of a single-stranded adaptor, or one strand of a double-stranded adaptor, can have a 5' phosphate group or lack a 5' phosphate group. Adaptors can include a 5' tail that does not hybridize to a target polynucleotide (e.g., a tailed adaptor), or adaptors can be non-tailed. At least a portion of the adaptor can comprise a known and pre-determined sequence. An adaptor can include a sequence that is complementary to at least a portion of a primer, such as an amplification primer, a sequencing primer, or a capture primer (e.g., soluble or immobilized capture primers). Adaptors can include a random sequence or degenerate sequence. Adaptors can include at least one inosine residue. Adaptors can include at least one phosphorothioate, phosphorothiolate and/or phosphoramidate linkage. Adaptors can include at least one barcode/index sequence which can be used to distinguish polynucleotides (e.g., insert sequences) from different sample sources in a multiplex assay. Adaptors can include at least one unique identification sequence (e.g., a molecular tag) that can be used to uniquely identify a nucleic acid molecule to which the adaptor is appended. An exemplary, but non limiting, unique identification sequence comprises 2-12 or more nucleotides having a known sequence. For example, the unique identification sequence comprises a known random sequence where a nucleotide at each position is randomly selected from nucleotides having a base A, G, C, T or U. Adaptors can include at least one restriction enzyme recognition sequence, including any one or any combination of two or more selected from a group consisting of type I, type II, type III, type IV, type IIs or type IIB.

The term "universal sequence" and related terms refers to a sequence in a nucleic acid molecule that is common among two or more polynucleotide molecules. For example, an adaptor having a universal sequence can be operably joined to a plurality of polynucleotides so that the population of co-joined molecules carry the same universal adaptor sequence. Examples of universal adaptor sequences include amplification primer sequences, sequencing primer sequences, for example those compatible with commercial sequencing platforms, or capture primer sequences (e.g., soluble or immobilized capture primers).

When used in reference to nucleic acid molecules, the terms "hybridize" or "hybridizing" or "hybridization" or other related terms refers to hydrogen bonding between two different nucleic acids to form a duplex nucleic acid. Hybridization also includes hydrogen bonding between two different regions of a single nucleic acid molecule to form a self-hybridizing molecule having a duplex region. Hybridization can comprise Watson-Crick or Hoogstein binding to form a duplex double-stranded nucleic acid, or a double-stranded region within a nucleic acid molecule. The double-stranded nucleic acid, or the two different regions of a single nucleic acid, may be wholly complementary, or partially complementary. Complementary nucleic acid strands need not hybridize with each other across their entire length. The complementary base pairing can be the standard A-T or C-G base pairing, or can be other forms of base-pairing interactions. Duplex nucleic acids can include mismatched base-paired nucleotides, which can form single-stranded regions in the duplex ("bubbles").

When used in reference to nucleic acids, the terms "extend", "extending", "extension" and other variants, refers to incorporation of one or more nucleotides into a nucleic acid molecule. Nucleotide incorporation comprises polymerization of one or more nucleotides into the terminal 3' OH end of a nucleic acid strand, resulting in extension of the nucleic acid strand. Nucleotide incorporation can be conducted with natural nucleotides and/or nucleotide analogs. Typically, but not necessarily, nucleotide incorporation occurs in a template-dependent fashion. Any suitable method of extending a nucleic acid molecule may be used, including primer extension catalyzed by a DNA polymerase or RNA polymerase.

The term "nucleotides" and related terms refers to a molecule comprising an aromatic base, a five carbon sugar (e.g., ribose or deoxyribose), and at least one phosphate group. Canonical or non-canonical nucleotides are consistent with use of the term. In some embodiments, the nucleotide comprises a monophosphate, diphosphate, or triphosphate, or corresponding phosphate analog. The term "nucleoside" refers to a molecule comprising an aromatic base and a sugar. Nucleotides and nucleosides can be non-labeled or labeled with a detectable reporter moiety.

Nucleotides (and nucleosides) typically comprise a heterocyclic base including substituted or unsubstituted nitrogen-containing parent heteroaromatic ring which are commonly found in nucleic acids, including naturally-occurring, substituted, modified, or engineered variants, or analogs of the same. The base of a nucleotide (or nucleoside) is capable of forming Watson-Crick and/or Hoogstein hydrogen bonds with an appropriate complementary base. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

Nucleotides (and nucleosides) typically comprise a sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other sugar moieties (Joeng, et al., 1993 J. Med. Chem. 36: 2627-2638; Kim, et al., 1993 J. Med. Chem. 36: 30-7; Eschenmosser 1999 Science 284:2118-2124; and U.S. Pat. No. 5,558,991). The sugar moiety comprises, without limitation: ribosyl; 2'-deoxyribosyl; 3'-deoxyribosyl; 2',3'-dideoxyribosyl; 2',3'-didehydrodideoxyribosyl; 2'-alkoxyribosyl; 2'-azidoribosyl; 2'-aminoribosyl; 2'-fluororibosyl; 2'-mercaptoribosyl; 2'-alkylthioribosyl; 3'-alkoxyribosyl; 3'-azidoribosyl; 3'-aminoribosyl; 3'-fluororibosyl; 3'-mercaptoribosyl; 3'-alkylthioribosyl carbocyclic; acyclic or other modified sugars.

Nucleotides can comprise a chain of one, two or three phosphorus atoms where the chain is typically attached to the 5' carbon of the sugar moiety via an ester or phosphoramide linkage. In some embodiments, the nucleotide is an analog having a phosphorus chain in which the phosphorus atoms are linked together with intervening O, S, NH, methylene or ethylene. The phosphorus atoms in the chain can include substituted side groups including O, S or $BH_3$. Alternatively, or in addition, the chain can include phosphate groups substituted with analogs including phosphoramidate, phosphorothioate, phosphordithioate, and O-methylphosphoroamidite groups.

Figure 31:
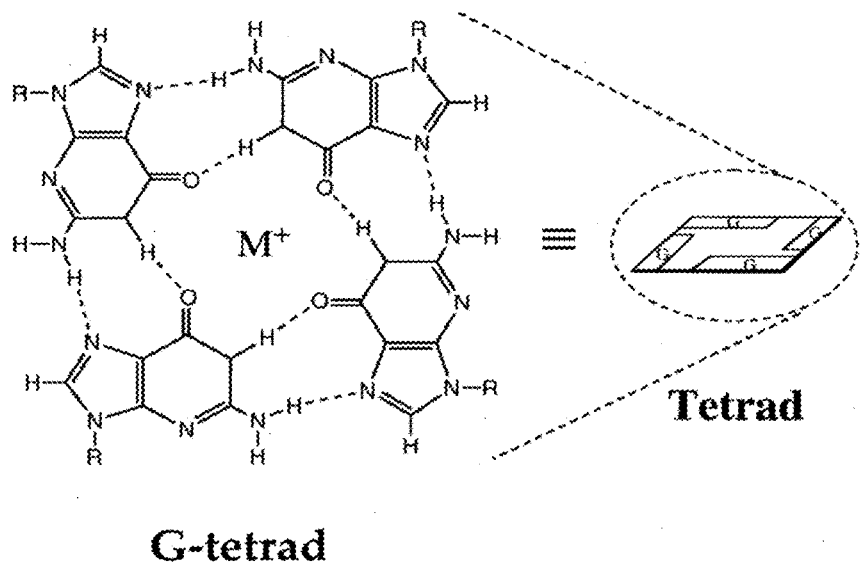
FIG. 31 is a schematic of a guanine tetrad (e.g., G-tetrad).
Figure 32:
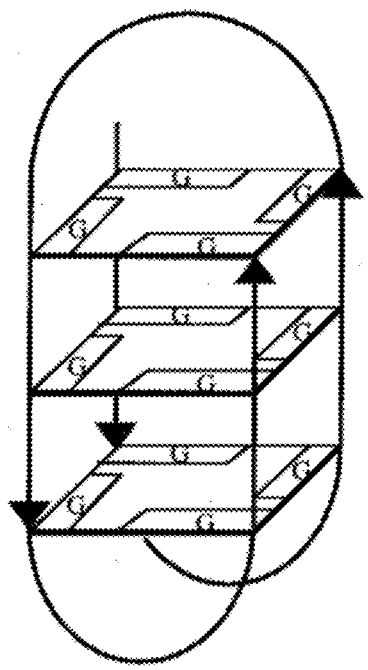
FIG. 32 is a schematic of an exemplary intramolecular G-quadruplex structure.

The term "rolling circle amplification" generally refers to an amplification method that employs a circularized nucleic acid template molecule containing a target sequence of interest, an amplification primer binding sequence, and optionally one or more adaptor sequences such as a sequencing primer binding sequence and/or a sample index sequence. The rolling circle amplification reaction can be conducted under isothermal amplification conditions, and includes the circularized nucleic acid template molecule, an amplification primer, a strand-displacing polymerase and a plurality of nucleotides, to generate a concatemer containing tandem repeat sequences of the circular template molecule and any adaptor sequences present in the original circularized nucleic acid template molecule. The concatemer can self-collapse to form a nucleic acid nanoball. The shape and size of the nanoball can be further compacted by including a pair of inverted repeat sequences in the circular template molecule, or by conducting the rolling circle amplification reaction with one or more compaction oligonucleotides. One of the advantages of using rolling circle amplification to generate clonal amplicons for a sequencing workflow is that the repeat copies of the target sequence in the nanoball can be simultaneously sequenced to increase signal intensity. In some embodiments, the rolling circle amplification reaction can be conducted in the presence of a plurality of compaction oligonucleotides having at least four consecutive guanines. The rolling circle amplification reaction generates concatemers comprising repeat copies of the universal binding sequence for the compaction oligonucleotide. At least one compaction oligonucleotide can form a guanine tetrad (FIG. 31) and hybridize to the universal binding sequences for the compaction oligonucleotide, and the resulting concatemer can fold to form an intramolecular G-quadruplex structure (FIG. 32). The concatemers can self-collapse to form compact nanoballs. Formation of the guanine tetrads and G-quadruplexes in the nanoballs may increase the stability of the nanoballs to retain their compact size and shape which can withstand repeated flows of reagents for conducting any of the sequencing workflows described herein.

When used in reference to nucleic acids, the terms "amplify", "amplifying", "amplification", and other related terms include producing multiple copies of an original polynucleotide template molecule, where the copies comprise a sequence that is complementary to the template sequence, and/or the copies comprise a sequence that is the same as the template sequence. In some embodiments, the copies comprise a sequence that is substantially identical to a template sequence, and/or is substantially identical to a sequence that is complementary to the template sequence.

The term "reporter moiety", "reporter moieties" or related terms refers to a compound that generates, or causes to generate, a detectable signal. A reporter moiety is sometimes called a "label". Any suitable reporter moiety may be used, including luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme. A reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. It is well known to one skilled in the art to select reporter moieties so that each absorbs excitation radiation and/or emits fluorescence at a wavelength distinguishable from the other reporter moieties to permit monitoring the presence of different reporter moieties in the same reaction or in different reactions. Two or more different reporter moieties can be selected having spectrally distinct emission profiles, or having minimal overlapping spectral emission profiles. Reporter moieties can be linked (e.g., operably linked) to nucleotides, nucleosides, nucleic acids, enzymes (e.g., polymerases or reverse transcriptases), or support (e.g., surfaces).

A reporter moiety (or label) can comprise a fluorescent label or a fluorophore. Exemplary fluorescent moieties which may serve as fluorescent labels or fluorophores include, but are not limited to fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue® and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor® dyes, DyLight® dyes, Atto™ dyes, LightCycler® Red dyes, CAL Flour dyes, JOE and derivatives thereof, Oregon Green™ dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

The term "support" as used herein refers to a substrate that is designed for deposition of biological molecules or biological samples for assays and/or analyses. Examples of biological molecules to be deposited onto a support include nucleic acids (e.g., DNA, RNA), polypeptides, saccharides, lipids, a single cell or multiple cells. Examples of biological samples include but are not limited to saliva, phlegm, mucus, blood, plasma, serum, urine, stool, sweat, tears and fluids from tissues or organs.

In some embodiments, the support is solid, semi-solid, or a combination of both. In some embodiments, the support is porous, semi-porous, non-porous, or any combination of porosity. In some embodiments, the support is substantially planar, concave, convex, or any combination thereof. In some embodiments, the support is cylindrical, for example comprising a capillary or interior surface of a capillary.

In some embodiments, the surface of the support can be substantially smooth. In some embodiments, the support can be regularly or irregularly textured, including bumps, etched, pores, three-dimensional scaffolds, or any combination thereof.

In some embodiments, the support comprises a bead having any shape, including spherical, hemi-spherical, cylindrical, barrel-shaped, toroidal, disc-shaped, rod-like, conical, triangular, cubical, polygonal, tubular or wire-like.

The support can be fabricated from any material, including but not limited to glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The present disclosure provides a plurality (e.g., two or more) of nucleic acid template molecules immobilized to a support. In some embodiments, the immobilized plurality of nucleic acid template molecules have the same sequence or have different sequences. In some embodiments, individual nucleic acid template molecules in the plurality of nucleic acid template molecules are immobilized to a different site on the support. In some embodiments, two or more individual nucleic acid template molecules in the plurality of nucleic acid templates are immobilized to a site on the support.

The term "array" refers to a support comprising a plurality of sites located at pre-determined locations on the support to form an array of sites. The sites can be discrete and separated by interstitial regions. In some embodiments, the pre-determined sites on the support can be arranged in one dimension in a row or a column, or arranged in two dimensions in rows and columns. In some embodiments, the plurality of pre-determined sites is arranged on the support in an organized fashion. In some embodiments, the plurality of pre-determined sites is arranged in any organized pattern, including rectilinear, hexagonal patterns, grid patterns, patterns having reflective symmetry, patterns having rotational symmetry, or the like. The pitch between different pairs of sites can be that same or can vary. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are located at pre-determined locations on the support. In some embodiments, a plurality of pre-determined sites on the support (e.g., $10^2$-$10^{15}$ sites or more) comprise immobilized nucleic acid template molecules at the sites to form a nucleic acid template array. In some embodiments, the nucleic acid template molecules that are immobilized at a plurality of pre-determined sites by hybridization to immobilized surface capture primers, or the nucleic acid template molecules are covalently attached to the surface capture primers. In some embodiments, the nucleic acid template molecules that are immobilized at a plurality of pre-determined sites, for example immobilized at $10^2$-$10^{15}$ sites or more. In some embodiments, the immobilized nucleic acid template molecules are clonally-amplified to generate immobilized nucleic acid clusters at the plurality of pre-determined sites. In some embodiments, individual immobilized nucleic acid clusters comprise linear clusters, or comprise single-stranded or double-stranded concatemers.

In some embodiments, a support comprises a plurality of sites located at random locations on the support, and is referred to herein as a support having randomly located sites thereon. The location of the randomly located sites on the support are not pre-determined. The plurality of randomly-located sites is arranged on the support in a disordered and/or unpredictable fashion. In some embodiments, the support comprises at least $10^2$ sites, at least $10^3$ sites, at least $10^4$ sites, at least $10^5$ sites, at least $10^6$ sites, at least $10^7$ sites, at least $10^8$ sites, at least $10^9$ sites, at least $10^{10}$ sites, at least $10^{11}$ sites, at least $10^{12}$ sites, at least $10^{13}$ sites, at least $10^{14}$ sites, at least $10^{15}$ sites, or more, where the sites are randomly located on the support. In some embodiments, a plurality of randomly located sites on the support (e.g., $10^2$-$10^{15}$ sites or more) comprise immobilized nucleic acid template molecules at the sites. In some embodiments, the nucleic acid template molecules are immobilized at a plurality of randomly located sites by hybridization to immobilized surface capture primers, or the nucleic acid template molecules are covalently attached to the surface capture primers. In some embodiments, the nucleic acid templates that are immobilized at a plurality of randomly located sites, for example immobilized at $10^2$-$10^{15}$ sites or more. In some embodiments, the immobilized nucleic acid templates are clonally-amplified to generate immobilized nucleic acid clusters at the plurality of randomly located sites. In some embodiments, individual immobilized nucleic acid clusters comprise linear clusters, or comprise single-stranded or double-stranded concatemers.

In some embodiments, the plurality of immobilized surface capture primers on the support (e.g., located at pre-determined or random locations on the support) are in fluid communication with each other to permit flowing a solution of reagents (e.g., nucleic acid template molecules, soluble primers, enzymes, nucleotides, divalent cations, buffers, and the like) onto the support so that the plurality of immobilized surface capture primers on the support can be essentially simultaneously reacted with the reagents in a massively parallel manner. In some embodiments, the fluid communication of the plurality of immobilized surface capture primers can be used to conduct nucleic acid amplification reactions (e.g., RCA, MDA, PCR and bridge amplification) essentially simultaneously on the plurality of immobilized surface capture primers. An exemplary support that allows fluid communication to permit flowing of a solution includes, but is not limited to, an interior surface of a flow cell or capillary.

In some embodiments, the plurality of immobilized nucleic acid clusters on the support are in fluid communication with each other to permit flowing a solution of reagents (e.g., enzymes, nucleotides, divalent cations, and the like) onto the support so that the plurality of immobilized nucleic acid clusters on the support can be essentially simultaneously reacted with the reagents in a massively parallel manner. In some embodiments, the fluid communication of the plurality of immobilized nucleic acid clusters can be used to conduct nucleotide binding assays and/or conduct nucleotide polymerization reactions (e.g., primer extension or sequencing) essentially simultaneously on the plurality of immobilized nucleic acid clusters, and optionally to conduct detection and imaging for massively parallel sequencing.

The term "immobilized" and related terms refer to nucleic acid molecules that are attached to a support through covalent bond or non-covalent interaction, or attached to a coating on the support, or buried within a matrix formed by a coating on the support, where the nucleic acid molecules include surface capture primers, nucleic acid template molecules and extension products of capture primers. Extension products of capture primers includes nucleic acid concatemers (e.g., nucleic acid clusters). The nucleic acid molecules can be immobilized at pre-determined or random locations on the support. The nucleic acid molecules can be immobilized at pre-determined or random locations on or within a coating passivated on the support.

The term "immobilized" and related terms can also refer to enzymes (e.g., polymerases) that are attached to a support through covalent bond or non-covalent interaction, or attached to a coating on the support, or buried within a matrix formed by a coating on the support. The enzymes can be immobilized at pre-determined or random locations on the support. The enzymes can be immobilized at pre-determined or random locations on or within a coating passivated on the support.

In some embodiments, one or more nucleic acid template molecules are immobilized on the support, for example immobilized at the random or pre-determined sites on the support. In some embodiments, the one or more nucleic acid template molecules are clonally-amplified. In some embodiments, the one or more nucleic acid template molecules are clonally-amplified off the support (e.g., in-solution) and then deposited onto the support and immobilized on the support. In some embodiments, the clonal amplification reaction of the one or more nucleic acid template molecules is conducted on the support resulting in immobilization on the support. In some embodiments, the one or more nucleic acid template molecules are clonally-amplified (e.g., in solution or on the support) using a nucleic acid amplification reaction, including any one or any combination of: polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification (RCA), circle-to-circle amplification, helicase-dependent amplification, recombinase-dependent amplification, and/or single-stranded binding (SSB) protein-dependent amplification.

The term "surface primer," "capture primer," "surface capture primer" and related terms refers to single-stranded oligonucleotides that are immobilized to a support and comprise a sequence that can hybridize to at least a portion of a nucleic acid template molecule. Surface capture primers can be used to immobilize template molecules to a support via hybridization. Surface capture primers can be immobilized to a support in a manner that resists primer removal during flowing, washing, aspirating, and changes in temperature, pH, salts, chemical and/or enzymatic conditions. Typically, but not necessarily, the 5' end of a surface capture primer can be immobilized to a support or to a coating on the support (or embedded in a coating on the support). Alternatively, or in addition, an interior portion or the 3' end of a surface capture primer can be immobilized to a support.

The sequence of surface capture primers can be wholly or partially complementary along their length to at least a portion of the nucleic acid template molecule. A support can include a plurality of immobilized surface capture primers having the same sequence, or having two or more different sequences. Surface capture primers can be any length, for example 4-50 nucleotides, or 50-100 nucleotides, or 100-150 nucleotides, or longer lengths.

A surface capture primer can have a terminal 3' nucleotide having a sugar 3' OH moiety which is extendible for nucleotide polymerization (e.g., polymerase catalyzed polymerization). A surface capture primer can have a terminal 3' nucleotide having the 3' sugar position linked to a chain-terminating moiety that inhibits nucleotide polymerization. The 3' chain-terminating moiety can be removed (e.g., de-blocked) to convert the 3' end to an extendible 3' OH end using a de-blocking agent. Examples of chain terminating moieties include alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. Azide type chain terminating moieties including azide, azido and azidomethyl groups. Examples of de-blocking agents include a phosphine compound, such as Tris(2-carboxyethyl)phosphine (TCEP) and bis-sulfo triphenyl phosphine (BS-TPP), for chain-terminating groups azide, azido and azidomethyl groups. Examples of de-blocking agents include tetrakis(triphenylphosphine)palladium(0) (Pd(PPh$_3$)$_4$) with piperidine, or with 2,3-Dichloro-5,6-dicyano-1,4-benzo-quinone (DDQ), for chain-terminating groups alkyl, alkenyl, alkynyl and allyl. Examples of a de-blocking agent includes Pd/C for chain-terminating groups aryl and benzyl. Examples of de-blocking agents include phosphine, beta-mercaptoethanol or dithiothritol (DTT), for chain-terminating groups amine, amide, keto, isocyanate, phosphate, thio and disulfide. Examples of de-blocking agents include potassium carbonate (K$_2$CO$_3$) in MeOH, triethylamine in pyridine, and Zn in acetic acid (AcOH), for carbonate chain-terminating groups. Examples of de-blocking agents include tetrabutylammonium fluoride, pyridine-HF, with ammonium fluoride, and triethylamine trihydrofluoride, for chain-terminating groups urea and silyl.

The term "sequencing" and related terms refers to a method for obtaining nucleotide sequence information from a nucleic acid molecule, typically by determining the identity of at least some nucleotides (including their nucleobase components) within the nucleic acid molecule. The sequence information of a given region of a nucleic acid molecule can include identifying each and every nucleotide within a region that is sequenced. Alternatively, sequencing information determines only some of the nucleotides a region, while the identity of some nucleotides remains undetermined or incorrectly determined. Any suitable method of sequencing may be used. For example, sequencing can include label-free or ion based sequencing methods. As a further example, sequencing can include labeled or dye-containing nucleotide or fluorescent based nucleotide sequencing methods. Sequencing can include polony-based sequencing or bridge sequencing methods. Sequencing can employ polymerases and multivalent molecules for generating at least one avidity complex, wherein individual multivalent molecules comprise a plurality of nucleotide units tethered to a core (FIGS. 20-24). Sequencing can employ polymerases and free nucleotides for performing sequencing-by-synthesis. Sequencing can also employs=a ligase enzyme and a plurality of sequence-specific oligonucleotides for performing sequence-by-ligation.

Double-Stranded Splint Adaptors

The present disclosure provides compositions comprising nucleic acid double-stranded splint adaptors, including kits, and methods that employ the double-stranded splint adaptors.

The double-stranded splint adaptors (200) can be used in a one-pot, multi-enzyme reaction to introduce one or more new adaptor sequences into a library molecule (100). The double-stranded splint adaptor (200) comprises a first splint strand (long splint strand (300)) and a second splint strand (short splint strand (400)), wherein the first and second splint strands are hybridized together to form the double-stranded splint adaptor (200) having a double-stranded region and two flanking single-stranded regions (e.g., see FIGS. 1-8). The second splint strand (400) carries the new adaptor sequence(s) to be introduced, such as for example a new universal binding sequence and/or a new index sequence. The first splint strand comprises a first region (320), an internal region (310), and a second region (330). The internal region of the first splint strand (310) is hybridized to the second splint strand (400). The two flanking single-stranded regions of the double-stranded splinted adaptor (e.g., (320) and (330)) are designed to hybridize to universal adaptor sequences at the ends of a single-stranded linear library molecule (100) having a sequence of interest (110). For example, the first region of the first splint strand (320) is hybridized to one end of the library molecule, and the second region of the first splint strand (330) is hybridized to the other end of the library molecule, thereby circularizing the library molecule to generate a library-splint complex (500) which includes two nicks (e.g., see FIGS. 1-8). The nicks can be enzymatically ligated to generate a covalently closed circular molecule (600) in which the second splint strand (400) is covalently joined at both ends to the library molecule, thereby introducing the new adaptor sequences into the library molecule (see FIG. 9).

Thus, the double-stranded splint adaptors and the methods described herein, can be used to convert any linear library molecule into a covalently closed circular molecule which can be used for a different workflow such as a different massively parallel sequencing platform. The double-stranded splint adaptors offer flexibility because the two flanking single-stranded regions (e.g., (320) and (330)), and the second splint strand (400) can be designed to include any combination of universal adaptor sequences. For example, the two flanking single-stranded regions (e.g., (320) and (330)) can comprise universal binding sequences (or complementary sequences thereof) for P5 and P7 sequences which bind to surface primers immobilized on a support (e.g., flow cell), where P5 and P7 sequences are typically used to construct library molecules for an Illumina sequencing platform. The second splint strand (400) can include at least one new universal adaptor sequence (e.g., a new surface primer sequence) that is not found on an Illumina sequencing platform, thereby permitting use of the covalently closed circular molecule (600) on a non-Illumina sequencing platform.

The methods described herein also offer the advantage of employing a ligation reaction rather than a gap fill-in reaction to introduce the new adaptor sequences. The ligation reaction gives a high efficiency circularization with as little as 0.25 pmol library molecules.

The methods described herein can be performed manually or adapted for automation because the annealing and multi-enzyme reactions can be conducted in a single reaction vessel (one-pot) by combining some enzymatic reactions (e.g., phosphorylation and ligation) and by adding subsequent enzymes (e.g., exonucleases) without intervening alcohol precipitations or organic extractions.

The present disclosure provides nucleic acid double-stranded splint adaptors (200), comprising: (i) a first splint strand (long splint strand (300)) which is hybridized to (ii) a second splint strand (short splint strand (400)) (e.g., see FIGS. 1-8). The first splint strand comprises a first region (320), an internal region (310), and a second region (330). The internal region of the first splint strand (310) is hybridized to the second splint strand (400) to form a double-stranded splint adaptor (200) having a double-stranded region and two flanking single-stranded regions. The two flanking single-stranded regions of the double-stranded splint adaptor (200) are designed to hybridize to the end sequences of a linear nucleic acid library molecule. The end sequences of the linear nucleic acid library molecule comprise first and sequence universal adaptor sequences, respectively. In some embodiments, the first and second universal adaptor sequences of the linear library molecule comprise binding sequences for immobilized first and second capture primers on a support, respectively.

The first region of the first splint strand (320) comprises a first universal adaptor sequence which can hybridize to a first universal binding sequence at one end of a linear nucleic acid library molecule (e.g., see FIGS. 1-8). The second region of the first splint strand (330) comprises a second universal adaptor sequence which can hybridize to a second universal binding sequence at the other end of the linear nucleic acid library molecule (e.g., see FIGS. 1-8). In some embodiments, the first region of the first splint strand (320) includes a first universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the second region of the first splint strand (330) includes a second universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the 5' end of the first splint strand (300) is phosphorylated or non-phosphorylated. In some embodiments, the 3' end of the first splint strand (300) comprises a terminal 3' OH group or a terminal 3' blocking group.

Figure 2:
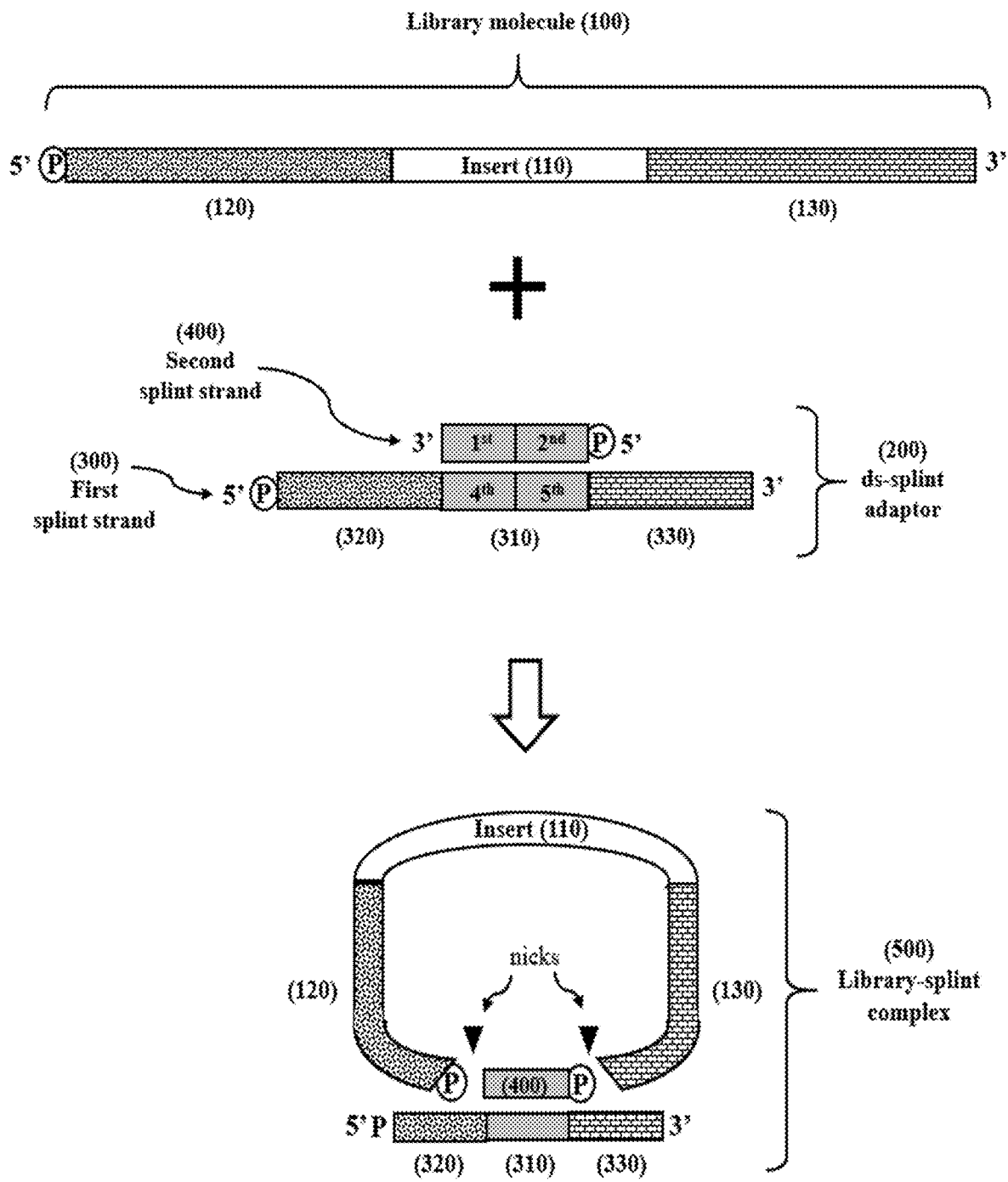
FIG. 2 is the same schematic shown in FIG. 1 with more detail pertaining to embodiments of the internal region (310) of the first splint strand (300), and the second splint strand (400). The second splint strand (400) can include two sub-regions, where the first sub-region comprises a universal binding sequence for a third surface primer, and the second sub-region comprises a universal binding sequence for a fourth surface primer. The internal region (310) of the first splint strand (300) can comprise two sub-regions, where the fourth sub-region hybridizes to the first sub-region of the second splint strand (400), and the fifth sub-region hybridizes to the second sub-region of the second splint strand (400).
Figure 3:
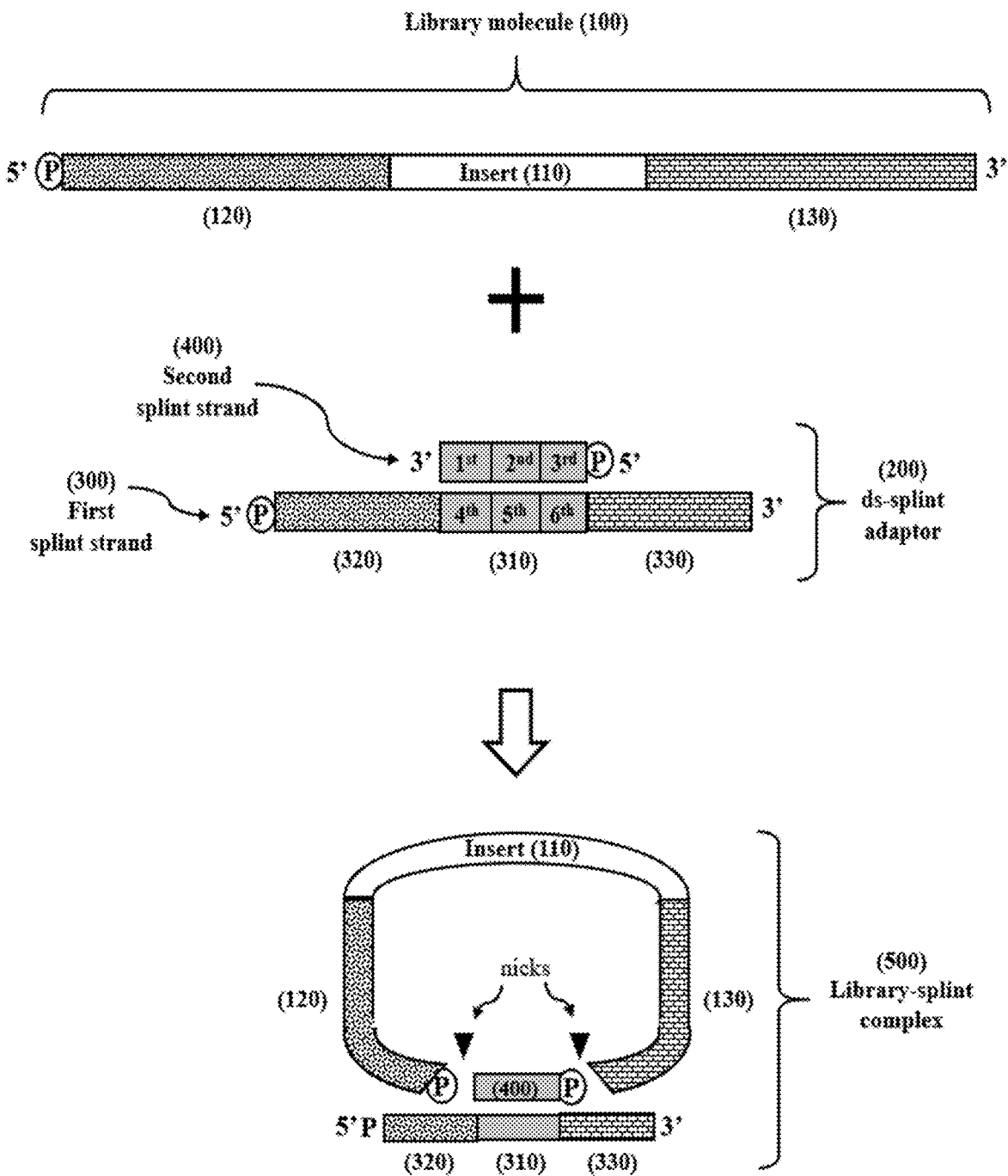
FIG. 3 is the same schematic shown in FIG. 1 with more detail pertaining to embodiments of the internal region (310) of the first splint strand (300), and the second splint strand (400). The second splint strand (400) can include three sub-regions, where the first sub-region comprises a universal binding sequence for a third surface primer, the second sub-region comprises a universal binding sequence for a fourth surface primer, and the third sub-region comprises a sample index sequence having 5-20 bases and/or a unique identification sequence having 2-10 or more bases (e.g., NN). The internal region (310) of the first splint strand (300) can comprise three sub-regions, where the fourth sub-region hybridizes to the first sub-region of the second splint strand (400), the fifth sub-region hybridizes to the second sub-region of the second splint strand (400), and the sixth sub-region hybridizes to the third sub-region of the second splint strand (400).
Figure 4:
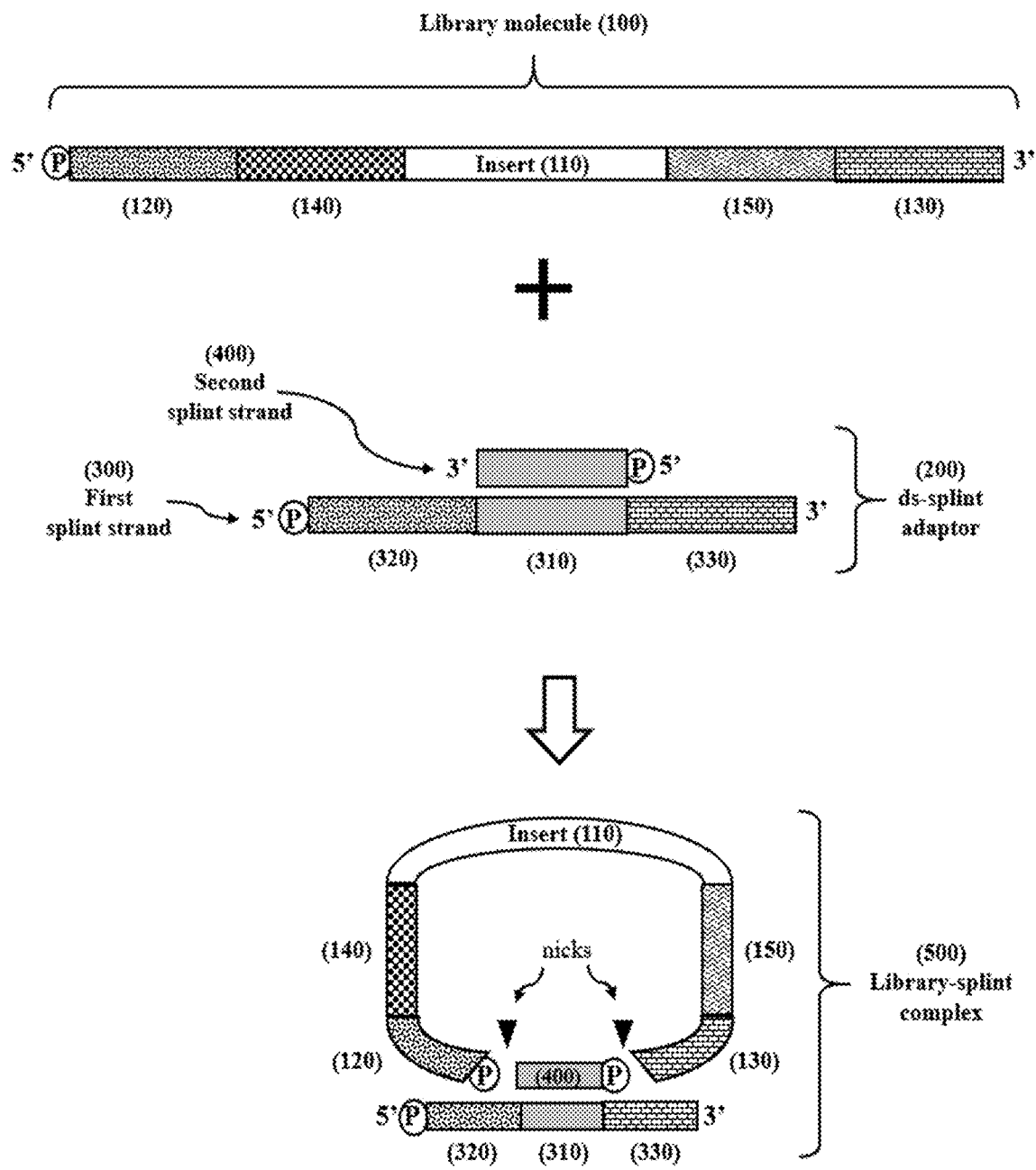
FIG. 4 is a schematic showing an exemplary linear single stranded library molecule (100) hybridizing with a double-stranded splint molecule (200) thereby circularizing the library molecule to form a library-splint complex (500) with two nicks. The library molecule (100) comprises a sequence of interest (Insert, 110) flanked on one side by a first left universal adaptor sequence (120) and a second left universal adaptor sequence (140), and flanked on the other side by a second right universal adaptor sequence (150) and a first right universal adaptor sequence (130). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400).

In some embodiments, the second splint strand (400) comprises at least two sub-regions, including a first and second sub-region (e.g., see FIGS. 2 and 3). In some embodiments, the first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN) (e.g., see FIG. 3). In some embodiments, the second splint strand (400) comprises only one sub-region and lacks a second and third sub-region, where the first sub-region comprises a sample index sequence having 5-20 bases. In some embodiments, the sample index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3'. Another exemplary arrangement of the sub-regions in the second splint strand (400), in a 5' to 3' orientation comprises: 5'-[third sub-region]-[second sub-region]-[first sub-region]-3' (e.g., see FIGS. 2 and 3). In some embodiments, the second splint strand (400) can be 20-100 nucleotides in length, or 30-80 nucleotides in length, or 40-60 nucleotides in length. In some embodiments, the 5' end of the second splint strand (400) is phosphorylated or non-phosphorylated. In some embodiments, the 3' end of the second splint strand (400) comprises a terminal 3' OH group or a terminal 3' blocking group. In some embodiments, the second splint strands (400) comprise one or more phosphorothioate linkage at the 5' and/or 3' ends to confer exonuclease resistance. In some embodiments, the second splint strands (400) comprise one or more phosphorothioate linkages at an internal position to confer endonuclease resistance. In some embodiments, the second splint strands (400) comprise one or more 2'-O-methylcytosine bases at the 5' and/or 3' end, or at an internal position.

In some embodiments, the first splint strand (300) includes an internal region (310) which comprises at least two sub-regions, including a fourth and fifth sub-region (e.g., see FIGS. 2 and 3). The fourth sub-region hybridizes to the first sub-region of the second splint strand (400). The fifth sub-region hybridizes to the second sub-region of the second splint strand (400). The fourth and fifth sub-regions do not hybridize (or at least exhibit very little hybridization to) the first and second surface primers. In some embodiments, the internal region (310) of the first splint strand further comprises an optional sixth sub-region which hybridizes to the third sub-region of the second splint strand (400) (e.g., see FIG. 3). An exemplary arrangement of the sub-regions of the first splint strand (300), in a 5' to 3' orientation comprises: 5'-[fourth sub-region]-[fifth sub-region]-3'. Another exemplary arrangement of the sub-regions of the first splint strand (300), in a 5' to 3' orientation comprises: 5'-[fourth sub-region]-[fifth sub-region]-[sixth sub-region]-3' (e.g., see FIGS. 2 and 3). In some embodiments, the first splint strand (300) can be 50-150 nucleotides in length, or 60-100 nucleotides in length, or 70-90 nucleotides in length. In some embodiments, the first splint strands (300) comprise one or more phosphorothioate linkages at the 5' and/or 3' ends to confer exonuclease resistance. In some embodiments, the first splint strands (300) comprise one or more phosphorothioate linkages at an internal position to confer endonuclease resistance. In some embodiments, the first splint strands (300) comprise one or more 2'-O-methylcytosine bases at the 5' and/or 3' end, or at an internal position.

Variants of Long Splint Strands: Truncations

Figure 11A:
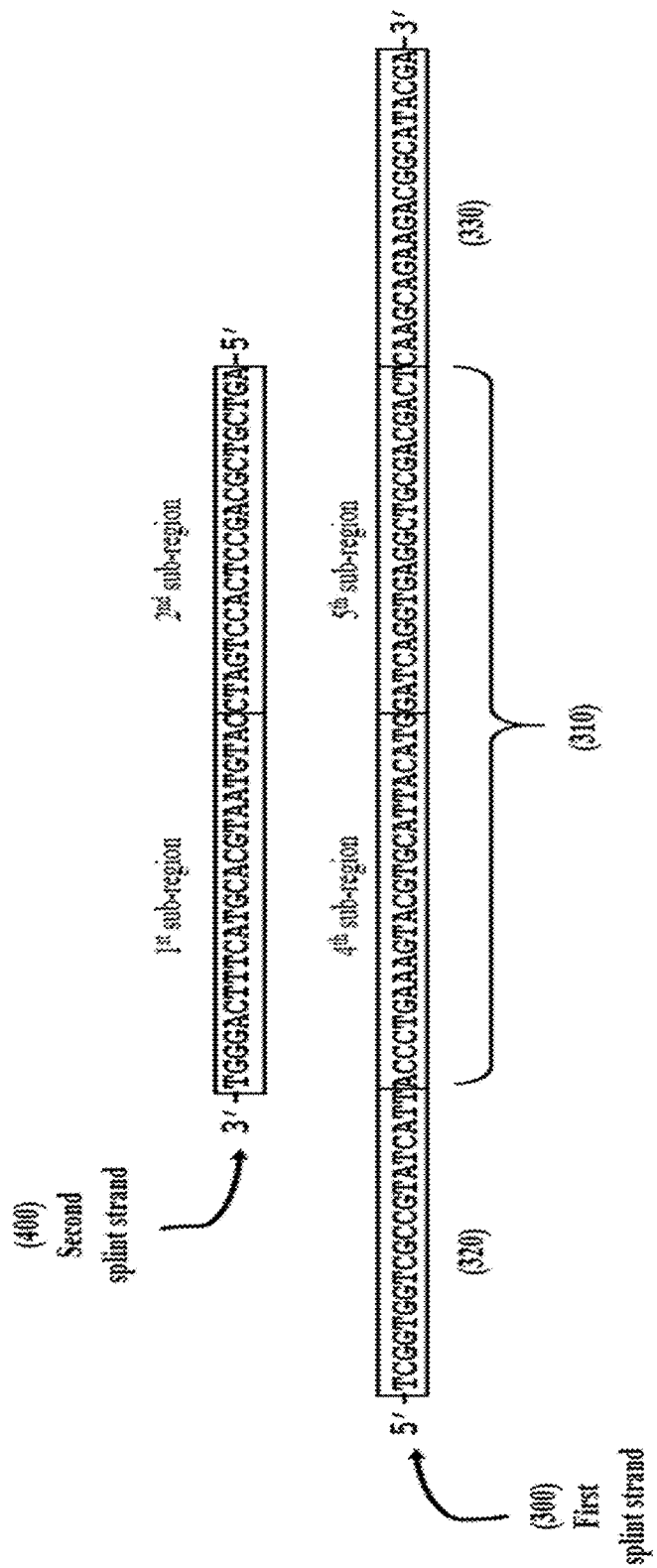
FIG. 11A shows the nucleotide sequences of an exemplary double-stranded splint molecule (200) having a first splint strand (300) and a second splint strand (400). The exemplary first splint strand comprises a first region (320; SEQ ID NO:4), a second region (330; SEQ ID NO:5), and an internal region (310) having a fourth sub-region (SEQ ID NO:6) and fifth sub-region (SEQ ID NO:7). The exemplary second splint strand (400) comprises a first sub-region (SEQ ID NO:1) and second sub-region (SEQ ID NO:2).
Figure 11B:
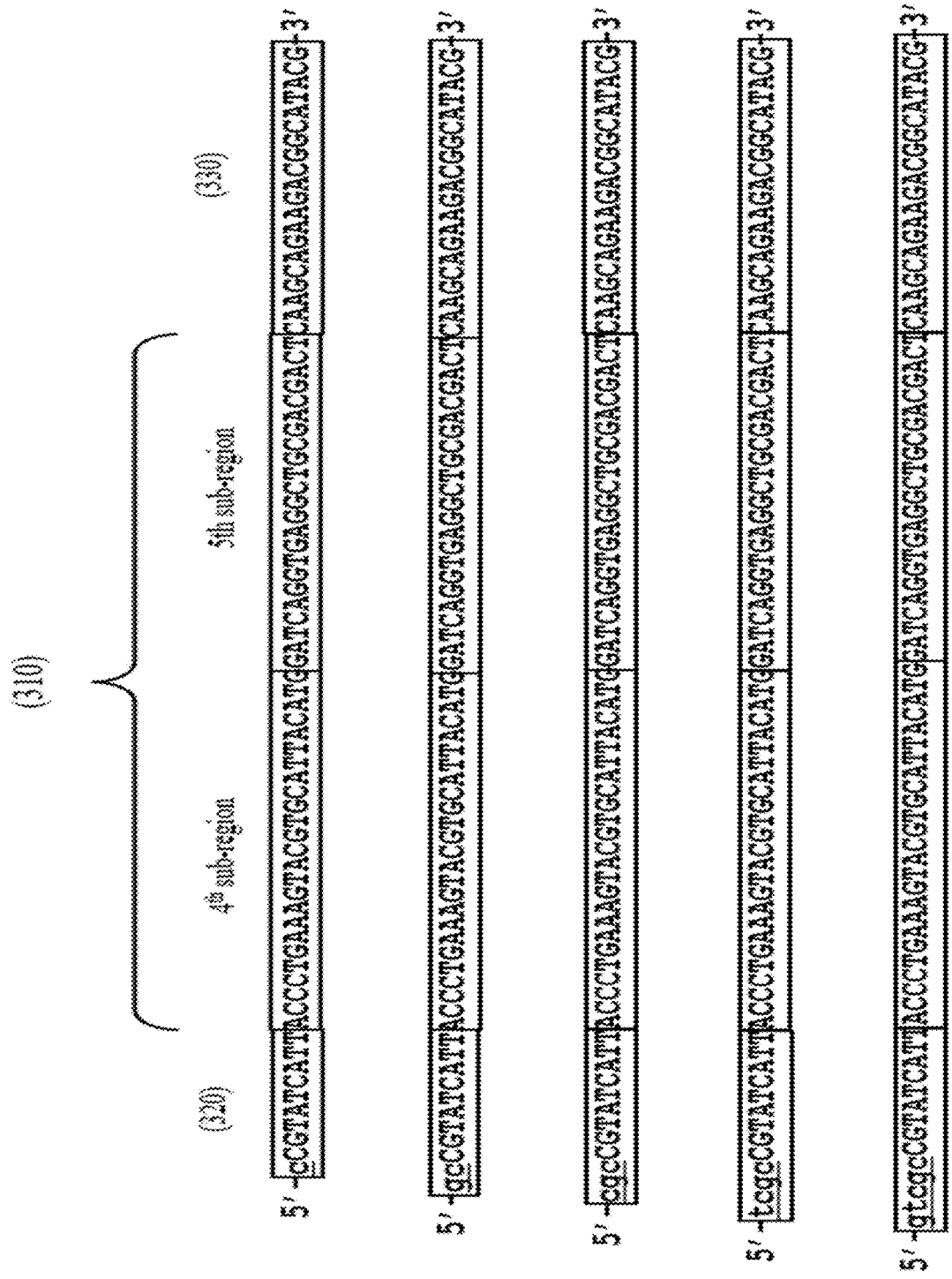
FIG. 11B shows the nucleotide sequences of exemplary first splint strands (300) each having a truncated sequence at the 5' end of the first region (320). The truncated sequences of the first regions (320) differ from SEQ ID NO:4 (see FIG. 11A). In the exemplary truncated first splint strands shown in FIG. 11B, the fourth sub-region comprises a sequence of SEQ ID NO:6, the fifth sub-region comprises a sequence of SEQ ID NO:7, and the second region (330) comprises the sequence SEQ ID NO:5. The truncated first strands (300) can hybridize with the second splint strand (400) shown in FIG. 11A, where the second splint strand comprises a first sub-region (SEQ ID NO:1) and a second sub-region (SEQ ID NO:2). The full length sequences in FIG. 11B, from top to bottom, are: SEQ ID NO:217, SEQ ID NO:218. SEQ ID NO:219, SEQ ID NO:220, SEQ ID NO:221.

In some embodiments, the first splint strand (300) comprises a truncated strand having a first region (320) having a truncated sequence at the 5' end (e.g., FIG. 11B). In some embodiments, the 5' end of the first region can have a truncation of any length for example a truncation of 1-10 nucleotides. In some embodiments, the truncated first splint strand (300) comprises a second region (330; e.g., SEQ ID NO:5), a fourth sub-region (e.g., SEQ ID NO:6) and a fifth sub-region (e.g., SEQ ID NO:7) that are not truncated and do not carry any sequence variants such as for example insertion, deletion or base-substitution. In some embodiments, the truncated first splint strand comprises a fourth sub-region and fifth sub-region that can hybridize with the first sub-region and second sub-region of a second splint strand (400) to form a double-stranded splint adaptor (200). In some embodiments, the truncated first splint strand comprises (300) comprises a truncated first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the truncated first splint strand, as part of a double-stranded splint adaptor (200) can hybridize to a library molecule (100) to form a library-splint complex (500).

Variants of Long Splint Strands: Mis-Match Sequences

Figure 11C:
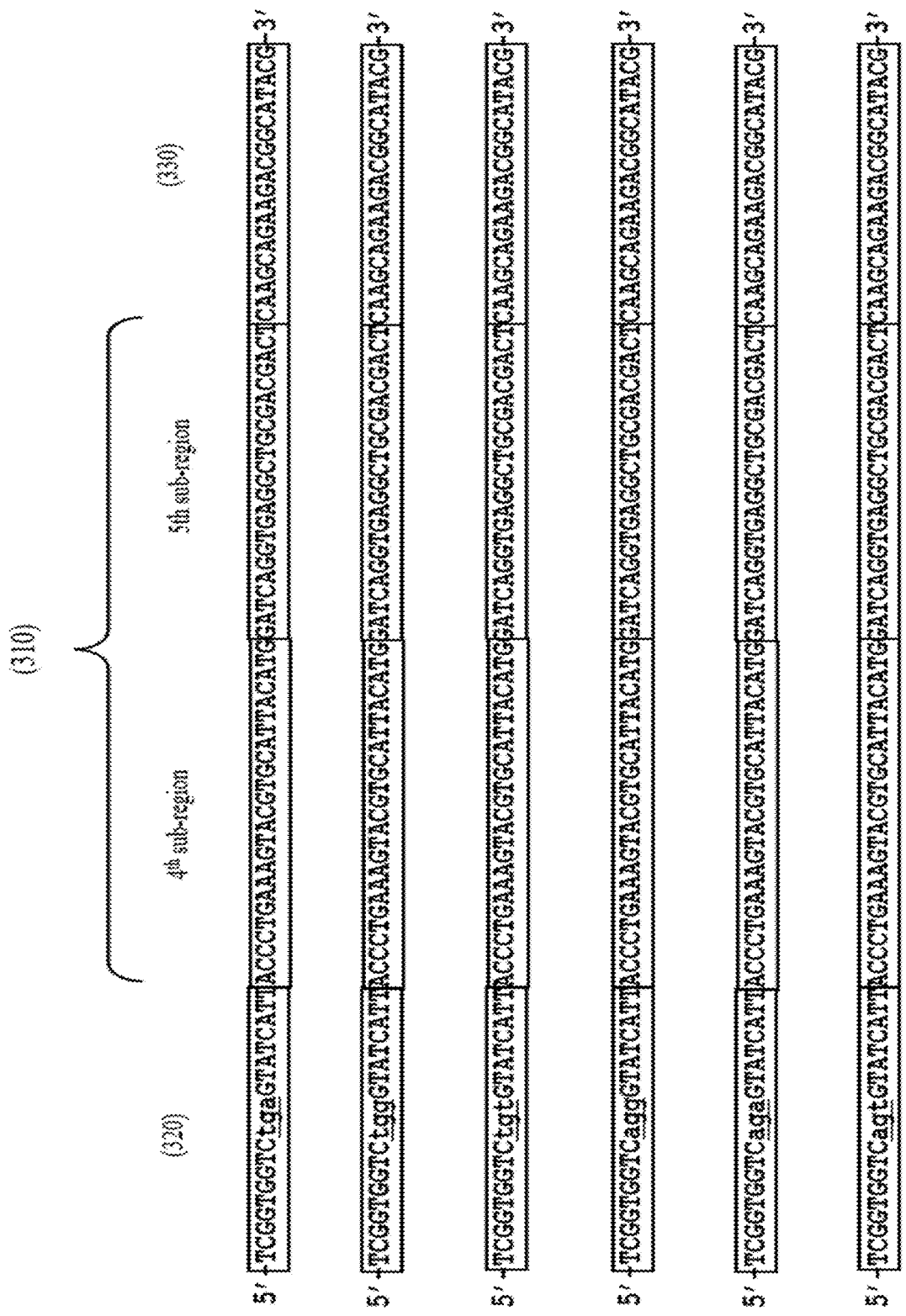
FIG. 11C shows the nucleotide sequences of exemplary first splint strands (300) each having a mis-match sequence within the first region (320). The mis-match sequences are indicated in small case letters and are underlined. The mis-match sequences differ from SEQ ID NO:4 (see FIG. 11A). The first region (320) can hybridize with the first left universal adaptor sequence (120) of a library molecule (100) to form a double-stranded portion having a bubble at the location of the mis-match sequence in the first region (320). In the exemplary mis-matched first splint strands shown in FIG. 11C, the fourth sub-region comprises a sequence of SEQ ID NO:6, the fifth sub-region comprises a sequence of SEQ ID NO:7, and the second region (330) comprises the sequence SEQ ID NO:5. The mis-matched first strands (300) can hybridize with the second splint strand (400) shown in FIG. 11A, where the second splint strand comprises a first sub-region (SEQ ID NO:1) and a second sub-region (SEQ ID NO:2). The full length sequences in FIG. 11C, from top to bottom, are: SEQ ID NO:222, SEQ ID NO:223, SEQ ID NO:224, SEQ ID NO:225, SEQ ID NO:226, SEQ ID NO:227.

In some embodiments, the first splint strand (300) comprises mis-match strand having a first region (320) having a mis-match sequence within the first region (320) (e.g., FIG. 11C). In some embodiments, the mis-match sequence is internal to the first region. In some embodiments, the mis-match sequence can be any length (e.g., 2-20 bases) and comprises any sequence that is not fully complementary to the left universal adaptor sequence (120) of a library molecule (100). Some embodiments of mis-match sequences in the first region (320) are shown in small case letters and underlined in FIG. 11C. In some embodiments, the mis-match first splint strand (300) comprises a second region (330; e.g., SEQ ID NO:5), a fourth sub-region (e.g., SEQ ID NO:6) and a fifth sub-region (e.g., SEQ ID NO:7) that do not carry any sequence variants such as for example an insertion, deletion or base-substitution. In some embodiments, the mis-match first splint strand comprises a fourth sub-region and fifth sub-region that can hybridize with the first sub-region and second sub-region of a second splint strand (400) to form a double-stranded splint adaptor (200). In some embodiments, the mis-match first splint strand comprises (300) comprises a mis-match first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the mis-match first region (320) can hybridize with the first left universal adaptor sequence (120) of a library molecule (100) to form a double-stranded portion having a bubble at the location of the mis-match sequence in the first region (320). In some embodiments, the mis-match first splint strand, as part of a double-stranded splint adaptor (200) can hybridize to a library molecule (100) to form a library-splint complex (500).

Variants of Long Splint Strands: Abasic Sites

In some embodiments, the first splint strand (300) comprises at least one abasic site which lacks a nitrogenous base. In some embodiments, the first splint strand (300) comprises at least one abasic site in the fourth sub-region and/or at least one abasic site in the fifth sub-region (e.g., top schematic of FIG. 11D, abasic sites are shown as solid black bars). In some embodiments, the abasic sites each comprise a 1',2'-dideoxyribose (e.g., dSpacer from Integrated DNA Technologies (IDT)).

In some embodiments, the abasic first splint strand (300) comprises a first region ((320); e.g., SEQ ID NO:4), and a second region ((330); e.g., SEQ ID NO:5) that do not carry any abasic sites and/or any sequence variants such as for example insertion, deletion or base-substitution. In some embodiments, the abasic first splint strand comprises a fourth sub-region and fifth sub-region that can hybridize with the first sub-region and second sub-region of a second splint strand (400) to form a double-stranded splint adaptor (200). In some embodiments, the abasic first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the abasic first splint strand, as part of a double-stranded splint adaptor (200) can hybridize to a library molecule (100) to form a library-splint complex (500).

Variants of Long Splint Strands: Uracil

Figure 11D:
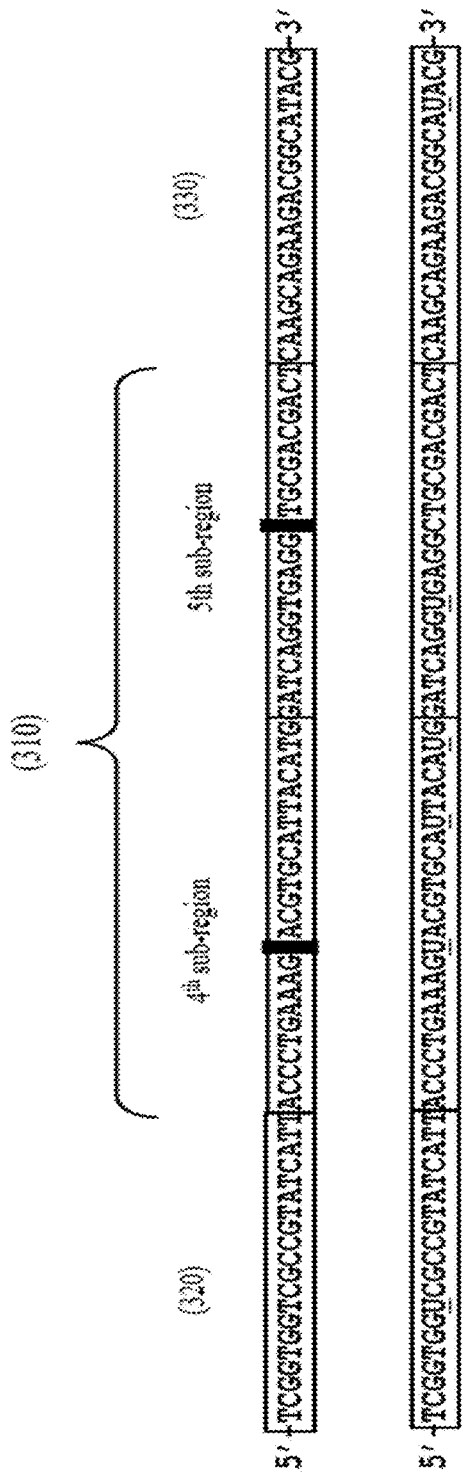
FIG. 11D shows the nucleotide sequences of exemplary first splint strands (300) having either abasic sites or uracils. The first splint strand shown at the top comprises abasic sites in the fourth and fifth sub-regions. The abasic sites are represented by the solid black bars. The first region (320) of the top first splint strand can hybridize with the first left universal adaptor sequence (120) of a library molecule (100). The second region (330) of the top first splint strand can hybridize with the first right universal adaptor sequence (130) of a library molecule (100). The first splint strand shown at the bottom comprises at least one uracil in the first region (320), the second region (330) and the internal region (310). The uracils are underlined. The first region (320) of the bottom first splint strand can hybridize with the first left universal adaptor sequence (120) of a library molecule (100). The second region (330) of the bottom first splint strand can hybridize with the first right universal adaptor sequence (130) of a library molecule (100). Top strand: SEQ ID NO:228-abasic site-SEQ ID NO:229-abasic site-SEQ ID NO:230; bottom strand: SEQ ID NO:231.

In some embodiments, the first splint strand (300) comprises at least one uracil. In some embodiments, the first splint strand (300) comprises at least one uracil in any one or any combination of regions including the first region (320), the second region (330), the fourth sub-region and/or the fifth sub-region. In some embodiments, at least one thymine base can be substituted with a uracil. An embodiment of a uracil-containing first splint strand is shown in FIG. 11D (bottom schematic). The skilled artisan will recognize that many other sequences of the first splint strand (300) comprising one or more uracils are possible.

In some embodiments, the uracil-containing first splint strand comprises a fourth sub-region and fifth sub-region that can hybridize with the first sub-region and second sub-region of a second splint strand (400) to form a double-stranded splint adaptor (200). In some embodiments, the uracil-containing first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the uracil-containing first splint strand, as part of a double-stranded splint adaptor (200) can hybridize to a library molecule (100) to form a library-splint complex (500).

Short Splint Strands (400) with Inserted or Replacing Random Sequences

Figure 7A:
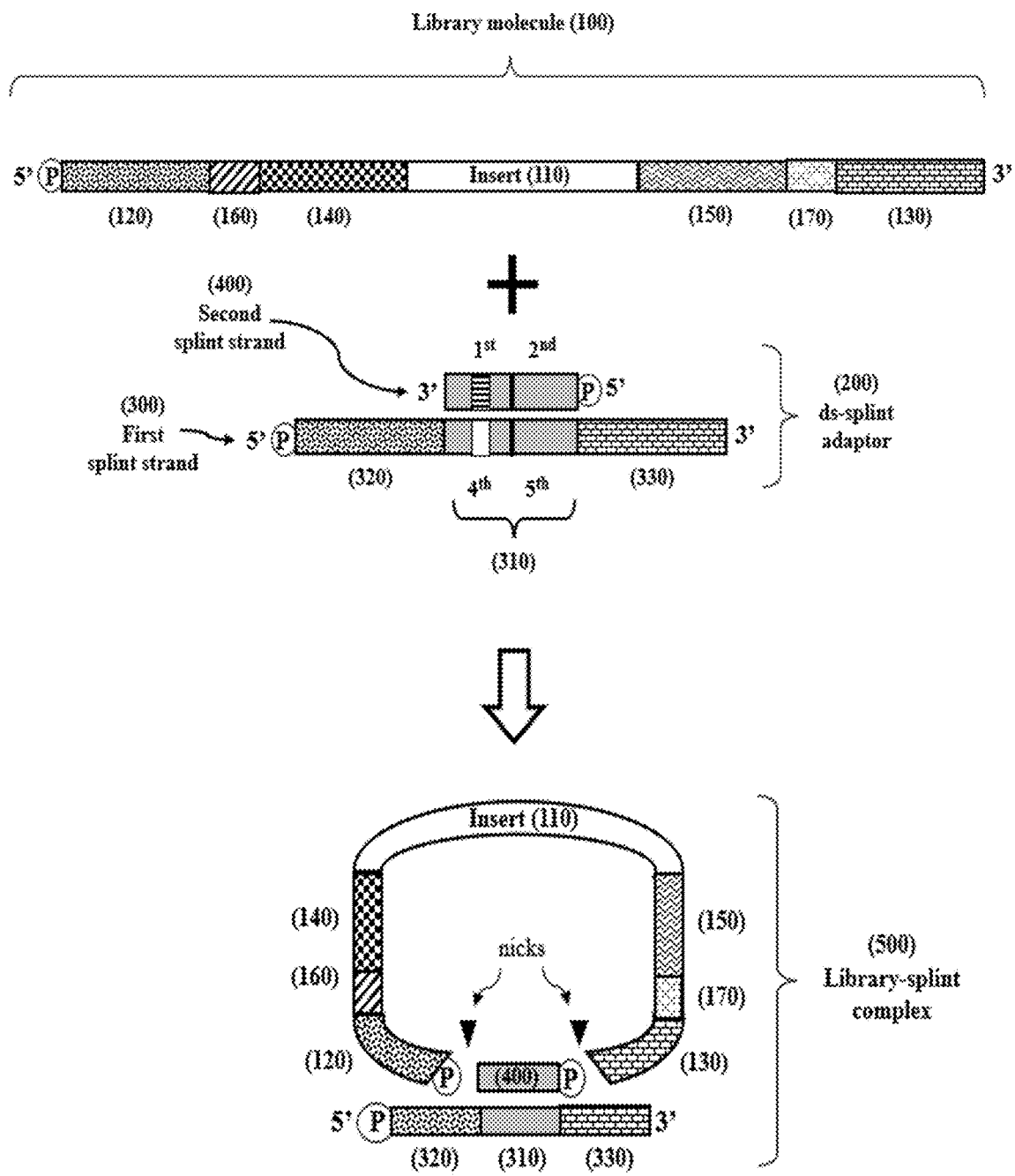
FIG. 7A is a schematic showing an exemplary linear single stranded library molecule (100) hybridizing with a double-stranded splint molecule (200) thereby circularizing the library molecule to form a library-splint complex (500) with two nicks. The library molecule (100) comprises: a first left universal adaptor sequence (120); a first left index sequence (160); a second left universal adaptor sequence (140); a sequence of interest (also termed insert, 110); a second right universal adaptor sequence (150); a first right index sequence (170); and a first right universal adaptor sequence (130). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400). The second splint strand (400) includes two sub-regions, where the first sub-region comprises a universal binding sequence for a fourth surface primer (e.g., surface pinning primer), and the second sub-region comprises a universal binding sequence for a third surface primer (e.g., surface capture primer). A random sequence (e.g., NNN) is inserted into the first sub-region, or a random sequence replaces a region in the first sub-region. The random sequence can comprise 3-20 bases. In some embodiments, the random sequence further comprises a sample index sequence. The random sequence can be sequenced and the sequence information can be used for polony mapping and/or template registration. The random sequence in the second splint strand (400) is represented by a horizontal-bar patterned region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A pre-determined sequence is inserted into the fourth sub-region or a pre-determined sequence replaces a region in the fourth sub-region. The pre-determined sequence in the first splint strand (300) comprises 3-20 bases and has a sequence that may or may not be complementary to the random sequence in the first sub-region of the second splint strand (400). The pre-determined sequence is represented by a non-patterned white region.
Figure 12A:
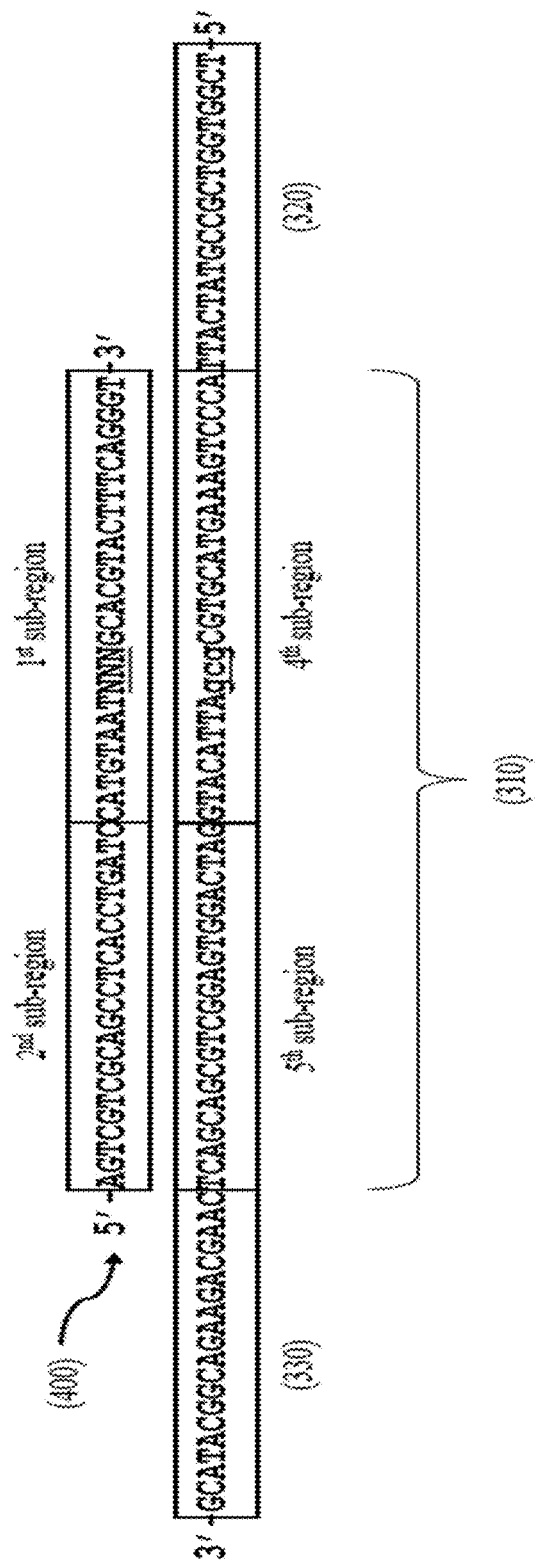
FIG. 12A shows the nucleotide sequences of an exemplary double-stranded splint molecule (200) having a first splint strand (300, bottom strand)) and a second splint strand (400, top strand). The exemplary first splint strand comprises a first region (320), a second region (330), and an internal region (310) having a fourth sub-region and a fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 3-mer random sequence (e.g., NNN) is inserted into the sequence of the first sub-region of the second splint strand (400). A 3-base pre-determined sequence (e.g., 5'-gcg-3') is inserted into the sequence of the fourth sub-region. The second splint strand (400) can hybridize with the first splint strand (300) to form a double-stranded molecule having a bubble at the location of the 3-mer random sequence (e.g., NNN) in the first sub-region of the second splint strand (400). Top strand: SEQ ID NO:232; bottom strand: SEQ ID NO:233.
Figure 12B:
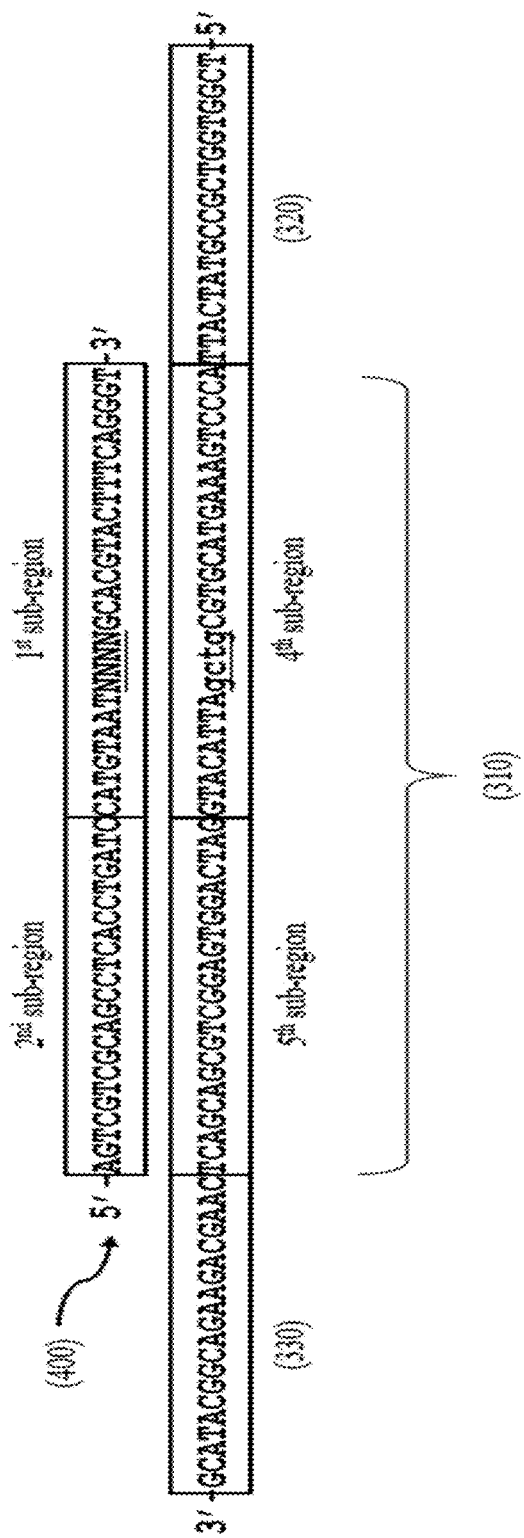
FIG. 12B shows the nucleotide sequences of an exemplary double-stranded splint molecule (200) having a first splint strand (300, bottom strand) and a second splint strand (400, top strand). The exemplary first splint strand comprises a first region (320), a second region (330), and an internal region (310) having a fourth sub-region and a fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 4-mer random sequence (e.g., NNNN) is inserted into the sequence of the first sub-region of the second splint strand (400). A 4-base pre-determined sequence (e.g., 5'-gtcg-3') is inserted into the sequence of the fourth sub-region. The second splint strand (400) can hybridize with the first splint strand (300) to form a double-stranded molecule having a bubble at the location of the 4-mer random sequence (e.g., NNNN) in the first sub-region of the second splint strand (400). Top strand: SEQ ID NO:234; bottom strand: SEQ ID NO:235.

In some embodiments, the second splint strand (400) comprises a random sequence inserted into the first sub-region of the second splint strand (e.g., FIGS. 7A, 12A and 12B). In some embodiments, a random sequence can replace a portion of the first sub-region of the second splint strand (e.g., FIGS. 7A, 13A and 13B).

In some embodiments, the second sub-region of the second splint strand (400) does not have an inserted random sequence. In some embodiments, a portion of the second sub-region of the second splint strand (400) is not replaced with a random sequence.

In some embodiments, the random sequence can be any length, for example 2-10 bases in length. For example, the random sequence can be 3 nucleotide in length (e.g., 'NNN' in FIGS. 12A and 13A) or 4 nucleotides in length (e.g., 'NNNN' in FIGS. 12B and 13B). In some embodiments, the random sequence can be inserted at any position in the first sub-region of the second splint strand (400).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110).

In some embodiments, a pre-determined sequence is inserted into the sequence of the fourth sub-region of the first splint strand (300). The length of the inserted pre-determined sequence can be the same length as the random sequence inserted into the first sub-region of the second splint strand (e.g., FIGS. 12A and 12B). The inserted pre-determined sequence can have any sequence. An exemplary pre-determined sequence is shown in FIGS. 12A and 12B.

Figure 13A:
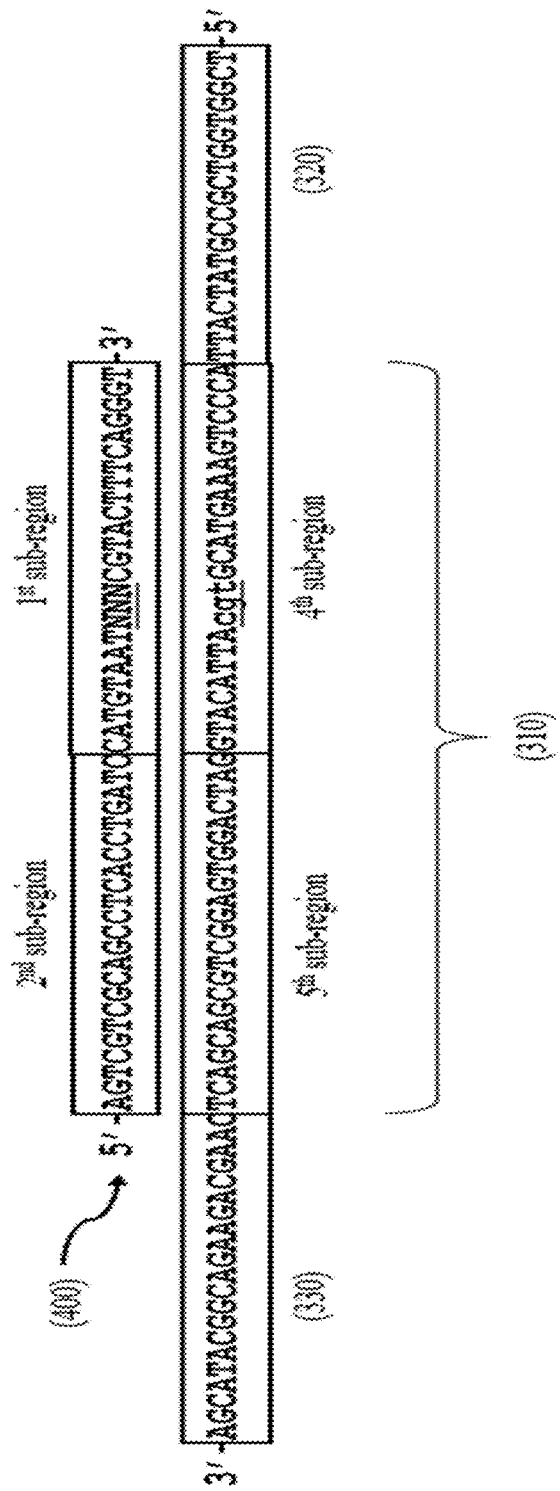
FIG. 13A shows the nucleotide sequences of an exemplary double-stranded splint molecule (200) having a first splint strand (300, bottom strand) and a second splint strand (400, top strand). The exemplary first splint strand comprises a first region (320), a second region (330), and an internal region (310) having a fourth sub-region and a fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 3-mer random sequence (e.g., NNN) replaces a portion of the sequence of the first sub-region of the second splint strand (400). A 3-base pre-determined sequence (e.g., 5'-tgc-3') replaces a portion of the sequence of the fourth sub-region. The second splint strand (400) can hybridize with the first splint strand (300) to form a double-stranded molecule having a bubble at the location of the 3-mer random sequence (e.g., NNN) in the first sub-region of the second splint strand (400). Top strand: SEQ ID NO:236; bottom strand: SEQ ID NO:237.
Figure 13B:
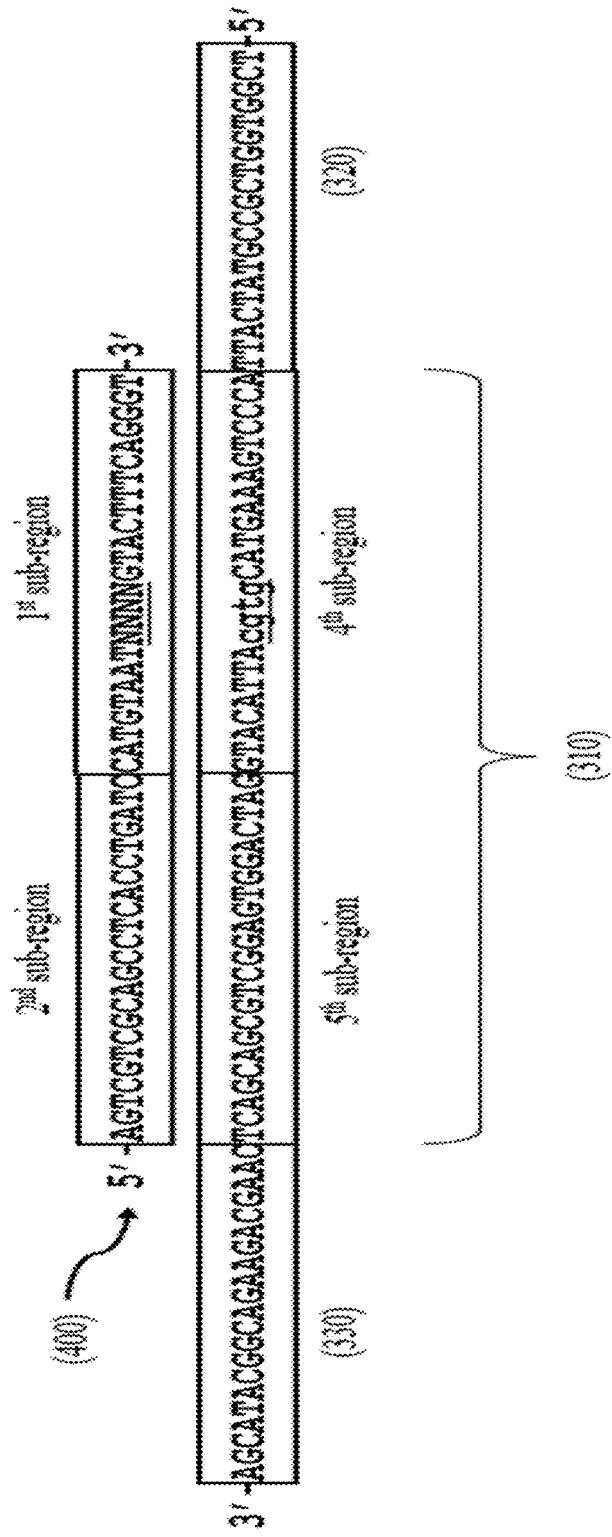
FIG. 13B shows the nucleotide sequences of an exemplary double-stranded splint molecule (200) having a first splint strand (bottom strand, 300) and a second splint strand (top strand, 400). The exemplary first splint strand comprises a first region (320), a second region (330), and an internal region (310) having a fourth sub-region and fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 4-mer random sequence (e.g., NNNN) replaces a portion of the sequence of the first sub-region of the second splint strand (400). A 4-base pre-determined sequence (e.g., 5'-gtgc-3') replaces a portion of the sequence of the fourth sub-region. The second splint strand (400) can hybridize with the first splint strand (300) to form a double-stranded molecule having a bubble at the location of the 4-mer random sequence (e.g., NNN) in the first sub-region of the second splint strand (400). Top strand: SEQ ID NO:238; bottom strand: SEQ ID NO:239.

In some embodiments, a portion of the fourth sub-region of the first splint strand (300) is replaced with a pre-determined sequence. The length of the pre-determined sequence which replaces a portion of the fourth sub-region is the same length as the random sequence that replaces a portion of the first sub-region of the second splint strand (e.g., FIGS. 13A and 13B). The replacing pre-determined sequence can have any sequence. An exemplary pre-determined sequence is shown in FIGS. 13A and 13B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 12A, 12B, 13A and 13B). In some embodiments, the double-stranded splint adaptor (200) forms a bubble at the location of the inserted or replacing random sequence.

In some embodiments, the second splint strand (400) carrying a random sequence, as part of a double-stranded splint adaptor (200), can hybridize to a library molecule (100) to form a library-splint complex (500).

Short Splint Strands (400) with Appended Random Sequences and Index Sequences

Figure 7B:
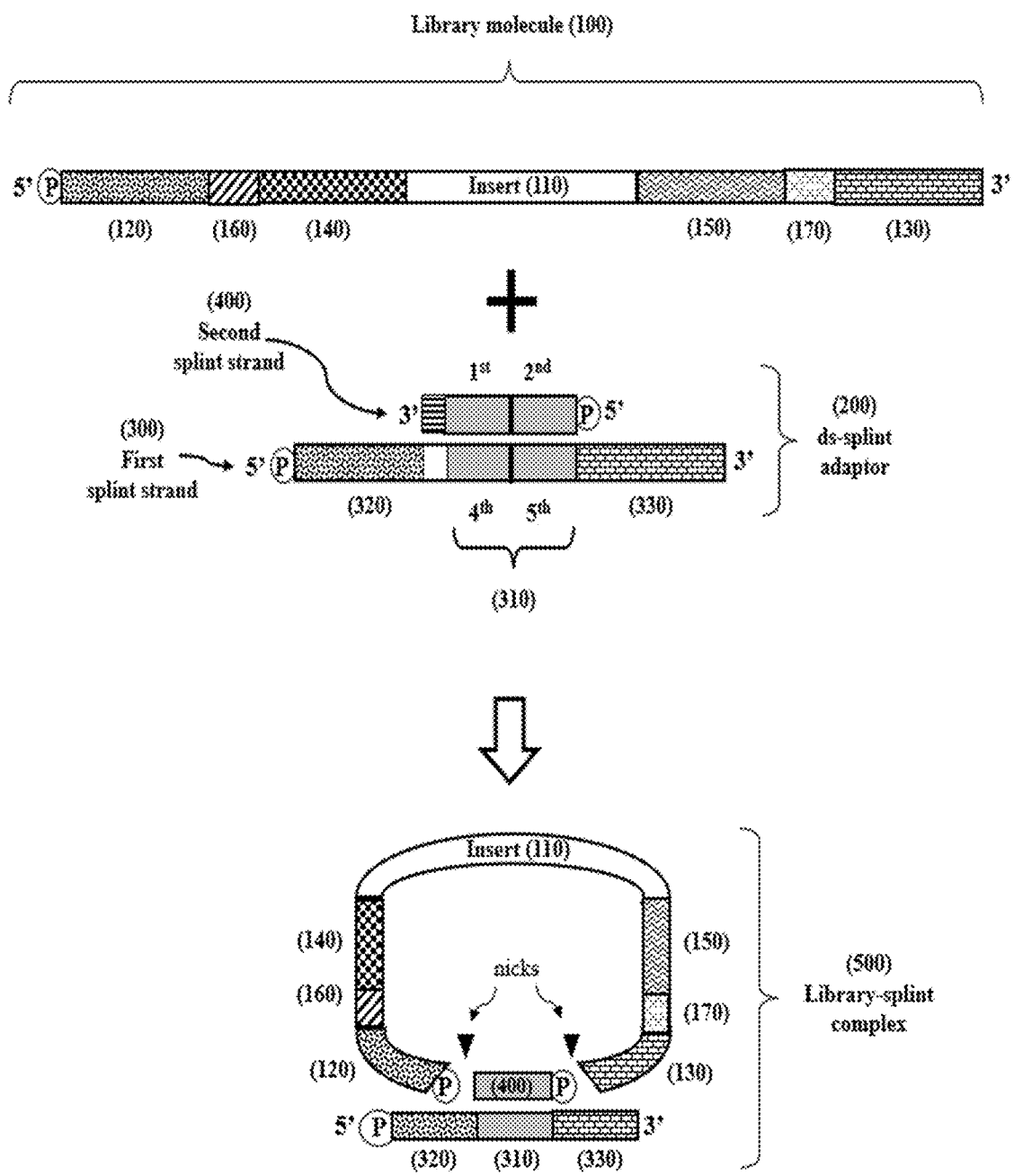
FIG. 7B is a schematic showing an exemplary linear single stranded library molecule (100) hybridizing with a double-stranded splint molecule (200) thereby circularizing the library molecule to form a library-splint complex (500) with two nicks. The library molecule (100) comprises: a first left universal adaptor sequence (120); a first left index sequence (160); a second left universal adaptor sequence (140); a sequence of interest (Insert, 110); a second right universal adaptor sequence (150); a first right index sequence (170); and a first right universal adaptor sequence (130). The double-stranded splint molecule comprises a first splint strand (long strand (300)) hybridized to a second splint strand (short splint strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400). The second splint strand (400) can include two sub-regions, where the first sub-region comprises a universal binding sequence for a fourth surface primer (e.g., surface pinning primer), and the second sub-region comprises a universal binding sequence for a third surface primer (e.g., surface capture primer). A random sequence (e.g., NNN) is appended to the 3' end of the first sub-region. The random sequence can comprise 3-20 bases. In some embodiments, the random sequence further comprises a sample index sequence. The random sequence can be sequenced and the sequence information can be used for polony mapping and/or template registration. The random sequence in the second splint strand (400) is represented by a horizontal-bar patterned region. The internal region (310) of the first splint strand (300) can comprise two sub-regions, where the fourth sub-region hybridizes to the first sub-region of the second splint strand (400), and the fifth sub-region hybridizes to the second sub-region of the second splint strand (400). A pre-determined sequence can be appended to the 5' end of the fourth sub-region. The pre-determined sequence in the first splint strand (300) can comprise 3-20 bases and has a sequence that may or may not be complementary to the random sequence in the first sub-region of the second splint strand (400). The pre-determined sequence is represented by a non-patterned white region.
Figure 14A:
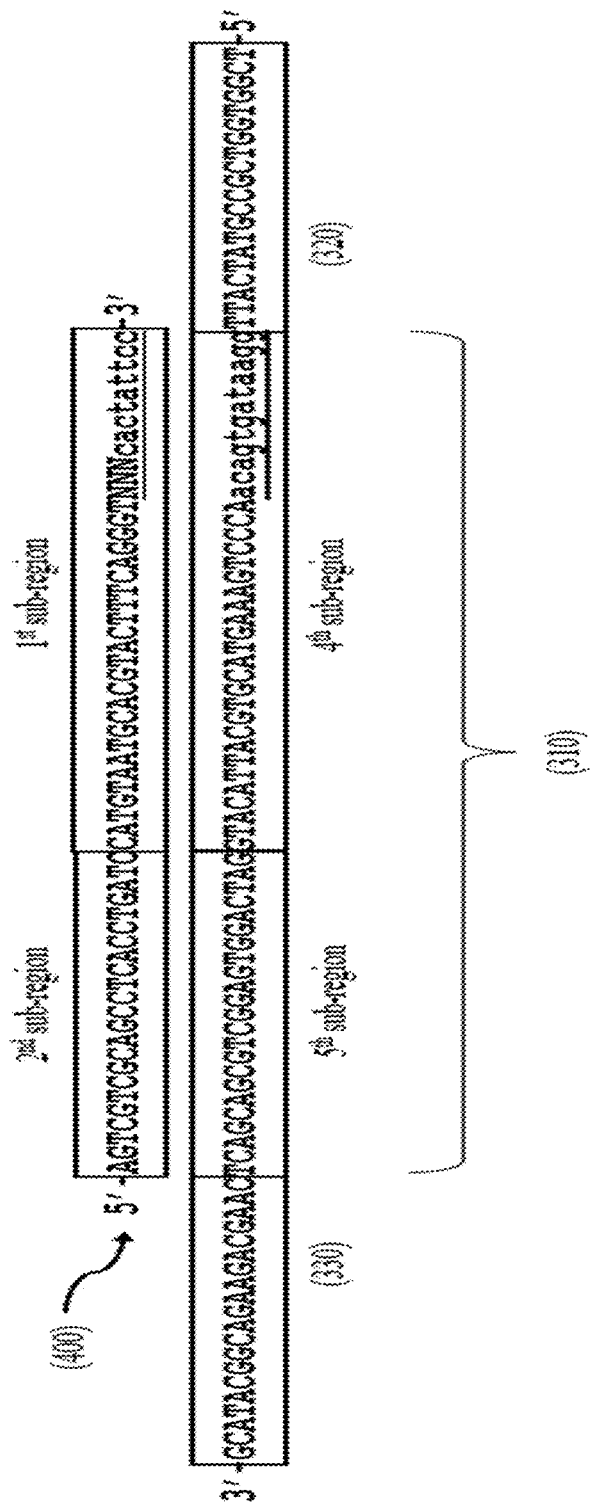
FIG. 14A shows the nucleotide sequences of an exemplary double-stranded splint molecule (200) having a first splint strand (bottom strand, 300) and a second splint strand (top strand, 400). The exemplary first splint strand comprises a first region (320), a second region (330), and an internal region (310) having a fourth sub-region and fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 3-mer random sequence (e.g., NNN) and an index sequence (e.g., 5'-cactattcc-3') is appended to the 3' end of the first sub-region of the second splint strand (400). A pre-determined sequence that is equivalent in length as the 3-mer random sequence and the index sequence (e.g., 5'-ggaatagtgaca-3') is appended to the 5' end of the sequence of the fourth sub-region. The second splint strand (400) can hybridize with the first splint strand (300) to form a double-stranded molecule having a bubble or a mis-matched end at the location of the 3-mer random sequence (e.g., NNN) and the index sequence in the first sub-region of the second splint strand (400). Top strand: SEQ ID NO:240; bottom strand: SEQ ID NO:241.
Figure 14B:
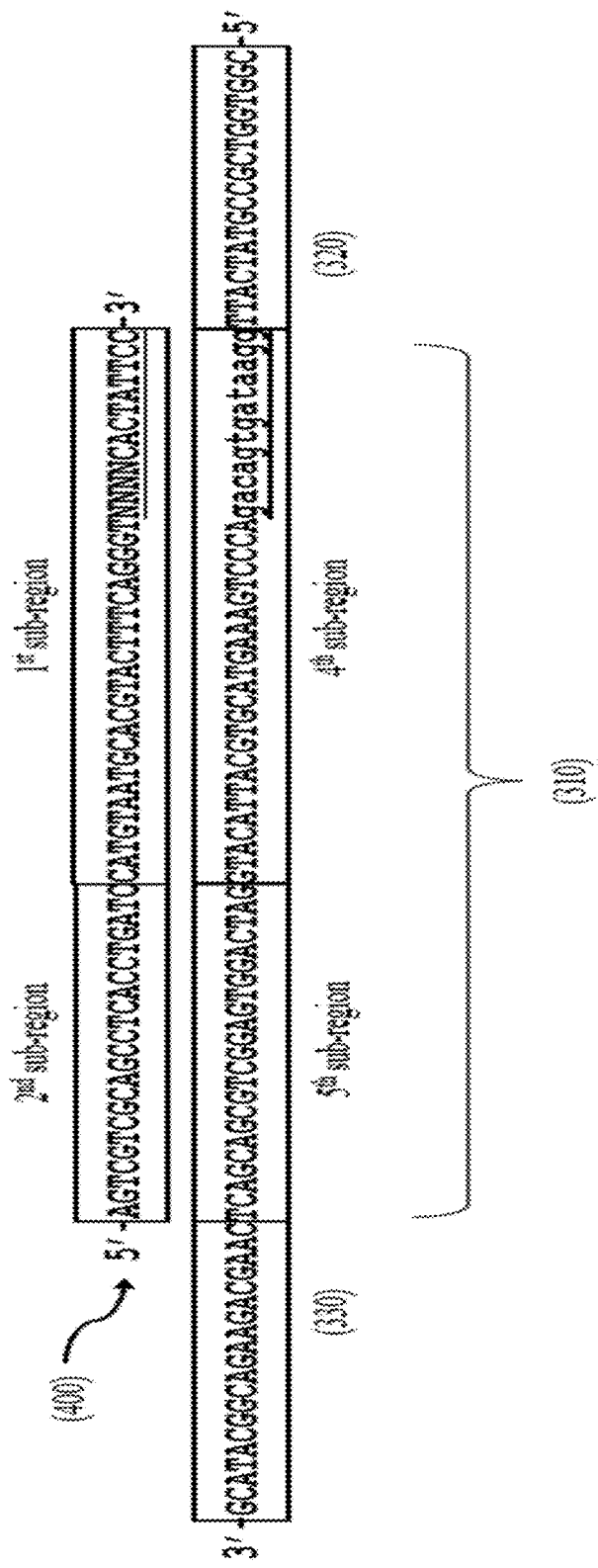
FIG. 14B shows the nucleotide sequences of an exemplary double-stranded splint molecule (200) having a first splint strand (bottom strand, 300) and a second splint strand (top strand, 400). The exemplary first splint strand comprises a first region (320), a second region (330), and an internal region (310) having a fourth sub-region and a fifth sub-region. The exemplary second splint strand (400) comprises a first sub-region and second sub-region. The internal region (310) of the first splint strand (300) comprises two sub-regions, where the fourth sub-region hybridizes to the first sub-region of the second splint strand (400), and the fifth sub-region hybridizes to the second sub-region of the second splint strand (400). A 4-mer random sequence (e.g., NNNN) and an index sequence (e.g., 5'-cactattcc-3') is appended to the 3' end of the first sub-region of the second splint strand (400). A pre-determined sequence that is equivalent in length as the 4-mer random sequence and the index sequence (e.g., 5'-ggaatagtgacag-3') is appended to the 5' end of the sequence of the fourth sub-region. The second splint strand (400) can hybridize with the first splint strand (300) to form a double-stranded molecule having a bubble or a mis-matched end at the location of the 4-mer random sequence (e.g., NNNN) and the index sequence in the first sub-region of the second splint strand (400). Top strand: SEQ ID NO:242; bottom strand: SEQ ID NO:243.
Figure 15A:
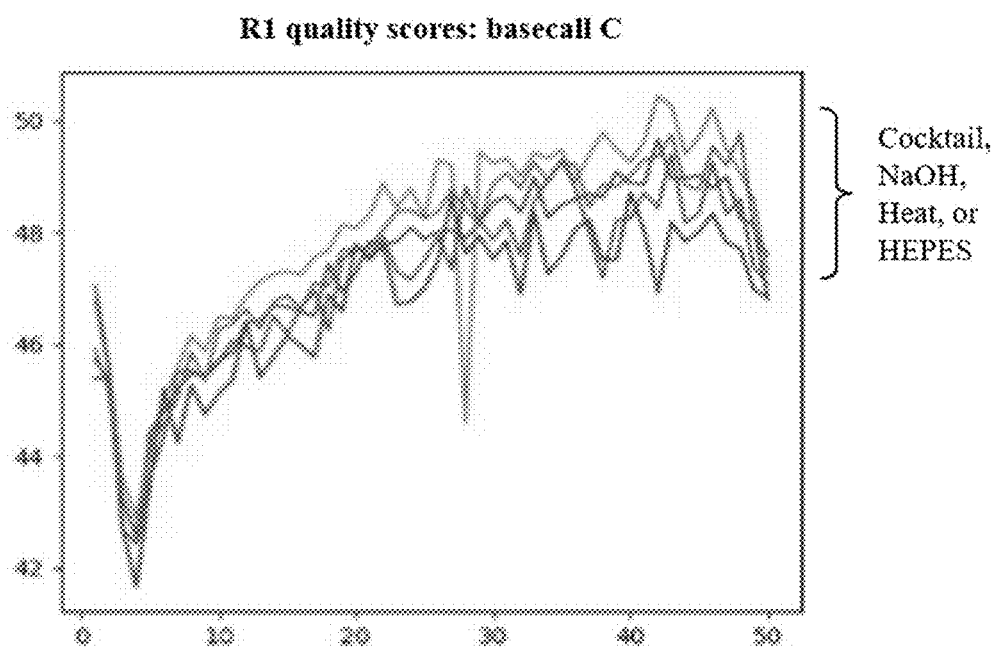
FIG. 15A is a graph showing sequencing quality scores of C base calls of first strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 15B:
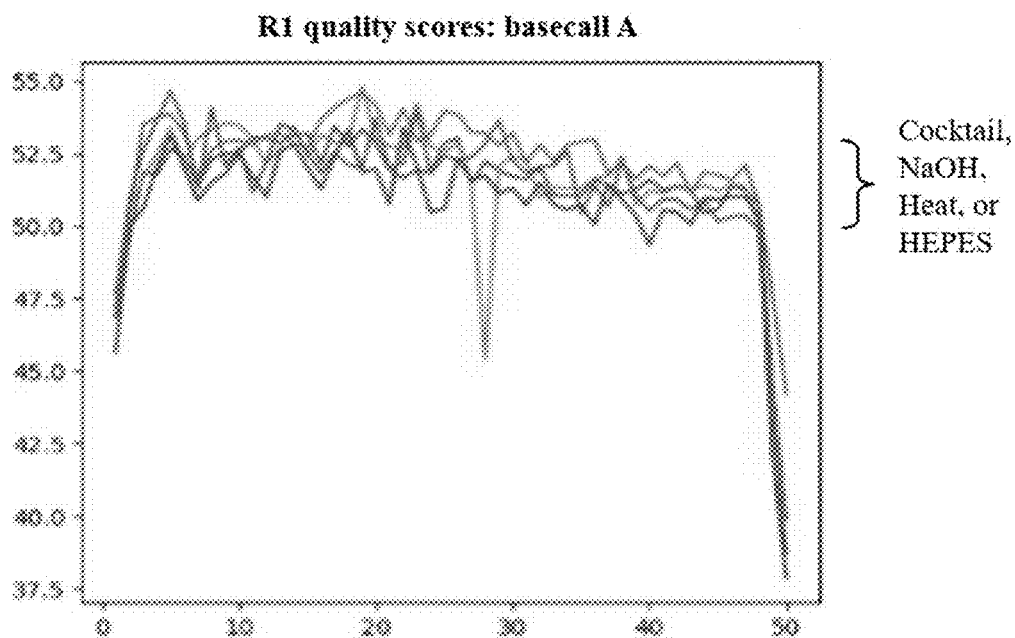
FIG. 15B is a graph showing sequencing quality scores of A base calls of first strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 15C:
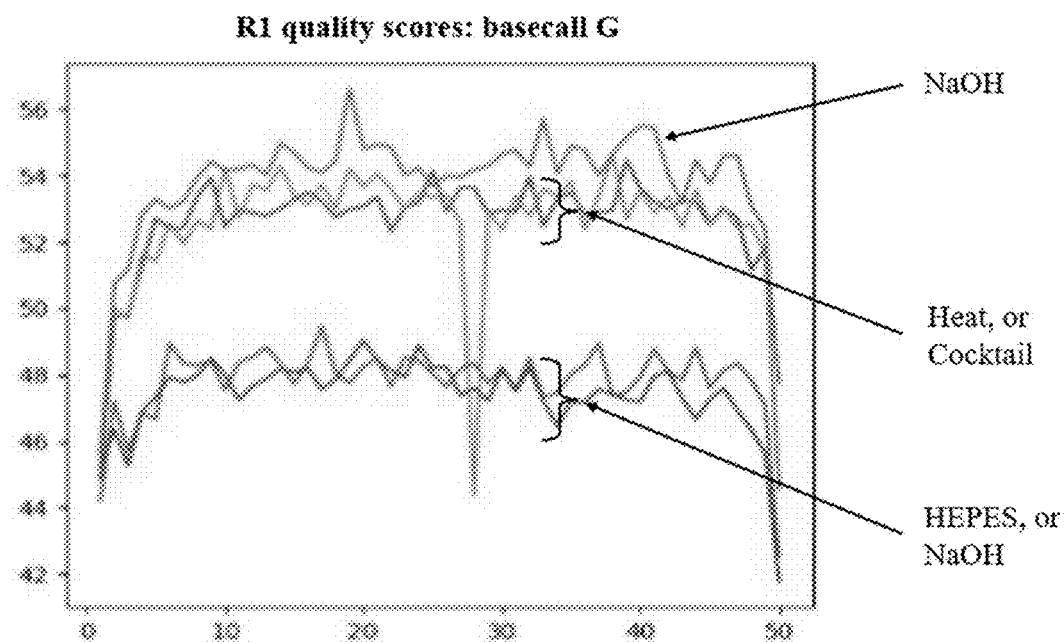
FIG. 15C is a graph showing sequencing quality scores of G base calls of first strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 15D:
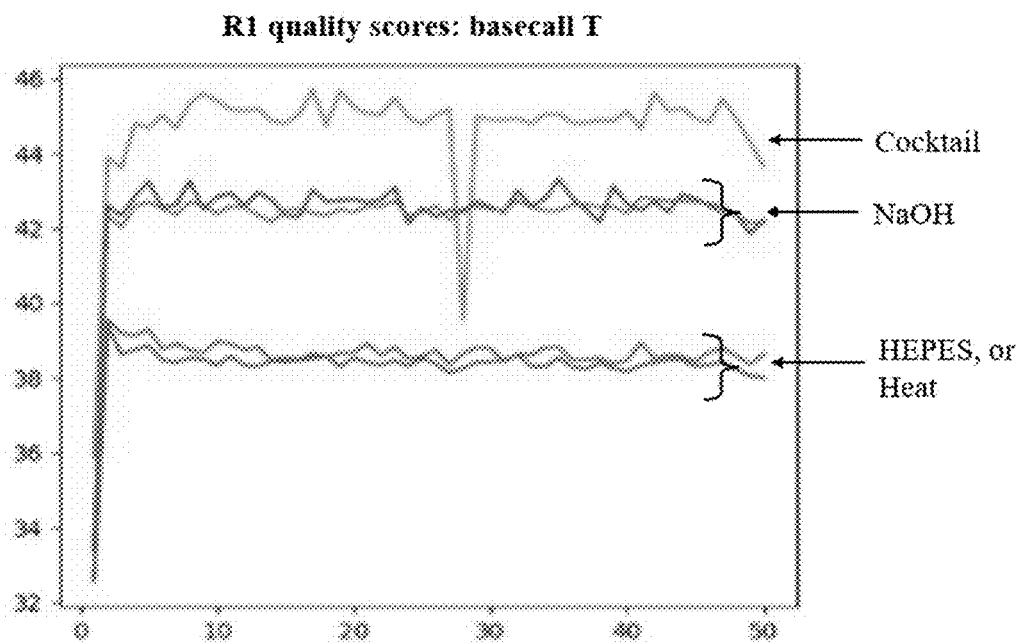
FIG. 15D is a graph showing sequencing quality scores of T base calls of first strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 16A:
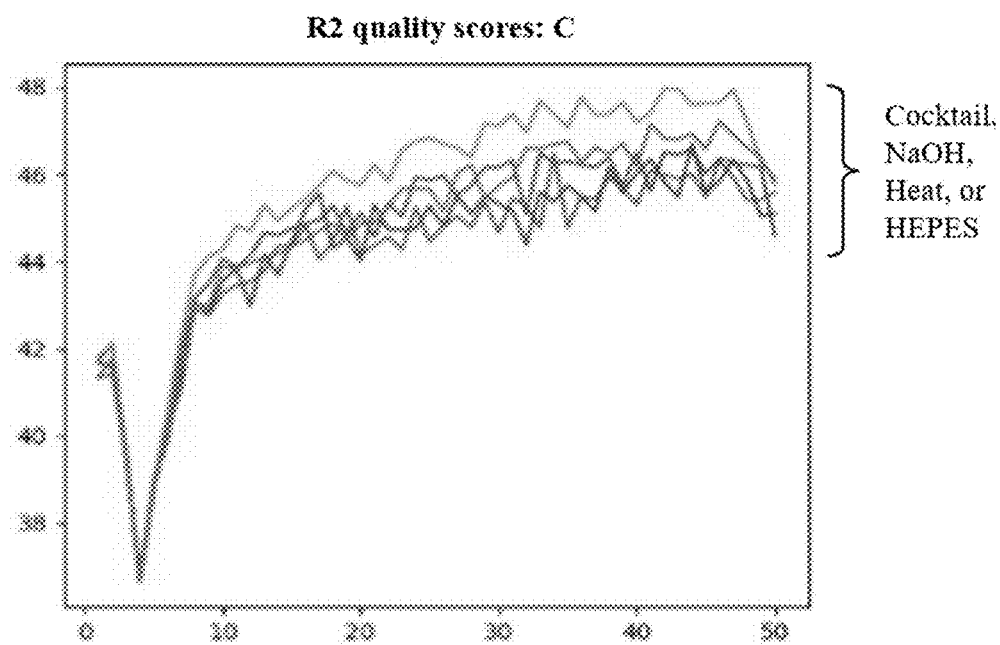
FIG. 16A is a graph showing sequencing quality scores of C base calls of second strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 16B:
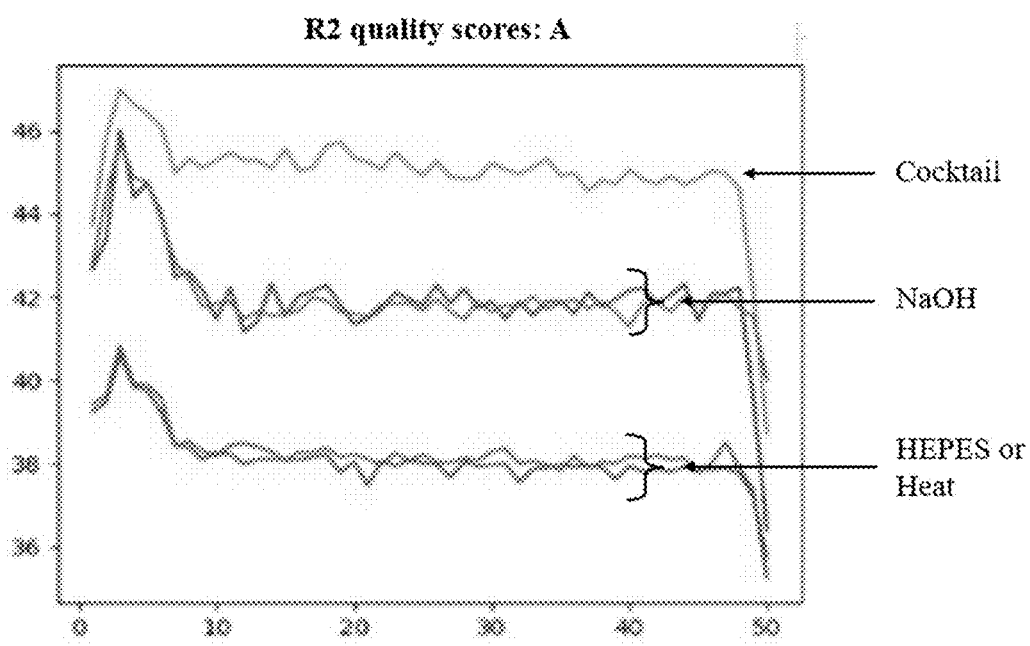
FIG. 16B is a graph showing sequencing quality scores of A base calls of second strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 16C:
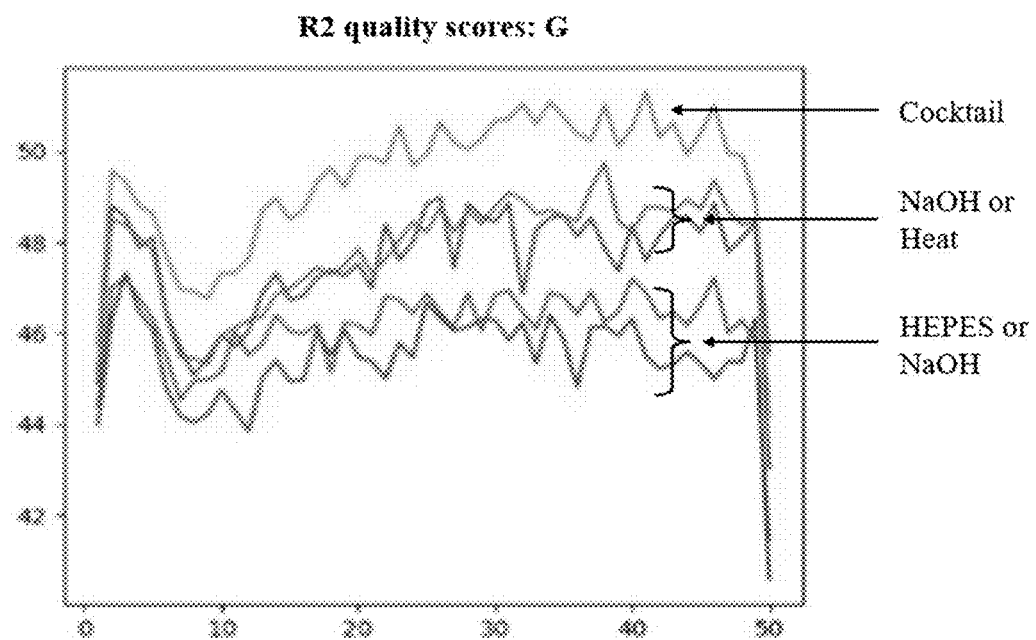
FIG. 16C is a graph showing sequencing quality scores of G base calls of second strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.
Figure 16D:
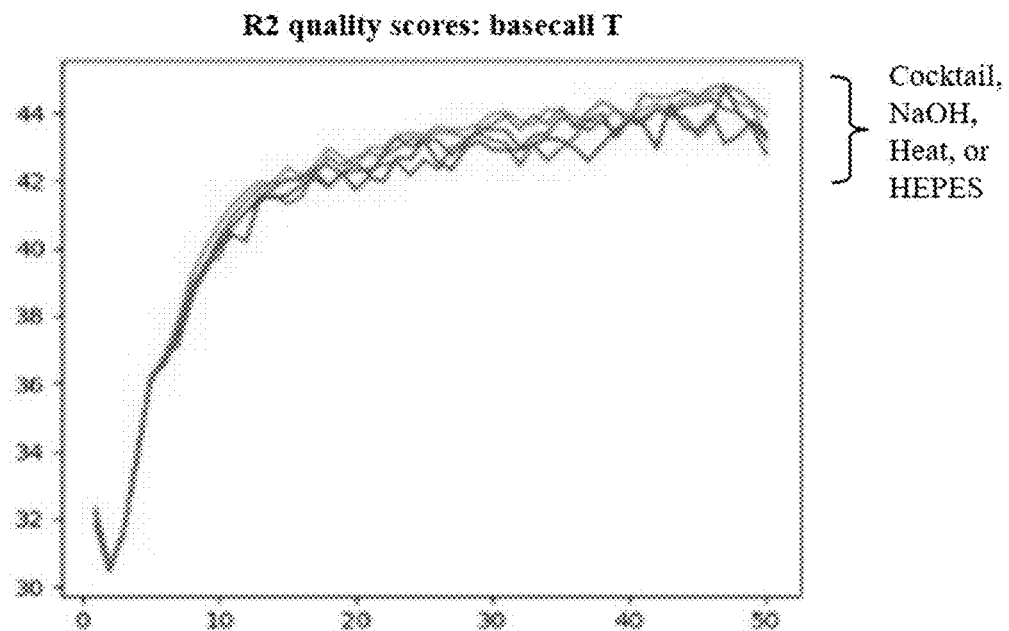
FIG. 16D is a graph showing sequencing quality scores of T base calls of second strand concatemer template molecules that were generated by a workflow that included circularizing linear library molecules using double-stranded splint adaptors (e.g., see FIG. 5 or 6, but without unique identification sequences (180) and (190)), with or without heat, and conducting on-support rolling circle amplification to generate concatemer template molecules immobilized to a coated support. The library preparation workflow compared the effect of heat, NaOH, HEPES buffer, or a cocktail mixture of enzymes that can generate abasic sites and remove the abasic sites. The X-axis is the number of sequencing cycles. The Y-axis is the quality scores.

In some embodiments, the second splint strand (400) comprises a random sequence which is appended to the 3' end of the first sub-region of the second splint strand (e.g., FIGS. 7B, 14A and 14B). In some embodiments, the random sequence comprises an index sequence.

In some embodiments, the second sub-region of the second splint strand (400) does not have an appended random sequence.

In some embodiments, the appended random sequence can be any length, for example 2-10 bases in length. For example, the random sequence can be 3 nucleotide in length (e.g., 'NNN' in FIG. 14A) or 4 nucleotides in length (e.g., 'NNNN' in FIG. 14B).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110).

In some embodiments, the index sequence can be used to distinguish polynucleotides (e.g., insert sequences) from different sample sources in a multiplex assay.

In some embodiments, a pre-determined sequence is appended to the 5' end of the fourth sub-region of the first splint strand (300). In some embodiments, the length of the appended pre-determined sequence can be the same length as the random sequence which is appended to the 3' end of the first sub-region of the second splint strand (e.g., FIGS. 14A and 14B). In some embodiments, the length of the appended pre-determined sequence can be the same length as the random sequence and index sequence which is appended to the 3' end of the first sub-region of the second splint strand (e.g., FIGS. 14A and 14B). The appended pre-determined sequence can have any sequence. An exemplary pre-determined sequence is shown in FIGS. 14A and 14B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 14A and 14B). In some embodiments, the double-stranded splint adaptor (200) forms a bubble or a mis-matched end at the location of the appended random sequence. In some embodiments, the double-stranded splint adaptor (200) forms a bubble or a mis-matched end at the location of the appended random sequence and index sequence.

In some embodiments, the second splint strand (400) appended with a random sequence (and optionally an index sequence), as part of a double-stranded splint adaptor (200), can hybridize to a library molecule (100) to form a library-splint complex (500).

Sequences of Short Splint Strand (400)

In some embodiments, the first sub-region of the second splint strand (400) comprises the sequence 5'-CATGTAATGCACGTACTTTCAGGGT-3' (SEQ ID NO:200). In some embodiments, the second sub-region of the second splint strand (400) comprises the sequence 5'-AGTCGTCGCAGCCTCACCTGATC-3' (SEQ ID NO:201). In some embodiments, the second splint strand (400) comprises a first and second sub-region comprising the sequence 5'-AGTCGTCGCAGCCTCACCTGATC-CATGTAATGCACGTACTTTCAGGGT-3' (SEQ ID NO:202). See FIG. 11A. In some embodiments, the 5' end of the second splint strand (400) can be phosphorylated or non-phosphorylated.

Sequences of Long Splint Strand (300)

In some embodiments, the first region of the first splint strand (320) includes a first universal adaptor sequence which comprises a universal binding sequence (or a complementary sequence thereof) for a first surface primer, where the first region (320) comprises the sequence 5'-TCGGTGGTCGCCGTATCATT-3' (SEQ ID NO:193). For example, the first region of the first splint strand (320) can hybridize to a P5 surface primer or a complementary sequence of the P5 surface primer. For example, the P5 surface primer comprises the sequence 5'-AATGA-TACGGCGACCACCGA-3' (SEQ ID NO:203; short P5), or the P5 surface primer comprises the sequence 5'-AATGA-TACGGCGACCACCGAGATC-3' (SEQ ID NO:194; long P5). In some embodiments, the second region of the first splint strand (330) includes a second universal adaptor sequence which comprises a universal binding sequence (or a complementary sequence thereof) for a second surface primer, where the second region (330) comprises the sequence 5'-CAAGCAGAAGACGGCATACGA-3' (SEQ ID NO:195). For example, the second region of the first splint strand (330) can hybridize to a P7 surface primer or a complementary sequence of the P7 surface primer. For example, the P7 surface primer comprises the sequence 5'-CAAGCAGAAGACGGCATACGA-3' (SEQ ID NO:195; short P7), or the P7 surface primer comprises the sequence 5'-CAAGCAGAAGACGGCATACGAGAT-3' (SEQ ID NO:196; long P7). In some embodiments, the first splint strand (300) includes an internal region (310) which comprises a fourth sub-region having the sequence 5'-ACCCT-GAAAGTACGTGCATTACATG-3' (SEQ ID NO:197). In some embodiments, the first splint strand (300) includes an internal region (310) which comprises a fifth sub-region having the sequence 5'-GATCAGGT-GAGGCTGCGACGACT-3' (SEQ ID NO:198). In some embodiments, the first splint strand (300) comprises a first region (320), an internal region (310) having a fourth and fifth sub-region, and a second region (330), having the sequence 5'-TCGGTGGTCGCCGTATCATTACCCT-GAAAGTACGTGCATTACATGGATCAGGTGAGG CTGCGACGACTCAAGCAGAAGACGGCATACGA-3' (SEQ ID NO:199). See FIG. 11A. In some embodiments, the 5' end of the first splint strand (300) can be phosphorylated or non-phosphorylated. In some embodiments, the first sub-region of the second splint strand (400) can hybridize to the fourth sub-region of the first splint strand (300). In some embodiments, the second sub-region of the second splint strand (400) can hybridize to the fifth sub-region of the first splint strand (300).

Library-Splint Complexes

The present disclosure provides a library-splint complex (500) comprising: (i) a single-stranded nucleic acid library molecule (100) which includes a sequence of interest (110) flanked on one side by at least a first left universal adaptor sequence (120) and flanked on the other side by at least a first right universal adaptor sequence (130); and (ii) a double-stranded splint adaptor (200) which includes a first splint strand (long splint strand (300)) and a second splint strand (short splint strand (400)), wherein the first splint strand comprises a first region (320), an internal region (310), and a second region (330), wherein the internal region of the first splint strand (310) is hybridized to the second splint strand (400) to form the double-stranded splint adaptor (200) having a double-stranded region flanked on either side by a single-stranded region. In the library-splint complex (500), the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) (e.g., see FIGS. 1-8).

In the library-splint complex (500), the first region of the first splint strand (320) comprises a first universal adaptor sequence which can hybridize to a first universal binding sequence at one end of a linear nucleic acid library molecule (e.g., see FIGS. 1-8). In some embodiments, the first region of the first splint strand (320) includes a first universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the first splint strand (300) can be 50-150 nucleotides in length, or 60-100 nucleotides in length, or 70-90 nucleotides in length. In some embodiments, the first splint strands (300) comprise one or more phosphorothioate linkages at the 5' and/or 3' ends to confer exonuclease resistance. In some embodiments, the first splint strands (300) comprise one or more phosphorothioate linkages at an internal position to confer endonuclease resistance. In some embodiments, the first splint strands (300) comprise one or more 2'-O-methylcytosine bases at the 5' and/or 3' end, or at an internal position. In some embodiments, the 5' end of the first splint strand (300) is phosphorylated or lacks a phosphate group. In some embodiments, the 3' end of the first splint strand (300) includes a terminal 3' OH group or a terminal 3' blocking group.

The second region of the first splint strand (330) comprises a second universal adaptor sequence which can hybridize to a second universal binding sequence at the other end of the linear nucleic acid library molecule (e.g., see FIGS. 1-8). In some embodiments, the second region of the first splint strand (330) includes a second universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the 5' end of the second splint strand (400) is phosphorylated or lacks a phosphate group. In some embodiments, the 3' end of the second splint strand (400) includes a terminal 3' OH group or a terminal 3' blocking group.

In the library-splint complex (500), the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500). The library-splint complex (500) comprises a first nick between the 5' end of the library molecule and the 3' end of the second splint strand. The library-splint complex (500) also comprises a second nick between the 5' end of the second splint strand and the 3' end of the library molecule (e.g., see FIGS. 1-8). In some embodiments, the first and second nicks are enzymatically ligatable.

In the library-splint complex (500), the first region of the first splint strand (320) can hybridize to a sense or anti-sense strand of a double-stranded nucleic acid library molecule. In the library-splint complex (500), the second region of the first splint strand (330) can hybridize to a sense or anti-sense strand of a double-stranded nucleic acid library molecule. The double-stranded nucleic acid library molecule can be denatured to generate the single-stranded sense and anti-sense library strands.

In the library-splint complex (500), the second splint strand (400) does not hybridize to the sequence of interest (110), and the internal region of the first splint strand (310) does not hybridize to the sequence of interest (110).

In the library-splint complex (500), the first region of the first splint strand (320) does not hybridize to the sequence of interest (110), and the second region of the first splint strand (330) does not hybridize to the sequence of interest (110).

In some embodiments, in the library-splint complex (500), the 5' end of the single-stranded library molecule (100) is phosphorylated or lacks a phosphate group. In some embodiments, the 3' end of the single-stranded library molecule includes a terminal 3' OH group or a terminal 3' blocking group.

In some embodiments, the nucleic acid library molecule (100) comprises a second left universal adaptor sequence (140). In some embodiments, the nucleic acid library molecule (100) comprises a second right universal adaptor sequence (150). Exemplary library molecules (100) are shown in FIGS. 4-8. In some embodiments, the nucleic acid library molecule (100) can further comprise additional left and/or right universal adaptor sequences.

In some embodiments, the nucleic acid library molecule (100) further comprises a first left index sequence (160). In some embodiments, the nucleic acid library molecule (100) further comprises a first right index sequence (170). In some embodiments, the first left index sequence (160) comprises a sample index sequence. In some embodiments, the first right index sequence (170) comprises another sample index sequence. In some embodiments, the first left index sequence (160) and the first right index sequence (170) are not the same sequence. In some embodiments, the nucleic acid library molecule (100) includes a first left index sequence (160) and/or a first right index sequence (170). The sample index sequences can be used to distinguish sequences of interest obtained from different sample sources in a multiplex assay. Exemplary library molecules (100) are shown in FIGS. 4-8. A list of exemplary first left index sequences (160) and first right index sequences (170) is provided in Table 1 at FIG. 33. The first left index sequence (160) can include a random sequence (e.g., NNN) or lack a random sequence. The first right index sequence (170) can include a random sequence (e.g., NNN) or lack a random sequence.

Figure 8:
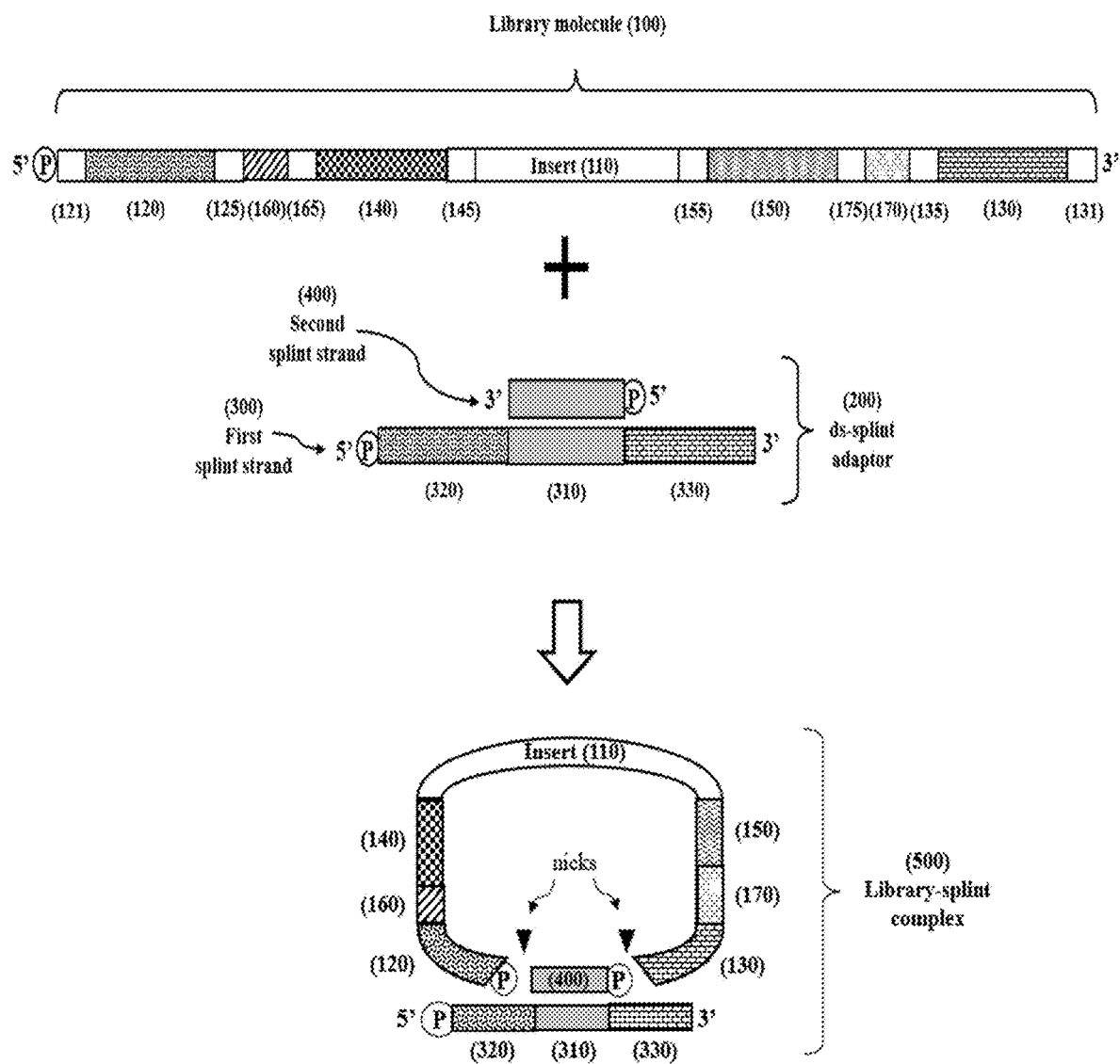
FIG. 8 is a schematic showing an exemplary linear single stranded library molecule (100) hybridizing with a double-stranded splint molecule (200) thereby circularizing the library molecule to form a library-splint complex (500) with two nicks. The library molecule (100) comprises: a first appended left universal adaptor sequence (121); a first left universal adaptor sequence (120); a first left junction adaptor sequence (125); a first left index sequence (160); a second left junction adaptor sequence (165); a second left universal adaptor sequence (140); a third left junction adaptor sequence (145); a sequence of interest (Insert, 110); a third right junction adaptor sequence (155); a second right universal adaptor sequence (150); a second right junction adaptor sequence (175); a first right index sequence (170); a first right junction adaptor sequence (135); a first right universal adaptor sequence (130); and a first appended right universal adaptor sequence (131). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400). For the sake of simplicity, the library-splint complex (500) does not show any of the junction adaptor sequences or the appended universal adaptor sequences. The skilled artisan will recognize that the linear library molecule (100) can include any one or any combination of two or more of the junction adaptors, with our without one or both of the appended universal adaptor sequences. The skilled artisan will recognize that the library-splint complex (500) can include any one or any combination of two or more of the junction adaptors, with our without one or both of the appended universal adaptor sequences, that are present in the library molecule (100).

In some embodiments, the nucleic acid library molecule (100) further comprises at least one junction adaptor sequence located between any of the universal adaptor sequences described herein (e.g., see FIG. 8). For example, a first left junction adaptor sequence (125) can be located between the first left universal adaptor sequence (120) and the first left index sequence (160). A second left junction adaptor sequence (165) can be located between the first left index sequence (160) and the second left universal adaptor sequence (140). A third left junction adaptor sequence (145) can be located between the second left universal adaptor sequence (140) and the sequence of interest (110). A first right junction adaptor sequence (135) can be located between the first right universal adaptor sequence (130) and the first right index sequence (170). A second right junction adaptor sequence (175) can be located between the first right index sequence (170) and the second right universal adaptor sequence (150). A third right junction adaptor sequence (155) can be located between the second right universal adaptor sequence (150) and the sequence-of-interest (110). In some embodiments, the nucleic acid library molecule (100) further comprises at least one, and up to ten, appended universal adaptor sequences located 5' (upstream) of the first left universal adaptor sequence (120) (e.g., see FIG. 8). In some embodiments, the nucleic acid library molecule (100) further comprises at least one and up to ten appended universal adaptor sequences located 3' (downstream) of the first right universal adaptor sequence (130) (e.g., see FIG. 8). Any of the junction adaptor sequences comprise any sequence and can be 3-60 nucleotides in length and/or appended universal adaptor sequences. Any of the junction adaptor sequences and/or appended universal adaptor sequences comprise a universal sequence or a unique sequence. Any of the junction adaptor sequences and/or appended universal adaptor sequences comprise a binding sequence for an amplification primer, a sequencing primer, a compaction oligonucleotide, or a combination thereof. Any of the junction adaptor sequences and/or appended universal adaptor sequences comprise a binding sequence for an immobilized surface primer (e.g., capture primer). Any of the junction adaptor sequences and/or appended universal adaptor sequences comprise a sample index sequence. Any of the junction adaptor sequences and/or appended universal adaptor sequences comprise a unique identification sequence. Any of the junction adaptor sequences and/or appended universal adaptor sequences, particularly junction adaptor sequence (145) as shown in FIG. 8 comprises a Tn5 transposon-end sequence 5'-AGATGTGTATAAGA-GACAG-3' (SEQ ID NO:211). Any of the junction adaptor sequences and/or appended universal adaptor sequences, particularly junction adaptor sequence (155) as shown in FIG. 8 comprises a Tn5 transposon-end sequence 5'-CTGTCTCTTATACACATCT-3' (SEQ ID NO:212). The Tn5 transposon-end sequences can be introduced into the library molecule (100) via a transposase-mediated reaction which includes contacting double-stranded input DNA (e.g., genomic DNA) with a Tn-5 type transposase enzyme, and a double-stranded oligonucleotide comprising the Tn transposon-end sequence (SEQ ID NO:211) linked to a universal adaptor sequence or a sample index sequence under a condition that is suitable to form a transposon synaptic complex. In the double-stranded oligonucleotide, the Tn transposon-end sequence (SEQ ID NO:211) can be located 5' or 3' relative to the universal adaptor sequence or a sample index sequence.

Multiplex workflows are enabled by preparing sample-indexed libraries using one or both index sequences (e.g., left and/or right index sequences). The first left index sequences (160) and/or first right index sequences (170) can be employed to prepare separate sample-indexed libraries using input nucleic acids isolated from different sources. The sample-indexed libraries can be pooled together to generate a multiplex library mixture, and the pooled libraries can be amplified and/or sequenced. The sequences of the insert region along with the first left index sequence (160) and/or first right index sequence (170) can be used to identify the source of the input nucleic acids. In some embodiments, any number of sample-indexed libraries can be pooled together, for example 2-10, or 10-50, or 50-100, or 100-200, or more than 200 sample-indexed libraries can be pooled. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

Figure 5:
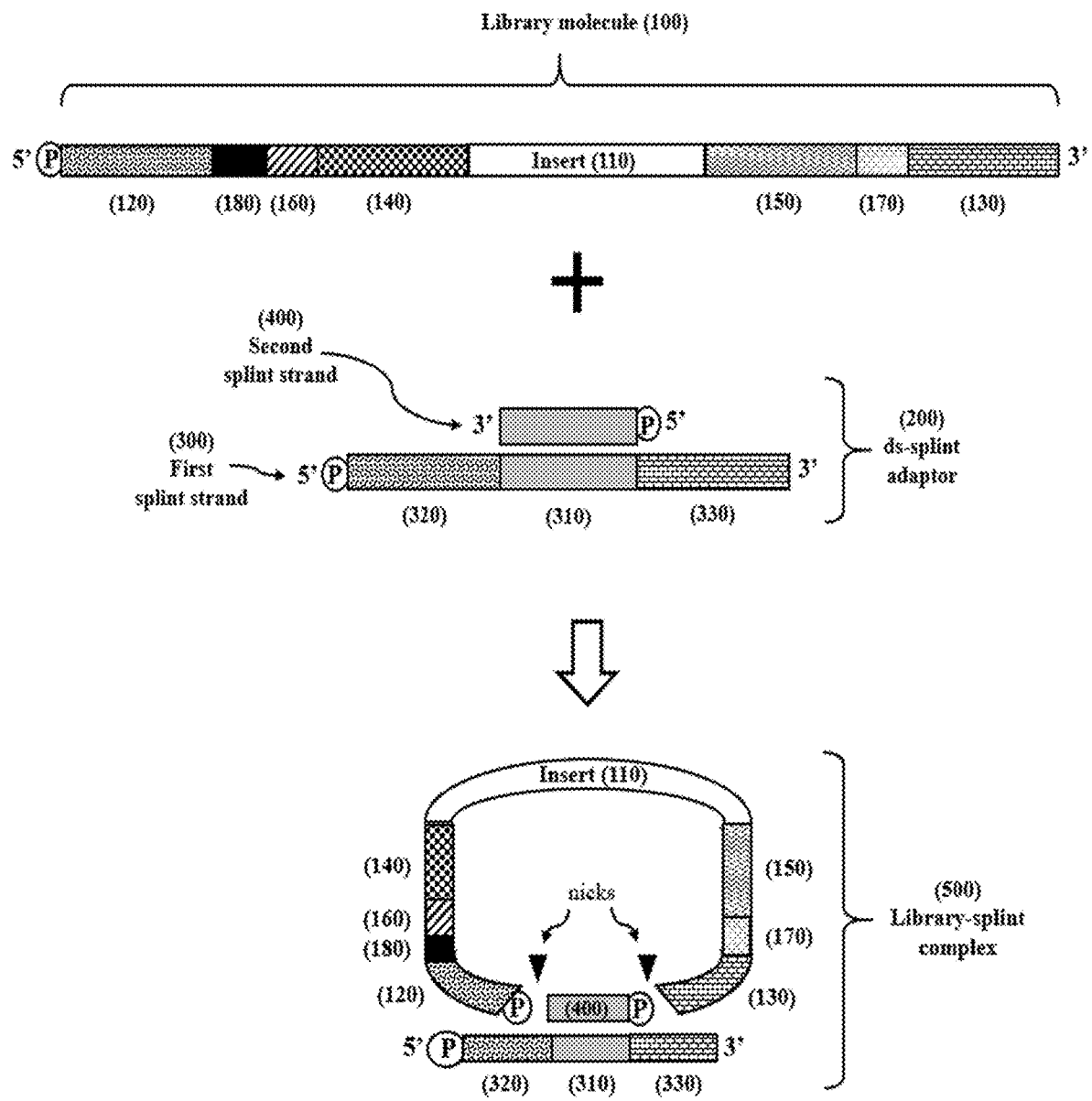
FIG. 5 is a schematic showing an exemplary linear single stranded library molecule (100) hybridizing with a double-stranded splint molecule (200) thereby circularizing the library molecule to form a library-splint complex (500) with two nicks. The library molecule (100) comprises: a first left universal adaptor sequence (120); a first left unique identification sequence (180); a first left index sequence (160); a second left universal adaptor sequence (140); a sequence of interest (110); a second right universal adaptor sequence (150); a first right index sequence (170); and a first right universal adaptor sequence (130). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400).
Figure 6:
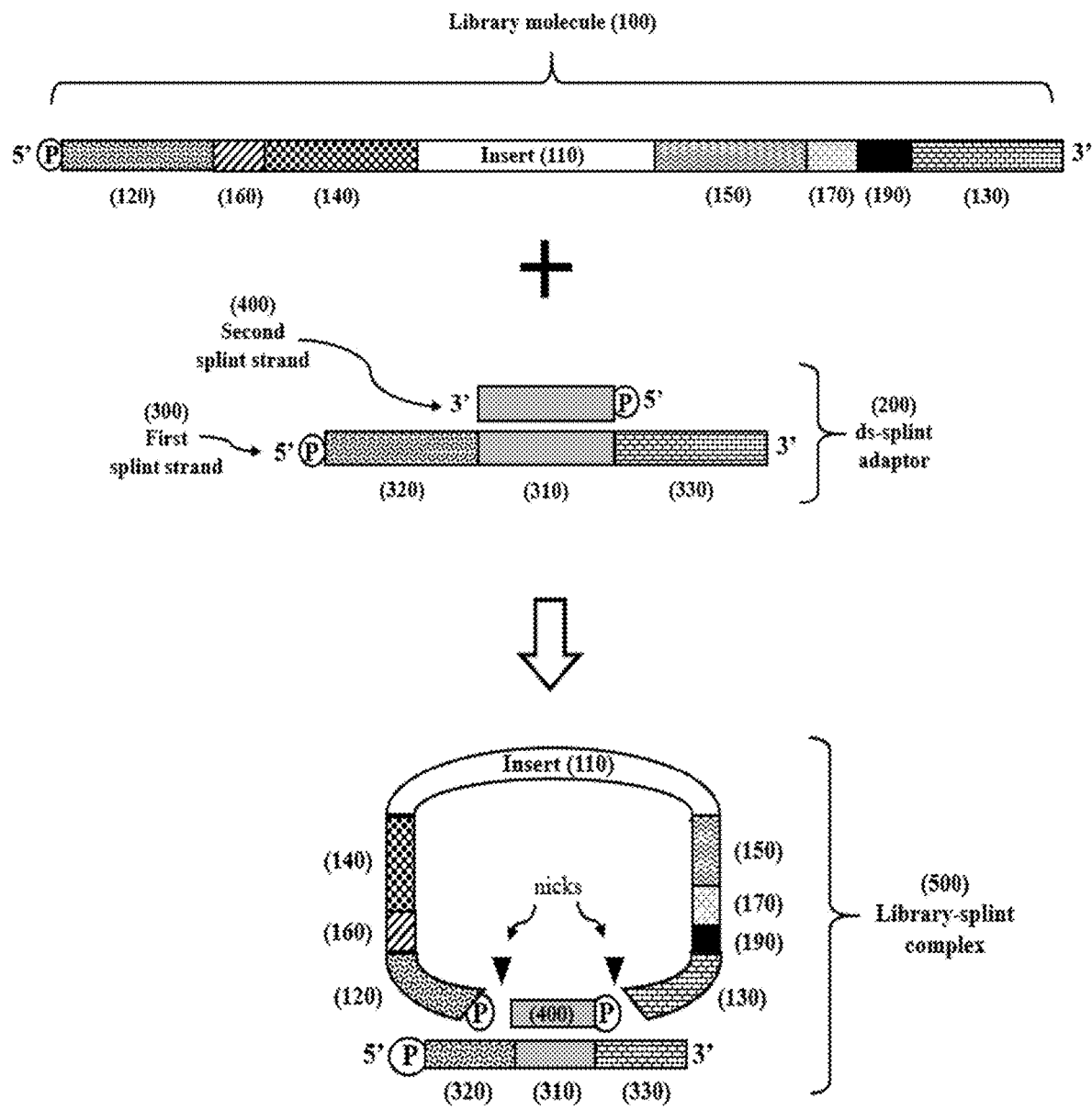
FIG. 6 is a schematic showing an exemplary linear single stranded library molecule (100) hybridizing with a double-stranded splint molecule (200) thereby circularizing the library molecule to form a library-splint complex (500) with two nicks. The library molecule (100) comprises: a first left universal adaptor sequence (120); a first left index sequence (160); a second left universal adaptor sequence (140); a sequence of interest (Insert, 110); a second right universal adaptor sequence (150); a first right index sequence (170); a first right unique identification sequence (190); and a first right universal adaptor sequence (130). The double-stranded splint molecule comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400).

In some embodiments, the nucleic acid library molecule (100) further comprises an optional first left unique identification sequence (180) as shown in FIG. 5. In some embodiments, the nucleic acid library molecule (100) further comprises an optional first right unique identification sequence (190) as shown in FIG. 6. In some embodiments, the first left unique identification sequence (180) and the first right unique identification sequence (190) each comprise a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging. Exemplary library molecules (100) are shown in FIGS. 4-8.

In some embodiments, the nucleic acid library molecule (100) comprises any one or any combination of two or more of: a first left universal adaptor sequence (120); a second left universal adaptor sequence (140); a first left index sequence (160); a first left unique identification sequence (180); a first right universal adaptor sequence (130); a second right universal adaptor sequence (150); a first right index sequence (170); and/or a first right unique identification sequence (190). Exemplary library molecules (100) are shown in FIGS. 4-8.

In some embodiments, the first left universal adaptor sequence (120) and/or the second left universal adaptor sequence (140), comprises a universal binding sequence for a forward or reverse sequencing primer; a universal binding sequence for a first or second surface primer; a universal binding sequence for a forward or reverse amplification primer; and/or a universal binding sequence for a compaction oligonucleotide. In some embodiments, the nucleic acid library molecule (100) comprises additional left universal adaptor sequences.

In some embodiments, the first right universal adaptor sequence (130) and/or the second right universal adaptor sequence (150), comprises a universal binding sequence for a forward or reverse sequencing primer; a universal binding sequence for a first or second surface primer; a universal binding sequence for a forward or reverse amplification primer; and/or a universal binding sequence for a compaction oligonucleotide. In some embodiments, the nucleic acid library molecule (100) comprises additional right universal adaptor sequences.

In some embodiments, the second splint strand (400) comprises at least two sub-regions, including a first and second sub-region (e.g., see FIGS. 2 and 3). In some embodiments, the first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN) (e.g., see FIGS. 2 and 3). In some embodiments, the second splint strand (400) comprises only one sub-region and lacks a second and third sub-region, where the first sub-region comprises a sample index sequence having 5-20 bases. In some embodiments, the sample index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3'. Another exemplary arrangement of the sub-regions in the second splint strand (400), in a 5' to 3' orientation comprises: 5'-[third sub-region]-[second sub-region]-[first sub-region]-3'. In some embodiments, the second splint strand (400) can be 20-100 nucleotides in length, or 30-80 nucleotides in length, or 40-60 nucleotides in length. In some embodiments, the second splint strands (400) comprise one or more phosphorothioate linkage at the 5' and/or 3' ends to confer exonuclease resistance. In some embodiments, the second splint strands (400) comprise one or more phosphorothioate linkages at an internal position to confer endonuclease resistance. In some embodiments, the second splint strands (400) comprise one or more 2'-O-methylcytosine bases at the 5' and/or 3' end, or at an internal position. In some embodiments, the 5' end of the second splint strand (400) is phosphorylated or non-phosphorylated.

In some embodiments, the 3' end of the second splint strand (400) comprises a terminal 3' OH group or a terminal 3' blocking group.

In some embodiments, the first splint strand (300) includes an internal region (310) which comprises at least two sub-regions, including a fourth and fifth sub-region (e.g., see FIGS. 2 and 3). The fourth sub-region hybridizes to the first sub-region of the second splint strand (400). The fifth sub-region hybridizes to the second sub-region of the second splint strand (400). The fourth and fifth sub-regions do not hybridize (or at least exhibit very little hybridization to) the first and second surface primers. In some embodiments, the internal region (310) of the first splint strand further comprises an optional sixth sub-region which hybridizes to the third sub-region of the second splint strand (400) (e.g., see FIGS. 2 and 3). An exemplary arrangement of the sub-regions of the first splint strand (300), in a 5' to 3' orientation comprises: 5'-[fourth sub-region]-[fifth sub-region]-3'. Another exemplary arrangement of the sub-regions of the first splint strand (300), in a 5' to 3' orientation comprises: 5'-[fourth sub-region]-[fifth sub-region]-[sixth sub-region]-3'.

In some embodiments, an exemplary library-splint complex (500) comprises: (a) single-stranded nucleic acid library molecule (100); (b) a first splint strand (300); and (c) a second splint strand (400).

In the exemplary library-splint complex (500), the single-stranded nucleic acid library molecule (100) comprises components arranged in a 5' to 3' order: (i) a first left universal adaptor sequence (120) having a binding sequence for a first surface primer; (ii) a second left universal adaptor sequence (140) having a binding sequence for a first sequencing primer; (iii) a sequence of interest (110); (iv) a second right universal adaptor sequence (150) having a binding sequence for a second sequencing primer; and (v) a first right universal adaptor sequence (130) having a binding sequence for a second surface primer.

In the exemplary library-splint complex (500), the first splint strand (300) comprises components arranged in a 5' to 3' order: a first region (320); an internal region (310); and a second region (330).

In the exemplary library-splint complex (500), the second splint strand (400) comprises sub-regions arranged in a 3' to 5' order: a first sub-region having a universal binding sequence for a third surface primer; and a second sub-region having a universal binding sequence for a fourth surface primer.

In the exemplary library-splint complex (500), portions of the first splint strand (300) are hybridized to portions of the library molecule (100) thereby circularizing the library molecule to generate a library-splint complex (500), such that the first region (320) of the first splint strand is hybridized to the binding sequence for the first surface primer (120), and the third region (330) of the first splint strand is hybridized to the binding sequence for the second surface primer (130). Additionally, the second splint strand (400) is hybridized to the internal region (310) of the first splint strand (300). The library-splint complex (500) comprises a first nick between the 5' end of the library molecule and the 3' end of the second splint strand, and a second nick between the 5' end of the second splint strand and the 3' end of the library molecule, and the first and second nicks are enzymatically ligatable.

In the exemplary library-splint complex (500), the second splint strand (400) does not hybridize to the sequence of interest (110), and the internal region of the first splint strand (310) does not hybridize to the sequence of interest (110).

In the exemplary library-splint complex (500), the first region of the first splint strand (320) does not hybridize to the sequence of interest (110), and the second region of the first splint strand (330) does not hybridize to the sequence of interest (110).

In some embodiments, any of the library-splint complexes (500) describe herein comprise a plurality of library-splint complexes (500), wherein the sequence of interest (110) of individual library-splint complexes in the plurality comprise the same sequence of interest or different sequences of interest.

Library Splint Complexes Formed with Double-Stranded Adaptors Having Truncated Long Splint Strands In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal sequence (130) of the library molecule, thereby circularizing the library molecule to generate a library-splint complex (500) having a first and second nick (e.g., FIGS. 1-6 and 8).

In some embodiments, the first splint strand (300) comprises a truncated strand having a first region (320) having a truncated sequence at the 5' end (e.g., FIG. 11B). In some embodiments, the first region has a truncated sequence at the 5' end when compared to SEQ ID NO: 199, as shown in FIG. 11A. In some embodiments, the 5' end of the first region can have a truncation of any length for example a truncation of 1-10 nucleotides. In some embodiments, the truncated first splint strand (300) comprises a second region (330; e.g., SEQ ID NO:5), a fourth sub-region (e.g., SEQ ID NO:6) and a fifth sub-region (e.g., SEQ ID NO:7) that are not truncated and do not carry any sequence variants such as for example insertion, deletion or base-substitution. In some embodiments, the truncated first splint strand comprises a fourth sub-region and fifth sub-region that can hybridize with the first sub-region and second sub-region of a second splint strand (400) to form a double-stranded splint adaptor (200). In some embodiments, the truncated first splint strand (300) comprises a truncated first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the truncated first splint strand, as part of a double-stranded splint adaptor (200) can hybridize to a library molecule (100) to form a library-splint complex (500) having a first and second nick.

Library Splint Complexes Formed with Double-Stranded Adaptors Having Long Splint Strands with Mis-Match Sequences In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) having a first and second nick (e.g., FIGS. 1-8).

In some embodiments, the first splint strand (300) comprises mis-match strand having a first region (320) having a mis-match sequence within the first region (320) (e.g., FIG. 11C). In some embodiments, the mis-match sequence can be any length (e.g., 2-20 bases) and comprises any sequence that is not fully complementary to the left universal adaptor sequence (120) of a library molecule (100). Some embodiments of mis-match sequences in the first region (320) are shown in small case letters and underlined in FIG. 11C. In some embodiments, the mis-match first splint strand (300) comprises a second region (330; e.g., SEQ ID NO:5), a fourth sub-region (e.g., SEQ ID NO:6) and a fifth sub-region (e.g., SEQ ID NO:7) that do not carry any sequence variants such as for example insertion, deletion or base-substitution. In some embodiments, the mis-match first splint strand comprises a fourth sub-region and fifth sub-region that can hybridize with the first sub-region and second sub-region of a second splint strand (400) to form a double-stranded splint adaptor (200). In some embodiments, the mis-match first splint strand comprises (300) comprises a mis-match first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the mis-match first region (320) can hybridize with the first left universal adaptor sequence (120) of a library molecule (100) to form a double-stranded portion having a bubble at the location of the mis-match sequence in the first region (320). In some embodiments, the mis-match first splint strand, as part of a double-stranded splint adaptor (200) can hybridize to a library molecule (100) to form a library-splint complex (500) with first and second nicks.

Library Splint Complexes Formed with Double-Stranded Adaptors Having Long Splint Strands with Abasic Sites In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) having a first and second nick (e.g., FIGS. 1-8).

In some embodiments, the first splint strand (300) comprises at least one abasic site which lacks a nitrogenous base. In some embodiments, the first splint strand (300) comprises at least one abasic site in the fourth sub-region and/or at least one abasic site in the fifth sub-region (e.g., top schematic of FIG. 11D, abasic sites are shown as solid black bars). In some embodiments, the abasic sites each comprise a 1',2'-dideoxyribose (e.g., dSpacer from Integrated DNA Technologies (IDT)).

In some embodiments, the abasic first splint strand (300) comprises a first region ((320); e.g., SEQ ID NO:4), and a second region ((330); e.g., SEQ ID NO:5) that do not carry any abasic sites and/or any sequence variants such as for example insertion, deletion or base-substitution. In some embodiments, the abasic first splint strand comprises a fourth sub-region and fifth sub-region that can hybridize with the first sub-region and second sub-region of a second splint strand (400) to form a double-stranded splint adaptor (200). In some embodiments, the abasic first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the abasic first splint strand, as part of a double-stranded splint adaptor (200) can hybridize to a library molecule (100) to form a library-splint complex (500) having first and second nicks.

Library Splint Complexes Formed with Double-Stranded Adaptors Having Long Splint Strands with Uracils In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) having a first and second nick (e.g., FIGS. 1-8).

In some embodiments, the first splint strand (300) comprises at least one uracil in any one or any combination of regions including the first region (320), the second region (330), the fourth sub-region and/or the fifth sub-region. In some embodiments, at least one thymine base can be substituted with a uracil. An embodiment of a uracil-containing first splint strand is shown in FIG. 11D (bottom schematic). The skilled artisan will recognize that many other sequences of the first splint strand (300) comprising one or more uracils are possible.

In some embodiments, the uracil-containing first splint strand comprises a fourth sub-region and fifth sub-region that can hybridize with the first sub-region and second sub-region of a second splint strand (400) to form a double-stranded splint adaptor (200). In some embodiments, the uracil-containing first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the uracil-containing first splint strand, as part of a double-stranded splint adaptor (200) can hybridize to a library molecule (100) to form a library-splint complex (500) having a first and second nick.

Library Splint Complexes Formed with Double-Stranded Adaptors Having Short Splint Strands with Random Sequences In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) having a first and second nick (e.g., FIGS. 1-8).

In some embodiments, the second splint strand (400) comprises a random sequence inserted into the first sub-region of the second splint strand (e.g., FIGS. 7A, 12A and 12B). In some embodiments, a random sequence can replace a portion of the first sub-region of the second splint strand (e.g., FIGS. 7A, 13A and 13B).

In some embodiments, the second sub-region of the second splint strand (400) does not have an inserted random sequence. In some embodiments, a portion of the second sub-region of the second splint strand (400) is not replaced with a random sequence.

In some embodiments, the random sequence can be any length, for example 2-10 bases in length. For example, the random sequence can be 3 nucleotide in length (e.g., 'NNN' in FIGS. 12A and 13A) or 4 nucleotides in length (e.g., 'NNNN' in FIGS. 12B and 13B). In some embodiments, the random sequence can be inserted at any position in the first sub-region of the second splint strand (400).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110).

In some embodiments, a pre-determined sequence is inserted into the sequence of the fourth sub-region of the first splint strand (300). The length of the inserted pre-determined sequence can be the same length as the random sequence inserted into the first sub-region of the second splint strand (e.g., FIGS. 12A and 12B). The inserted pre-determined sequence can have any sequence. An exemplary pre-determined sequence is shown in FIGS. 12A and 12B.

In some embodiments, a portion of the fourth sub-region of the first splint strand (300) is replaced with a pre-determined sequence. The length of the pre-determined sequence which replaces a portion of the fourth sub-region is the same length as the random sequence that replaces a portion of the first sub-region of the second splint strand (e.g., FIGS. 13A and 13B). The replacing pre-determined sequence can have any sequence. An exemplary pre-determined sequence is shown in FIGS. 13A and 13B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 12A, 12B, 13A and 13B). In some embodiments, the double-stranded splint adaptor (200) forms a bubble at the location of the inserted or replacing random sequence.

In some embodiments, the second splint strand (400) carrying a random sequence, as part of a double-stranded splint adaptor (200), can hybridize to a library molecule (100) to form a library-splint complex (500) having a first and second nick.

Library Splint Complexes Formed with Double-Stranded Adaptors Having Short Splint Strands with Appended Random Sequences and Index Sequences In some embodiments, the library-splint complex (500) comprises a library molecule (100) hybridized to the first splint strand (300) of a double-stranded splint adaptor (200). In some embodiments, the first region of the first splint strand (320) is hybridized to the at least first left universal adaptor sequence (120) of the library molecule, and a second region of the first splint strand (330) is hybridized to the at least first right universal adaptor sequence (130) of the library molecule, thereby circularizing the library molecule to generate a library-splint complex (500) having a first and second nick (e.g., FIGS. 1-8).

In some embodiments, the second splint strand (400) comprises a random sequence which is appended to the 3' end of the first sub-region of the second splint strand (e.g., FIGS. 7B, 14A and 14B). In some embodiments, the random sequence further comprises an index sequence.

In some embodiments, the second sub-region of the second splint strand (400) does not have an appended random sequence.

In some embodiments, the appended random sequence can be any length, for example 2-10 bases in length. For example, the random sequence can be 3 nucleotide in length (e.g., 'NNN' in FIG. 14A) or 4 nucleotides in length (e.g., 'NNNN' in FIG. 14B).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110).

In some embodiments, the index sequence can be used to distinguish polynucleotides (e.g., insert sequences) from different sample sources in a multiplex assay.

In some embodiments, a pre-determined sequence is appended to the 5' end of the fourth sub-region of the first splint strand (300). In some embodiments, the length of the appended pre-determined sequence can be the same length as the random sequence which is appended to the 3' end of the first sub-region of the second splint strand (e.g., FIGS. 14A and 14B). In some embodiments, the length of the appended pre-determined sequence can be the same length as the random sequence and index sequence which is appended to the 3' end of the first sub-region of the second splint strand (e.g., FIGS. 14A and 14B). The appended pre-determined sequence can have any sequence. An exemplary pre-determined sequence is shown in FIGS. 14A and 14B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 14A and 14B). In some embodiments, the double-stranded splint adaptor (200) forms a bubble or a mis-matched end at the location of the appended random sequence. In some embodiments, the double-stranded splint adaptor (200) forms a bubble or a mismatched end at the location of the appended random sequence and index sequence.

In some embodiments, the second splint strand (400) appended with a random sequence (and optionally an index sequence), as part of a double-stranded splint adaptor (200), can hybridize to a library molecule (100) to form a library-splint complex (500) having a first and second nick.

Sequences of Short Splint Strand (400)

In some embodiments of the library-splint complexes (500) described herein, the first sub-region of the second splint strand (400) comprises the sequence 5'-CATGTAATGCACGTACTTTCAGGGT-3' (SEQ ID NO:200). In some embodiments, the second sub-region of the second splint strand (400) comprises the sequence 5'-AGTCGTCGCAGCCTCACCTGATC-3' (SEQ ID NO:201). In some embodiments, the second splint strand (400) comprises a first and second sub-region comprising the sequence 5'-AGTCGTCGCAGCCTCACCTGATC-CATGTAATGCACGTACTTTCAGGGT-3' (SEQ ID NO:202). See FIG. 11A. In some embodiments, the 5' end of the second splint strand (400) can be phosphorylated or non-phosphorylated.

In some embodiments, the second splint strand (400) comprises only one sub-region and lacks a second and third sub-region, where the first sub-region comprises a sample index sequence having 5-20 bases.

Sequences of Long Splint Strand (300)

In some embodiments of the library-splint complexes (500) describe herein, the first region of the first splint strand (320) includes a first universal adaptor sequence which comprises a universal binding sequence (or a complementary sequence thereof) for a first surface primer, where the first region (320) comprises the sequence 5'-TCGGTGGTCGCCGTATCATT-3' (SEQ ID NO:193). For example, the first region of the first splint strand (320) can hybridize to a P5 surface primer or a complementary sequence of the P5 surface primer. For example, the P5 surface primer comprises the sequence 5'-AATGA-TACGGCGACCACCGA-3' (SEQ ID NO:203; short P5), or the P5 surface primer comprises the sequence 5'-AATGA-TACGGCGACCACCGAGATC-3' (SEQ ID NO:194; long P5). In some embodiments, the second region of the first splint strand (330) includes a second universal adaptor sequence which comprises a universal binding sequence (or a complementary sequence thereof) for a second surface primer, where the second region (330) comprises the sequence 5'-CAAGCAGAAGACGGCATACGA-3' (SEQ ID NO:195). For example, the second region of the first splint strand (330) can hybridize to a P7 surface primer or a complementary sequence of the P7 surface primer. For example, the P7 surface primer comprises the sequence 5'-CAAGCAGAAGACGGCATACGA-3' (SEQ ID NO:195; short P7), or the P7 surface primer comprises the sequence 5'-CAAGCAGAAGACGGCATACGAGAT-3' (SEQ ID NO:196; long P7). In some embodiments, the first splint strand (300) includes an internal region (310) which comprises a fourth sub-region having the sequence 5'-ACCCT-GAAAGTACGTGCATTACATG-3' (SEQ ID NO:197). In some embodiments, the first splint strand (300) includes an internal region (310) which comprises a fifth sub-region having the sequence 5'-GATCAGGT-GAGGCTGCGACGACT'3' (SEQ ID NO:198). In some embodiments, the first splint strand (300) comprises a first region (320), an internal region (310) having a fourth and fifth sub-region, and a second region (330), having the sequence 5'-TCGGTGGTCGCCGTATCATTACCCT-GAAAGTACGTGCATTACATGGATCAGGTGAGG CTGCGACGACTCAAGCAGAAGACGGCATACGA-3' (SEQ ID NO:199). See FIG. 11A. In some embodiments, the 5' end of the first splint strand (300) can be phosphorylated or non-phosphorylated. In some embodiments, the first sub-region of the second splint strand (400) can hybridize to the fourth sub-region of the first splint strand (300). In some embodiments, the second sub-region of the second splint strand (400) can hybridize to the fifth sub-region of the first splint strand (300).

Sequences of Library-Splint Complexes

In some embodiments of the library-splint complexes (500) describe herein, the first region of the first splint strand (320) comprises a sequence that can bind a first left universal adaptor sequence (120) of a library molecules, wherein the first region of the first splint strand (320) comprises the sequence 5'-ACCCTGAAAGTACGTGCATTACATG-3' (SEQ ID NO:215) or a complementary sequence thereof.

In some embodiments of the library-splint complexes (500) describe herein, the second region of the first splint strand (330) comprises a sequence that can bind a first right universal adaptor sequence (130) of a library molecules, wherein the second region of the first splint strand (330) comprises the sequence 5'-GATCAGGT-GAGGCTGCGACGACT-3' (SEQ ID NO:216) or a complementary sequence thereof.

In some embodiments, in any of the library-splint complexes (500) describe herein, the library molecule includes a first left universal adaptor sequence (120) which binds the first region of the first splint strand (320), wherein the left universal binding sequence (120) comprises the sequence 5'-AATGATACGGCGACCACCGA-3' (SEQ ID NO:203).

In some embodiments, in any of the library-splint complexes (500) describe herein, the library molecule includes a first left universal adaptor sequence (120) which binds the first region of the first splint strand (320), wherein the first left universal adaptor sequence (120) comprises the sequence 5'-CATGTAATGCACGTACTTTCAGGGT-3' (SEQ ID NO:213) or a complementary sequence thereof.

In some embodiments of the library-splint complexes (500) describe herein, the library molecule includes a second left universal adaptor sequence comprising a sequence for binding a sequencing primer (140), wherein the second left universal adaptor sequence comprises the sequence

5'-ACACTCTTTCCCTACACGACGCTCTTCCGATCT-3'. (SEQ ID NO: 204)

In some embodiments of the library-splint complexes (500) describe herein, the library molecule includes a second left universal adaptor sequence comprising a sequence for binding a sequencing primer (140), wherein the second left universal adaptor sequence comprises the sequence

5'-TCGTCGGCAGCGTCAGATGTGTATAAGAGACAG-3'. (SEQ ID NO: 207)

In some embodiments of the library-splint complexes (500) describe herein, the library molecule includes a second left universal adaptor sequence comprising a sequence for binding a sequencing primer (140), wherein the second left universal adaptor sequence comprises the sequence

5'-CGTGCTGGATTGGCTCACCAGACACCTTCCGACAT-3'. (SEQ ID NO: 208)

In some embodiments of the library-splint complexes (500) describe herein, the library molecule includes a second right universal adaptor sequence comprising a sequence for binding a sequencing primer (150), wherein the right universal adaptor sequence comprises the sequence

5'-AGATCGGAAGAGCACACGTCTGAACTCCAGTCAC-3'. (SEQ ID NO: 205)

In some embodiments of the library-splint complexes (500) describe herein, the library molecule includes a second right universal adaptor sequence comprising a sequence for binding a sequencing primer (150), wherein the second right universal adaptor sequence comprises the sequence

5'-CTGTCTCTTATACACATCTCCGAGCCCACGAGAC-3'. (SEQ ID NO: 209)

In some embodiments of the library-splint complexes (500) describe herein, the library molecule includes a second right universal adaptor sequence comprising a sequence for binding a sequencing primer (150), wherein the second right universal adaptor sequence comprises the sequence

5'-ATGTCGGAAGGTGTGCAGGCTACCGCTTGTCAACT-3'. (SEQ ID NO: 210)

In some embodiments of the library-splint complexes (500) describe herein, the library molecule includes a first right universal adaptor sequence (130) which binds the first region of the first splint strand (330), wherein the first right universal adaptor sequence (130) comprises the sequence 5'-TCGTATGCCGTCTTCTGCTTG-3' (SEQ ID NO:206).

In some embodiments of the library-splint complexes (500) describe herein, the library molecule includes a first right universal adaptor sequence (130) which binds the first region of the first splint strand (330), wherein the first right universal adaptor sequence (130) comprises the sequence 5'-AGTCGTCGCAGCCTCACCTGATC-3' (SEQ ID NO:214) or a complementary sequence thereof.

The present disclosure provides a reaction mixture comprising a plurality of any of the library-splint complexes (500) described herein. In some embodiments, the reaction mixture comprises a plurality of any of the library-splint complexes (500) described herein, and a T4 polynucleotide kinase. In some embodiments, the reaction mixture comprises a plurality of any of the library-splint complexes (500) described herein, and a ligase enzyme. In some embodiments, the reaction mixture comprises a plurality of any of the library-splint complexes (500) described herein, and a T4 polynucleotide kinase and a ligase enzyme. In some embodiments, the ligase enzyme comprises T7 DNA ligase, T3 ligase, T4 ligase, or Taq ligase.

Covalently Closed Circular Molecules

Figure 9:
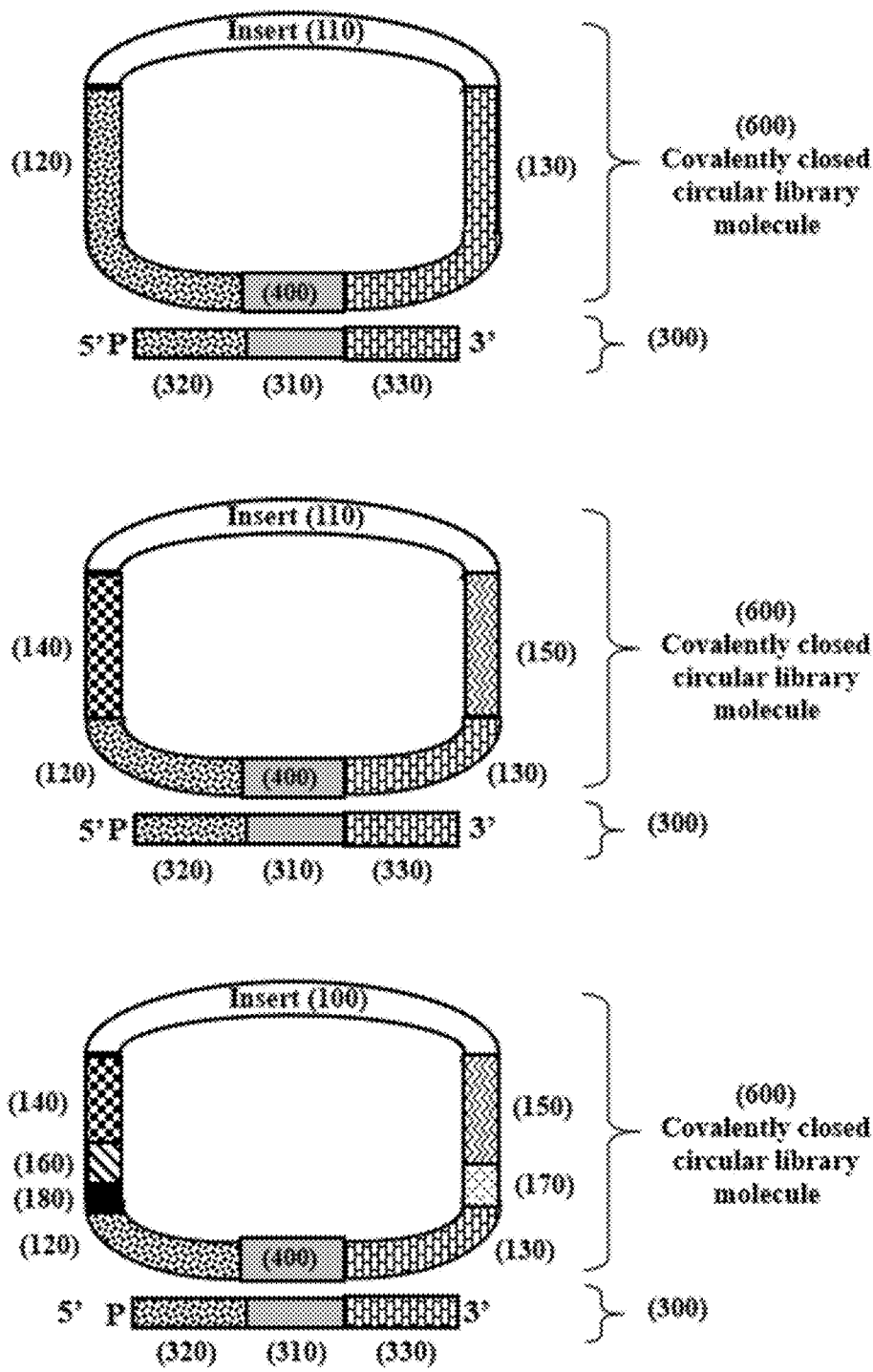
FIG. 9 shows three schematics of exemplary covalently closed circular library molecules (600), each hybridized to a first splint strand (300). The top schematic shows a covalently closed circular library molecule (600) having a sequence of interest (Insert, 110), a first right universal adaptor sequence (130), a second splint strand sequence (400), and a first left universal adaptor sequence (120). The middle schematic shows a covalently closed circular library molecule (600) having a sequence of interest (110), a second right universal adaptor sequence (150), a first right universal adaptor sequence (130), a second splint strand sequence (400), a first left universal adaptor sequence (120), and a second left universal adaptor sequence (140). The bottom schematic shows a covalently closed circular library molecule (600) having a sequence of interest (110), a second right universal adaptor sequence (150), a first right index sequence (170), a first right universal adaptor sequence (130), a second splint strand sequence (400), a first left universal adaptor sequence (120), a first left unique identification sequence (180), a first left index sequence (160), and a second left universal adaptor sequence (140).

The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently close circular molecule (600) further comprises a first left index sequence (160) and/or a first right index sequence (170). The index sequences can be used to distinguish sequences of interest obtained from different sample sources in a multiplex assay. A list of exemplary first left index sequences (160) and first right index sequences (170) is provided in Table 1 at FIGS. 33-1 to 33-6. The first left index sequence (160) can include a random sequence (e.g., NNN) or lack a random sequence. The first right index sequence (170) can include a random sequence (e.g., NNN) or lack a random sequence.

Multiplex workflows are enabled by preparing sample-indexed libraries using one or both index sequences (e.g., left and/or right index sequences). The first left index sequences (160) and/or first right index sequences (170) can be employed to prepare separate sample-indexed libraries using input nucleic acids isolated from different sources. The sample-indexed libraries can be pooled together to generate a multiplex library mixture, and the pooled libraries can be amplified and/or sequenced. The sequences of the insert region along with the first left index sequence (160) and/or first right index sequence (170) can be used to identify the source of the input nucleic acids. In some embodiments, any number of sample-indexed libraries can be pooled together, for example 2-10, or 10-50, or 50-100, or 100-200, or more than 200 sample-indexed libraries can be pooled. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

In some embodiments, the covalently close circular molecule (600) further comprises an optional first left unique identification sequence (180) and/or an optional first right unique identification sequence (190), as shown in FIGS. 5 and 6. In some embodiments, the first left unique identification sequence (180) and the first right unique identification sequence (190) each comprise a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging.

In some embodiments, the covalently close circular molecule (600) comprises any one or any combination of two or more: a first left universal adaptor sequence (120); a second left universal adaptor sequence (140); a first left index sequence (160); a first left unique identification sequence (180); a first right universal adaptor sequence (130); a second right universal adaptor sequence (150); a first right index sequence (170); and/or a first right unique identification sequence (190). In some embodiments, the first left index sequence (160) comprises a sample index sequence. In some embodiments, the first right index sequence (170) comprises another sample index sequence. The sample index sequences can be used to distinguish sequences of interest obtained from different sample sources in a multiplex assay. In some embodiments, the first left unique identification sequence (180) and the first right unique identification sequence (190) each comprise a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging.

In some embodiments, in the covalently close circular molecule (600), the first left universal adaptor sequence (120) and/or the second left universal adaptor sequence (140), comprises: a universal binding sequence for a forward or reverse sequencing primer; a universal binding sequence for a first or second surface primer; a universal binding sequence for a forward or reverse amplification primer; and/or a universal binding sequence for a compaction oligonucleotide. In some embodiments, the covalently close circular molecule (600) can further comprise additional left universal adaptor sequences.

In some embodiments, in the covalently close circular molecule (600), the first right universal adaptor sequence (130) and/or the second right universal adaptor sequence (150), comprises: a universal binding sequence for a forward or reverse sequencing primer; a universal binding sequence for a first or second surface primer; a universal binding sequence for a forward or reverse amplification primer; a universal binding sequence for a compaction oligonucleotide, or a combination thereof. In some embodiments, the covalently close circular molecule (600) can further comprise additional right universal adaptor sequences.

In some embodiments, the covalently close circular molecule (600) further comprises at least one junction adaptor sequence located between any of the universal adaptor sequences described herein (e.g., see FIG. 8). For example, a first left junction adaptor sequence (125) can be located between the first left universal adaptor sequence (120) and the first left index sequence (160). A second left junction adaptor sequence (165) can be located between the first left index sequence (160) and the second left universal adaptor sequence (140). A third junction adaptor sequence (145) can be located between the second left universal adaptor sequence (140) and the sequence of interest (110). A first right junction adaptor sequence (135) can be located between the first right universal adaptor sequence (130) and the first right index sequence (170). A second right junction adaptor sequence (175) can be located between the first right index sequence (170) and the second right universal adaptor sequence (150). A third right junction adaptor sequence (155) can be located between the second right universal adaptor sequence (150) and the sequence-of-interest (110). In some embodiments, the covalently close circular molecule (600) further comprises at least one and up to ten appended universal adaptor sequences located 5' (upstream) of the first left universal adaptor sequence (120) (e.g., see FIG. 8). In some embodiments, the covalently close circular molecule (600) further comprises at least one and up to ten appended universal adaptor sequences located 3' (downstream) of the first right universal adaptor sequence (130) (e.g., see FIG. 8). Any of the junction adaptor sequences and/or appended universal adaptor sequences comprise any sequence and can be 3-60 nucleotides in length. Any of the junction adaptor sequences and/or appended universal adaptor sequences comprise a universal sequence or a unique sequence. Any of the junction adaptor sequences and/or appended universal adaptor sequences comprise a binding sequence for an amplification primer, a sequencing primer or a compaction oligonucleotide. Any of the junction adaptor sequences and/or appended universal adaptor sequences comprise a binding sequence for an immobilized surface primer (e.g., capture primer). Any of the junction adaptor sequences and/or appended universal adaptor sequences comprise a sample index sequence. Any of the junction adaptor sequences and/or appended universal adaptor sequences comprise a unique identification sequence. Any of the junction adaptor sequences and/or appended universal adaptor sequences, particularly junction adaptor sequence (145) as shown in FIG. 8 comprises a Tn5 transposon-end sequence 5'-AGATGTGTATAAGAGACAG-3' (SEQ ID NO:211). Any of the junction adaptor sequences and/or appended universal adaptor sequences, particularly junction adaptor sequence (155) as shown in FIG. 8 comprises a Tn5 transposon-end sequence 5'-CTGTCTCTTATACACATCT-3' (SEQ ID NO:212). The Tn5 transposon-end sequences can be introduced into the library molecule (100) via a transposase-mediated reaction which includes contacting double-stranded input DNA (e.g., genomic DNA) with a Tn-5 type transposase enzyme, and a double-stranded oligonucleotide comprising the Tn transposon-end sequence (SEQ ID NO:211) linked to a universal adaptor sequence or a sample index sequence under a condition that is suitable to form a transposon synaptic complex. In the double-stranded oligonucleotide, the Tn transposon-end sequence (SEQ ID NO:211) can be located 5' or 3' relative to the universal adaptor sequence or a sample index sequence.

In some embodiments, the second splint strand sequence (400) of the covalently closed circular molecule comprises at least two sub-regions, including a first and second sub-region. In some embodiments, the first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN). In some embodiments, the second splint strand (400) comprises only one sub-region and lacks a second and third sub-region, where the first sub-region comprises an index sequence (e.g., a sample index sequence) having 5-20 bases. In some embodiments, the index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3' (e.g., FIG. 2). Another exemplary arrangement of the sub-regions in the second splint strand (400), in a 5' to 3' orientation comprises: 5'-[third sub-region]-[second sub-region]-[first sub-region]-3' (e.g., FIG. 3).

In some embodiments, the second splint strand sequence (400) of the covalently closed circular library molecule (600) can be hybridized to a first splint strand (300). In some embodiments, the first splint strand (300) includes an internal region (310) which comprises at least two sub-regions, including a fourth and fifth sub-region. The fourth sub-region hybridizes to the first sub-region of the second splint strand (400). The fifth sub-region hybridizes to the second sub-region of the second splint strand (400). The fourth and fifth sub-regions do not hybridize (or at least exhibit very little hybridization to) the first and second surface primers. In some embodiments, the internal region (310) of the first splint strand further comprises an optional sixth sub-region which hybridizes to the third sub-region of the second splint strand (400). An exemplary arrangement of the sub-regions of the first splint strand (300), in a 5' to 3' orientation comprises: 5'-[fourth sub-region]-[fifth sub-region]-3' (e.g., FIG. 2). Another exemplary arrangement of the sub-regions of the first splint strand (300), in a 5' to 3' orientation comprises: 5'-[fourth sub-region]-[fifth sub-region]-[sixth sub-region]-3' (e.g., FIG. 3).

In some embodiments, an exemplary covalently closed circular molecule (600) comprises: (i) a first left universal adaptor sequence (120) having a binding sequence for a first surface primer; (ii) a second left universal adaptor sequence (140) having a binding sequence for a first sequencing primer; (iii) a sequence of interest (110); (iv) a second right universal adaptor sequence (150) having a binding sequence for a second sequencing primer; (v) a first right universal adaptor sequence (130) having a binding sequence for a second surface primer; and (vi) a second splint strand sequence (400), wherein the covalently closed circular molecule (600) is optionally hybridized to the first splint strand (300).

In the exemplary covalently closed circular molecule (600), the second splint strand region (400) comprises at least two sub-regions, including a first and second sub-region. The first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN). In some embodiments, the second splint strand (400) comprises only one sub-region and lacks a second and third sub-region, where the first sub-region comprises a sample index sequence having 5-20 bases. In some embodiments, the sample index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3'. Another exemplary arrangement of the sub-regions in the second splint strand (400), in a 5' to 3' orientation comprises: 5'-[third sub-region]-[second sub-region]-[first sub-region]-3'.

The disclosure provides pluralities of the covalently closed circular library molecules described herein. In some embodiments of the pluralities of covalently closed circular molecules (600), the sequence of interest (110) of individual covalently closed circular molecules (600) in the plurality comprise the same sequence of interest or different sequences of interest.

Covalently Closed Circular Molecules Formed with Double-Stranded Adaptors Having Truncated Long Splint Strands The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) is hybridized to a first splint strand. In some embodiments, the first splint strand (300) comprises a truncated strand having a first region (320) having a truncated sequence at the 5' end (e.g., FIG. 11B, showing exemplary truncations compared to SEQ ID NO:199, as shown in FIG. 11A). In some embodiments, the 5' end of the first region can have a truncation of any length for example a truncation of 1-10 nucleotides. In some embodiments, the truncated first splint strand (300) comprises a second region (330; e.g., SEQ ID NO:5), a fourth sub-region (e.g., SEQ ID NO:6) and a fifth sub-region (e.g., SEQ ID NO:7) that are not truncated and do not carry any sequence variants such as for example insertion, deletion or base-substitution. In some embodiments, the truncated first splint strand comprises a fourth sub-region and fifth sub-region that can hybridize with the first sub-region and second sub-region of a second splint strand (400) as part of the covalently closed circular library molecule (600) (e.g., FIG. 9). In some embodiments, the truncated first splint strand comprises (300) comprises a truncated first region (320) that hybridizes with a sequence (e.g., 120) as part of the covalently closed circular library molecule (600), and a second region (330) that hybridizes with a sequence (e.g., 130) as part of the covalently closed circular library molecule (600).

Covalently Closed Circular Molecules Formed with Double-Stranded Adaptors Having Long Splint Strands with Mis-Match Sequences The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) is hybridized to a first splint strand. In some embodiments, the first splint strand (300) comprises mis-match strand having a first region (320) having a mis-match sequence within the first region (320) (e.g., FIG. 11C). In some embodiments, the mis-match sequence can be any length (e.g., 2-20 bases) and comprises any sequence that is not fully complementary to the left universal adaptor sequence (120) of a library molecule (100). Some embodiments of mis-match sequences in the first region (320) are shown in small case letters and underlined in FIG. 11C. In some embodiments, the mis-match first splint strand (300) comprises a second region (330; e.g., SEQ ID NO:5), a fourth sub-region (e.g., SEQ ID NO:6) and a fifth sub-region (e.g., SEQ ID NO:7) that do not carry any sequence variants such as for example insertion, deletion or base-substitution. In some embodiments, the mis-match first splint strand comprises a fourth sub-region and fifth sub-region that can hybridize with the first sub-region and second sub-region of a second splint strand (400) as part of the covalently closed circular library molecule (600) (e.g., FIG. 9). In some embodiments, the mis-match first splint strand comprises (300) comprises a mis-match first region (320) that hybridizes with a sequence (e.g., 120) as part of the covalently closed circular library molecule (600), and a second region (330) that hybridizes with a sequence (e.g., 130) as part of the covalently closed circular library molecule (600). In some embodiments, the mis-match first region (320) can hybridize with the first left universal adaptor sequence (120) of a covalently closed circular library molecule (600) to form a double-stranded portion having a bubble at the location of the mis-match sequence in the first region (320).

Covalently Closed Circular Molecules Formed with Double-Stranded Adaptors Having Long Splint Strands with Abasic Sites The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) is hybridized to a first splint strand. In some embodiments, the first splint strand (300) comprises at least one abasic site which lacks a nitrogenous base. In some embodiments, the first splint strand (300) comprises at least one abasic site in the fourth sub-region and/or at least one abasic site in the fifth sub-region (e.g., top schematic of FIG. 11D, abasic sites are shown as solid black bars). In some embodiments, the abasic sites each comprise a 1',2'-dideoxyribose (e.g., dSpacer from Integrated DNA Technologies (IDT)). In some embodiments, the abasic first splint strand (300) comprises a first region ((320); e.g., SEQ ID NO:4), and a second region ((330); e.g., SEQ ID NO:5) that do not carry any abasic sites and/or any sequence variants such as for example an insertion, deletion or base-substitution. In some embodiments, the abasic first splint strand comprises a fourth sub-region and fifth sub-region that can hybridize with the first sub-region and second sub-region of a second splint strand (400) as part of the covalently closed circular library molecule (600) (e.g., FIG. 9). In some embodiments, the abasic first splint strand comprises (300) comprises a first region (320) that hybridizes with a sequence (e.g., 120) as part of the covalently closed circular library molecule (600), and a second region (330) that hybridizes with a sequence (e.g., 130) as part of the covalently closed circular library molecule (600).

Covalently Closed Circular Molecules Formed with Double-Stranded Adaptors Having Long Splint Strands with Uracil The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) is hybridized to a first splint strand. In some embodiments, the first splint strand (300) comprises at least one uracil. In some embodiments, the first splint strand (300) comprises at least one uracil in any one or any combination of regions including the first region (320), the second region (330), the fourth sub-region and/or the fifth sub-region. In some embodiments, at least one thymine base can be substituted with a uracil. An embodiment of a uracil-containing first splint strand is shown in FIG. 11D (bottom schematic). The skilled artisan will recognize that many other sequences of the first splint strand (300) comprising one or more uracils are possible. In some embodiments, the uracil-containing first splint strand comprises a fourth sub-region and fifth sub-region that can hybridize with the first sub-region and second sub-region of a second splint strand (400) as part of the covalently closed circular library molecule (600) (e.g., FIG. 9). In some embodiments, the uracil-containing first splint strand comprises (300) comprises a first region (320) that hybridizes with a sequence (e.g., 120) as part of the covalently closed circular library molecule (600), and a second region (330) that hybridizes with a sequence (e.g., 130) as part of the covalently closed circular library molecule (600).

Covalently Closed Circular Molecules Formed with Double-Stranded Adaptors Having Short Splint Strands with Random Sequences and Index Sequences The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) comprises a second splint strand sequence (400) covalently joined to a first left universal adaptor sequence (120) and a first right universal adaptor sequence (130) (e.g., FIGS. 7A and 9). In some embodiments, the covalently closed circular library molecule (600) is hybridized to a first splint strand (300). In some embodiments, the second splint strand (400) comprises a random sequence inserted into the first sub-region of the second splint strand (e.g., FIGS. 7A, 12A and 12B). In some embodiments, a random sequence can replace a portion of the first sub-region of the second splint strand (e.g., FIGS. 7A, 13A and 13B). In some embodiments, the second sub-region of the second splint strand (400) does not have an inserted random sequence. In some embodiments, a portion of the second sub-region of the second splint strand (400) is not replaced with a random sequence.

In some embodiments, the random sequence can be any length, for example 2-10 bases in length. For example, the random sequence can be 3 nucleotide in length (e.g., 'NNN' in FIGS. 12A and 13A) or 4 nucleotides in length (e.g., 'NNNN' in FIGS. 12B and 13B). In some embodiments, the random sequence can be inserted at any position in the first sub-region of the second splint strand (400).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110). In some embodiments, the covalently closed circular library molecule can be subjected to an rolling circle amplification reaction to generate a concatemer immobilized to a support. The concatemer comprises tandem repeat sequences of the circular library molecule including any insert sequence and adaptor sequences (e.g., random sequence) present in the original circularized nucleic acid template molecule. In some embodiments, the random index sequence can be sequence prior to sequencing the insert region, where the random index is located in the first sub-region of the second splint strand (400).

In some embodiments, the random sequence can be sequenced prior to sequencing the insert region. In some embodiments, the sequencing data from the random sequence can be used for polony mapping and/or template registration because the random sequence provides sufficient nucleotide diversity and color balance.

In some embodiments, a pre-determined sequence is inserted into the sequence of the fourth sub-region of the first splint strand (300) (e.g., FIG. 7A). The length of the inserted pre-determined sequence can be the same length as the random sequence inserted into the first sub-region of the second splint strand (e.g., FIGS. 12A and 12B). The inserted pre-determined sequence can have any sequence. An exemplary pre-determined sequence is shown in FIGS. 12A and 12B.

In some embodiments, a portion of the fourth sub-region of the first splint strand (300) is replaced with a pre-determined sequence. The length of the pre-determined sequence which replaces a portion of the fourth sub-region is the same length as the random sequence that replaces a portion of the first sub-region of the second splint strand (e.g., FIGS. 7A, 13A and 13B). The replacing pre-determined sequence can have any sequence. An exemplary pre-determined sequence is shown in FIGS. 13A and 13B.

In some embodiments, the second splint strand (400) comprises a first sub-region and second sub-region that can hybridize with the fourth sub-region and fifth sub-region of a first splint strand (300) as part of the covalently closed circular library molecule (600) (e.g., FIGS. 7A, 12A, 12B, 13A and 13B) which can include a bubble at the location of the inserted or replacing random sequence.

Covalently Closed Circular Molecules Formed with Double-Stranded Adaptors Having Short Splint Strands with Appended Random Sequences and Index Sequences The present disclosure provides a covalently closed circular library molecule (600) comprising: a sequence of interest (110), at least a first left universal adaptor sequence (120), at least a first right universal adaptor sequence (130), and a second splint strand sequence (400). Exemplary covalently closed circular library molecules are shown in FIG. 9. In some embodiments, the covalently closed circular library molecule (600) further comprises a second left universal adaptor sequence (140). In some embodiments, the covalently close circular molecule (600) further comprises a second right universal adaptor sequence (150). In some embodiments, the covalently close circular molecule (600) further comprise additional left and/or right universal adaptor sequences.

In some embodiments, the covalently closed circular library molecule (600) comprises a second splint strand sequence (400) covalently joined to a first left universal adaptor sequence (120) and a first right universal adaptor sequence (130) (e.g., FIGS. 7B and 9). In some embodiments, the covalently closed circular library molecule (600) is hybridized to a first splint strand (300). In some embodiments, the second splint strand (400) comprises a random sequence which is appended to the 3' end of the first sub-region of the second splint strand (e.g., FIGS. 7B, 14A and 14B). In some embodiments, the random sequence further comprises an index sequence. In some embodiments, the second sub-region of the second splint strand (400) does not have an appended random sequence.

In some embodiments, the appended random sequence can be any length, for example 2-10 bases in length. For example, the random sequence can be 3 nucleotide in length (e.g., 'NNN' in FIG. 14A) or 4 nucleotides in length (e.g., 'NNNN' in FIG. 14B).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance. In some embodiments, the sequences of the left index (160), the right index (170) and/or any portion of the insert region (110), do not provide sufficient nucleotide diversity to enable polony mapping and/or template registration. In some embodiments, the random sequence provides a higher level of nucleotide diversity compared to the left index (160), the right index (170) and/or any portion of the insert region (110). In some embodiments, the covalently closed circular library molecule can be subjected to an rolling circle amplification reaction to generate a concatemer immobilized to a support. The concatemer comprises tandem repeat sequences of the circular library molecule including any insert sequence and adaptor sequences (e.g., random sequence) present in the original circularized nucleic acid template molecule. In some embodiments, the random index sequence can be sequence prior to sequencing the insert region, where the random index is located at the 3' end of the first sub-region of the second splint strand (400).

In some embodiments, the index sequence can be used to distinguish polynucleotides (e.g., insert sequences) from different sample sources in a multiplex assay.

In some embodiments, a pre-determined sequence is appended to the 5' end of the fourth sub-region of the first splint strand (300) (e.g., FIG. 7B). In some embodiments, the length of the appended pre-determined sequence can be the same length as the random sequence which is appended to the 3' end of the first sub-region of the second splint strand (e.g., FIGS. 7B, 14A and 14B). In some embodiments, the length of the appended pre-determined sequence can be the same length as the random sequence and index sequence which is appended to the 3' end of the first sub-region of the second splint strand (e.g., FIGS. 7B, 14A and 14B). The appended pre-determined sequence can have any sequence. An exemplary pre-determined sequence is shown in FIGS. 14A and 14B.

In some embodiments, the second splint strand (400) comprises a first sub-region and second sub-region that can hybridize with the fourth sub-region and fifth sub-region of a first splint strand (300) as part of the covalently closed circular library molecule (600) (e.g., FIGS. 7B, 14A and 14B) which can include a bubble at the location of the appended random sequence.

Sequences of Short Splint Strands

In some embodiments of the covalently closed circular molecules (600) described herein, the first sub-region of the second splint strand (400) comprises the sequence 5'-CATGTAATGCACGTACTTTCAGGGT-3' (SEQ ID NO:200). In some embodiments, the second sub-region of the second splint strand (400) comprises the sequence 5'-AGTCGTCGCAGCCTCACCTGATC-3' (SEQ ID NO:201). In some embodiments, the second splint strand (400) comprises a first and second sub-region comprising the sequence 5'-AGTCGTCGCAGCCTCACCTGATC-CATGTAATGCACGTACTTTCAGGGT-3' (SEQ ID NO:202). See FIG. 11A. In some embodiments, the 5' end of the second splint strand (400) can be phosphorylated or non-phosphorylated.

Sequences of Long Splint Strands

In some embodiments of the covalently closed circular molecules (600) described herein, the first region of the first splint strand (320) includes a first universal adaptor sequence which comprises a universal binding sequence (or a complementary sequence thereof) for a first surface primer, where the first region (320) comprises the sequence 5'-TCGGTGGTCGCCGTATCATT-3' (SEQ ID NO:193). For example, the first region of the first splint strand (320) can hybridize to a P5 surface primer or a complementary sequence of the P5 surface primer. For example, the P5 surface primer comprises the sequence 5'-AATGA-TACGGCGACCACCGA-3' (SEQ ID NO:203; short P5), or the P5 surface primer comprises the sequence 5'-AATGA-TACGGCGACCACCGAGATC-3' (SEQ ID NO:194; long P5). In some embodiments, the second region of the first splint strand (330) includes a second universal adaptor sequence which comprises a universal binding sequence (or a complementary sequence thereof) for a second surface primer, where the second region (330) comprises the sequence 5'-CAAGCAGAAGACGGCATACGA-3' (SEQ ID NO:195). For example, the second region of the first splint strand (330) can hybridize to a P7 surface primer or a complementary sequence of the P7 surface primer. For example, the P7 surface primer comprises the sequence 5'-CAAGCAGAAGACGGCATACGA-3' (SEQ ID NO:195; short P7), or the P7 surface primer comprises the sequence 5'-CAAGCAGAAGACGGCATACGAGAT-3' (SEQ ID NO:196; long P7). In some embodiments, the first splint strand (300) includes an internal region (310) which comprises a fourth sub-region having the sequence 5'-ACCCT-GAAAGTACGTGCATTACATG-3' (SEQ ID NO:197). In some embodiments, the first splint strand (300) includes an internal region (310) which comprises a fifth sub-region having the sequence 5'-GATCAGGT-GAGGCTGCGACGACT'3' (SEQ ID NO:198). In some embodiments, the first splint strand (300) comprises a first region (320), an internal region (310) having a fourth and fifth sub-region, and a second region (330), having the sequence 5'-TCGGTGGTCGCCGTATCATTACCCT-GAAAGTACGTGCATTACATGGATCAGGTGAGG CTGCGACGACTCAAGCAGAAGACGGCATACGA-3' (SEQ ID NO:199). See FIG. 11A. In some embodiments, the 5' end of the first splint strand (300) can be phosphorylated or non-phosphorylated. In some embodiments, the first sub-region of the second splint strand (400) can hybridize to the fourth sub-region of the first splint strand (300). In some embodiments, the second sub-region of the second splint strand (400) can hybridize to the fifth sub-region of the first splint strand (300).

Sequences of Covalently Closed Circular Molecules

In some embodiments of the covalently closed circular molecules (600) described herein, the first region of the first splint strand (320) comprises a sequence that can bind a first left universal adaptor sequence (120) of a library molecules, wherein the first region of the first splint strand (320)

comprises the sequence 5'-ACCCTGAAAGTACGTGCAT-TACATG-3' (SEQ ID NO:215) or a complementary sequence thereof.

In some embodiments of the covalently closed circular molecules (600) described herein, the second region of the first splint strand (330) comprises a sequence that can bind a first right universal adaptor sequence (130) of a library molecules, wherein the second region of the first splint strand (330) comprises the sequence 5'-GATCAGGT-GAGGCTGCGACGACT-3' (SEQ ID NO:216) or a complementary sequence thereof.

In some embodiments of the covalently closed circular molecules (600) described herein, the library molecule includes a first left universal adaptor sequence (120) which comprises the sequence 5'-AATGATACGGCGAC-CACCGA-3' (SEQ ID NO:203).

In some embodiments of the covalently closed circular molecules (600) described herein, the library molecule includes a first left universal adaptor sequence (120) which binds the first region of the first splint strand (320), wherein the first left universal adaptor sequence (120) comprises the sequence 5'-CATGTAATGCACGTACTTTCAGGGT-3' (SEQ ID NO:213) or a complementary sequence thereof.

In some embodiments of the covalently closed circular molecules (600) described herein, the library molecule includes a second left universal adaptor sequence comprising a sequence for binding a sequencing primer (140) wherein the second left universal adaptor sequence comprises the sequence (SEQ ID NO: 204)
5'-ACACTCTTTCCCTACACGACGCTCTTCCGATCT-3'.

In some embodiments of the covalently closed circular molecules (600) described herein, the library molecule includes a second left universal adaptor sequence comprising a sequence for binding a sequencing primer (140) wherein the second left universal binding sequence comprises the sequence (SEQ ID NO: 207)
5'-TCGTCGGCAGCGTCAGATGTGTATAAGAGACAG-3'.

In some embodiments of the covalently closed circular molecules (600) described herein, the library molecule includes a second left universal adaptor sequence comprising a sequence for binding a sequencing primer (140) wherein the second left universal adaptor sequence comprises the sequence (SEQ ID NO: 208)
5'-CGTGCTGGATTGGCTCACCAGACACCTTCCGACAT-3'.

In some embodiments of the covalently closed circular molecules (600) described herein, the library molecule includes a first right universal adaptor sequence comprising a sequence for binding a sequencing primer (150) wherein the first right universal adaptor sequence comprises the sequence (SEQ ID NO: 205)
5'-AGATCGGAAGAGCACACGTCTGAACTCCAGTCAC-3'.

In some embodiments of the covalently closed circular molecules (600) described herein, the library molecule includes a first right universal adaptor sequence comprising a sequence for binding a sequencing primer (150) wherein the first right universal adaptor sequence comprises the sequence (SEQ ID NO: 209)
5'-CTGTCTCTTATACACATCTCCGAGCCCACGAGAC-3'.

In some embodiments of the covalently closed circular molecules (600) described herein, the library molecule includes a first right universal adaptor sequence comprising a sequence for binding a sequencing primer (150) wherein the first right universal adaptor sequence comprises the sequence (SEQ ID NO: 210)
5'-ATGTCGGAAGGTGTGCAGGCTACCGCTTGTCAACT-3'.

In some embodiments of the covalently closed circular molecules (600) described herein, the library molecule includes a first right universal adaptor sequence (130) which comprises the sequence 5'-TCGTATGCCGTCTTCTGCTTG-3' (SEQ ID NO:206).

In some embodiments of the covalently closed circular molecules (600) described herein, the library molecule includes a first right universal adaptor sequence (130) which binds the first region of the first splint strand (330), wherein the first right universal adaptor sequence (130) comprises the sequence 5'-AGTCGTCGCAGCCTCACCTGATC-3' (SEQ ID NO:214) or a complementary sequence thereof.

The present disclosure provides a reaction mixture comprising a plurality of any of the covalently closed circular molecules (600) described herein and at least one exonuclease enzyme. In some embodiments, the exonuclease enzyme comprises any one or any combination of two or more of exonuclease I, thermolabile exonuclease I and/or T7 exonuclease.

Kits Comprising Double-Stranded Splint Adaptors

The present disclosure provides kits for the use of introducing one or more new adaptor sequences into linear nucleic acid library molecules. In some embodiments, the kit can be used to circularize single-stranded nucleic acid library molecules having a sequence of interest (110) flanked on one side by at least a first left universal adaptor sequence (120) and flanked on the other side by at least a first right universal adaptor sequence (130). In some embodiments, the circularized library molecules can be converted to covalently closed circular molecules which can be subjected to a rolling circle amplification (RCA) reaction to generate nucleic acid concatemers. The concatemers can be immobilized to a support for massively parallel sequencing.

The present disclosure provides kits comprising nucleic acid double-stranded splint adaptors (200), comprising: (i) a first splint strand (long splint strand (300)) which is hybridized to (ii) a second splint strand (short splint strand (400)). In some embodiments, the first splint strand comprises a first region (320), an internal region (310), and a second region (330). The internal region of the first splint strand (310) is hybridized to the second splint strand (400) to form a double-stranded splint adaptor (200) having a double-stranded region and two flanking single-stranded regions. The second splint strand (400) includes a new adaptor sequence that can be introduced the linear nucleic acid library molecules. Exemplary double-stranded splint adaptors are shown in FIGS. 1-8. The kits can include a container which contains the first splint strands (300) hybridized to the second splint strands (400). The kits can include a first container which contains the first splint strands (300) and a second container which contains the second splint strands (400).

In some embodiments of the kits of the disclosure, the second splint strand (400) comprises at least two sub-regions, including a first and second sub-region (e.g., see FIGS. 2 and 3). The first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN) (e.g., see FIG. 3). In some embodiments, the second splint strand (400) comprises only one sub-region and lacks a second and third sub-region, where the first sub-region comprises a index sequence (e.g. a sample index) having 5-20 bases. In some embodiments, the sample index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3'. Another exemplary arrangement of the sub-regions in the second splint strand (400), in a 5' to 3' orientation comprises: 5'-[third sub-region]-[second sub-region]-[first sub-region]-3'. Exemplary first (300) and second (400) splint strands are shown in FIGS. 2 and 3. In some embodiments, the second splint strand (400) can be 20-100 nucleotides in length, or 30-80 nucleotides in length, or 40-60 nucleotides in length. In some embodiments, the second splint strands (400) comprise one or more phosphorothioate linkages at the 5' and/or 3' ends to confer exonuclease resistance. In some embodiments, the second splint strands (400) comprise one or more phosphorothioate linkage sat an internal position to confer endonuclease resistance. In some embodiments, the second splint strands (400) comprise one or more 2'-O-methylcytosine bases at the 5' and/or 3' end, or at an internal position. In some embodiments, the 5' end of the second splint strand (400) is phosphorylated or non-phosphorylated. In some embodiments, the 3' end of the second splint strand (400) comprises a terminal 3' OH group or a terminal 3' blocking group.

In some embodiments of the kits of the disclosure, the first splint strand (300) comprises a first region (320), a second region (330), and internal region (310). The first region (320) comprises a first universal adaptor sequence which can hybridize to the first universal binding sequence at one end of the linear nucleic acid library molecule. The second region (330) comprises a second universal adaptor sequence which can hybridize to the second universal binding sequence at the other end of the linear nucleic acid library molecule. In some embodiments, the first region of the first splint strand (320) includes a first universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the second region of the first splint strand (330) includes a second universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the first splint strand (300) can be 50-150 nucleotides in length, or 60-100 nucleotides in length, or 70-90 nucleotides in length. In some embodiments, the first splint strands (300) comprise one or more phosphorothioate linkages at the 5' and/or 3' ends to confer exonuclease resistance. In some embodiments, the first splint strands (300) comprise one or more phosphorothioate linkages at an internal position to confer endonuclease resistance. In some embodiments, the first splint strands (300) comprise one or more 2'-O-methylcytosine bases at the 5' and/or 3' end, or at an internal position. In some embodiments, the 5' end of the first splint strand (300) is phosphorylated or non-phosphorylated. In some embodiments, the 3' end of the first splint strand (300) comprises a terminal 3' OH group or a terminal 3' blocking group.

In some embodiments of the kits of the disclosure, the first splint strand (300) includes an internal region (310) which comprises at least two sub-regions, including a fourth and fifth sub-region (e.g., FIGS. 2 and 3). The fourth sub-region hybridizes to the first sub-region of the second splint strand (400). The fifth sub-region hybridizes to the second sub-region of the second splint strand (400). The fourth and fifth sub-regions do not hybridize (or at least exhibit very little hybridization to) the first and second surface primers. In some embodiments, the internal region (310) of the first splint strand further comprises an optional sixth sub-region which hybridizes to the third sub-region of the second splint strand (400). An exemplary arrangement of the sub-regions of the first splint strand (300), in a 5' to 3' orientation comprises: 5'-[fourth sub-region]-[fifth sub-region]-3'. Another exemplary arrangement of the sub-regions of the first splint strand (300), in a 5' to 3' orientation comprises: 5'-[fourth sub-region]-[fifth sub-region]-[sixth sub-region]-3'. Exemplary first splint strands (300) are shown in FIGS. 2 and 3.

In some embodiments of the kits described herein, the first sub-region of the second splint strand (400) comprises the sequence 5'-CATGTAATGCACGTACTTTCAGGGT-3' (SEQ ID NO:200). In some embodiments, the second sub-region of the second splint strand (400) comprises the sequence 5'-AGTCGTCGCAGCCTCACCTGATC-3' (SEQ ID NO:201). In some embodiments, the second splint strand (400) comprises a first and second sub-region comprising the sequence 5'-AGTCGTCGCAGCCTCACCTGATC-CATGTAATGCACGTACTTTCAGGGT-3' (SEQ ID NO:202). See FIG. 11A. In some embodiments, the 5' end of the second splint strand (400) can be phosphorylated or non-phosphorylated.

In some embodiments of the kits described herein, the first region of the first splint strand (320) includes a first universal adaptor sequence which comprises a universal binding sequence (or a complementary sequence thereof) for a first surface primer, where the first region (320) comprises the sequence 5'-TCGGTGGTCGCCGTATCATT-3' (SEQ ID NO:193). For example, the first region of the first splint strand (320) can hybridize to a P5 surface primer or a complementary sequence of the P5 surface primer. For example, the P5 surface primer comprises the sequence 5'-AATGATACGGCGACCACCGA-3' (SEQ ID NO:203; short P5), or the P5 surface primer comprises the sequence 5'-AATGATACGGCGACCACCGAGATC-3' (SEQ ID NO:194; long P5). In some embodiments, the second region of the first splint strand (330) includes a second universal adaptor sequence which comprises a universal binding sequence (or a complementary sequence thereof) for a second surface primer, where the second region (330) comprises the sequence 5'-CAAGCAGAAGACGGCATACGA-3' (SEQ ID NO:195). For example, the second region of the first splint strand (330) can hybridize to a P7 surface primer or a complementary sequence of the P7 surface primer. For example, the P7 surface primer comprises the sequence 5'-CAAGCAGAAGACGGCATACGA-3' (SEQ ID NO:195; short P7), or the P7 surface primer comprises the sequence 5'-CAAGCAGAAGACGGCATACGAGAT-3' (SEQ ID NO:196; long P7). In some embodiments, the first splint strand (300) includes an internal region (310) which comprises a fourth sub-region having the sequence 5'-ACCCT-GAAAGTACGTGCATTACATG-3' (SEQ ID NO:197). In some embodiments, the first splint strand (300) includes an internal region (310) which comprises a fifth sub-region having the sequence 5'-GATCAGGT-GAGGCTGCGACGACT'3' (SEQ ID NO:198). In some embodiments, the first splint strand (300) comprises a first region (320), an internal region (310) having a fourth and fifth sub-region, and a second region (330), having the sequence 5'-TCGGTGGTCGCCGTATCATTACCCT-GAAAGTACGTGCATTACATGGATCAGGTGAGG CTGCGACGACTCAAGCAGAAGACGGCATACGA-3' (SEQ ID NO:199). See FIG. 11A. In some embodiments, the 5' end of the first splint strand (300) can be phosphorylated or non-phosphorylated. In some embodiments, the first sub-region of the second splint strand (400) can hybridize to the fourth sub-region of the first splint strand (300). In some embodiments, the second sub-region of the second splint strand (400) can hybridize to the fifth sub-region of the first splint strand (300).

In some embodiments of the kits described herein, the first region of the first splint strand (320) comprises a sequence that can bind a first left universal adaptor sequence (120) of a library molecules, wherein the first region of the first splint strand (320) comprises the sequence 5'-ACCCT-GAAAGTACGTGCATTACATG-3' (SEQ ID NO:215) or a complementary sequence thereof.

In some embodiments of the kits described herein, the second region of the first splint strand (330) comprises a sequence that can bind a first right universal adaptor sequence (130) of a library molecules, wherein the second region of the first splint strand (330) comprises the sequence 5'-GATCAGGTGAGGCTGCGACGACT-3' (SEQ ID NO:216) or a complementary sequence thereof.

In some embodiments, the kits comprise an adaptor having a first left universal adaptor sequence (120) which binds the first region of the first splint strand (320) for use in preparing a plurality of library molecules, wherein the library molecules comprise the sequence 5'-AATGA-TACGGCGACCACCGA-3' (SEQ ID NO:203). The adaptor can be a single-stranded adaptor (e.g., PCR primer), double-stranded adaptor, bubble adaptor, or Y-shaped adaptor.

In some embodiments of the kits described herein, the library molecule includes a first left universal adaptor sequence (120) which binds the first region of the first splint strand (320), wherein the first left universal adaptor sequence (120) comprises the sequence 5'-CATGTAATGCACGTACTTTCAGGGT-3' (SEQ ID NO:213) or a complementary sequence thereof.

In some embodiments, the kits comprise an adaptor having a second left universal adaptor sequence for a sequencing primer (140) for use in preparing a plurality of library molecules, wherein the library molecules comprise the sequence 5'-ACACTCTTTCCCTA-CACGACGCTCTTCCGATCT-3' (SEQ ID NO:204). In some embodiments, the adaptor having a second left universal adaptor sequence for a sequencing primer (140) also includes a first left index sequence (160). The adaptor can be a single-stranded adaptor (e.g., PCR primer), double-stranded adaptor, bubble adaptor, or Y-shaped adaptor.

In some embodiments, the kits comprise an adaptor having a second left universal adaptor sequence comprising a sequence for binding a sequencing primer (140) for use in preparing a plurality of library molecules, wherein the library molecules comprise the sequence 5'-TCGTCGGCAGCGTCAGATGTGTATAAGAGACAG-3' (SEQ ID NO:207). In some embodiments, the adaptor having a second left universal adaptor sequence for a sequencing primer (140) also includes a first left index sequence (160). The adaptor can be a single-stranded adaptor (e.g., PCR primer), double-stranded adaptor, bubble adaptor, or Y-shaped adaptor.

In some embodiments, the kits comprise an adaptor having a second left universal adaptor sequence comprising a sequence for binding a sequencing primer (140) for use in preparing a plurality of library molecules, wherein the library molecules comprise the sequence 5'-CGTGCTG-GATTGGCTCACCAGACACCTTCCGACAT-3' (SEQ ID NO:208). In some embodiments, the adaptor having a second left universal adaptor sequence for a sequencing primer (140) also includes a first left index sequence (160). The adaptor can be a single-stranded adaptor (e.g., PCR primer), double-stranded adaptor, bubble adaptor, or Y-shaped adaptor.

In some embodiments, the kits comprise an adaptor having a second right universal adaptor sequence comprising a sequence for binding a sequencing primer (150) for use in preparing a plurality of library molecules, wherein the library molecules comprise the sequence 5'-AGATCG-GAAGAGCACACGTCTGAACTCCAGTCAC-3' (SEQ ID NO:205). In some embodiments, the adaptor having a second right universal adaptor sequence for a sequencing primer (150) also includes a first right index sequence (170). The adaptor can be a single-stranded adaptor (e.g., PCR primer), double-stranded adaptor, bubble adaptor, or Y-shaped adaptor.

In some embodiments, the kits comprise an adaptor having a second right universal adaptor sequence comprising a sequence for binding a sequencing primer (150) for use in preparing a plurality of library molecules, where the library molecules comprise the sequence 5'-CTGTCTCT-TATACACATCTCCGAGCCCACGAGAC-3' (SEQ ID NO:209). In some embodiments, the adaptor having a second right universal adaptor sequence for a sequencing primer (150) also includes a first right index sequence (170). The adaptor can be a single-stranded adaptor (e.g., PCR primer), double-stranded adaptor, bubble adaptor, or Y-shaped adaptor.

In some embodiments, the kits comprise an adaptor having a second right universal adaptor sequence comprising a sequence for binding a sequencing primer (150) for use in preparing a plurality of library molecules, wherein the library molecules comprise the sequence 5'-ATGTCG-GAAGGTGTGCAGGCTACCGCTTGTCAACT-3' (SEQ ID NO:210). In some embodiments, the adaptor having a second right universal adaptor sequence for a sequencing primer (150) also includes a first right index sequence (170).

The adaptor can be a single-stranded adaptor (e.g., PCR primer), double-stranded adaptor, bubble adaptor, or Y-shaped adaptor.

In some embodiments, the kits comprise an adaptor having a first right universal adaptor sequence (130) which binds the first region of the first splint strand (330), for use in preparing a plurality of library molecules, where the library molecules comprise the sequence 5'-TCGTATGCCGTCTTCTGCTTG-3' (SEQ ID NO:206). The adaptor can be a single-stranded adaptor (e.g., PCR primer), double-stranded adaptor, bubble adaptor, or Y-shaped adaptor.

In some embodiments of the kits described herein, the library molecule includes a first right universal adaptor sequence (130) which binds the first region of the first splint strand (330), where the first right universal adaptor sequence (130) comprises the sequence 5'-AGTCGTCGCAGCCT-CACCTGATC-3' (SEQ ID NO:214) or a complementary sequence thereof.

In some embodiments, the kit comprises a plurality polynucleotides comprising a first left index sequences (160) and/or a plurality of first right index sequences (170). In some embodiments, the kit can include separate containers holding polynucleotides comprising individual first left index (160) or individual first right index (170) sequences. In some embodiments, the kit can include separate containers holding a pair of polynucleotides comprising individual first left index (160) and individual first right index (170) sequences. In some embodiments, the kit contains the polynucleotides comprising first left indexes (160) and/or a plurality of first right index sequences (170) in multi-well plates (e.g., 96-well plate). A list of exemplary first left index sequences (160) and first right index sequences (170) is provided in Table 1 at FIGS. 33-1 to 33-6. The first left index sequence (160) can include a random sequence (e.g., NNN) or lack a random sequence. The first right index sequence (170) can include a random or sequence (e.g., NNN) or lack a random sequence.

In some embodiments, the kit comprises nucleic acid double-stranded splint adaptors (200) and a T4 polynucleotide kinase. In some embodiments, the kit f comprises a ligase enzyme, wherein the ligase enzyme comprises T7 DNA ligase, T3 ligase, T4 ligase, or Taq ligase. In some embodiments, the kit comprises at least one endonuclease, which comprises any one or any combination of two or more of exonuclease I, thermolabile exonuclease I and/or T7 exonuclease.

In some embodiments, the kit comprises at least one buffer for hybridizing the plurality of the double-stranded splint adaptors (200) and the plurality of nucleic acid library molecules (100). In some embodiments, the kit comprises one buffer for conducting multiple enzymatic reactions in a single reaction vessel, including any combination of (i) phosphorylating the 5' ends of the first and/or second splint strands (e.g., (300) and/or (400)), (ii) ligating the nicks in the library-splint complex (500), and/or (iii) exonuclease digestion of the first splint strand (300) from the covalently closed circular molecule (600). Alternatively, the kit comprises two or more separate buffers, where the first buffer can be used to conduct the phosphorylation reaction, the second buffer can be used to conduct the ligation reaction, and a third buffer can be used to conduct the exonuclease digestion reaction.

In some embodiments, the kit comprises one or more containers that contain any of the double-stranded splint adaptors (200) described herein, or any of the first and second splint strands (300) and (400), described herein. The kit can further comprise one or more containers that contain a T4 polynucleotide kinase, at least one ligase and/or at least one exonuclease. The kit can comprise any of these components in any combination and can be contained in a single container, or can be contained in separate container, or any combination thereof.

The kit can include instructions for use of the kit for conducting reactions to introduce one or more new adaptor sequences into linear nucleic acid library molecules.

The kit can include polynucleotides encoding one or more exemplary sequences of interest, for use as a positive control.

Methods for Forming a Plurality of Library-Splint Complexes

The present disclosure provides methods for forming a plurality of library-splint complexes (500) comprising: (a) providing a plurality of double-stranded splint adaptors (200) wherein individual double-stranded splint adaptors (200) in the plurality comprise a first splint strand (300) hybridized to a second splint strand (400), wherein the double-stranded splint adaptor includes a double-stranded region and two flanking single-stranded regions, wherein the first splint strand comprises a first region (320), an internal region (310), and a second region (330), and wherein the internal region of the first splint strand (310) is hybridized to the second splint strand (400). Exemplary double-stranded splint adaptors (200) are shown in FIGS. 1-8.

In some embodiments, the methods for forming a plurality of library-splint complexes (500) comprise step (b): hybridizing the plurality of double-stranded splint adaptors with a plurality of single-stranded nucleic acid library molecules (100) wherein individual library molecules include a sequence of interest (110) flanked on one side by at least a first left universal adaptor sequence (120) and flanked on the other side by at least a first right universal adaptor sequence (130) (e.g., FIGS. 1-8). The hybridizing is conducted under conditions suitable for hybridizing the first region of the first splint strand (320) to the at least first left universal adaptor sequence (120) of the library molecule, and hybridizing the second region of the first splint strand (330) to the at least first right universal sequence (130) of the library molecule, thereby circularizing the plurality of library molecules to form a plurality of library-splint complexes (500).

In some embodiments of the methods for forming a plurality of library-splint complexes (500), the first region of the first splint strand (320) comprises a first universal adaptor sequence which can hybridize to a first universal binding sequence at one end of a linear nucleic acid library molecule. In some embodiments, the first region of the first splint strand (320) includes a first universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the 5' end of the first splint strand (300) is phosphorylated or lacks a phosphate group. In some embodiments, the 3' end of the first splint strand (300) includes a terminal 3' OH group or a terminal 3' blocking group.

In some embodiments of the methods for forming a plurality of library-splint complexes (500), the second region of the first splint strand (330) comprises a second universal adaptor sequence which can hybridize to a second universal binding sequence at the other end of the linear nucleic acid library molecule. In some embodiments, the second region of the first splint strand (330) includes a second universal adaptor sequence which comprises a universal binding sequence for a forward or reverse sequencing primer, a universal binding sequence for a first or second surface primer, a universal binding sequence for a forward or reverse amplification primer, a universal binding sequence for a compaction oligonucleotide, or a combination thereof. In some embodiments, the 5' end of the second splint strand (400) is phosphorylated or lacks a phosphate group. In some embodiments, the 3' end of the second splint strand (400) includes a terminal 3' OH group or a terminal 3' blocking group.

In some embodiments of the methods for forming a plurality of library-splint complexes (500), the first region of the first splint strand (320) is hybridized to the at least first left universal adaptor sequence (120) of the library molecule, and a second region of the first splint strand (330) is hybridized to the at least first right universal sequence (130) of the library molecule, thereby circularizing the library molecule to generate a library-splint complex (500). The library-splint complex (500) comprises a first nick between the 5' end of the library molecule and the 3' end of the second splint strand (e.g., FIGS. 1-8). The library-splint complex (500) also comprises a second nick between the 5' end of the second splint strand and the 3' end of the library molecule (e.g., FIGS. 1-8). In some embodiments, the first and second nicks are enzymatically ligatable.

In some embodiments of the methods for forming a plurality of library-splint complexes (500), the first region of the first splint strand (320) can hybridize to a sense or anti-sense strand of a double-stranded nucleic acid library molecule. In the library-splint complex (500), the second region of the first splint strand (330) can hybridize to a sense or anti-sense strand of a double-stranded nucleic acid library molecule. The double-stranded nucleic acid library molecule can be denatured to generate the single-stranded sense and anti-sense library strands.

In some embodiments of the methods for forming a plurality of library-splint complexes (500), the second splint strand (400) does not hybridize to the sequence of interest (110), and the internal region of the first splint strand (310) does not hybridize to the sequence of interest (110).

In some embodiments of the methods for forming a plurality of library-splint complexes (500), the first region of the first splint strand (320) does not hybridize to the sequence of interest (110), and the second region of the first splint strand (330) does not hybridize to the sequence of interest (110).

In some embodiments of the methods for forming a plurality of library-splint complexes (500), the 5' end of the single-stranded library molecule (100) is phosphorylated or lacks a phosphate group. In some embodiments, the 3' end of the single-stranded library molecule includes a terminal 3' OH group or a terminal 3' blocking group.

In some embodiments of the methods for forming a plurality of library-splint complexes (500), the individual nucleic acid library molecules (100) comprise a second left universal adaptor sequence (140). In some embodiments, the individual nucleic acid library molecules (100) comprise a second right universal adaptor sequence (150). In some embodiments, the nucleic acid library molecules (100) comprise additional left and/or right universal adaptor sequences.

In some embodiments of the methods for forming a plurality of library-splint complexes (500), the nucleic acid library molecule (100) comprises a first left index sequence (160). In some embodiments, the nucleic acid library molecule (100) comprises a first right index sequence (170). In some embodiments, the first left index sequence (160) comprises a sample index sequence. In some embodiments, the first right index sequence (170) comprises another sample index sequence. In some embodiments, the sequence of the first left index sequence is not the same as the sequence of the first right index sequence. The sample index sequences can be used to distinguish sequences of interest obtained from different sample sources in a multiplex assay. A list of exemplary first left index sequences (160) and first right index sequences (170) is provided in Table 1 at FIGS. 33-1 to 33-6. The first left index sequence (160) can include a random sequence (e.g., NNN) or lack a random sequence. The first right index sequence (170) can include a random sequence (e.g., NNN) or lack a random sequence.

Multiplex workflows are enabled by preparing sample-indexed libraries using one or both index sequences (e.g., left and/or right index sequences). The first left index sequences (160) and/or first right index sequences (170) can be employed to prepare separate sample-indexed libraries using input nucleic acids isolated from different sources. The sample-indexed libraries can be pooled together to generate a multiplex library mixture, and the pooled libraries can be amplified and/or sequenced. The sequences of the insert region along with the first left index sequence (160) and/or first right index sequence (170) can be used to identify the source of the input nucleic acids. In some embodiments, any number of sample-indexed libraries can be pooled together, for example 2-10, or 10-50, or 50-100, or 100-200, or more than 200 sample-indexed libraries can be pooled. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

In some embodiments of the methods for forming a plurality of library-splint complexes (500), the nucleic acid library molecule (100) comprises a first left unique identification sequence (180). In some embodiments, the nucleic acid library molecule (100) comprises a first right unique identification sequence (190). In some embodiments, the first left unique identification sequence (180) and the first right unique identification sequence (190) each comprise a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging.

In some embodiments of the methods for forming a plurality of library-splint complexes (500), the nucleic acid library molecule (100) comprises any one or any combination of two or more: a first left universal adaptor sequence (120); a second left universal adaptor sequence (140); a first left index sequence (160); a first left unique identification sequence (180); a first right universal adaptor sequence (130); a second right universal adaptor sequence (150); a first right index sequence (170); and/or a first right unique identification sequence (190).

In some embodiments of the methods for forming a plurality of library-splint complexes (500), the first left universal adaptor sequence (120) and/or the second left universal adaptor sequence (140), comprises a universal binding sequence for a forward or reverse sequencing primer; a universal binding sequence for a first or second surface primer; a universal binding sequence for a forward or reverse amplification primer; and/or a universal binding sequence for a compaction oligonucleotide. In some embodiments, the nucleic acid library molecule (100) comprises additional left universal adaptor sequences.

In some embodiments of the methods for forming a plurality of library-splint complexes (500), the first right universal adaptor sequence (130) and/or the second right universal adaptor sequence (150), comprises a universal binding sequence for a forward or reverse sequencing primer; a universal binding sequence for a first or second surface primer; a universal binding sequence for a forward or reverse amplification primer; and/or a universal binding sequence for a compaction oligonucleotide. In some embodiments, the nucleic acid library molecule (100) comprises additional right universal adaptor sequences.

In some embodiments of the methods for forming a plurality of library-splint complexes (500), the nucleic acid library molecule (100) comprises at least one junction adaptor sequence located between any of the universal adaptor sequences described herein (e.g., see FIG. 8). For example, a first left junction adaptor sequence (125) can be located between the first left universal adaptor sequence (120) and the first left index sequence (160). A second left junction adaptor sequence (165) can be located between the first left index sequence (160) and the second left universal adaptor sequence (140). A third left junction adaptor sequence (145) can be located between the second left universal adaptor sequence (140) and the sequence-of-interest (110). A first right junction adaptor sequence (135) can be located between the first right universal sequence (130) and the first right index sequence (170). A second right junction adaptor sequence (175) can be located between the first right index sequence (170) and the second right universal adaptor sequence (150). A third right junction adaptor sequence (155) can be located between the second right universal adaptor sequence (150) and the sequence of interest (110). In some embodiments, the nucleic acid library molecule (100) further comprises at least one and up to ten appended universal adaptor sequences located 5' (upstream) of the first left universal adaptor sequence (120) (e.g., see FIG. 8). In some embodiments, the nucleic acid library molecule (100) further comprises at least one and up to ten appended universal adaptor sequences located 3' (downstream) of the first right universal sequence (130) (e.g., see FIG. 8). Any of the junction adaptor sequences and/or appended universal adaptor sequences comprise any sequence and can be 3-60 nucleotides in length. Any of the junction adaptor sequences and/or appended universal adaptor sequences comprise a universal sequence or a unique sequence. Any of the junction adaptor sequences and/or appended universal adaptor sequences comprise a binding sequence for an amplification primer, a sequencing primer, a compaction oligonucleotide, or a combination thereof. Any of the junction adaptor sequences and/or appended universal adaptor sequences comprise a binding sequence for an immobilized surface primer (e.g., capture primer). Any of the junction adaptor sequences and/or appended universal adaptor sequences comprise a sample index sequence. Any of the junction adaptor sequences and/or appended universal adaptor sequences comprise a unique identification sequence. Any of the junction adaptor sequences and/or appended universal adaptor sequences, particularly junction adaptor sequence (145) comprises a Tn5 transposon-end sequence 5'-AGATGTGTATAAGAGACAG-3' (SEQ ID NO:211). Any of the junction adaptor sequences and/or appended universal adaptor sequences, particularly junction adaptor sequence (155) comprises a Tn5 transposon-end sequence 5'-CTGTCTCTTATACACATCT-3' (SEQ ID NO:212). The Tn5 transposon-end sequences can be introduced into the library molecule (100) via a transposase-mediated reaction which includes contacting double-stranded input DNA (e.g., genomic DNA) with a Tn-5 type transposase enzyme, and a double-stranded oligonucleotide comprising the Tn transposon-end sequence (SEQ ID NO:211) linked to a universal adaptor sequence or a sample index sequence under a condition that is suitable to form a transposon synaptic complex. In the double-stranded oligonucleotide, the Tn transposon-end sequence (SEQ ID NO:211) can be located 5' or 3' relative to the universal adaptor sequence or a sample index sequence.

In some embodiments of the methods for forming a plurality of library-splint complexes (500), the second splint strand (400) comprises at least two sub-regions, including a first and second sub-region (e.g., FIGS. 2 and 3). The first sub-region comprises a universal binding sequence for a third surface primer, and the second sub-region comprises a universal binding sequence for a fourth surface primer, wherein the first and second sub-regions do not hybridize (or at least exhibit very little hybridization to) the first and second surface primers. In some embodiments, the second splint strand (400) further comprises an optional third sub-region which includes a sample index sequence having 5-20 bases and/or a unique identification sequence having 2-10 or more bases (e.g., NN) (e.g., FIG. 3). In some embodiments, the second splint strand (400) comprises only one sub-region and lacks a second and third sub-region, where the first sub-region comprises a sample index sequence having 5-20 bases. In some embodiments, the sample index sequence can be used to distinguish sequences of interest obtained from different sample sources in a multiplex assay. In some embodiments, the unique identification sequence comprises a random sequence. The unique identification sequence can be designed to exhibit reduced or no hybridization to the first, second, third and fourth surface primers. An exemplary arrangement of the sub-regions in the second splint strand (400), in a 5' to 3' orientation comprises: 5'-[second sub-region]-[first sub-region]-3'. Another exemplary arrangement of the sub-regions in the second splint strand (400), in a 5' to 3' orientation comprises: 5'-[third sub-region]-[second sub-region]-[first sub-region]-3'. In some embodiments, the second splint strand (400) can be 20-100 nucleotides in length, or 30-80 nucleotides in length, or 40-60 nucleotides in length. In some embodiments, the second splint strands (400) comprise one or more phosphorothioate linkages at the 5' and/or 3' ends to confer exonuclease resistance. In some embodiments, the second splint strands (400) comprise one or more phosphorothioate linkages at an internal position to confer endonuclease resistance. In some embodiments, the second splint strands (400) comprise one or more 2'-O-methylcytosine bases at the 5' and/or 3' end, or at an internal position. In some embodiments, the 5' end of the second splint strand (400) is phosphorylated or non-phosphorylated. In some embodiments, the 3' end of the second splint strand (400) comprises a terminal 3' OH group or a terminal 3' blocking group.

In some embodiments of the methods for forming a plurality of library-splint complexes (500), the first splint strand (300) includes an internal region (310) which comprises at least two sub-regions, including a fourth and fifth sub-region (e.g., FIGS. 2 and 3). The fourth sub-region hybridizes to the first sub-region of the second splint strand (400). The fifth sub-region hybridizes to the second sub-region of the second splint strand (400). The fourth and fifth sub-regions do not hybridize (or at least exhibit very little hybridization to) the first and second surface primers. In some embodiments, the internal region (310) of the first splint strand further comprises an optional sixth sub-region which hybridizes to the third sub-region of the second splint strand (400) (e.g., FIG. 3). An exemplary arrangement of the sub-regions of the first splint strand (300), in a 5' to 3' orientation comprises: 5'-[fourth sub-region]-[fifth sub-region]-5'. Another exemplary arrangement of the sub-regions of the first splint strand (300), in a 5' to 3' orientation comprises: 5'-[fourth sub-region]-[fifth sub-region]-[sixth sub-region]-3'. In some embodiments, the first splint strand (300) can be 50-150 nucleotides in length, or 60-100 nucleotides in length, or 70-90 nucleotides in length. In some embodiments, the first splint strands (300) comprise one or more phosphorothioate linkages at the 5' and/or 3' ends to confer exonuclease resistance. In some embodiments, the first splint strands (300) comprise one or more phosphorothioate linkages at an internal position to confer endonuclease resistance. In some embodiments, the first splint strands (300) comprise one or more 2'-O-methylcytosine bases at the 5' and/or 3' end, or at an internal position.

The present disclosure provides methods for forming a plurality of library-splint complexes (500) comprising: (a) providing a plurality of double-stranded splint adaptors (200) wherein individual double-stranded splint adaptors (200) comprise a first splint strand (300) hybridized to a second splint strand (400), wherein the first splint strand (300) comprises regions arranged in a 5' to 3' order a first region (320), an internal region (310), and a second region (330), and wherein the internal region of the first splint strand (310) is hybridized to the second splint strand (400), wherein the second splint strand comprises regions arranged in a 5' to 3' order (i) a second sub-region having a universal binding sequence for a fourth surface primer, and (ii) a first sub-region having a universal binding sequence for a third surface primer. In some embodiments, the methods for forming a plurality of library-splint complexes (500) further comprises step (b): hybridizing the plurality of double-stranded splint adaptors with a plurality of single-stranded nucleic acid library molecules (100) wherein individual library molecules comprise regions arranged in a 5' to 3' order: (i) a first left universal adaptor sequence (120) having a binding sequence for a first surface primer; (ii) a second left universal adaptor sequence (140) having a binding sequence for a first sequencing primer; (iii) a sequence of interest (110); (iv) a second right universal adaptor sequence (150) having a binding sequence for a second sequencing primer; and (v) a first right universal adaptor sequence (130) having a binding sequence for a second surface primer, wherein the hybridizing is conducted under a conditions suitable to hybridize the first splint strand (300) to the library molecule (100) thereby circularizing the library molecule to generate a library-splint complex (500), such that the first region (320) of the first splint strand is hybridized to the binding sequence for the first surface primer (120), and the third region (330) of the first splint strand is hybridized to the binding sequence for the second surface primer (130), wherein the library-splint complex (500) comprises a first nick between the 5' end of the library molecule and the 3' end of the second splint strand (300), wherein the library-splint complex (500) comprises a second nick between the 5' end of the second splint strand (300) and the 3' end of the library molecule (100), and wherein the first and second nicks are enzymatically ligatable. In some embodiments, the plurality of single-stranded nucleic acid library molecules (100) comprise a first left index sequence (160) and/or a first right index sequence (170) (e.g., see FIG. 5). A list of exemplary first left index sequences (160) and first right index sequences (170) is provided in Table 1 at FIGS. 33-1 to 33-6. In some embodiments, the first left index sequences (160) include or lack a short random sequence (e.g., NNN). In some embodiments, the first right index sequences (170) include or lack a short random sequence (e.g., NNN). In some embodiments, the plurality of single-stranded nucleic acid library molecules (100) comprise a first left unique identification sequence (180) and/or a first right unique identification sequence (190) each comprising a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging. (e.g., see FIG. 6).

Multiplex workflows are enabled by preparing sample-indexed libraries using one or both index sequences (e.g., left and/or right index sequences). The first left index sequences (160) and/or first right index sequences (170) can be employed to prepare separate sample-indexed libraries using input nucleic acids isolated from different sources. The sample-indexed libraries can be pooled together to generate a multiplex library mixture, and the pooled libraries can be amplified and/or sequenced. The sequences of the insert region along with the first left index sequence (160) and/or first right index sequence (170) can be used to identify the source of the input nucleic acids. In some embodiments, any number of sample-indexed libraries can be pooled together, for example 2-10, or 10-50, or 50-100, or 100-200, or more than 200 sample-indexed libraries can be pooled. Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The nucleic acid library molecules can be prepared in single-stranded or double-stranded form.

In some embodiments, the plurality of single-stranded nucleic acid library molecules (100) further comprise a first left unique identification sequence (180) and/or a first right unique identification sequence (190) (e.g., see FIG. 6). In some embodiments, the first left unique identification sequence (180) and the first right unique identification sequence (190) each comprise a sequence that is used to uniquely identify an individual sequence of interest (e.g., insert sequence) to which the unique adaptors are appended in a population of other sequence of interest molecules. In some embodiments, the first left unique identification sequence (180) and/or the first right unique identification sequence (190) can be used for molecular tagging.

Methods for Forming Library-Splint Complexes Using Double-Stranded Adaptors Having Truncated Long Splints In some embodiments of the methods for forming library-splint complexes (500), the single-stranded library molecules (100) can be hybridized with a plurality of double-stranded splint adaptors (200). In some embodiments, the first splint strand (300) of individual double-stranded splint adaptors (200) comprise a truncated strand having a first region (320) having a truncated sequence at the 5' end (e.g., FIG. 11B, e.g. compared to SEQ ID NO:199 shown in FIG. 11A). In some embodiments, the 5' end of the first region can have a truncation of any length for example a truncation of 1-10 nucleotides. In some embodiments, the truncated first splint strand (300) comprises a second region (330; e.g., SEQ ID NO:5), a fourth sub-region (e.g., SEQ ID NO:6) and a fifth sub-region (e.g., SEQ ID NO:7) that are not truncated and do not carry any sequence variants such as for example an insertion, deletion or base-substitution. In some embodiments, the truncated first splint strand comprises a fourth sub-region and fifth sub-region that can hybridize with the first sub-region and second sub-region of a second splint strand (400) to form a double-stranded splint adaptor (200). In some embodiments, the truncated first splint strand comprises (300) comprises a truncated first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the truncated first splint strand, as part of a double-stranded splint adaptor (200) can hybridize to a library molecule (100) to form a library-splint complex (500).

Methods for Forming Library-Splint Complexes Using Double-Stranded Adaptors Having Long Splint Strands with Mis-Match Sequences In some embodiments of the methods for forming library-splint complexes (500), the single-stranded library molecules (100) can be hybridized with a plurality of double-stranded splint adaptors (200). In some embodiments, the first splint strand (300) of individual double-stranded splint adaptors (200) comprise a first region (320) having a mis-match sequence within the first region (320) (e.g., FIG. 11C). In some embodiments, the mis-match sequence can be any length (e.g., 2-20 bases) and comprises any sequence that is not fully complementary to the left universal adaptor sequence (120) of a library molecule (100). Some embodiments of mis-match sequences in the first region (320) are shown in small case letters and underlined in FIG. 11C. In some embodiments, the mis-match first splint strand (300) comprises a second region (330; e.g., SEQ ID NO:5), a fourth sub-region (e.g., SEQ ID NO:6) and a fifth sub-region (e.g., SEQ ID NO:7) that do not carry any sequence variants such as for example an insertion, deletion or base-substitution. In some embodiments, the mis-match first splint strand comprises a fourth sub-region and fifth sub-region that can hybridize with the first sub-region and second sub-region of a second splint strand (400) to form a double-stranded splint adaptor (200). In some embodiments, the mis-match first splint strand comprises (300) comprises a mis-match first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the mis-match first region (320) can hybridize with the first left universal adaptor sequence (120) of a library molecule (100) to form a double-stranded portion having a bubble at the location of the mis-match sequence in the first region (320). In some embodiments, the mis-match first splint strand, as part of a double-stranded splint adaptor (200) can hybridize to a library molecule (100) to form a library-splint complex (500).

Methods for Forming Library-Splint Complexes Using Double-Stranded Adaptors Having Long Splint Strands with Abasic Sites In some embodiments of the methods for forming library-splint complexes (500), the single-stranded library molecules (100) can be hybridized with a plurality of double-stranded splint adaptors (200). In some embodiments, the first splint strand (300) of individual double-stranded splint adaptors (200) comprise at least one abasic site which lacks a nitrogenous base. In some embodiments, the first splint strand (300) comprises at least one abasic site in the fourth sub-region and/or at least one abasic site in the fifth sub-region (e.g., top schematic of FIG. 11D, abasic sites are shown as solid black bars). In some embodiments, the abasic sites each comprise a 1',2'-dideoxyribose (e.g., dSpacer from Integrated DNA Technologies (IDT)). In some embodiments, the abasic first splint strand (300) comprises a first region ((320); e.g., SEQ ID NO:4), and a second region ((330); e.g., SEQ ID NO:5) that do not carry any abasic sites and/or any sequence variants such as for example insertion, deletion or base-substitution. In some embodiments, the abasic first splint strand comprises a fourth sub-region and fifth sub-region that can hybridize with the first sub-region and second sub-region of a second splint strand (400) to form a double-stranded splint adaptor (200). In some embodiments, the abasic first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the abasic first splint strand, as part of a double-stranded splint adaptor (200) can hybridize to a library molecule (100) to form a library-splint complex (500).

Methods for Forming Library-Splint Complexes Using Double-Stranded Adaptors Having Long Splint Strands with Uracil In some embodiments of the methods for forming library-splint complexes (500), the single-stranded library molecules (100) can be hybridized with a plurality of double-stranded splint adaptors (200). In some embodiments, the first splint strand (300) of individual double-stranded splint adaptors (200) comprise at least one uracil. In some embodiments, the first splint strand (300) of individual double-stranded splint adaptors (200) comprise at least one uracil in any one or any combination of regions including the first region (320), the second region (330), the fourth sub-region and/or the fifth sub-region. In some embodiments, at least one thymine base can be substituted with a uracil. An embodiment of a uracil-containing first splint strand is shown in FIG. 11D (bottom schematic). The skilled artisan will recognize that many other sequences of the first splint strand (300) comprising one or more uracils are possible. In some embodiments, the uracil-containing first splint strand comprises a fourth sub-region and fifth sub-region that can hybridize with the first sub-region and second sub-region of a second splint strand (400) to form a double-stranded splint adaptor (200). In some embodiments, the uracil-containing first splint strand comprises (300) comprises a first region (320) that hybridizes with a sequence (e.g., 120) on one end of the linear single stranded library molecule (100), and a second region (330) that hybridizes with a sequence (e.g., 130) on the other end of the linear single stranded library molecule (100). In some embodiments, the uracil-containing first splint strand, as part of a double-stranded splint adaptor (200) can hybridize to a library molecule (100) to form a library-splint complex (500).

Methods for Forming Library-Splint Complexes Using Double-Stranded Adaptors Having Short Splint Strands Inserted with Random Sequences and Index Sequences In some embodiments of the methods for forming library-splint complexes (500), the single-stranded library molecules (100) can be hybridized with a plurality of double-stranded splint adaptors (200). In some embodiments, the second splint strand (400) of individual double-stranded splint adaptors (200) comprise a random sequence inserted into the first sub-region of the second splint strand (e.g., FIGS. 12A and 12B). In some embodiments, a random sequence can replace a portion of the first sub-region of the second splint strand (e.g., FIGS. 13A and 13B). In some embodiments, the second sub-region of the second splint strand (400) does not have an inserted random sequence. In some embodiments, a portion of the second sub-region of the second splint strand (400) is not replaced with a random sequence.

In some embodiments, the random sequence can be any length, for example 2-10 bases in length. For example, the random sequence can be 3 nucleotide in length (e.g., 'NNN' in FIGS. 12A and 13A) or 4 nucleotides in length (e.g., 'NNNN' in FIGS. 12B and 13B). In some embodiments, the random sequence can be inserted at any position in the first sub-region of the second splint strand (400).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance.

In some embodiments, a pre-determined sequence is inserted into the sequence of the fourth sub-region of the first splint strand (300). The length of the inserted pre-determined sequence can be the same length as the random sequence inserted into the first sub-region of the second splint strand (e.g., FIGS. 12A and 12B). The inserted pre-determined sequence can have any sequence. An exemplary pre-determined sequence is shown in FIGS. 12A and 12B.

In some embodiments, a portion of the fourth sub-region of the first splint strand (300) is replaced with a pre-determined sequence. The length of the pre-determined sequence which replaces a portion of the fourth sub-region is the same length as the random sequence that replaces a portion of the first sub-region of the second splint strand (e.g., FIGS. 13A and 13B). The replacing pre-determined sequence can have any sequence. An exemplary pre-determined sequence is shown in FIGS. 13A and 13B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 12A, 12B, 13A and 13B). In some embodiments, the double-stranded splint adaptor (200) forms a bubble at the location of the inserted or replacing random sequence.

In some embodiments, the second splint strand (400) carrying a random sequence, as part of a double-stranded splint adaptor (200), can hybridize to a library molecule (100) to form a library-splint complex (500).

Methods for Forming Library-Splint Complexes Using Double-Stranded Adaptors Having Short Splint Strands Appended with Random Sequences and Index Sequences In any of the methods for forming library-splint complexes (500), as described herein, the single-stranded library molecules (100) can be hybridized with a plurality of double-stranded splint adaptors (200). In some embodiments, the second splint strand (400) of individual double-stranded splint adaptors (200) comprise a random sequence which is appended to the 3' end of the first sub-region of the second splint strand (e.g., FIGS. 14A and 14B). In some embodiments, the random sequence further comprises an index sequence. In some embodiments, the second sub-region of the second splint strand (400) does not have an appended random sequence.

In some embodiments, the appended random sequence can be any length, for example 2-10 bases in length. For example, the random sequence can be 3 nucleotide in length (e.g., 'NNN' in FIG. 14A) or 4 nucleotides in length (e.g., 'NNNN' in FIG. 14B).

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, a population of second splint strands (400) include a random sequence having a high diversity sequence which includes approximately equal proportions of all four nucleotides (e.g., A, G, C, T and/or U) that will be represented in each cycle of a sequencing run.

In some embodiments, the random sequence provides nucleotide diversity and color balance for a sequencing reaction. In some embodiments, the random sequence provides high nucleotide diversity which includes approximately equal proportions of all four nucleotides (e.g., A, G, C, T and/or U) that will be represented in each cycle of a sequencing run.

In some embodiments, the random sequence can be sequenced prior to sequencing the insert region. In some embodiments, the sequencing data from the random sequence can be used for polony mapping and/or template registration because the random sequence provides sufficient nucleotide diversity and color balance.

In some embodiments, the index sequence can be used to distinguish polynucleotides (e.g., insert sequences) from different sample sources in a multiplex assay.

In some embodiments, a pre-determined sequence is appended to the 5' end of the fourth sub-region of the first splint strand (300). In some embodiments, the length of the appended pre-determined sequence can be the same length as the random sequence which is appended to the 3' end of the first sub-region of the second splint strand (e.g., FIGS.

14A and 14B). In some embodiments, the length of the appended pre-determined sequence can be the same length as the random sequence and index sequence which is appended to the 3' end of the first sub-region of the second splint strand (e.g., FIGS. 14A and 14B). The appended pre-determined sequence can have any sequence. An exemplary pre-determined sequence is shown in FIGS. 14A and 14B.

In some embodiments, the second splint strand (400) comprises a first sub-region and second sub-region that can hybridize with the fourth sub-region and fifth sub-region of a first splint strand (300) to form a double-stranded splint adaptor (200) (e.g., FIGS. 14A and 14B). In some embodiments, the double-stranded splint adaptor (200) forms a bubble or a mis-matched end at the location of the appended random sequence. In some embodiments, the double-stranded splint adaptor (200) forms a bubble or a mis-matched end at the location of the appended random sequence and index sequence.

In some embodiments, the second splint strand (400) appended with a random sequence (and optionally an index sequence), as part of a double-stranded splint adaptor (200), can hybridize to a library molecule (100) to form a library-splint complex (500).

Sequences of Short Splint Strands

In some embodiments of the methods for forming a plurality of library-splint complexes (500) described herein, the first sub-region of the second splint strand (400) comprises the sequence 5'-CATGTAATGCACGTACTTTCAGGGT-3' (SEQ ID NO:200). In some embodiments, the second sub-region of the second splint strand (400) comprises the sequence 5'-AGTCGTCGCAGCCTCACCTGATC-3' (SEQ ID NO:201). In some embodiments, the second splint strand (400) comprises a first and second sub-region comprising the sequence 5'-AGTCGTCGCAGCCTCACCTGATC-CATGTAATGCACGTACTTTCAGGGT-3' (SEQ ID NO:202). See FIG. 11A. In some embodiments, the 5' end of the second splint strand (400) can be phosphorylated or non-phosphorylated.

Sequences of Long Splint Strands

In some embodiments of the methods for forming a plurality of library-splint complexes (500) described herein, the first region of the first splint strand (320) includes a first universal adaptor sequence which comprises a universal binding sequence (or a complementary sequence thereof) for a first surface primer, where the first region (320) comprises the sequence 5'-TCGGTGGTCGCCGTATCATT-3' (SEQ ID NO:193). For example, the first region of the first splint strand (320) can hybridize to a P5 surface primer or a complementary sequence of the P5 surface primer. For example, the P5 surface primer comprises the sequence 5'-AATGATACGGCGACCACCGA-3' (SEQ ID NO:203; short P5), or the P5 surface primer comprises the sequence 5'-AATGATACGGCGACCACCGAGATC-3' (SEQ ID NO:194; long P5). In some embodiments, the second region of the first splint strand (330) includes a second universal adaptor sequence which comprises a universal binding sequence (or a complementary sequence thereof) for a second surface primer, where the second region (330) comprises the sequence 5'-CAAGCAGAAGACGGCATACGA-3' (SEQ ID NO:195). For example, the second region of the first splint strand (330) can hybridize to a P7 surface primer or a complementary sequence of the P7 surface primer. For example, the P7 surface primer comprises the sequence 5'-CAAGCAGAAGACGGCATACGA-3' (SEQ ID NO:195; short P7), or the P7 surface primer comprises the sequence 5'-CAAGCAGAAGACGGCATACGAGAT-3' (SEQ ID NO:196; long P7). In some embodiments, the first splint strand (300) includes an internal region (310) which comprises a fourth sub-region having the sequence 5'-ACCCT-GAAAGTACGTGCATTACATG-3' (SEQ ID NO:197). In some embodiments, the first splint strand (300) includes an internal region (310) which comprises a fifth sub-region having the sequence 5'-GATCAGGT-GAGGCTGCGACGACT'3' (SEQ ID NO:198). In some embodiments, the first splint strand (300) comprises a first region (320), an internal region (310) having a fourth and fifth sub-region, and a second region (330), having the sequence 5'-TCGGTGGTCGCCGTATCATTACCCT-GAAAGTACGTGCATTACATGGATCAGGTGAGG CTGCGACGACTCAAGCAGAAGACGGCATACGA-3' (SEQ ID NO:199). See FIG. 11A. In some embodiments, the 5' end of the first splint strand (300) can be phosphorylated or non-phosphorylated. In some embodiments, the first sub-region of the second splint strand (400) can hybridize to the fourth sub-region of the first splint strand (300). In some embodiments, the second sub-region of the second splint strand (400) can hybridize to the fifth sub-region of the first splint strand (300).

In some embodiments of the methods for forming a plurality of library-splint complexes (500) described herein, the first region of the first splint strand (320) comprises a sequence that can bind a first left universal adaptor sequence (120) of a library molecules, where the first region of the first splint strand (320) comprises the sequence 5'-ACCCT-GAAAGTACGTGCATTACATG-3' (SEQ ID NO:215) or a complementary sequence thereof.

In some embodiments of the methods for forming a plurality of library-splint complexes (500) described herein, the second region of the first splint strand (330) comprises a sequence that can bind a first right universal adaptor sequence (130) of a library molecules, where the second region of the first splint strand (330) comprises the sequence 5'-GATCAGGTGAGGCTGCGACGACT-3' (SEQ ID NO:216) or a complementary sequence thereof.

Sequences of Library-Splint Complex

In some embodiments of the methods for forming a plurality of library-splint complexes (500) described herein, the library molecule includes a first left universal adaptor sequence (120) which binds the first region of the first splint strand (320), wherein the first left universal adaptor sequence (120) comprises the sequence (SEQ ID NO: 203)
5'-AATGATACGGCGACCACCGA-3'.

In some embodiments of the methods for forming a plurality of library-splint complexes (500) described herein, the library molecule includes a first left universal adaptor sequence (120) which binds the first region of the first splint strand (320), wherein the first left universal adaptor sequence (120) comprises the sequence 5'-CATGTAATGCACGTACTTTCAGGGT-3' (SEQ ID NO:213) or a complementary sequence thereof.

In some embodiments of the methods for forming a plurality of library-splint complexes (500) described herein, the library molecule includes a second left universal adaptor sequence comprising a sequence for binding a sequencing primer (140) where the second left universal adaptor sequence comprises the sequence 5'-ACACTCTTTCCCTA-CACGACGCTCTTCCGATCT-3' (SEQ ID NO:204).

In some embodiments of the methods for forming a plurality of library-splint complexes (500) described herein, the library molecule includes a second left universal adaptor sequence comprising a sequence for binding a sequencing primer (140) wherein the second left universal adaptor sequence comprises the sequence 5'-TCGTCGGCAGCGTCAGATGTGTATAAGAGACAG-3' (SEQ ID NO:207).

In some embodiments of the methods for forming a plurality of library-splint complexes (500) described herein, the library molecule includes a second left universal adaptor sequence comprising a sequence for binding a sequencing primer (140) where the second left universal adaptor sequence comprises the sequence 5'-CGTGCTGGAT-TGGCTCACCAGACACCTTCCGACAT-3' (SEQ ID NO:208).

In some embodiments, in any of the methods for forming a plurality of library-splint complexes (500) described herein, the library molecule includes a second right universal adaptor sequence comprising a sequence for binding a sequencing primer (150) wherein the second right universal adaptor sequence comprises the sequence 5'-AGATCG-GAAGAGCACACGTCTGAACTCCAGTCAC-3' (SEQ ID NO:205).

In some embodiments of the methods for forming a plurality of library-splint complexes (500) described herein, the library molecule includes a second right universal adaptor sequence comprising a sequence for binding a sequencing primer (150) wherein the second right universal adaptor sequence comprises the sequence 5'-CTGTCTCTTATACA-CATCTCCGAGCCCACGAGAC-3' (SEQ ID NO:209).

In some embodiments of the methods for forming a plurality of library-splint complexes (500) described herein, the library molecule includes a second right universal adaptor sequence comprising a sequence for binding a sequencing primer (150) wherein the second right universal adaptor sequence comprises the sequence 5'-ATGTCG-GAAGGTGTGCAGGCTACCGCTTGTCAACT-3' (SEQ ID NO:210).

In some embodiments of the methods for forming a plurality of library-splint complexes (500) described herein, the library molecule includes a first right universal adaptor sequence (130) which binds the first region of the first splint strand (330), wherein the right universal binding sequence (130) comprises the sequence (SEQ ID NO: 206)
5'-TCGTATGCCGTCTTCTGCTTG-3'.

In some embodiments of the methods for forming a plurality of library-splint complexes (500) described herein, the library molecule includes a first right universal adaptor sequence (130) which binds the first region of the first splint strand (330), where the right universal binding sequence (130) comprises the sequence 5'-AGTCGTCGCAGCCT-CACCTGATC-3' (SEQ ID NO:214) or a complementary sequence thereof.

Methods for Generating Covalently Closed Circular Library Molecules

In some embodiments of the methods for forming a plurality of library-splint complexes (500) described herein, the methods comprise at least one enzymatic reaction, including a phosphorylation reaction, ligation reaction and/or exonuclease reaction. The enzymatic reactions can be conducted sequentially or essentially simultaneously. The enzymatic reactions can be conducted in a single reaction vessel. Alternatively, a first enzymatic reaction can be conducted in a first reaction vessel, then transferred to a second reaction vessel where the second enzymatic reaction is conducted, then transferred to a third reaction vessel where the third enzymatic reaction is conducted.

In some embodiments of the methods for forming a plurality of library-splint complexes (500), the methods comprise conducting separate and sequential phosphorylation and ligation reactions which are conducted in separate reaction vessels. In some embodiments, the methods for forming a plurality of library-splint complexes (500) comprise step (c1): contacting in a first reaction vessel the plurality of the double-stranded splint adaptors (200) and the plurality of the single-stranded nucleic acid library molecules (100) with a T4 polynucleotide kinase enzyme under conditions suitable to phosphorylate the 5' ends of the plurality of double-stranded splint adaptors (200) and/or the plurality of single-stranded nucleic acid library molecules (100); and transferring the phosphorylation reaction to a second reaction vessel. In some embodiments, the methods comprise step (d1): contacting in the second reaction vessel the plurality of phosphorylated double-stranded splint adaptors (200) and the plurality of phosphorylated single-stranded nucleic acid library molecules (100) with a ligase, under a condition suitable to enzymatically ligate the first and second nicks, thereby generating a plurality of covalently closed circular library molecules (600) each hybridized to the first splint strand (300). In some embodiments, the ligase enzyme comprises T7 DNA ligase, T3 ligase, T4 ligase, or Taq ligase.

In some embodiments of the methods for forming a plurality of library-splint complexes (500), the methods comprise conducting sequential phosphorylation and ligation reactions which are conducted sequentially in the same reaction vessel. In some embodiments, the methods comprise step (c2): contacting in a first reaction vessel the plurality of the double-stranded splint adaptors (200) and the plurality of the single-stranded nucleic acid library molecules (100) with a T4 polynucleotide kinase enzyme under conditions suitable to phosphorylate the 5' ends of the plurality of double-stranded splint adaptors (200) and the plurality of single-stranded nucleic acid library molecules (100). In some embodiments, the methods comprise step (d2): contacting in the same first reaction vessel the phosphorylated double-stranded splint adaptors (200) and the phosphorylated single-stranded nucleic acid library molecules (100) with a ligase under a condition suitable to enzymatically ligate the first and second nicks, thereby generating a plurality of covalently closed circular library molecules (600) each hybridized to the first splint strand (300). In some embodiments, the ligase enzyme comprises T7 DNA ligase, T3 ligase, T4 ligase, or Taq ligase.

In some embodiments of the methods for forming a plurality of library-splint complexes (500) described herein, the methods comprise conducting essentially simultaneous phosphorylation and ligation reactions which are conducted together in the same reaction vessel. In some embodiments, the methods comprise step (c3): contacting in a first reaction vessel the plurality of the double-stranded splint adaptors (200) and the plurality of the single-stranded nucleic acid library molecules (100) with a (i) T4 polynucleotide kinase enzyme and (ii) a ligase enzyme, under conditions suitable to phosphorylate the 5' ends of the plurality of double-stranded splint adaptors (200) and the plurality of single-stranded nucleic acid library molecules (100), and the conditions are suitable to enzymatically ligate the first and second nicks, thereby generating a plurality of covalently closed circular library molecules (600) each hybridized to the first splint strand (300). In some embodiments, the ligase enzyme comprises T7 DNA ligase, T3 ligase, T4 ligase, or Taq ligase.

In some embodiments of the methods for forming a plurality of library-splint complexes (500) described herein, the methods comprise the optional step of enzymatically removing the plurality of first splint strands (300) from the plurality of covalently closed circular library molecules (600), which comprises: contacting the plurality of covalently closed circular library molecules (600) with at least one exonuclease enzyme to remove the plurality of first splint strands (300) and retaining the plurality of covalently closed circular library molecules (600). In some embodiments, the exonuclease reaction can be conducted in the same reaction buffer used to conduct the phosphorylation and/or ligation reactions, or in a different reaction buffer. In some embodiments, the exonuclease reaction can be conducted in a third reaction vessel after conducting the phosphorylation reaction in the first reaction vessel (c1), and conducting the ligation reaction in the second reaction vessel (d1). In some embodiments, the exonuclease reaction can be conducted in the first reaction vessel after conducting the phosphorylation reaction in the first reaction vessel (c2), and conducting the sequential ligation reaction in the first reaction vessel (d2). In some embodiments, the exonuclease reaction can be conducted in the first reaction vessel after conducting the essentially simultaneous phosphorylation and ligation reactions in the first reaction vessel (c3). In some embodiments, the at least one exonuclease enzyme comprises any combination of two or more of exonuclease I, thermolabile exonuclease I and/or T7 exonuclease.

Rolling Circle Amplification

The present disclosure provides methods for conducting rolling circle amplification reaction on the covalently closed circular library molecules (600). The rolling circle amplification reaction can be conducted after the phosphorylation and ligation reactions, or after the ligation reaction. In some embodiments, the rolling circle amplification reaction can be conducted on covalently closed circular library molecules (600) that are no longer hybridized to the first splint strands (300) following the exonuclease reaction. In some embodiments, the rolling circle amplification reaction can be conducted on covalently closed circular library molecules (600) that are hybridized to the first splint strands (300). In some embodiments, the covalently closed circular library molecules (600) can be distributed onto a support and then be subjected to rolling circle amplification reaction. In some embodiments, the covalently closed circular library molecules (600) can be subjected to rolling circle amplification reaction in-solution and then distributed onto a support. In some embodiments, the rolling circle amplification reactions can employ the retained first splint strand (300) as an amplification primer, or the first splint strand (300) can be removed (e.g., via exonuclease digestion) and replaced with a soluble amplification primer.

On-Support Rolling Circle Amplification

In some embodiments, the methods for conducting rolling circle amplification reaction comprise conducting rolling circle amplification on a plurality of covalently closed circular library molecules which lack hybridized first splint strands (300). In some embodiments, individual covalently closed circular library molecules (600) in the plurality comprise a second splint strand region (400) which includes a universal binding sequence for a third surface primer. In some embodiments, the methods comprise (a): distributing the plurality of covalently closed circular library molecules (600) onto a support having a plurality of the third surface primers immobilized on the support, under conditions suitable for hybridizing individual covalently closed circular library molecules (600) to individual immobilized third surface primers thereby immobilizing the plurality of covalently closed circular library molecules (600).

In some embodiments, the plurality of the third surface primers immobilized on the support comprise the sequence 5'-GATCAGGTGAGGCTGCGACGACT-3' (SEQ ID NO:198). Individual third surface primers can hybridize to a covalently closed circular library molecule (600) having a second splint strand region (400) which includes a universal binding sequence for a third surface primer, where the universal binding sequence for a third surface primer comprises a second sub-region which comprises the sequence 5'-AGTCGTCGCAGCCTCACCTGATC-3' (SEQ ID NO:201). In some embodiments, the immobilized third surface primers comprise immobilized surface capture primers.

Figure 19:
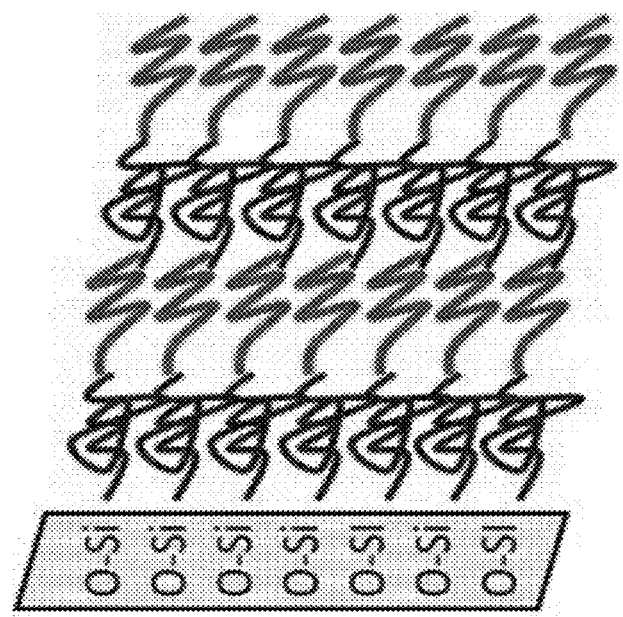
FIG. 19 is a schematic of an exemplary low binding support comprising a glass substrate and alternating layers of hydrophilic coatings which are covalently or non-covalently adhered to the glass, and which further comprises chemically-reactive functional groups that serve as attachment sites for oligonucleotide primers (e.g., capture oligonucleotides and circularization oligonucleotides). In alternative embodiments, the support can be made of any material such as glass, plastic or a polymer material.
Figure 20:
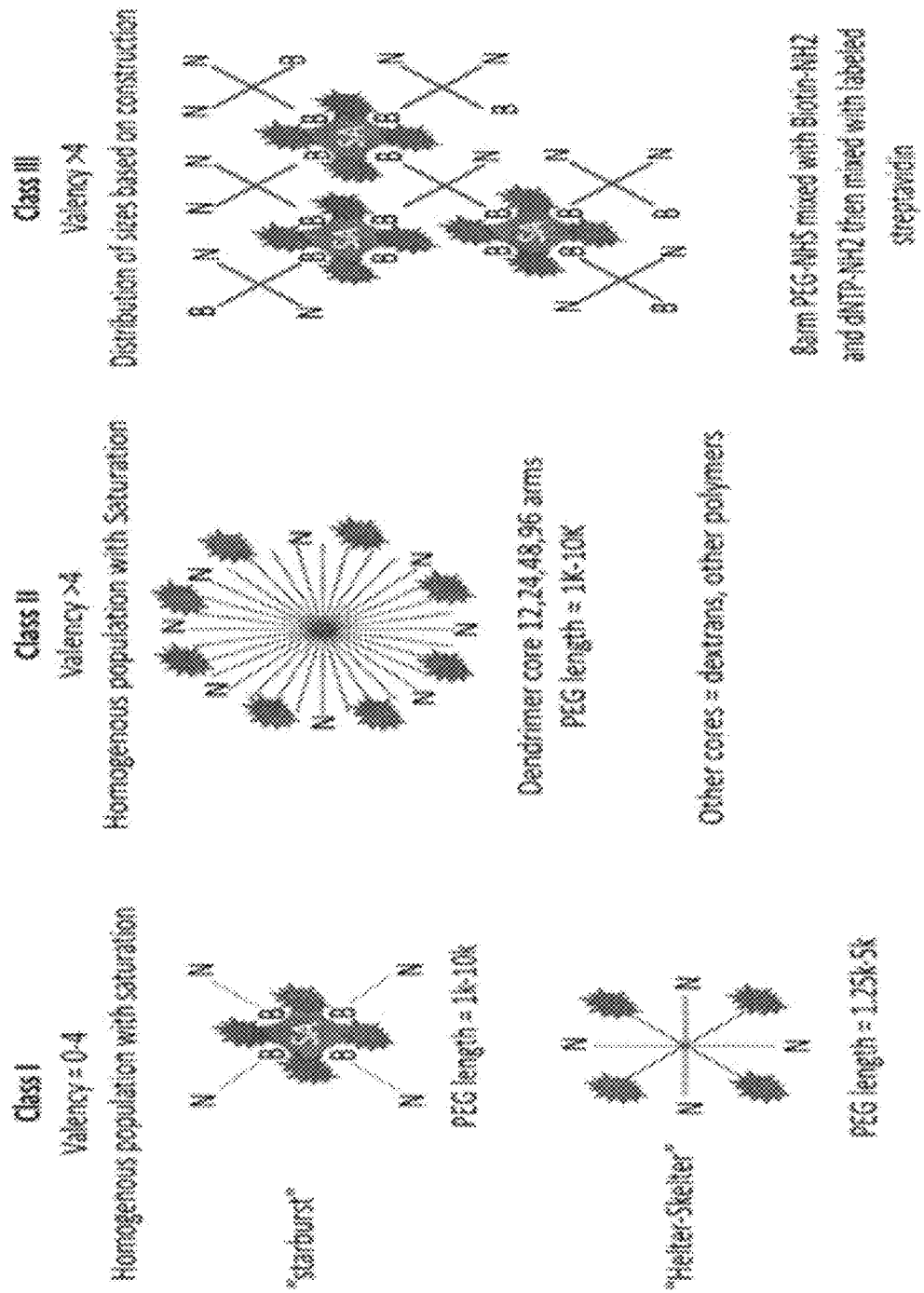
FIG. 20 is a schematic of various exemplary configurations of multivalent molecules. Left: schematics of multivalent molecules having a starburst or helter-skelter configuration. Center: a schematic of a multivalent molecule having a dendrimer configuration. Right: a schematic of multiple multivalent molecules formed by reacting streptavidin with 4-arm or 8-arm PEG-NHS with biotin and dNTPs. Nucleotide units are designated 'N', biotin is designated 'B', and streptavidin is designated 'SA'.
Figure 21:
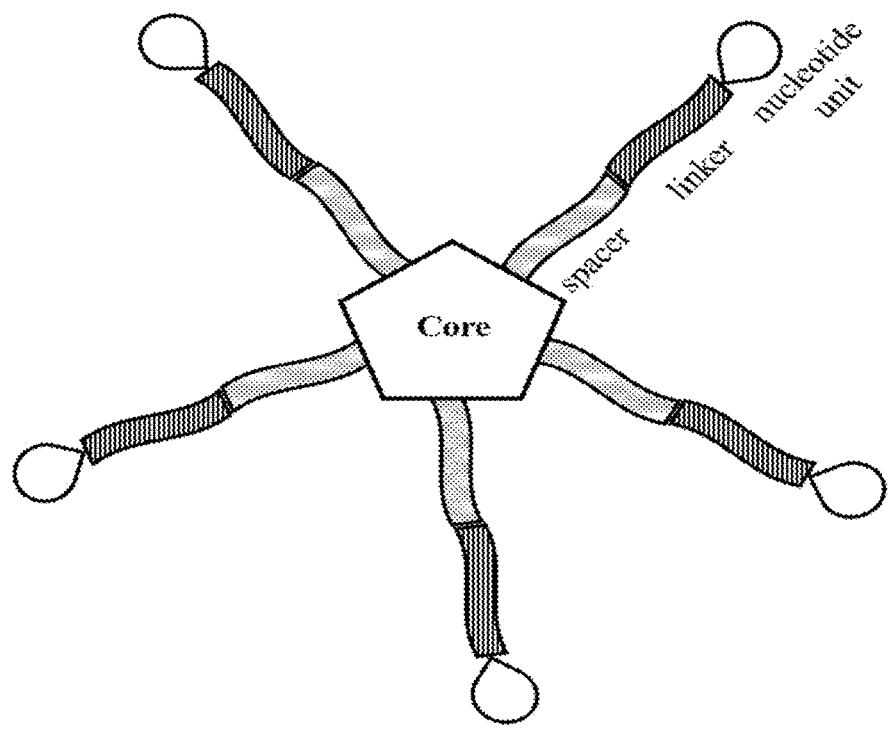
FIG. 21 is a schematic of an exemplary multivalent molecule comprising a generic core attached to a plurality of nucleotide-arms.
Figure 22:
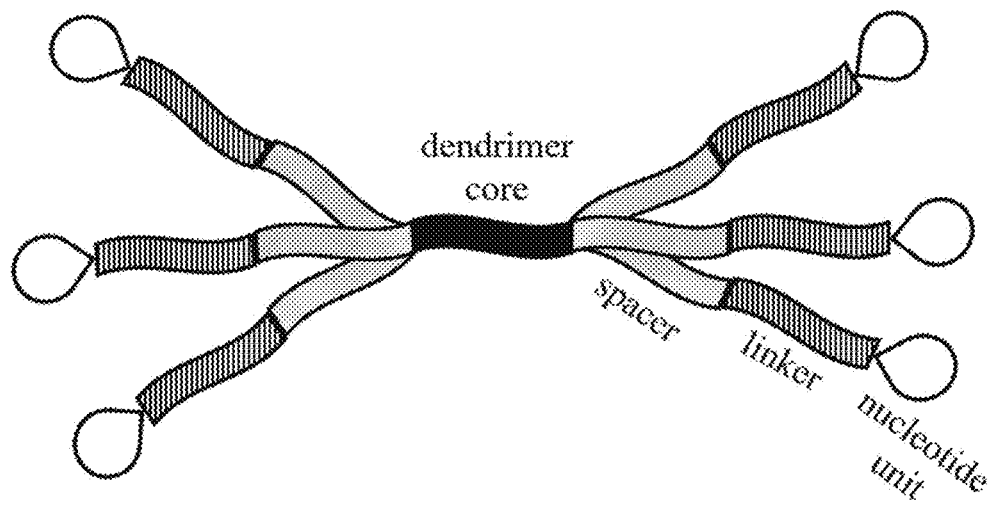
FIG. 22 is a schematic of an exemplary multivalent molecule comprising a dendrimer core attached to a plurality of nucleotide-arms.
Figure 23:
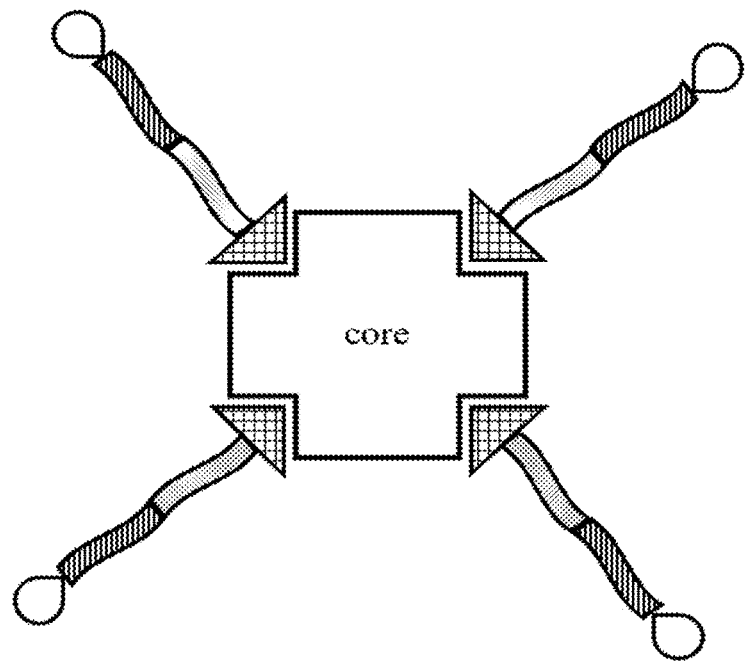
FIG. 23 shows a schematic of an exemplary multivalent molecule comprising a core attached to a plurality of nucleotide-arms, where the nucleotide arms comprise biotin, spacer, linker and a nucleotide unit.

In some embodiments, the plurality of covalently closed circular library molecules (600) can be distributed onto a support that is coated with one or more compounds to produce a passivated layer on the support (e.g., FIG. 19). In some embodiments, the passivated layer forms a porous or semi-porous layer. In some embodiments, the surface primer, concatemer template molecule and/or polymerase, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees. In some embodiments, the density of the covalently closed circular library molecules (600) immobilized to the support or immobilized to the coating on the support is about $10^2$-$10^6$ per $mm^2$, or about $10^6$-$10^9$ per $mm^2$, or about $10^9$-$10^{12}$ per $mm^2$. In some embodiments, the plurality of covalently closed circular library molecules (600) are immobilized to the support or immobilized to the coating on the support at pre-determined sites on the support (or the coating on the support), or immobilized to the coating on the support at random sites on the support (or the coating on the support).

In some embodiments, the distributing of step (a) can be conducted in the presence of a high-efficiency hybridization buffer which comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, the methods for conducting rolling circle amplification reaction comprises step (b): contacting the plurality of immobilized covalently closed circular library molecules (600) with a plurality of strand-displacing polymerases and a plurality of nucleotides, under conditions suitable to conduct a rolling circle amplification reaction on the support using the plurality of third surface primers as immobilized amplification primers and the plurality of covalently closed circular library molecules (600) as template molecules, thereby generating a plurality of nucleic acid concatemer molecules immobilized to the third surface primers. In some embodiments, the plurality of nucleotides comprises any combination of two or more of dATP, dGTP, dCTP, dTTP and/or dUTP. In some embodiments, individual immobilized concatemers are covalently joined to individual third surface primers. In some embodiments, individual covalently closed circular library molecules (600) in the plurality comprise a second splint strand region (400) which also include a universal binding sequence for a fourth surface primer so that the rolling circle amplification reaction generates concatemer molecules having multiple copies of universal binding sequences for third and fourth surface primers. In some embodiments, the method comprises distributing the covalently closed circular library molecules (600) onto a support comprising a plurality of immobilized third and fourth surface primers, conducting a rolling circle amplification reaction to generate concatemer molecules under a condition suitable for hybridizing at least one second splint strand region (400) of the concatemer molecules to immobilized third and fourth surface primers thereby pinning down at least one portion of the concatemer molecules to the support. In some embodiments, the immobilized concatemers can be subjected to sequencing reactions.

In some embodiments, the plurality of the fourth surface primers immobilized on the support comprise the sequence 5'-CATGTAATGCACGTACTTTCAGGGT-3' (SEQ ID NO:200) or a complementary sequence thereof. Individual fourth surface primers can hybridize to a portion of the concatemer molecules having a second splint strand region (400) which includes a universal binding sequence for a fourth surface primer or a complementary sequence thereof, where the universal binding sequence for the fourth surface primer comprises a first sub-region which comprises the sequence 5'-CATGTAATGCACGTACTTTCAGGGT-3' (SEQ ID NO:200). In some embodiments, the immobilized fourth surface primers comprise immobilized surface pinning primers.

In-Solution Rolling Circle Amplification Using Soluble Amplification Primers

In some embodiments, the methods for conducting rolling circle amplification reaction comprise conducting rolling circle amplification on a plurality of covalently closed circular library molecules which lack hybridized first splint strands (300). In some embodiments, individual covalently closed circular library molecules (600) in the plurality comprise a first (120) or second (140) left universal adaptor sequence of a universal binding sequence for a forward amplification primer, and wherein individual covalently closed circular library molecules (600) in the plurality comprise a second splint strand region (400) which includes a universal binding sequence for a third surface primer. In some embodiments, the methods comprise (a) hybridizing in solution a plurality of soluble forward amplification primers to the first or second left universal adaptor sequence which comprise the universal binding sequence for a forward amplification primer; and (b) conducting a first rolling circle amplification reaction by contacting the plurality of covalently closed circular library molecules (600) with a plurality of strand-displacing polymerases and a plurality of nucleotides, under conditions suitable to conduct a rolling circle amplification reaction in solution using the plurality of forward amplification primers and the plurality of covalently closed circular library molecules (600) as template molecules, thereby generating a plurality of nucleic acid concatemer molecules which are still hybridized to covalently closed circular library molecules (600). In some embodiments, the methods for conducting rolling circle amplification reaction comprises step (c): distributing the plurality of concatemer molecules onto a support having a plurality of the third surface primers immobilized thereon, under a condition suitable for hybridizing at least a portion of the concatemers to the plurality of the immobilized third surface primers thereby immobilizing the plurality of concatemer molecules. The plurality of immobilized concatemer molecules are still hybridized to covalently closed circular library molecules (600). In some embodiments, the methods for conducting rolling circle amplification reaction comprise step (d): contacting the immobilized plurality of concatemer molecules with a plurality of strand-displacing polymerases and a plurality of nucleotides, under a condition suitable to conduct a second rolling circle amplification reaction on the support using the plurality of covalently closed circular library molecules (600) as template molecules, thereby extending the plurality of immobilized nucleic acid concatemer molecules. In some embodiments, the first and/or the second rolling circle amplification reactions can be conducted with a plurality of nucleotides which comprise any combination of two or more of dATP, dGTP, dCTP, dTTP and/or dUTP. In some embodiments, individual immobilized concatemers are hybridized to individual third surface primers. In some embodiments, individual covalently closed circular library molecules (600) in the plurality comprise a second splint strand region (400) which also include a universal binding sequence for a fourth surface primer so that the first rolling circle amplification reaction in solution generates concatemer molecules having multiple copies of universal binding sequences for third and fourth surface primers. In some embodiments, the method comprises distributing the concatemer molecules onto a support comprising a plurality of immobilized third and fourth surface primers, and incubating the concatemer molecules under a condition suitable for hybridizing at least one second splint strand region (400) of the concatemer molecules to immobilized third and fourth surface primers thereby pinning down at least one portion of the concatemer molecules to the support. In some embodiments, the immobilized concatemers can be subjected to sequencing reactions.

In some embodiments, the plurality of concatemer molecules of step (c) can be distributed onto a support comprising a plurality of the third surface primers immobilized on the support, wherein individual third surface primers comprise the sequence 5'-GATCAGGT-GAGGCTGCGACGACT-3' (SEQ ID NO:198). Individual third surface primers can hybridize to a portion of a concatemer molecule having a universal binding sequence for a third surface primer, where the universal binding sequence for a third surface primer comprises the sequence 5'-AGTCGTCGCAGCCTCACCTGATC-3' (SEQ ID NO:201 or a complementary sequence thereof). In some embodiments, the immobilized third surface primers comprise immobilized surface capture primers.

In some embodiments, the plurality of concatemer molecules of step (c) can be distributed onto a support comprising a plurality of the fourth surface primers immobilized on the support wherein individual fourth surface primers comprise the sequence 5'-CATGTAATGCACGTACTTTCAGGGT-3' (SEQ ID NO:200 or a complementary sequence thereof). Individual fourth surface primers can hybridize to a portion of the concatemer molecules having a universal binding sequence for a fourth surface primer (or a complementary sequence thereof), where the universal binding sequence for the fourth surface primer comprises the sequence 5'-CATGTAATGCACGTACTTTCAGGGT-3' (SEQ ID NO:200). In some embodiments, the immobilized fourth surface primers comprise immobilized surface pinning primers.

In some embodiments, the plurality of concatemer molecules of step (c) can be distributed onto a support that is coated with one or more compounds to produce a passivated layer on the support (e.g., FIG. 19). In some embodiments, the passivated layer forms a porous or semi-porous layer. In some embodiments, the surface primer, concatemer template molecule and/or polymerase, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees. In some embodiments, the density of the concatemer molecules immobilized to the support or immobilized to the coating on the support is about $10^2$-$10^6$ per $mm^2$, or about $10^6$-$10^9$ per $mm^2$, or about $10^9$-$10^{12}$ per $mm^2$. In some embodiments, the plurality of the concatemer molecules are immobilized to the support or immobilized to the coating on the support at pre-determined sites on the support (or the coating on the support), or immobilized to the coating on the support at random sites on the support (or the coating on the support).

In some embodiments, the distributing of step (c) can be conducted in the presence of a high-efficiency hybridization buffer which comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, the methods for conducting rolling circle amplification reaction comprise conducting rolling circle amplification on a plurality of covalently closed circular library molecules which lack hybridized first splint strands (300). In some embodiments, individual covalently closed circular library molecules (600) in the plurality comprise a first (130) or second (150) right universal adaptor sequence of a universal binding sequence for a forward amplification primer, and individual covalently closed circular library molecules (600) in the plurality comprise a second splint strand region (400) which includes a universal binding sequence for a third surface primer. In some embodiments, the methods comprise (a) hybridizing in solution a plurality of soluble forward amplification primers to the first or second right universal adaptor sequence which comprise the universal binding sequence for a forward amplification primer; and (b) conducting a first rolling circle amplification reaction by contacting the plurality of covalently closed circular library molecules (600) with a plurality of strand-displacing polymerases and a plurality of nucleotides, under conditions suitable to conduct a rolling circle amplification reaction in solution using the plurality of forward amplification primers and the plurality of covalently closed circular library molecules (600) as template molecules, thereby generating a plurality of nucleic acid concatemer molecules which are still hybridized to covalently closed circular library molecules (600). In some embodiments, the methods for conducting rolling circle amplification reaction comprise step (c): distributing the plurality of concatemer molecules onto a support having a plurality of the third surface primers immobilized thereon, under a condition suitable for hybridizing at least a portion of the concatemers to the plurality of the immobilized third surface primers thereby immobilizing the plurality of concatemer molecules. The plurality of immobilized concatemer molecules are still hybridized to covalently closed circular library molecules (600). In some embodiments, the methods comprise step (d): contacting the immobilized plurality of concatemer molecules with a plurality of strand-displacing polymerases and a plurality of nucleotides, under a condition suitable to conduct a second rolling circle amplification reaction on the support using the plurality of covalently closed circular library molecules (600) as template molecules, thereby extending the plurality of immobilized nucleic acid concatemer molecules. In some embodiments, the first and/or the second rolling circle amplification reactions can be conducted with a plurality of nucleotides which comprise any combination of two or more of dATP, dGTP, dCTP, dTTP and/or dUTP. In some embodiments, individual immobilized concatemers are hybridized to individual third surface primers. In some embodiments, individual covalently closed circular library molecules (600) in the plurality comprise a second splint strand region (400) which also include a universal binding sequence for a fourth surface primer so that the first rolling circle amplification reaction in solution generates concatemer molecules having multiple copies of universal binding sequences for third and fourth surface primers. In some embodiments, the method comprises distributing the concatemer molecules onto a support comprising a plurality of immobilized third and fourth surface primers, and incubating the concatemer molecules under a condition suitable for hybridizing at least one second splint strand region (400) of the concatemer molecules to immobilized third and fourth surface primers thereby pinning down at least one portion of the concatemer molecules to the support. In some embodiments, the immobilized concatemers can be subjected to sequencing reactions.

In some embodiments, the plurality of concatemer molecules of step (c) can be distributed onto a support comprising a plurality of the third surface primers immobilized on the support, wherein individual third surface primers comprise the sequence 5'-GATCAGGT-GAGGCTGCGACGACT-3' (SEQ ID NO:198). Individual third surface primers can hybridize to a portion of a concatemer molecule having a universal binding sequence for a third surface primer, where the universal binding sequence for a third surface primer comprises the sequence 5'-AGTCGTCGCAGCCTCACCTGATC-3' (SEQ ID NO:201 or a complementary sequence thereof).

In some embodiments, the plurality of concatemer molecules of step (c) can be distributed onto a support comprising a plurality of the fourth surface primers immobilized on the support, wherein individual fourth surface primer comprise the sequence 5'-CATGTAATGCACGTACTTTCAGGGT-3' (SEQ ID NO:200 or a complementary sequence thereof). Individual fourth surface primers can hybridize to a portion of the concatemer molecules having a universal binding sequence for a fourth surface primer (or a complementary sequence thereof), where the universal binding sequence for the fourth surface primer comprises the sequence 5'-CATGTAATGCACGTACTTTCAGGGT-3' (SEQ ID NO:200).

In some embodiments, the plurality of concatemer molecules of step (c) can be distributed onto a support that is coated with one or more compounds to produce a passivated layer on the support (e.g., FIG. 19). In some embodiments, the passivated layer forms a porous or semi-porous layer. In some embodiments, the surface primer, concatemer template molecule and/or polymerase, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees. In some embodiments, the density of the concatemer molecules immobilized to the support or immobilized to the coating on the support is about $10^2$-$10^6$ per mm$^2$, or about $10^6$-$10^9$ per mm$^2$, or about $10^9$-$10^{12}$ per mm$^2$. In some embodiments, the plurality of the concatemer molecules are immobilized to the support or immobilized to the coating on the support at pre-determined sites on the support (or the coating on the support), or immobilized to the coating on the support at random sites on the support (or the coating on the support).

In some embodiments, the distributing of step (c) can be conducted in the presence of a high-efficiency hybridization buffer which comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In-Solution Rolling Circle Amplification Using First Splint Strands

Figure 10:
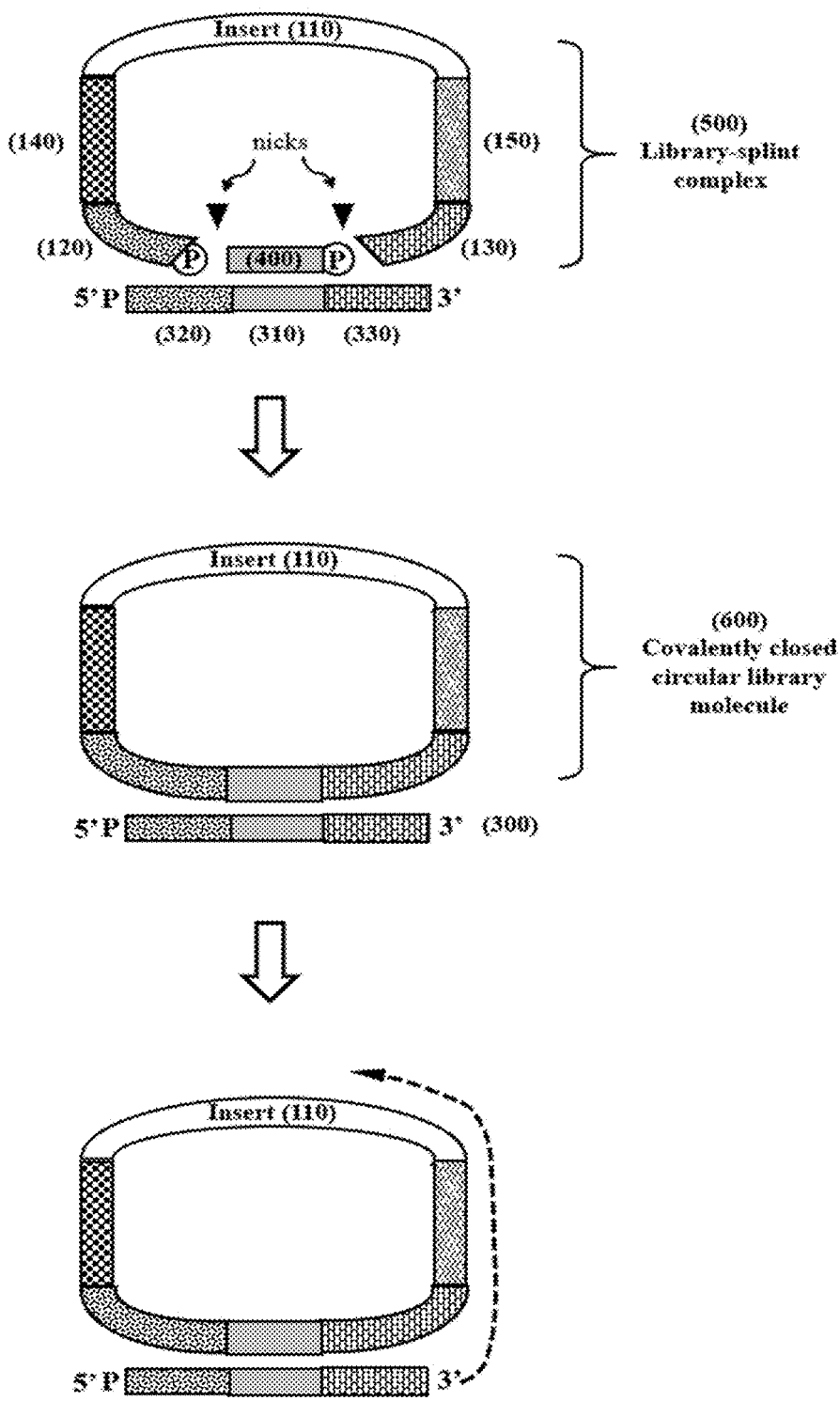
FIG. 10 is a schematic showing an exemplary library-splint complex (500) undergoing a ligation reaction to close the nicks to form a covalently closed circular library molecule (600) which is hybridized to a first splint strand (300), where the first splint strand (300) is used as an amplification primer to conduct a rolling circle amplification reaction. The dotted line represents the nascent extension product.

In some embodiments, the methods comprise conducting rolling circle amplification reaction on a plurality of covalently closed circular library molecules which are hybridized to first splint strands (300). In some embodiments, individual covalently closed circular library molecules (600) in the plurality comprise a second splint strand region (400) which includes a universal binding sequence for a third surface primer. In some embodiments, the methods comprise (a): contacting in solution the plurality of covalently closed circular library molecules (600) which are hybridized to first splint strands (300) with a plurality of strand-displacing polymerases and a plurality of nucleotides under a condition suitable for conducting a first rolling circle amplification reaction using the first splint strand (300) as an amplification primer thereby generating a plurality of concatemer molecules which are still hybridized to covalently closed circular library molecules (600). See FIG. 10.

In some embodiments, the methods comprise step (b): distributing the plurality of concatemer molecules which are hybridized to a covalently closed circular library molecule (600) onto a support having a plurality of the third surface primers immobilized thereon, under a condition suitable for hybridizing at least a portion of the concatemers to the plurality of the immobilized third surface primers thereby immobilizing the plurality of concatemer molecules which are hybridized to a covalently closed circular library molecule (600).

In some embodiments, the plurality of concatemer molecules of step (b) can be distributed onto a support comprising a plurality of the third surface primers immobilized on the support, wherein individual third surface primers comprise the sequence 5'-GATCAGGT-GAGGCTGCGACGACT-3' (SEQ ID NO:198). Individual third surface primers can hybridize to a portion of a concatemer molecule having a universal binding sequence for a third surface primer, where the universal binding sequence for a third surface primer comprises the sequence 5'-AGTCGTCGCAGCCTCACCTGATC-3' (SEQ ID NO:201 or a complementary sequence thereof). In some embodiments, the immobilized third surface primers comprise immobilized surface capture primers.

In some embodiments, the plurality of concatemer molecules of step (b) can be distributed onto a support comprising a plurality of the fourth surface primers immobilized on the support, wherein individual fourth surface primers comprise the sequence 5'-CATGTAATGCACGTACTTTCAGGGT-3' (SEQ ID NO:200 or a complementary sequence thereof). Individual fourth surface primers can hybridize to a portion of the concatemer molecules having a universal binding sequence for a fourth surface primer (or a complementary sequence thereof), where the universal binding sequence for the fourth surface primer comprises the sequence 5'-CATGTAATGCACGTACTTTCAGGGT-3' (SEQ ID NO:200). In some embodiments, the immobilized fourth surface primers comprise immobilized surface pinning primers.

In some embodiments, the plurality of concatemer molecules of step (b) can be distributed onto a support that is coated with one or more compounds to produce a passivated layer on the support (e.g., FIG. 19). In some embodiments, the passivated layer forms a porous or semi-porous layer. In some embodiments, the surface primer, concatemer template molecule and/or polymerase, can be attached to the passivated layer for immobilization to the support. In some embodiments, the support comprises a low non-specific binding surface that enable improved nucleic acid hybridization and amplification performance on the support. In general, the support may comprise one or more layers of a covalently or non-covalently attached low-binding, chemical modification layers, e.g., silane layers, polymer films, and one or more covalently or non-covalently attached oligonucleotides that can be used for immobilizing a plurality of nucleic acid concatemer molecules to the support. In some embodiments, the support can comprise a functionalized polymer coating layer covalently bound at least to a portion of the support via a chemical group on the support, a primer grafted to the functionalized polymer coating, and a water-soluble protective coating on the primer and the functionalized polymer coating. In some embodiments, the functionalized polymer coating comprises a poly(N-(5-azidoacetamidylpentyl)acrylamide-co-acrylamide (PAZAM). In some embodiments, the support comprises a surface coating having at least one hydrophilic polymer coating layer and at least one layer of a plurality of oligonucleotides. The hydrophilic polymer coating layer can comprise polyethylene glycol (PEG). The hydrophilic polymer coating layer can comprise branched PEG having at least 4 branches. In some embodiments, the low non-specific binding coating has a degree of hydrophilicity which can be measured as a water contact angle, where the water contact angle is no more than 45 degrees. In some embodiments, the density of the concatemer molecules immobilized to the support or immobilized to the coating on the support is about $10^2$-$10^6$ per mm$^2$, or about $10^6$-$10^9$ per mm$^2$, or about $10^9$-$10^{12}$ per mm$^2$. In some embodiments, the plurality of the concatemer molecules are immobilized to the support or immobilized to the coating on the support at pre-determined sites on the support (or the coating on the support), or immobilized to the coating on the support at random sites on the support (or the coating on the support).

In some embodiments, the distributing of step (b) can be conducted in the presence of a high-efficiency hybridization buffer which comprises: (i) a first polar aprotic solvent having a dielectric constant that is no greater than 40 and having a polarity index of 4-9; (ii) a second polar aprotic solvent having a dielectric constant that is no greater than 115 and is present in the hybridization buffer formulation in an amount effective to denature double-stranded nucleic acids; (iii) a pH buffer system that maintains the pH of the hybridization buffer formulation in a range of about 4-8; and (iv) a crowding agent in an amount sufficient to enhance or facilitate molecular crowding. In some embodiments, the high efficiency hybridization buffer comprises: (i) the first polar aprotic solvent comprises acetonitrile at 25-50% by volume of the hybridization buffer; (ii) the second polar aprotic solvent comprises formamide at 5-10% by volume of the hybridization buffer; (iii) the pH buffer system comprises 2-(N-morpholino)ethanesulfonic acid (MES) at a pH of 5-6.5; and (iv) the crowding agent comprises polyethylene glycol (PEG) at 5-35% by volume of the hybridization buffer. In some embodiments, the high efficiency hybridization buffer further comprises betaine.

In some embodiments, the methods for conducting rolling circle amplification reaction further comprises step (c): contacting the plurality of immobilized concatemer molecules with a plurality of strand-displacing polymerases and a plurality of nucleotides, under a condition suitable to conduct a second rolling circle amplification reaction on the support using the plurality of covalently closed circular library molecules (600) as template molecules, thereby extending the plurality of immobilized nucleic acid concatemer molecules.

In some embodiments, the first and/or the second rolling circle amplification reactions can be conducted with a plurality of nucleotides which comprise any combination of two or more of dATP, dGTP, dCTP, dTTP and/or dUTP. In some embodiments, individual covalently closed circular library molecules (600) in the plurality comprise a second splint strand region (400) which also include a universal binding sequence for a fourth surface primer so that the first rolling circle amplification reaction in solution generates concatemer molecules having multiple copies of universal binding sequences for third and fourth surface primers. In some embodiments, the method comprises distributing the concatemer molecules onto a support comprising a plurality of immobilized third and fourth surface primers, and incubating the plurality of immobilized nucleic acid concatemer molecules under a condition suitable for hybridizing at least one second splint strand region (400) of the concatemer molecules to the immobilized third and fourth surface primers thereby pinning down at least one portion of the concatemer molecules to the support. In some embodiments, individual immobilized concatemers are hybridized to individual third surface primers. In some embodiments, the immobilized concatemers can be subjected to sequencing reactions.

Methods for Sequencing

The present disclosure provides methods for sequencing any of the immobilized concatemer molecules described herein. Any of the methods for conducting rolling circle amplification reaction described herein can be used to generate a plurality of concatemer molecules immobilized to a support, and the immobilized concatemers can be subjected to sequencing reactions. In some embodiments, the sequencing reactions employ detectably labeled nucleotide analogs. In some embodiments, the sequencing reactions employ a two-stage sequencing reaction comprising binding detectably labeled multivalent molecules, and incorporating nucleotide analogs. The terms concatemer molecule and template molecule are used interchangeably.

In some embodiments, any of the rolling circle amplification reaction described herein (e.g., RCA conducted on-support or in-solution) can be used to generate immobilized concatemers each containing tandem repeat units of the sequence-of-interest and any adaptor sequences present in the covalently closed circular library molecules (600). For example, the tandem repeat unit comprises: (i) a first left universal adaptor sequence (120) having a binding sequence for a first surface primer, (ii) a second left universal adaptor sequence (140) having a binding sequence for a first sequencing primer, (iii) a sequence-of-interest (110), (iv) a second right universal adaptor sequence (150) having a binding sequence for a second sequencing primer, (v) a first right universal adaptor sequence (130) having a binding sequence for a second surface primer, and (vii) a first left index sequence (160) and/or a first right index sequence (170) (e.g., see FIGS. 5-8). In some embodiments, the tandem repeat unit further comprises a first left unique identification sequence (180) and/or a first right unique identification sequence (190).

The immobilized concatemer can self-collapse into a compact nucleic acid nanoball. Inclusion of one or more compaction oligonucleotides during the RCA reaction can further compact the size and/or shape of the nanoball. An increase in the number of tandem repeat units in a given concatemer increases the number of sites along the concatemer for hybridizing to multiple sequencing primers (e.g., sequencing primers having a universal sequence) which serve as multiple initiation sites for polymerase-catalyzed sequencing reactions. When the sequencing reaction employs detectably labeled nucleotides and/or detectably labeled multivalent molecules (e.g., having nucleotide units), the signals emitted by the nucleotides or nucleotide units that participate in the parallel sequencing reactions along the concatemer yields an increased signal intensity for each concatemer. Multiple portions of a given concatemer can be simultaneously sequenced. Furthermore, a plurality of binding complexes can form along a particular concatemer molecule, each binding complex comprising a sequencing polymerase bound to a multivalent molecule wherein the plurality of binding complexes remain stable without dissociation resulting in increased persistence time which increases signal intensity and reduces imaging time.

Methods for Sequencing Using Nucleotide Analogs

The present disclosure provides methods for sequencing, comprising step (a): contacting a sequencing polymerase with (i) a nucleic acid concatemer molecule and (ii) a nucleic acid primer, wherein the contacting is conducted under conditions suitable to bind the sequencing polymerase to the nucleic acid concatemer molecule which is hybridized to the nucleic acid primer, wherein the nucleic acid concatemer molecule hybridized to the nucleic acid primer forms the nucleic acid duplex. In some embodiments, the sequencing polymerase comprises a recombinant mutant sequencing polymerase. In some embodiments, the primer comprises a 3' extendible end.

In some embodiments, the methods for sequencing comprise step (b): contacting the sequencing polymerase with a plurality of nucleotides under conditions suitable for binding at least one nucleotide to the sequencing polymerase which is bound to the nucleic acid duplex, and which are suitable for polymerase-catalyzed nucleotide incorporation. In some embodiments, the sequencing polymerase is contacted with the plurality of nucleotides in the presence of at least one catalytic cation comprising magnesium and/or manganese. In some embodiments, the plurality of nucleotides comprises at least one nucleotide analog having a chain terminating moiety at the sugar 2' or 3' position. In some embodiments, the plurality of nucleotides comprises at least one nucleotide that lacks a chain terminating moiety.

In some embodiments, the methods for sequencing comprise step (c): incorporating at least one nucleotide into the 3' end of the extendible primer under conditions suitable for incorporating the at least one nucleotide. In some embodiments, the suitable conditions for nucleotide binding the polymerase and for incorporation the nucleotide can be the same or different. In some embodiments, conditions suitable for incorporating the nucleotide comprise inclusion of at least one catalytic cation comprising magnesium and/or manganese. In some embodiments, the at least one nucleotide binds the sequencing polymerase and incorporates into the 3' end of the extendible primer. In some embodiments, the incorporating the nucleotide into the 3' end of the primer in step (c) comprises a primer extension reaction.

In some embodiments, the methods for sequencing comprise step (d): repeating the incorporating at least one nucleotide into the 3' end of the extendible primer of step (c) at least once. In some embodiments, the plurality of nucleotides comprise a plurality of nucleotides labeled with detectable reporter moiety. The detectable reporter moiety can comprise a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base. In some embodiments, the method further comprises detecting the at least one incorporated nucleotide at step (c) and/or (d). In some embodiments, the method further comprises identifying the at least one incorporated nucleotide at step (c) and/or (d). In some embodiments, the sequence of the nucleic acid concatemer molecule can be determined by detecting and identifying the nucleotide that binds the sequencing polymerase, thereby determining the sequence of the concatemer molecule. In some embodiments, the sequence of the nucleic acid concatemer molecule can be determined by detecting and identifying the nucleotide that incorporates into the 3' end of the primer, thereby determining the sequence of the concatemer molecule.

In some embodiments, in the methods for sequencing, the plurality of sequencing polymerases that are bound to the nucleic acid duplexes comprise a plurality of complexed polymerases, having at least a first and second complexed polymerase, wherein (a) the first complexed polymerases comprises a first sequencing polymerase bound to a first nucleic acid duplex comprising a first nucleic acid template sequence which is hybridized to a first nucleic acid primer, (b) the second complexed polymerases comprises a second sequencing polymerase bound to a second nucleic acid duplex comprising a second nucleic acid template sequence which is hybridized to a second nucleic acid primer, (c) the first and second nucleic acid template sequences comprise the same or different sequences, (d) the first and second nucleic acid concatemers are clonally-amplified, (e) the first and second primers comprise extendible 3' ends or non-extendible 3' ends, and (f) the plurality of complexed polymerases are immobilized to a support. In some embodiments, the density of the plurality of complexed polymerases is about $10^2$-$10^{15}$ complexed polymerases per $mm^2$ that are immobilized to the support.

Two-Stage Methods for Nucleic Acid Sequencing

The present disclosure provides a two-stage method for sequencing nucleic acid molecules. In some embodiments, the first stage generally comprises binding multivalent molecules to complexed polymerases to form multivalent-complexed polymerases, and detecting the multivalent-complexed polymerases.

In some embodiments, the first stage comprises step (a): contacting a plurality of a first sequencing polymerase with (i) a plurality of nucleic acid concatemer molecules and (ii) a plurality of nucleic acid primers, wherein the contacting is conducted under conditions suitable to bind the plurality of first sequencing polymerases to the plurality of nucleic acid concatemer molecules and the plurality of nucleic acid primers thereby forming a plurality of first complexed polymerases each comprising a first sequencing polymerase bound to a nucleic acid duplex wherein the nucleic acid duplex comprises a nucleic acid concatemer molecule hybridized to a nucleic acid primer. In some embodiments, the first polymerase comprises a recombinant mutant sequencing polymerase.

In some embodiments of the methods for sequencing concatemer molecules, the primer comprises a 3' extendible end or a 3' non-extendible end. In some embodiments, the plurality of nucleic acid concatemer molecules comprise amplified template molecules (e.g., clonally amplified template molecules). In some embodiments, the plurality of nucleic acid concatemer molecules comprise one copy of a target sequence of interest. In some embodiments, the plurality of nucleic acid molecules comprise two or more tandem copies of a target sequence of interest (e.g., concatemers). In some embodiments, the nucleic acid concatemer molecules in the plurality of nucleic acid concatemer molecules comprise the same target sequence of interest or different target sequences of interest. In some embodiments, the plurality of nucleic acid concatemer molecules and/or the plurality of nucleic acid primers are in solution or are immobilized to a support. In some embodiments, when the plurality of nucleic acid concatemer molecules and/or the plurality of nucleic acid primers are immobilized to a support, the binding with the first sequencing polymerase generates a plurality of immobilized first complexed polymerases. In some embodiments, the plurality of nucleic acid concatemer molecules and/or nucleic acid primers are immobilized to $10^2$-$10^{15}$ different sites on a support. In some embodiments, the binding of the plurality of concatemer molecules and nucleic acid primers with the plurality of first sequencing polymerases generates a plurality of first complexed polymerases immobilized to $10^2$-$10^{15}$ different sites on the support. In some embodiments, the plurality of immobilized first complexed polymerases on the support are immobilized to pre-determined or to random sites on the support. In some embodiments, the plurality of immobilized first complexed polymerases are in fluid communication with each other to permit flowing a solution of reagents (e.g., enzymes including sequencing polymerases, multivalent molecules, nucleotides, and/or divalent cations) onto the support so that the plurality of immobilized complexed polymerases on the support are reacted with the solution of reagents in a massively parallel manner.

In some embodiments, the methods for sequencing comprise step (b): contacting the plurality of first complexed polymerases with a plurality of multivalent molecules to form a plurality of multivalent-complexed polymerases (e.g., binding complexes). In some embodiments, individual multivalent molecules in the plurality of multivalent molecules comprise a core attached to multiple nucleotide arms and each nucleotide arm is attached to a nucleotide (e.g., nucleotide unit) (e.g., FIGS. 20-23). In some embodiments, the contacting of step (b) is conducted under conditions suitable for binding complementary nucleotide units of the multivalent molecules to at least two of the plurality of first complexed polymerases thereby forming a plurality of multivalent-complexed polymerases. In some embodiments, the conditions are suitable for inhibiting polymerase-catalyzed incorporation of the complementary nucleotide units into the primers of the plurality of multivalent-complexed polymerases. In some embodiments, the plurality of multivalent molecules comprise at least one multivalent molecule having multiple nucleotide arms (e.g., FIG. 24) each attached with a nucleotide analog (e.g., nucleotide analog unit), where the nucleotide analog includes a chain terminating moiety at the sugar 2' and/or 3' position. In some embodiments, the plurality of multivalent molecules comprises at least one multivalent molecule comprising multiple nucleotide arms each attached with a nucleotide unit that lacks a chain terminating moiety. In some embodiments, at least one of the multivalent molecules in the plurality of multivalent molecules is labeled with a detectable reporter moiety. Any portion of the multivalent molecule can be labeled including the core, nucleotide arm or nucleo-base. In some embodiments, the detectable reporter moiety comprises a fluorophore. In some embodiments, the contacting of step (b) is conducted in the presence of at least one non-catalytic cation comprising strontium, barium and/or calcium.

In some embodiments, the methods for sequencing comprise step (c): detecting the plurality of multivalent-complexed polymerases. In some embodiments, the detecting includes detecting the multivalent molecules that are bound to the complexed polymerases, where the complementary nucleotide units of the multivalent molecules are bound to the primers but incorporation of the complementary nucleotide units is inhibited. In some embodiments, the multivalent molecules are labeled with a detectable reporter moiety to permit detection. In some embodiments, the labeled multivalent molecules comprise a fluorophore attached to the core, linker and/or nucleotide unit of the multivalent molecules.

In some embodiments, the methods for sequencing comprise step (d): identifying the base of the complementary nucleotide units that are bound to the plurality of first complexed polymerases, thereby determining the sequence of the concatemer molecule. In some embodiments, the multivalent molecules are labeled with a detectable reporter moiety that corresponds to the particular nucleotide units attached to the nucleotide arms to permit identification of the complementary nucleotide units (e.g., nucleotide base adenine, guanine, cytosine, thymine or uracil) that are bound to the plurality of first complexed polymerases.

In some embodiments, the second stage of the two-stage sequencing method generally comprises nucleotide incorporation. In some embodiments, the methods for sequencing comprise step (e): dissociating the plurality of multivalent-complexed polymerases and removing the plurality of first sequencing polymerases and their bound multivalent molecules, and retaining the plurality of nucleic acid duplexes.

In some embodiments, the methods for sequencing comprise step (f): contacting the plurality of the retained nucleic acid duplexes of step (e) with a plurality of second sequencing polymerases, wherein the contacting is conducted under conditions suitable for binding the plurality of second sequencing polymerases to the plurality of the retained nucleic acid duplexes, thereby forming a plurality of second complexed polymerases each comprising a second sequencing polymerase bound to a nucleic acid duplex. In some embodiments, the second sequencing polymerase comprises a recombinant mutant sequencing polymerase.

In some embodiments, the plurality of first sequencing polymerases of step (a) have an amino acid sequence that is 100% identical to the amino acid sequence as the plurality of the second sequencing polymerases of step (f). In some embodiments, the plurality of first sequencing polymerases of step (a) have an amino acid sequence that differs from the amino acid sequence of the plurality of the second sequencing polymerases of step (f).

In some embodiments, the methods for sequencing comprise step (g): contacting the plurality of second complexed polymerases with a plurality of nucleotides, wherein the contacting is conducted under conditions suitable for binding complementary nucleotides from the plurality of nucleotides to at least two of the second complexed polymerases thereby forming a plurality of nucleotide-complexed polymerases. In some embodiments, the contacting of step (g) is conducted under conditions that are suitable for promoting polymerase-catalyzed incorporation of the bound complementary nucleotides into the primers of the nucleotide-complexed polymerases thereby forming a plurality of nucleotide-complexed polymerases. In some embodiments, the incorporating the nucleotide into the 3' end of the primer in step (g) comprises a primer extension reaction. In some embodiments, the contacting of step (g) is conducted in the presence of at least one catalytic cation comprising magnesium and/or manganese. In some embodiments, the contacting of step (g) is conducted in the presence of magnesium and/or manganese. In some embodiments, the plurality of nucleotides comprise native nucleotides (e.g., non-analog nucleotides) or nucleotide analogs. In some embodiments, the plurality of nucleotides comprise a 2' and/or 3' chain terminating moiety which is removable or is not removable. In some embodiments, the plurality of nucleotides comprises a plurality of nucleotides labeled with detectable reporter moiety, e.g. a fluorophore. In some embodiments, the fluorophore is attached to the nucleotide base. In some embodiments, the fluorophore is attached to the nucleotide base with a linker which is cleavable/removable from the base or is not removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base.

In some embodiments, the methods for sequencing comprise step (h): detecting the complementary nucleotides which are incorporated into the primers of the nucleotide-complexed polymerases. In some embodiments, the plurality of nucleotides are labeled with a detectable reporter moiety to permit detection. In some embodiments, in the methods for sequencing concatemer molecules, the detecting step is omitted.

In some embodiments, the methods for sequencing further comprise step (i): identifying the bases of the complementary nucleotides which are incorporated into the primers of the nucleotide-complexed polymerases. In some embodiments, the identification of the incorporated complementary nucleotides in step (i) can be used to confirm the identity of the complementary nucleotides of the multivalent molecules that are bound to the plurality of first complexed polymerases in step (d). In some embodiments, the identifying of step (i) can be used to determine the sequence of the nucleic acid concatemer molecules. In some embodiments, in the methods for sequencing concatemer molecules, the identifying step is omitted.

In some embodiments, the methods for sequencing further comprise step (j): removing the chain terminating moiety from the incorporated nucleotide when step (g) is conducted by contacting the plurality of second complexed polymerases with a plurality of nucleotides that comprise at least one nucleotide having a 2' and/or 3' chain terminating moiety.

In some embodiments, the methods for sequencing comprise step (k): repeating steps (a)-(j) at least once. In some embodiments, the sequence of the nucleic acid concatemer molecules can be determined by detecting and identifying the multivalent molecules that bind the sequencing polymerases but do not incorporate into the 3' end of the primer at steps (c) and (d). In some embodiments, the sequence of the nucleic acid concatemer molecule can be determined (or confirmed) by detecting and identifying the nucleotide that incorporates into the 3' end of the primer at steps (h) and (i).

In some embodiments of the methods for sequencing nucleic acid molecules, the binding of the plurality of first complexed polymerases with the plurality of multivalent molecules forms at least one avidity complex, the method comprising the steps: (a) binding a first nucleic acid primer, a first sequencing polymerase, and a first multivalent molecule to a first portion of a concatemer template molecule thereby forming a first binding complex, wherein a first nucleotide unit of the first multivalent molecule binds to the first sequencing polymerase; and (b) binding a second nucleic acid primer, a second sequencing polymerase, and the first multivalent molecule to a second portion of the same concatemer template molecule thereby forming a second binding complex, wherein a second nucleotide unit of the first multivalent molecule binds to the second sequencing polymerase, wherein the first and second binding complexes which include the same multivalent molecule forms an avidity complex. In some embodiments, the first sequencing polymerase comprises any wild type or mutant polymerase described herein. In some embodiments, the second sequencing polymerase comprises any wild type or mutant polymerase described herein. The concatemer template molecule comprises tandem repeat sequences of a sequence of interest and at least one universal sequencing primer binding site. The first and second nucleic acid primers can bind to a sequencing primer binding site along the concatemer template molecule. Exemplary multivalent molecules are shown in FIGS. 20-23.

In some embodiments of the methods for sequencing nucleic acid molecules, the methods include binding the plurality of first complexed polymerases with the plurality of multivalent molecules to form at least one avidity complex, and the methods comprise the steps: (a) contacting the plurality of sequencing polymerases and the plurality of nucleic acid primers with different portions of a concatemer nucleic acid concatemer molecule to form at least first and second complexed polymerases on the same concatemer template molecule; (b) contacting a plurality of multivalent molecules to the at least first and second complexed polymerases on the same concatemer template molecule, under conditions suitable to bind a single multivalent molecule from the plurality to the first and second complexed polymerases, wherein at least a first nucleotide unit of the single multivalent molecule is bound to the first complexed polymerase which includes a first primer hybridized to a first portion of the concatemer template molecule thereby forming a first binding complex (e.g., first ternary complex), and wherein at least a second nucleotide unit of the single multivalent molecule is bound to the second complexed polymerase which includes a second primer hybridized to a second portion of the concatemer template molecule thereby forming a second binding complex (e.g., second ternary complex), wherein the contacting is conducted under a condition suitable to inhibit polymerase-catalyzed incorporation of the bound first and second nucleotide units in the first and second binding complexes, and wherein the first and second binding complexes which are bound to the same multivalent molecule forms an avidity complex; and (c) detecting the first and second binding complexes on the same concatemer template molecule, and (d) identifying the first nucleotide unit in the first binding complex thereby determining the sequence of the first portion of the concatemer template molecule, and identifying the second nucleotide unit in the second binding complex thereby determining the sequence of the second portion of the concatemer template molecule. In some embodiments, the plurality of sequencing polymerases comprise any wild type or mutant sequencing polymerase described herein. The concatemer template molecule comprises tandem repeat sequences of a sequence of interest and at least one universal sequencing primer binding site. The plurality of nucleic acid primers can bind to a sequencing primer binding site along the concatemer template molecule. Exemplary multivalent molecules are shown in FIGS. 20-23.

Sequencing-by-Binding

The present disclosure provides methods for sequencing any of the immobilized concatemer molecules described herein, wherein the sequencing methods comprise a sequencing-by-binding (SBB) procedure. In some embodiments, the SBB procedure employs non-labeled chain-terminating nucleotide. In some embodiments, the sequencing-by-binding (SBB) method comprises the steps of (a) sequentially contacting a primed template nucleic acid with at least two separate mixtures under ternary complex stabilizing conditions, wherein the at least two separate mixtures each include a polymerase and a nucleotide, whereby the sequentially contacting results in the primed template nucleic acid being contacted, under the ternary complex stabilizing conditions, with nucleotide cognates for first, second and third base type base types in the template; (b) examining the at least two separate mixtures to determine whether a ternary complex formed; and (c) identifying the next correct nucleotide for the primed template nucleic acid molecule, wherein the next correct nucleotide is identified as a cognate of the first, second or third base type if ternary complex is detected in step (b), and wherein the next correct nucleotide is imputed to be a nucleotide cognate of a fourth base type based on the absence of a ternary complex in step (b); (d) adding a next correct nucleotide to the primer of the primed template nucleic acid after step (b), thereby producing an extended primer; and (e) repeating steps (a) through (d) at least once on the primed template nucleic acid that comprises the extended primer. Exemplary sequencing-by-binding methods are described in U.S. Pat. No. 10,246,744 and 10,731,141 (where the contents of both patents are hereby incorporated by reference in their entireties).

Multiplex Workflows

The present disclosure provides multiplex workflows comprising preparing separate populations of sample-indexed covalently closed circular library molecules using double-stranded splint adaptors (200) and sample-indexed nucleic acid libraries carrying one or both index sequences (e.g., left (160) and/or right (170) sample index sequences). The first left index sequence (160) and the first right index sequence (170) are known sequences. Separate sample-indexed libraries can be prepared from input nucleic acids isolated from different sources where the sample index sequences are used to distinguish the different sources. The pooling step can be conducted either after generating sample-indexed covalently closed circular library molecules or before generating sample-indexed library-splint complexes. The pooled molecules can be subjected to downstream multiplex amplification and/or multiplex sequencing reactions.

An Exemplary Pooling Workflow for Multiplexing

In one embodiment, a method for preparing a multiplex mixture of sequences of interest isolated from a plurality of sample sources comprises: (a) providing two or more populations of single-stranded nucleic acid library molecules (100), each population of library molecules (100) contained in a separate compartment, wherein the nucleic acid library molecules in a given population comprise (i) a first left universal adaptor sequence (120) having a binding sequence for a first surface primer, (ii) a second left universal adaptor sequence (140) having a binding sequence for a first sequencing primer, (iii) a sequence of interest (110) isolated from a sample source, (iv) a second right universal adaptor sequence (150) having a binding sequence for a second sequencing primer, (v) a first right universal adaptor sequence (130) having a binding sequence for a second surface primer, and (vii) a first left index sequence (160) and/or a first right index sequence (170), wherein the sequences of the left (160) and/or right (170) indexes separately or in combination identify the sample source from which the sequences of interest (110) have been isolated (e.g., see FIGS. 5-8). In some embodiments, the single-stranded nucleic acid library molecules (100) further comprises a first left unique identification sequence (180) and/or a first right unique identification sequence (190).

In some embodiments, the method for preparing a multiplex mixture of sequences-of-interest isolated from a plurality of sample sources comprises step (b): providing a plurality of double-stranded splint adaptors (200) wherein individual double-stranded splint adaptors (200) comprise a first splint strand (300) hybridized to a second splint strand (400), wherein the first splint strand (300) comprises regions arranged in a 5' to 3' order a first region (320), an internal region (310), and a second region (330), and wherein the internal region of the first splint strand (310) is hybridized to the second splint strand (400), wherein the second splint strand comprises regions arranged in a 5' to 3' order (i) a second sub-region having a universal binding sequence for a fourth surface primer, and (ii) a first sub-region having a universal binding sequence for a third surface primer.

In some embodiments, the method for preparing a multiplex mixture of sequences-of-interest isolated from a plurality of sample sources comprises step (c): contacting in the separate compartments the population of single-stranded nucleic acid library molecules (100) with an allotment of the plurality of double-stranded splint adaptors (200), wherein the contacting is conducted under conditions suitable to hybridize portions of the first splint strand (300) to portions of the library molecules (100) thereby circularizing the library molecules to generate a population of library-splint complexes (500), such that the first region (320) of an individual first splint strand is hybridized to the binding sequence for the first surface primer (120) of an individual library molecule (100), and the third region (330) of the individual first splint strand is hybridized to the binding sequence for the second surface primer (130) of the individual library molecule (100), wherein each of the library-splint complexes (500) comprise a first nick between the 5' end of the library molecule and the 3' end of the second splint strand (300), wherein each of the library-splint complexes (500) comprises a second nick between the 5' end of the second splint strand (300) and the 3' end of the library molecule (100), and wherein the first and second nicks are enzymatically ligatable (e.g., see FIGS. 5-8).

In some embodiments, the method for preparing a multiplex mixture of sequences-of-interest isolated from a plurality of sample sources comprises step (d): contacting in the separate compartments the populations of library-splint complexes (500) with a ligase, under a condition suitable to enzymatically ligate the first and second nicks, thereby generating a population of covalently closed circular library molecules (600) each hybridized to the first splint strand (300) (e.g., see FIGS. 5-8).

In some embodiments, the method for preparing a multiplex mixture of sequences-of-interest isolated from a plurality of sample sources comprises step (e): pooling together the population of covalently closed circular library molecules (600) from the separate compartments to generate a multiplex mixture of covalently closed circular library molecules (600) which comprise the multiplex mixture of sequences-of-interest isolated from a plurality of sample sources.

In some embodiments, the sequences of interest can be isolated from two or more different sample sources (e.g., 2-10, or 10-50, or 50-100, or 100-250, or more than 250 different sample sources). Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The sequences of interest in a given population have the same or different sequences.

In some embodiments, the number of populations of single-stranded nucleic acid library molecules (100) of step (a) can be 2-10, or 10-50, or 50-100, or 100-250, or more than 250 different population of single-stranded nucleic acid library molecules (100). In some embodiments, any number of different populations of covalently closed circular library molecules (600) can be pooled together in step (e), for example 2-10, or 10-50, or 50-100, or 100-200, or more than 200 different populations of covalently closed circular library molecules (600) can be pooled together.

The skilled artisan will recognize that any number of separate compartments can be used in step (a) (e.g., 2-10, or 10-50, or 50-100, or 100-250, or more separate compartments) (e.g., multi-well plate such as for example a 96-well plate).

In some embodiments, the 3' end of the first splint strand (300) that are hybridized to the covalently closed circular library molecules (600) of step (d) or (e) comprise an extendible 3'OH ends which can serve as an initiation point for a primer extension reaction (e.g., rolling circle amplification reaction).

In some embodiments, at step (d) or (e) the population of covalently closed circular library molecules (600) that are hybridized to the first splint strand (300) can optionally be reacted with at least one exonuclease enzyme to remove the plurality of first splint strands (300) and retaining the plurality of covalently closed circular library molecules (600). In some embodiments, the at least one exonuclease enzyme comprises exonuclease I, thermolabile exonuclease I and/or T7 exonuclease.

In some embodiments, the single-stranded nucleic acid library molecules (100) of step (a) further comprise any one or any combination of two or more of: a universal binding sequence for a forward amplification primer; a universal binding sequence for a reverse amplification primer; and/or a universal binding sequence for a compaction oligonucleotide.

In some embodiments, individual covalently closed circular library molecules (600) in the multiplex mixture of step (e) comprise a second splint strand region (400) which includes a universal binding sequence for a third surface primer.

An Additional Exemplary Pooling Workflow for Multiplexing

In one embodiment, a method for preparing a multiplex mixture of sequences-of-interest isolated from a plurality of sample sources, comprises: (a) providing two or more populations of single-stranded nucleic acid library molecules (100), each population of library molecules (100), each population of single-stranded nucleic acid library molecules is contained in a separate compartment, wherein the nucleic acid library molecules in a given population comprise (i) a first left universal adaptor sequence (120) having a binding sequence for a first surface primer, (ii) a second left universal adaptor sequence (140) having a binding sequence for a first sequencing primer, (iii) a sequence of interest (110) isolated from a sample source, (iv) a second right universal adaptor sequence (150) having a binding sequence for a second sequencing primer, (v) a first right universal adaptor sequence (130) having a binding sequence for a second surface primer, and (vii) a first left index sequence (160) and/or a first right index sequence (170), wherein the sequences of the left (160) and/or right (170) indexes separately or in combination identify the sample source from which the sequences of interest (110) are isolated (e.g., see FIGS. 5-8). In some embodiments, the single-stranded nucleic acid library molecules (100) further comprises a first left unique identification sequence (180) and/or a first right unique identification sequence (190).

In some embodiments, the method for preparing a multiplex mixture of sequences-of-interest isolated from a plurality of sample sources comprises step (b): pooling together the two or more populations of single-stranded nucleic acid library molecules (100) into the same compartment.

In some embodiments, the method for preparing a multiplex mixture of sequences-of-interest isolated from a plurality of sample sources comprises step (c): adding to the compartment of step (b) a plurality of double-stranded splint adaptors (200) wherein individual double-stranded splint adaptors (200) comprise a first splint strand (300) hybridized to a second splint strand (400), wherein the first splint strand (300) comprises regions arranged in a 5' to 3' order a first region (320), an internal region (310), and a second region (330), and wherein the internal region of the first splint strand (310) is hybridized to the second splint strand (400), wherein the second splint strand comprises regions arranged in a 5' to 3' order (i) a second sub-region having a universal binding sequence for a fourth surface primer, and (ii) a first sub-region having a universal binding sequence for a third surface primer.

In some embodiments, the method for preparing a multiplex mixture of sequences-of-interest isolated from a plurality of sample sources comprises step (d): incubating the population of single-stranded nucleic acid library molecules (100) and the plurality of double-stranded splint adaptors (200) which are in the same compartment of step (c) under a condition suitable to hybridize portions of the first splint strand (300) to portions of the library molecules (100) thereby circularizing the library molecules to generate a population of library-splint complexes (500), such that the first region (320) of an individual first splint strand is hybridized to the binding sequence for the first surface primer (120) of an individual library molecule (100), and the third region (330) of the individual first splint strand is hybridized to the binding sequence for the second surface primer (130) of the individual library molecule (100), wherein each of the library-splint complexes (500) comprise a first nick between the 5' end of the library molecule and the 3' end of the second splint strand (300), wherein each of the library-splint complexes (500) comprises a second nick between the 5' end of the second splint strand (300) and the 3' end of the library molecule (100), and wherein the first and second nicks are enzymatically ligatable.

In some embodiments, the method for preparing a multiplex mixture of sequences-of-interest isolated from a plurality of sample sources comprises step (e): contacting the populations of library-splint complexes (500) in the compartment of step (d) with a ligase, under a condition suitable to enzymatically ligate the first and second nicks, thereby generating a population of covalently closed circular library molecules (600) each hybridized to the first splint strand (300), thereby generating a multiplex mixture of covalently closed circular library molecules (600) which comprise the multiplex mixture of sequences-of-interest isolated from a plurality of sample sources (e.g., see FIGS. 5-8).

In some embodiments, the sequences of interest can be isolated from two or more different sample sources (e.g., 2-10, or 10-50, or 50-100, or 100-250, or more than 250 different sample sources). Exemplary nucleic acid sources include naturally-occurring, recombinant, or chemically-synthesized sources. Exemplary nucleic acid sources include single cells, a plurality of cells, tissue, biological fluid, environmental sample or whole organism. Exemplary nucleic acid sources include fresh, frozen, fresh-frozen or archived sources (e.g., formalin-fixed paraffin-embedded; FFPE). The skilled artisan will recognize that the nucleic acids can be isolated from many other sources. The sequences of interest in a given population have the same or different sequences.

In some embodiments, the number of populations of single-stranded nucleic acid library molecules (100) of step (a) can be 2-10, or 10-50, or 50-100, or 100-250, or more than 250 different population of single-stranded nucleic acid library molecules (100). In some embodiments, any number of different populations of single-stranded nucleic acid library molecules can be pooled together in step (b), for example 2-10, or 10-50, or 50-100, or 100-200, or more than 200 different populations of covalently closed circular library molecules (600) can be pooled together.

The skilled artisan will recognize that any number of separate compartments can be used in step (a) (e.g., 2-10, or 10-50, or 50-100, or 100-250, or more separate compartments) (e.g., multi-well plate such as for example a 96-well plate).

In some embodiments, the 3' end of the first splint strand (300) that are hybridized to the covalently closed circular library molecules (600) of step (e) comprise an extendible 3'OH ends which can serve as an initiation point for a primer extension reaction (e.g., rolling circle amplification reaction).

In some embodiments, at step (e) the population of covalently closed circular library molecules (600) that are hybridized to the first splint strand (300) can optionally be reacted with at least one exonuclease enzyme to remove the plurality of first splint strands (300) and retaining the plurality of covalently closed circular library molecules (600). In some embodiments, the at least one exonuclease enzyme comprises exonuclease I, thermolabile exonuclease I and/or T7 exonuclease.

In some embodiments, the single-stranded nucleic acid library molecules (100) of step (a) further comprise any one or any combination of two or more of: a universal binding sequence for a forward amplification primer; a universal binding sequence for a reverse amplification primer; and/or a universal binding sequence for a compaction oligonucleotide.

In some embodiments, individual covalently closed circular library molecules (600) in the multiplex mixture of step (e) comprise a second splint strand region (400) which includes a universal binding sequence for a third surface primer.

On-Support Multiplex Rolling Circle Amplification Reaction

In some embodiments, the multivalent mixtures of covalently closed circular library molecules (600) described herein can be distributed onto a support, wherein the method comprises: distributing the plurality of covalently closed circular library molecules (600) onto a support having a plurality of the third surface primers immobilized on the support, under a condition suitable for hybridizing individual covalently closed circular library molecules (600) to individual immobilized third surface primers thereby immobilizing the plurality of covalently closed circular library molecules (600); and contacting the plurality of immobilized covalently closed circular library molecules (600) with a plurality of strand-displacing polymerases and a plurality of nucleotides, under conditions suitable to conduct a rolling circle amplification reaction on the support using the plurality of third surface primers as immobilized amplification primers and the plurality of covalently closed circular library molecules (600) as template molecules, thereby generating a plurality of immobilized nucleic acid concatemer molecules, wherein the plurality of nucleotides comprises dATP, dGTP, dCTP, dTTP and/or dUTP. In some embodiments, the population of covalently closed circular library molecules are still hybridized to the first splint strand (300) and are distributed onto the support. In some embodiments, the first splint strands have been removed from the population of covalently closed circular library molecules (600) using at least one exonuclease enzyme under a condition suitable to remove the plurality of first splint strands (300) and retain the population of covalently closed circular library molecules (600).

In-Solution Multiplex Rolling Circle Amplification Reaction Using Soluble Amplification Primers and Immobilizing on a Support In some embodiments, the multivalent mixtures of covalently closed circular library molecules (600) described herein can be subjected to methods comprising an in-solution rolling circle amplification reaction, the method comprising: contacting the population of covalently closed circular library molecules (600) that are hybridized to the first splint strand (300) with at least one exonuclease enzyme under a condition suitable to remove the plurality of first splint strands (300) and retaining the population of covalently closed circular library molecules (600); and contacting the retained population of covalently closed circular library molecules (600) with a plurality of soluble amplification primers, a plurality of strand-displacing polymerases, and a plurality of nucleotides, under conditions suitable to conduct a rolling circle amplification reaction thereby generating a plurality of nucleic acid concatemer molecules, wherein the plurality of nucleotides comprises dATP, dGTP, dCTP, dTTP and/or dUTP. In some embodiments, the covalently closed circular library molecules (600) comprise a universal binding sequence for a forward amplification primer and/or a universal binding sequence for a reverse amplification primer. In some embodiments, the soluble amplification primers can hybridize to the universal binding sequence for a forward amplification primer or the universal binding sequence for a reverse amplification primer. In some embodiments, the at least one exonuclease enzyme comprises exonuclease I, thermolabile exonuclease I and/or T7 exonuclease.

In some embodiments, the methods comprise distributing the plurality of nucleic acid concatemer molecules onto a support, and the methods comprise: distributing the plurality of concatemer molecules onto a support having a plurality of the third surface primers immobilized thereon, under a condition suitable for hybridizing at least a portion of the concatemers to at least a portion of the plurality of the immobilized third surface primers thereby immobilizing the plurality of concatemer molecules; and contacting the immobilized plurality of concatemer molecules (which are hybridized to a covalently closed circular library molecule (600)) with a plurality of strand-displacing polymerases and a plurality of nucleotides, under a condition suitable to conduct a rolling circle amplification reaction on the support using the plurality of covalently closed circular library molecules (600) as template molecules, thereby extending the plurality of immobilized nucleic acid concatemer molecules, wherein the plurality of nucleotides comprises dATP, dGTP, dCTP, dTTP and/or dUTP.

In-Solution Multiplex Rolling Circle Amplification Reaction Using First Splint Strands and Immobilizing on a Support In some embodiments, the multivalent mixtures of covalently closed circular library molecules (600) described herein can be subjected to an in-solution rolling circle amplification reaction. In some embodiments, the methods comprise: conducting a rolling circle amplification reaction by contacting the population of covalently closed circular library molecules (600) which are hybridized to the first splint strand (300) with a plurality of strand-displacing polymerases and a plurality of nucleotides, under conditions suitable to conduct a rolling circle amplification reaction thereby generating a plurality of concatemer molecules, wherein the plurality of nucleotides comprises dATP, dGTP, dCTP, dTTP and/or dUTP.

In some embodiments, the plurality of concatemer molecules can be distributed onto a support, and the method comprises: distributing the plurality of concatemer molecules which are hybridized to a covalently closed circular library molecule (600) onto a support having a plurality of the third surface primers immobilized thereon, under conditions suitable for hybridizing at least a portion of the concatemers to at least a portion of the plurality of the immobilized third surface primers thereby immobilizing the plurality of concatemer molecules which are hybridized to a covalently closed circular library molecule (600); and contacting the plurality of immobilized concatemer molecules with a plurality of strand-displacing polymerases and a plurality of nucleotides, under a condition suitable to conduct a rolling circle amplification reaction on the support using the plurality of covalently closed circular library molecules (600) as template molecules, thereby extending the plurality of immobilized nucleic acid concatemer molecules, wherein the plurality of nucleotides comprises dATP, dGTP, dCTP, dTTP and/or dUTP.

Multiplex Sequencing of Immobilized Concatemer Molecules

Any of the multiplex immobilized concatemer molecules described herein can be subjected to sequencing reactions. In some embodiments, the sequencing reactions comprise: sequencing the insert region (110) and the first left index sequence (160) and/or the first right index sequence (170) of the plurality of immobilized nucleic acid concatemer molecules, wherein the sequences of the insert region (110) along with the first left index sequence (160) and/or first right index sequence (170) can be used to identify the sample source of the sequence of interest of a given immobilized concatemer molecule. The immobilized nucleic acid concatemer molecules comprise the insert region (110) and one or both of the sample index sequences (e.g., first left index sequence (160) and/or the first right index sequence (170)). The insert region (110), the first left index sequence (160) and/or the first right index sequence (170) can be sequenced in any order. In some embodiments, the insert region (110) can be sequenced first, the first left index sequence (160) can be sequenced second, and the first right index sequence (170) can be sequenced third if it is present in the immobilized nucleic acid concatemer molecule. In some embodiments, the first left index sequence (160) can be sequenced first, the insert region (110) can be sequenced second, and the first right index sequence (170) can be sequenced third if it is present in the immobilized nucleic acid concatemer molecule.

In some embodiments, the sequencing reads of the first left index (160) and the first right index (170) can be aligned with their respective known sequences and assigned an alignment score, where the alignment score indicates the similarity between the known index sequence and the sequencing read of that index. The alignment score(s) of the first left index (160) and/or the first right index (170), along with the sequence read of the associated insert region (110), can be used to determine the sample source of the insert region.

Multiplex Sequencing Using Nucleotide Analogs

In some embodiments the sequencing method comprising: (a) binding the plurality of immobilized nucleic acid concatemer molecules with a plurality of sequencing primers, a plurality of sequencing polymerases, and a plurality of detectably labeled nucleotide analogs each comprising a 2' or 3' chain terminating moiety, under conditions suitable for incorporating the detectably labeled nucleotide analogs into the 3' end of the sequencing primers; (b) detecting the incorporated detectably labeled nucleotide analog; and (c) identifying the nucleo-base of the incorporated detectably labeled nucleotide analog. Sequencing methods that employ nucleotide analogs are described in detail above.

Multiplex Sequencing Using a Two-Stage Sequencing Method

In some embodiments, any of the multiplex immobilized concatemer molecules described herein can be sequenced using a two-stage sequencing method, wherein the first stage comprises: (a) binding the plurality of immobilized nucleic acid concatemer molecules with a plurality of sequencing primers, a plurality of a first sequencing polymerase, and a plurality of detectably labeled multivalent molecules, under a condition suitable to bind individual concatemer molecules to a sequencing primer, a first sequencing polymerase, and a detectably labeled multivalent molecule (e.g., forming a plurality of multivalent-complexed polymerases), where the suitable conditions inhibit polymerase-catalyzed incorporation of the nucleotide unit of the detectably labeled multivalent molecule; (b) detecting the bound detectably labeled multivalent molecule; and (c) identifying the nucleo-base of the detectably labeled multivalent molecule. In some embodiments, individual detectably labeled multivalent molecules comprise a core attached to multiple nucleotide arms and each nucleotide arm is attached to a nucleotide (e.g., nucleotide unit) (e.g., see FIGS. 20-23). In some embodiments, at least one of the multivalent molecules in the plurality of multivalent molecules is labeled with a detectable reporter moiety. Any portion of the multivalent molecule can be labeled including the core, nucleotide arm or nucleo-base. In some embodiments, the detectable reporter moiety comprises a fluorophore. In some embodiments, the binding of step (a) is conducted in the presence of at least one non-catalytic cation comprising strontium, barium and/or calcium. In some embodiments, the binding of the detectably labeled multivalent molecules to the plurality of immobilized nucleic acid concatemer molecules forms at least one avidity complex as described above.

In some embodiments, the second stage of the two-stage sequencing method comprises: (d) removing the plurality of first sequencing polymerases and the plurality of bound multivalent molecules from the plurality of immobilized nucleic acid concatemer molecules and retaining the immobilized concatemer molecules each hybridized to a sequencing primer (nucleic acid duplex); and (e) contacting the retained immobilized concatemer molecules and hybridized sequencing primers with a plurality of second polymerases and a plurality of nucleotides under a condition suitable for incorporating the nucleotides into the 3' end of the sequencing primers. Sequencing methods that employ the two-stage methods are described in detail above.

Sample Indexes for Improved Base Calling

Generally, it is desirable to prepare nucleic acid libraries that will be distributed onto a support (e.g., coated flowcell). The library molecules are converted into template molecules that are immobilized at a high density on the support for massively parallel sequencing. For template molecules that are immobilized at high densities at random locations on the support, resolving high density fluorescent images for accurate base calling during sequencing runs becomes challenging.

The nucleotide diversity of a population of immobilized template molecules refers to the relative proportion of nucleotides A, G, C and T that are present in each sequencing cycle. An optimal high diversity library will generally include sequence of interest (insert) regions having approximately equal proportions of all four nucleotides represented in each cycle of a sequencing run. A low diversity library will generally include sequence of interest (insert) regions having a high proportion of certain nucleotides and low proportion of other nucleotides. To overcome the problem of low diversity libraries, a small amount of a high diversity library prepared from PhiX bacteriophage is typically mixed with the library of sequences of interest (e.g., PhiX spike-in library) and sequenced together on the same flowcell. While the PhiX library spike-in library provides nucleotide diversity, it also occupies space on the flowcell thereby replacing the target libraries carrying the sequence of interest and reduces the amount of sequencing data obtainable from the target libraries (e.g., reduces sequencing throughput). Another method to overcome the problem of low diversity libraries is to prepare target library molecules having at least one sample index sequence that is designed to be color-balanced. However it may be desirable to design a large number of sample index sets, for example a set of single index sample sequences or paired index sample sequences for 16-plex, 24-plex, 96-plex or larger plexy levels. It is challenging to design sample index sequences, as a single or paired sample indexes, for large sample index sets where all of the sample index sequences are color-balanced (e.g., see FIGS. 36 and 37).

An alternative method to overcome the challenges of sequencing low diversity library molecules (e.g., at high density on the support) is to prepare libraries having at least one sample index sequence comprising a short random sequence (e.g., NNN) linked directly to a universal sample index sequence, wherein the short random sequence provides nucleotide diversity and color balance. Table 1, at FIGS. 33-1 to 33-6, provides a list of exemplary right index sequences (170) having a short random sequence (e.g., NNN) and a universal sample index sequence. In a population of sample-indexed library molecules, the short random sequence of the sample index (e.g., (170)) provides high nucleotide diversity which includes approximately equal proportions of all four nucleotides (e.g., A, G, C, T and/or U) that will be represented in each cycle of a sequencing run (see FIG. 36). The high nucleotide diversity of the short random sequence also provide color balance during each cycle of the sequencing run. The advantage of designing sample indexes (e.g., (160) and/or (170)) to include a short random sequence (e.g., NNN) is that, in a low-plexy population of library molecules (e.g., 2-plex or 4-plex), the universal sample index sequences that identify the two or four different samples need not exhibit nucleotide diversity (e.g., see FIG. 36). Additionally, the nucleotide diversity of the short random sequence (e.g., NNN) can obviate the need to include a PhiX spike-in library, or permits use of a reduced amount of PhiX spike-in library to be distributed onto the flowcell and sequenced.

The target library molecule can include a single sample index sequence which includes a short random sequence (e.g., sample index (170)) and a universal sample index sequence. In some embodiments, the sequencing data from only the single sample index sequence (e.g., (170)) is used for polony mapping and template registration because the short random sequence (e.g., NNN) provides sufficient nucleotide diversity and color balance. The sequencing data from the universal sample index sequence (e.g., (170)) can be used to distinguish sequences of interest obtained from different sample sources in a multiplex assay.

The target library molecule can further include a second sample index sequence (e.g., dual sample index) comprising a second universal sample index sequence (e.g., (160)). In some embodiments, the sequencing data from only the single sample index sequence (e.g., (170)) is used for polony mapping and/or template registration because the short random sequence provides sufficient nucleotide diversity and color balance. The sequencing data from the first universal sample index sequence (170) and the second universal sample index sequence (160) can be used as dual sample indexes to distinguish sequences of interest obtained from different sample sources in a multiplex assay. In some embodiments, the second sample index sequence (e.g., (160)) may or may not include a second short random sequence (e.g., NNN).

The order of sequencing the sequence of interest region and the sample index region(s) can also be used to improve the challenges of sequencing low diversity library molecules. For example, the sample index region can be sequenced first, before sequencing the sequence of interest region of the concatemer molecule, and the sample index sequence can be associated with the sequence-of-interest region. For example, sample index region can be sequenced first including sequencing the short random sequence (e.g., NNN) and optionally sequencing at least a portion of the universal sample index), and then sequencing the sequence of interest. In a population of sample indexed library molecules, the short random sequence (e.g., NNN) provides nucleotide diversity which may not be provided the sequence of interest regions of the library molecules. The sequence of the sample index provides improved nucleotide diversity and color balance for polony mapping and template registration.

Additionally, when sequencing the sample index region first, the length of the sequenced sample index region is relatively short (e.g., less than 30 nucleotides in length) so that de-hybridization of the product of the sequenced sample index region is more complete. Gentler de-hybridization conditions can be used to remove most or all of the product of the sequenced sample index region which reduces the level of residual signals from any sequencing products remaining hybridized to the template molecules. By contrast, the sequence of interest region of the concatemer molecule is typically much longer than the sample index region (e.g., more than 100 nucleotides in length). When the sequence of interest region is sequenced before the sample index region, the product of the sequenced sequence of interest region must be subjected to harsher de-hybridization conditions to remove any products remaining hybridized to the template molecules which may damage the template molecules.

The present disclosure provides nucleic acid library molecules (100) each comprising at least one sample index sequence that can be used to distinguish sequences of interest obtained from different sample sources in a multiplex assay, where the at least one sample index sequence comprises a short random sequence (e.g., NNN) linked to a universal sample index sequence. In some embodiments, the left sample index (160) comprises a short random sequence (e.g., NNN) linked to a universal left sample index sequence and/or the right sample index (170) comprises a short random sequence (e.g., NNN) linked to a right universal sample index sequence. The at least one sample index sequence can include sequence diversity for improved base calling. The at least one sample index sequence can be used to improve base calling accuracy.

In some embodiments, the short random sequence (e.g., NNN) is positioned upstream of the universal sample index sequence (e.g., (170) and/or (160)) so that during a sequencing run the random sequence portion is sequenced before the universal sample index sequence. In some embodiments, the short random sequence is positioned downstream of the universal sample index sequence so that during a sequencing run the random portion is sequenced after the universal sample index sequence.

In some embodiments, in the random sequence each base "N" at a given position is independently selected from A, G, C, T or U. In some embodiments, the random sequence lacks consecutive repeat sequences having 2 or 3 of the same nucleo-base, for example AA, TT, CC, GG, UU, AAA, TTT, CCC, GGG or UUU. In some embodiments, in a population of library molecules the universal sample index sequences (e.g., (170) and/or (160)) include a short random sequence having a high diversity sequence which includes approximately equal proportions of all four nucleotides (e.g., A, G, C, T and/or U) that will be represented in each cycle of a sequencing run.

In some embodiments, the short random sequence (e.g., NNN) comprises 3-20 nucleotides, or 3-10 nucleotides, or 3-8 nucleotides, or 3-6 nucleotides, or 3-5 nucleotides, or 3-4 nucleotides.

In some embodiments, the short random sequence (e.g., NNN) includes, but is not limited to, AGC, AGT, GAC, GAT, CAT, CAG, TAG, TAC. The skilled artisan will recognize that many more random sequences can be prepared (e.g., 64 possible combinations) where each base "N" at a given position in the random sequence is independently selected from A, G, C, T or U.

In some embodiments, the universal sample index sequence comprises 5-20 nucleotides, or 7-18 nucleotides, or 9-16 nucleotides.

In some embodiments, individual right sample index sequences (e.g., first right index (170)) in a population of right sample index sequences comprise a universal sample index sequence and a short random sequence (e.g., NNN). In some embodiments, the short random sequences in the population of right sample index sequences have an overall base composition of about 25% or about 20-30% of all four nucleotide bases (e.g., A, G, C and T/U) to provide nucleotide diversity at each sequencing cycle during sequencing the short random sequence (e.g., NNN).

In some embodiments, in the population of right sample index sequences the proportion of adenine (A) at any given position in the short random sequence is about 20-30% or about 15-35% or about 10-40%. In some embodiments, in the population of right sample index sequences the proportion of guanine (G) at any given position in the short random sequence is about 20-30% or about 15-35% or about 10-40%. In some embodiments, in the population of right sample index sequences the proportion of cytosine (C) at any given position in the short random sequence is about 20-30% or about 15-35% or about 10-40%. In some embodiments, in the population of right sample index sequences the proportion of thymine (T) or uracil (U) at any given position in the short random sequence is about 20-30% or about 15-35% or about 10-40%.

In some embodiments, in the population of right sample index sequences the proportion of adenine (A) and thymine (T), or the proportion of adenine (A) and uracil (U), at any given position in the short random sequence is about 10-65%. In some embodiments, in the population of right sample index sequences the proportion of guanine (G) and cytosine (C) at any given position in the short random sequence is about 10-65%.

In some embodiments, in the population of right sample index sequences the sequence diversity of the short random sequences ensures that no sequencing cycle is presented with fewer than four different nucleotide bases during sequencing at least the short random sequence (e.g., NNN).

Exemplary sample index sequence that include a short random sequence NNN linked directly to a universal sample index sequence include but are not limited to: NNNGTAGGAGCC (SEQ ID NO:97); NNNCCGCTGCTA (SEQ ID NO:98); NNNAACAACAAG (SEQ ID NO:99); NNNGGTGGTCTA (SEQ ID NO:100); NNNTTGGCCAAC (SEQ ID NO:101); NNNCAGGAGTGC (SEQ ID NO:105); and NNNATCACACTA (SEQ ID NO:106). The skilled artisan will recognize that the universal sample index can be any length and have any sequence that can be used to distinguish sequences of interest obtained from different sample sources in a multiplex assay. In a population of a given sample index, for example NNNGTAGGAGCC (SEQ ID NO:97), the population contains a mixture of individual sample index molecules each carrying the same universal sample index sequence (e.g., GTAGGAGCC) and a different short random sequence (e.g., NNN) where up to 64 different short random sequences may be present in the population of the given sample index.

Exemplary sample index sequence that include a short random sequence NNN are listed in Table 1 at FIGS. 33-1 to 33-6. In some embodiments, at least one library molecule comprises a right sample index comprising a short random sequence (e.g., NNN) directly linked to a right universal sample index sequence. In some embodiments, the at least one library molecule further comprises a left sample index comprising a left universal sample index sequence that differs from the right universal sample index sequence.

Figure 36:
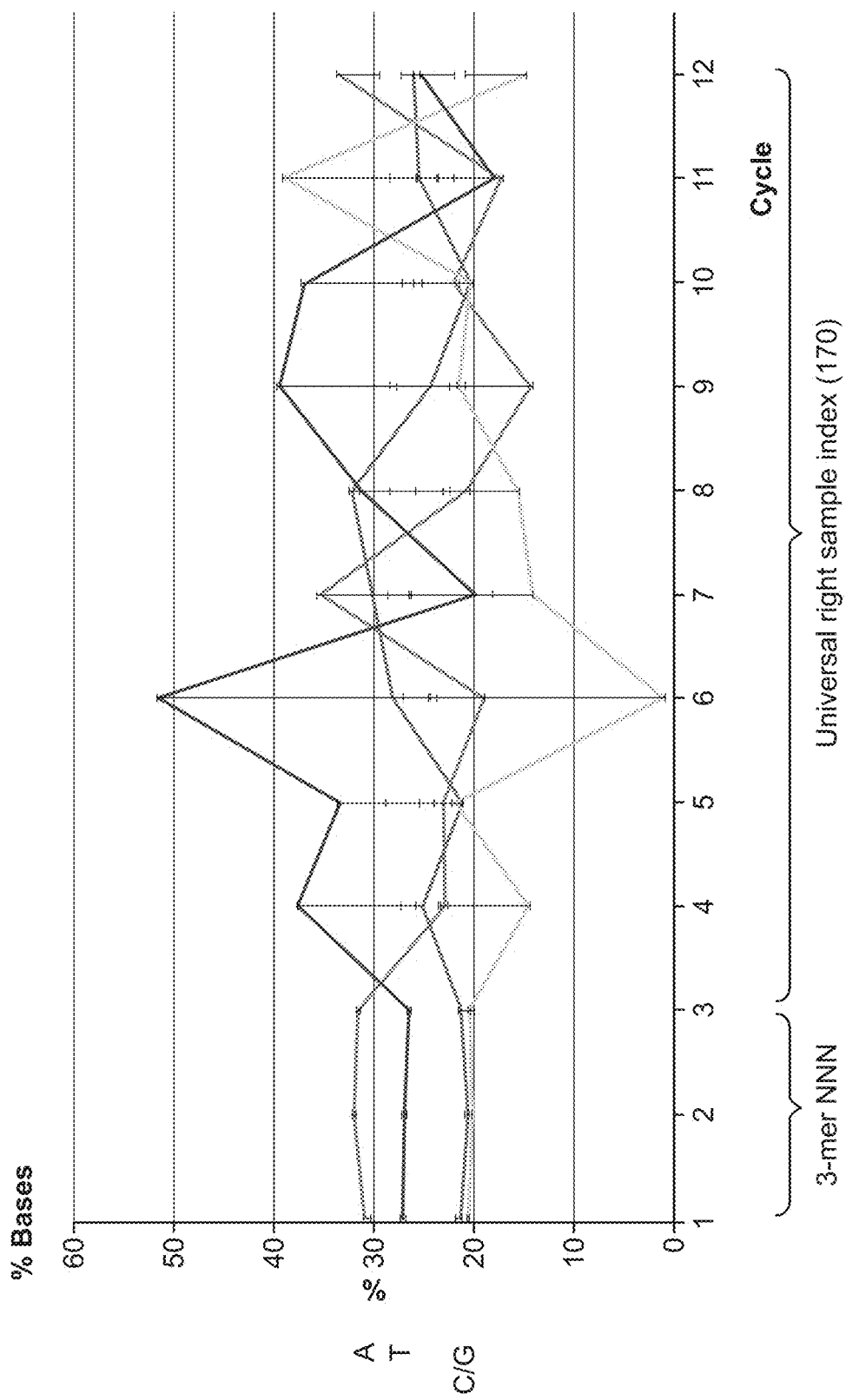
FIG. 36 is a graph showing the nucleotide base diversity of a right index sequence (170) including the 3-mer random sequence (NNN). The graph shows a nucleotide diversity of the 3-mer random sequence (NNN) of approximately 30% for A and T base calls, and approximately 20% for C and G base calls.
Figure 37:
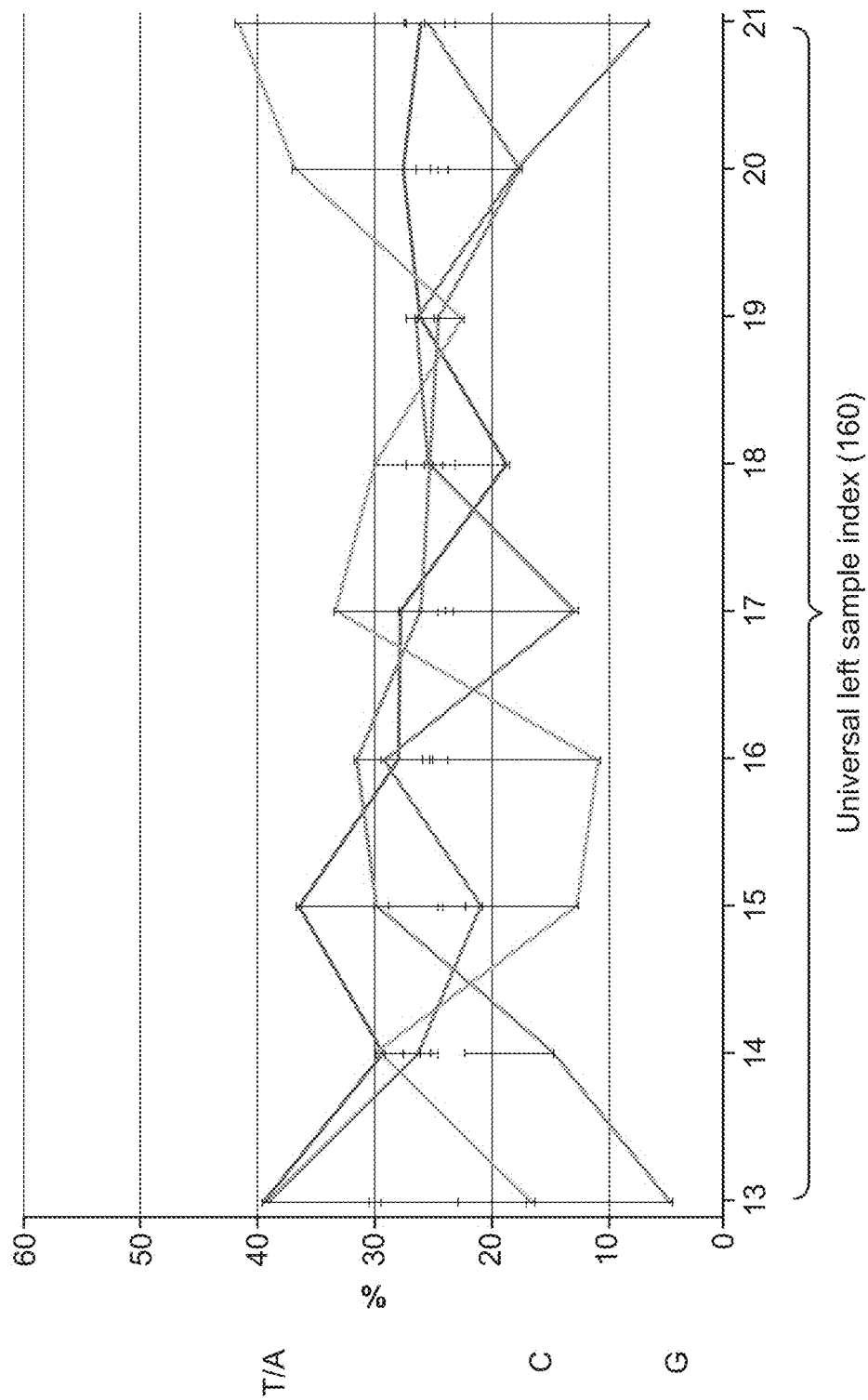
FIG. 37 is a graph showing the nucleotide base diversity of a left index sequence (160) which lacks a 3-mer random sequence (NNN). The graph shows a nucleotide diversity of approximately 40% for A and T base calls, approximately 15% for C base calls, and approximately 5% for G base calls.

In some embodiments, the random sequence (e.g., NNN) provides a balanced ratio of nucleo-bases adenine, cytosine, guanine, thymine and/or uracil (see FIG. 36). In some embodiments, in a population of sample-indexed library molecules, the random sequence (e.g., NNN) together with at least a portion of the universal sample index sequence provide a balanced ratio of nucleo-bases adenine, cytosine, guanine, thymine and/or uracil represented in each cycle of a sequencing run.

In some embodiments, a sequencing reaction includes use of polymerases and nucleotides (e.g., nucleotide analogs) that are labeled with a different fluorophore that corresponds to the nucleo-base. In some embodiments, sequencing the random sequence (e.g., NNN) using labeled nucleotides provides a balanced ratio of fluorescent colors that correspond to the nucleo-bases adenine, cytosine, guanine, thymine and/or uracil in each cycle of a sequencing run. In some embodiments, sequencing the random sequence (e.g., NNN) and at least a portion of the universal sample index sequence using labeled nucleotides provides a balanced ratio of fluorescent colors that correspond to nucleo-bases adenine, cytosine, guanine, thymine and/or uracil (e.g., see FIG. 36). The labeled nucleotides emit fluorescent signals during the sequencing reactions. In some embodiments, the sequencing reaction is conducted on a sequencing apparatus having a detector that captures fluorescent images from sequencing reactions on the immobilized template molecules. The sequencing apparatus can be configured to relay the fluorescent imaging data captured by the detector to a computer system that is programmed to determine the location (e.g., mapping) of the immobilized template molecules on the flowcell. The computer system can generate a map of the locations of the immobilized template molecules based on the fluorescent imaging data of only the random sequence (e.g., NNN), or based on the random sequence (e.g., NNN) and at least a portion the universal sample index sequence. Thus the few numbers of sequencing cycles used to sequence the random sequence (e.g., NNN) and optionally a portion of the universal sample index sequence can be used to generate a map of the location of the immobilized template molecules. The computer system can be configured to extract the fluorescent color and intensity of only the random sequence (e.g., NNN), or the random sequence (e.g., NNN) and at least a portion of the universal sample index sequence. The computer system can be configured to use the location of a given immobilized template molecule and the fluorescent color and intensity associated with the given template molecule (which were established while sequencing the random sequence) for base calling while sequencing the sequence of interest region (110). The computer system can be configured to detect phasing and pre-phasing while sequencing the random sequence (e.g., NNN) and the universal sample index sequence, and the sequence of interest region (110). In some embodiments, the balanced ratio of fluorescent colors provided by the random sequence (e.g., NNN) at each sequencing cycle can improve the quality of the data which is processed from the fluorescent images captured by the detector, and can in turn improve the capability by the computer system to determine the location of the immobilized template molecules on the flowcell, and the color and intensity, all of which can improve base calling accuracy and quality scores of the sequenced sequence of interest region (110).

In some embodiments, a sequencing reaction includes use of polymerases and multivalent molecules that are labeled with a different fluorophore that corresponds to the nucleobase (e.g., adenine, guanine, cytosine, thymine or uracil) of the nucleotide units that are attached to the nucleotide arms in a given multivalent molecule. In some embodiments, the core of individual multivalent molecules is attached to a fluorophore which corresponds to the nucleotide units (e.g., adenine, guanine, cytosine, thymine or uracil) that are attached to the nucleotide arms in a given multivalent molecule (e.g., see FIGS. 20-23). In some embodiments, at least one of the nucleotide arms of the multivalent molecule comprises a linker and/or nucleotide base that is attached to a fluorophore, and wherein the fluorophore which is attached to a given linker or nucleotide base corresponds to the nucleotide base (e.g., adenine, guanine, cytosine, thymine or uracil) of the nucleotide arm. In some embodiments, sequencing the random sequence (e.g., NNN) using labeled multivalent molecules provides a balanced ratio of fluorescent colors that correspond to the nucleo-bases adenine, cytosine, guanine, thymine and/or uracil in each cycle of a sequencing run. In some embodiments, sequencing the random sequence (e.g., NNN) and at least a portion of the universal sample index sequence using labeled multivalent molecules provides a balanced ratio of fluorescent colors that correspond to nucleo-bases adenine, cytosine, guanine, thymine and/or uracil (e.g., see FIG. 36). The labeled multivalent molecules emit fluorescent signals during the sequencing reactions. In some embodiments, the sequencing reaction is conducted on a sequencing apparatus having a detector that captures fluorescent images from sequencing reactions on the immobilized template molecules. The sequencing apparatus can be configured to relay the fluorescent imaging data captured by the detector to a computer system that is programmed to determine the location (e.g., mapping) of the immobilized template molecules (polonies) on the flowcell. The computer system can generate a map of the locations of the immobilized template molecules based on the fluorescent imaging data of only the random sequence (e.g., NNN), or based on the random sequence (e.g., NNN) and at least a portion of the universal sample index sequence. Thus the few numbers of sequencing cycles used to sequence the random sequence (e.g., NNN) and optionally a portion of the universal sample index sequence can be used to generate a map of the location of the immobilized template molecules. The computer system can be configured to extract the fluorescent color and intensity of only the random sequence (e.g., NNN) or the random sequence (e.g., NNN) and the universal sample index sequence. The computer system can be configured to use the location of a given immobilized template molecule and the fluorescent color and intensity associated with the given template molecule (which were established while sequencing the random sequence) for base calling while sequencing the sequence of interest region (110). The computer system can be configured to detect phasing and pre-phasing while sequencing the random sequence (e.g., NNN) and the universal sample index sequence, and the sequence of interest region (110). In some embodiments, the balanced ratio of fluorescent colors provided by the random sequence (e.g., NNN) at each sequencing cycle can improve the quality of the data which is processed from the fluorescent images captured by the detector, and can in turn improve the capability by the computer system to determine the location of the immobilized template molecules on the flowcell, and the color and intensity, all of which can improve base calling accuracy and quality scores of the sequenced sequence of interest region (110).

A First Embodiment: Order of Sequencing Sample Index Sequences

In some embodiments, the order of sequencing comprises: (1) sequencing the first right sample index (170) wherein the right index comprises a first random sequence (e.g., NNN) and a right universal sample index sequence; (2) sequencing the first left sample index (160); and (3) sequencing the sequence of interest region (110). In some embodiments, the first left sample index (160) comprises a left universal sample index sequence. In some embodiments, the first left sample index (160) comprises a second random sequence (e.g., NNN) and a left universal sample index sequence. In some embodiments, sequencing the first right sample index region (170), including the first random sequence (e.g., NNN) and right universal sample index sequence, may provide enough nucleotide diversity so that sequencing the first left sample index (160) can be omitted.

In some embodiments of the methods for sequencing the template molecules immobilized to a support, individual template molecules comprise: (i) a universal binding sequence for a first surface primer (120), (ii) a first left sample index sequence (160) having a universal left sample index sequence, (iii) a second universal adaptor sequence for binding a forward sequencing primer (140), (iv) a sequence of interest (110), (v) a second universal adaptor sequence for binding a reverse sequencing primer (150), (vi) a first right sample index sequence having a short random sequence (e.g., NNN) linked directly to a right universal sample index sequence (170), and (vii) a first universal adaptor sequence for binding a second surface primer (130) (e.g., see FIGS. 5 and 6), wherein the method comprises step (a): hybridizing the template molecules with a first plurality of soluble sequencing primers that hybridize to the universal binding sequence for a reverse sequencing primer (150) and sequencing the first right sample index sequence (170) including sequencing the short random sequence (e.g., NNN) and the right universal sample index sequence, thereby generating a first plurality of sample index extension products that are hybridized to the immobilized template molecules, wherein the first plurality of sample index extension products are complementary to the right sample index sequence having a short random sequence (e.g., NNN) linked directly to a first right universal sample index sequence (170).

In some embodiments, the methods for sequencing comprise step (b): removing the first plurality of sample index extension products and retaining the immobilized template molecules.

In some embodiments, the methods for sequencing comprise step (c): hybridizing the retained immobilized template molecules with a second plurality of soluble sequencing primers that hybridize to the universal binding sequence for the first surface primer (120) and sequencing the first left sample index sequence (160) thereby generating a second plurality of sample index extension products that are hybridized to the immobilized template molecules, wherein the second plurality of sample index extension products are complementary to the first left sample index sequence (160) having a left universal sample index sequence.

In some embodiments, the methods for sequencing further comprise step (d): removing the second plurality of sample index extension products and retaining the immobilized template molecules.

In some embodiments, the methods for sequencing comprise step (e): hybridizing the retained immobilized template molecules with a third plurality of soluble sequencing primers that hybridize to the universal binding sequence for the forward sequencing primer (140) and sequencing the insert region (110) thereby generating a plurality of insert extension products that are hybridized to the immobilized template molecules, wherein the plurality of insert extension products are complementary to the sequence of interest (110).

In some embodiments, the methods for sequencing further comprise step (f1): assigning the sequence of (i) the insert region (110) to (ii) the right sample index sequence having a short random sequence (e.g., NNN) linked directly to a right universal sample index sequence (170), thereby identifying the insert region as being obtained from a first source.

In some embodiments, the methods for sequencing further comprise step (f2): assigning the sequence of (i) the insert region (110) to (ii) the right sample index sequence having a short random sequence (e.g., NNN) linked directly to a right universal sample index sequence (170), and (iii) the left sample index sequence (160), thereby identifying the insert region as being obtained from a first source.

In some embodiments, the removing of the plurality of sequencing extension products of steps (b) and (d) can be conducted using a denaturation reagent comprising SSC (e.g., saline-sodium citrate) buffer with or without formamide, at a temperature that promotes nucleic acid denaturation such as for example 50-90° C.

In some embodiments, the sequencing of steps (a), (c) and (e) include conducting any of the sequencing methods described herein that employ sequencing polymerases and detectably labeled nucleotide analogs. In some embodiments, the sequencing of steps (a), (c) and (e) include conducting any of the two-stage sequencing methods described herein that employ sequencing polymerases, detectably labeled multivalent molecules, and nucleotide analogs. In some embodiments, the sequencing of steps (a), (c) and (e) include conducting any of the sequencing-by-binding methods described herein.

In some embodiments, the density of the plurality of template molecules immobilized to the support is about $10^2$-$10^{15}$ per mm$^2$. In some embodiments, the plurality of template molecules are immobilized at random locations on the support. In some embodiments, the plurality of template molecules are immobilized on the support in a predetermined pattern.

A Second Embodiment: Order of Sequencing Sample Index Sequences

In some embodiments, the order of sequencing comprises: (1) sequencing the first right sample index (170) where the right index comprises a random sequence (e.g., NNN) and a universal sample index sequence; (2) sequencing the sequence of interest region (110); and (3) sequencing the first left sample index (160). In some embodiments, the first left sample index (160) comprises a left universal sample index sequence. In some embodiments, the first left sample index (160) comprises a second random sequence (e.g., NNN) and a left universal sample index sequence. In some embodiments, sequencing the first right sample index region (170), including the first random sequence (e.g., NNN) and right universal sample index sequence, may provide enough nucleotide diversity so that sequencing the left sample index (160) can be omitted.

In some embodiments of the methods for sequencing the template molecules immobilized to a support, individual template molecules comprise: (i) a first left universal adaptor sequence comprising a universal binding sequence for a first surface primer (120), (ii) a first left sample index sequence (160) having a left universal sample index sequence (iii) a second left universal adaptor sequence comprising a universal binding sequence for a forward sequencing primer (140), (iv) a sequence of interest (110), (v) a second right universal adaptor sequence comprising universal binding sequence for a reverse sequencing primer (150), (vi) a first right sample index sequence having a short random sequence (e.g., NNN) linked directly to a right universal sample index sequence (170), and (vii) a first right universal adaptor sequence comprising universal binding sequence for a second surface primer (130) (e.g., see FIGS. 5 and 6), wherein the method comprises step (a): hybridizing the template molecules with a first plurality of soluble sequencing primers that hybridize to the universal binding sequence for a reverse sequencing primer (150) and sequencing the right sample index sequence (170) including sequencing the short random sequence (e.g., NNN) and the right universal sample index sequence thereby generating a first plurality of sample index extension products that are hybridized to the immobilized template molecules, wherein the first plurality of sample index extension products are complementary to the right sample index sequence having a short random sequence (e.g., NNN) linked directly to a right universal sample index sequence (170).

In some embodiments, the methods for sequencing comprise step (b): removing the first plurality of sample index extension products and retaining the immobilized template molecules.

In some embodiments, the methods for sequencing comprise step (c): hybridizing the retained immobilized template molecules with a second plurality of soluble sequencing primers that hybridize to the universal binding sequence for a forward sequencing primer (140) and sequencing the sequence of interest region (110) thereby generating a plurality of insert extension products that are hybridized to the immobilized template molecules, wherein the plurality of insert extension products are complementary to the sequence of interest (110).

In some embodiments, the methods for sequencing comprise step (d): removing the plurality of insert extension products and retaining the immobilized template molecules.

In some embodiments, the methods for sequencing comprise step (e): hybridizing the retained immobilized template molecules with a third plurality of soluble sequencing primers that hybridize to the universal binding sequence for a first surface primer (120) and sequencing the left sample index sequence (160) thereby generating a second plurality of sample index extension products that are hybridized to the immobilized template molecules, wherein the second plurality of sample index extension products are complementary to the left sample index sequence (160) having a left universal sample index sequence.

In some embodiments, the methods for sequencing comprise step (f1): assigning the sequence of (i) the sequence of interest region (110) to (ii) the right sample index sequence having a short random sequence (e.g., NNN) linked directly to a right universal sample index sequence (170), thereby identifying the insert region as being obtained from a first source.

In some embodiments, the methods for sequencing comprise step (f2): assigning the sequence of (i) the sequence of interest region (110) to (ii) the right sample index sequence having a short random sequence (e.g., NNN) linked directly to a right universal sample index sequence (170), and (iii) the left sample index sequence (160), thereby identifying the insert region as being obtained from a first source.

In some embodiments, the removing of the plurality of sequencing extension products of steps (b) and (d) can be conducted using a denaturation reagent comprising SSC (e.g., saline-sodium citrate) buffer with or without formamide, at a temperature that promotes nucleic acid denaturation such as for example 50-90° C.

In some embodiments, the sequencing of steps (a), (c) and (e) include conducting any of the sequencing methods described herein that employ sequencing polymerases and detectably labeled nucleotide analogs. In some embodiments, the sequencing of steps (a), (c) and (e) include conducting any of the two-stage sequencing methods described herein that employ sequencing polymerases, detectably labeled multivalent molecules, and nucleotide analogs. In some embodiments, the sequencing of steps (a), (c) and (e) include conducting any of the sequencing-by-binding methods described herein.

In some embodiments, the density of the plurality of template molecules immobilized to the support is about $10^2$-$10^{15}$ per mm$^2$. In some embodiments, the plurality of template molecules are immobilized at random locations on the support. In some embodiments, the plurality of template molecules are immobilized on the support in a predetermined pattern.

A Third Embodiment: Order of Sequencing Sample Index Sequences

In some embodiments, the order of sequencing comprises: (1) sequencing the sequence of interest region (110); (2) sequencing the first right sample index (170) wherein the right index comprises a random sequence (e.g., NNN) and a universal sample index sequence; and (3) sequencing the first left sample index (160). In some embodiments, the left sample index (160) comprises a left universal sample index sequence. In some embodiments, the left sample index (160) comprises a second random sequence (e.g., NNN) and a left universal sample index sequence. In some embodiments, sequencing the right sample index region (170), including the first random sequence (e.g., NNN) and right universal sample index sequence, may provide enough nucleotide diversity so that sequencing the left sample index (160) can be omitted.

In some embodiments, of the methods for sequencing the template molecules immobilized to a support, individual template molecules comprise: (i) a first left universal adaptor sequence comprising a universal binding sequence for a first surface primer (120), (ii) a first left sample index sequence (160) having a left universal sample index sequence (iii) a second left universal adaptor sequence comprising a universal binding sequence for a forward sequencing primer (140), (iv) a sequence of interest (110), (v) a second right universal adaptor sequence comprising a universal binding sequence for a reverse sequencing primer (150), (vi) a first right sample index sequence having a short random sequence (e.g., NNN) linked directly to a right universal sample index sequence (170), and (vii) a first right universal adaptor sequence comprising a universal binding sequence for a second surface primer (130) (e.g., see FIGS. 5 and 6), wherein the method comprises step (a): hybridizing the template molecules with a first plurality of soluble sequencing primers that hybridize to the universal binding sequence for a forward sequencing primer (140) and sequencing the sequence of interest region (110) thereby generating a plurality of insert extension products that are hybridized to the immobilized template molecules, wherein the plurality of insert extension products are complementary to the sequence of interest (110).

In some embodiments, the methods for sequencing comprise step (b): removing the plurality of insert extension products and retaining the immobilized template molecules.

In some embodiments, the methods for sequencing comprise step (c): hybridizing the template molecules with a second plurality of soluble sequencing primers that hybridize to the universal binding sequence for a reverse sequencing primer (150) and sequencing the right sample index sequence (170) including sequencing the short random sequence (e.g., NNN) and the right universal sample index sequence thereby generating a first plurality of sample index extension products that are hybridized to the immobilized template molecules, wherein the first plurality of sample index extension products are complementary to the right sample index sequence having a short random sequence (e.g., NNN) linked directly to a right universal sample index sequence (170).

In some embodiments, the methods for sequencing comprise step (d): removing the first plurality of sample index extension products and retaining the immobilized template molecules.

In some embodiments, the methods for sequencing comprise step (e): hybridizing the retained immobilized template molecules with a third plurality of soluble sequencing primers that hybridize to the universal binding sequence for a first surface primer (120) and sequencing the left sample index sequence (160) thereby generating a second plurality of sample index extension products that are hybridized to the immobilized template molecules, wherein the second plurality of sample index extension products are complementary to the left sample index sequence (160) having a left universal sample index sequence.

In some embodiments, the methods for sequencing comprise step (f1): assigning the sequence of (i) the sequence of interest region (110) to (ii) the right sample index sequence having a short random sequence (e.g., NNN) linked directly to a right universal sample index sequence (170), thereby identifying the insert region as being obtained from a first source.

In some embodiments, the methods for sequencing comprise step (f2): assigning the sequence of (i) the insert region (110) to (ii) the right sample index sequence having a short random sequence (e.g., NNN) linked directly to a right universal sample index sequence (170), and (iii) the left sample index sequence (160), thereby identifying the insert region as being obtained from a first source.

In some embodiments, the removing of the plurality of sequencing extension products of steps (b) and (d) can be conducted using a denaturation reagent comprising SSC (e.g., saline-sodium citrate) buffer with or without formamide, at a temperature that promotes nucleic acid denaturation such as for example 50-90° C.

In some embodiments, the sequencing of steps (a), (c) and (e) include conducting any of the sequencing methods described herein that employ sequencing polymerases and detectably labeled nucleotide analogs. In some embodiments, the sequencing of steps (a), (c) and (e) include conducting any of the two-stage sequencing methods described herein that employ sequencing polymerases, detectably labeled multivalent molecules, and nucleotide analogs. In some embodiments, the sequencing of steps (a), (c) and (e) include conducting any of the sequencing-by-binding methods described herein.

In some embodiments, the density of the plurality of template molecules immobilized to the support is about $10^2$-$10^{15}$ per mm$^2$. In some embodiments, the plurality of template molecules are immobilized at random locations on the support. In some embodiments, the plurality of template molecules are immobilized on the support in a predetermined pattern.

A Fourth Embodiment: Order of Sequencing

In some embodiments, the order of sequencing comprises: (1) sequencing the first 3-5 bases of the sequence of interest region (110); (2) sequencing the first right sample index (170) wherein the right index comprises an optional random sequence (e.g., NNN) and a universal sample index sequence; and (3) sequencing the first left sample index (160). In some embodiments, the left sample index (160) comprises a left universal sample index sequence. In some embodiments, the left sample index (160) comprises a second random sequence (e.g., NNN) and a left universal sample index sequence. In some embodiments, sequencing the first 3-5 bases of the insert region (110) may provide enough sequence diversity so that the right sample index (170) and the left sample index (160) do not include a short random sequence (e.g., NNN). In some embodiments, sequencing the right sample index region (170), including the first random sequence (e.g., NNN) and right universal sample index sequence, may provide enough nucleotide diversity so that sequencing the left sample index (160) can be omitted.

In some embodiments of the methods for sequencing the template molecules immobilized to a support, individual template molecules comprise: (i) a first left universal adaptor sequence comprising a universal binding sequence for a first surface primer (120), (ii) a first left sample index sequence (160) having a left universal sample index sequence (iii) a second left universal adaptor sequence comprising a universal binding sequence for a forward sequencing primer (140), (iv) a sequence of interest (110), (v) a second right universal adaptor sequence comprising a universal binding sequence for a reverse sequencing primer (150), (vi) a first right sample index sequence having a short random sequence (e.g., NNN) linked directly to a right universal sample index sequence (170), and (vii) a first right universal adaptor sequence comprising a universal binding sequence for a second surface primer (130) (e.g., see FIGS. 5 and 6), wherein the method comprises step (a): hybridizing the template molecules with a first plurality of soluble sequencing primers that hybridize to the universal binding sequence for a forward sequencing primer (140) and sequencing the first 3-5 bases of the sequence of interest region (110) thereby generating a plurality of insert extension products that are hybridized to the immobilized template molecules, wherein the plurality of insert extension products are complementary to the sequence of interest (110). The sequence of the first 3-5 bases of the insert region (110) may provide sufficient sequence diversity and color balance for polony mapping and template registration.

In some embodiments, the methods for sequencing comprise step (b): removing the plurality of insert extension products and retaining the immobilized template molecules.

In some embodiments, the methods for sequencing comprise step (c): hybridizing the template molecules with a second plurality of soluble sequencing primers that hybridize to the universal binding sequence for a reverse sequencing primer (150) and sequencing the right sample index sequence (170) including sequencing the short random sequence (e.g., NNN) if present and the right universal sample index sequence thereby generating a first plurality of sample index extension products that are hybridized to the immobilized template molecules, wherein the first plurality of sample index extension products are complementary to the right sample index sequence (170).

In some embodiments, the methods for sequencing comprise step (d): removing the first plurality of sample index extension products and retaining the immobilized template molecules.

In some embodiments, the methods for sequencing comprise step (e): hybridizing the retained immobilized template molecules with a third plurality of soluble sequencing primers that hybridize to the universal binding sequence for a first surface primer (120) and sequencing the left sample index sequence (160) thereby generating a second plurality of sample index extension products that are hybridized to the immobilized template molecules, wherein the second plurality of sample index extension products are complementary to the left sample index sequence (160) having a left universal sample index sequence.

In some embodiments, the methods for sequencing comprise step (f): removing the second plurality of sample index extension products and retaining the immobilized template molecules.

In some embodiments, the methods for sequencing comprise step (g): hybridizing the template molecules with a fourth plurality of soluble sequencing primers that hybridize to the universal binding sequence for a forward sequencing primer (140) and sequencing the full length of the sequence of interest (110) thereby generating a plurality of full length insert extension products that are hybridized to the immobilized template molecules, wherein the plurality of full length insert extension products are complementary to the sequence of interest (110).

In some embodiments, the methods for sequencing comprise step (h1): assigning the full length sequence of (i) the sequence of interest region (110) to (ii) the right sample index sequence (170), thereby identifying the insert region as being obtained from a first source.

In some embodiments, the methods for sequencing comprise step (h2): assigning the full length sequence of (i) the sequence of interest region (110) to (ii) the right sample index sequence (170), and (iii) the left sample index sequence (160), thereby identifying the insert region as being obtained from a first source.

In some embodiments, the removing of the plurality of sequencing extension products of steps (b), (d) and (f) can be conducted using a denaturation reagent comprising SSC (e.g., saline-sodium citrate) buffer with or without formamide, at a temperature that promotes nucleic acid denaturation such as for example 50-90° C.

In some embodiments, the sequencing of steps (a), (c), (e) and (g) include conducting any of the sequencing methods described herein that employ sequencing polymerases and detectably labeled nucleotide analogs. In some embodiments, the sequencing of steps (a), (c), (e) and (g) include conducting any of the two-stage sequencing methods described herein that employ sequencing polymerases, detectably labeled multivalent molecules, and nucleotide analogs. In some embodiments, the sequencing of steps (a), (c), (e) and (g) include conducting any of the sequencing-by-binding methods described herein.

In some embodiments, the density of the plurality of template molecules immobilized to the support is about $10^2$-$10^{15}$ per $mm^2$. In some embodiments, the plurality of template molecules are immobilized at random locations on the support. In some embodiments, the plurality of template molecules are immobilized on the support in a predetermined pattern.

A Fifth Embodiment: Order of Sequencing

In some embodiments, the order of sequencing comprises: (1) sequencing the first 3-5 bases of the sequence of interest region (110) of the immobilized template molecule (e.g., sequencing in a forward direction); (2) sequencing the first right sample index (170) where the right index comprises a first random sequence (e.g., NNN) and a right universal sample index sequence; (3) sequencing the first left sample index (160); (4) conducting a pairwise turn reaction so that the immobilized template molecule is replaced with an immobilized strand that is complementary to the template molecule; and (5) sequencing the full-length of the sequence of interest region (110) of the immobilized complementary strand (e.g., sequencing in the reverse direction). In some embodiments, the sequences of the first 3-5 bases of the sequence of interest region (110) of a population of library molecules may provide enough sequence diversity for improved base-calling accuracy. In some embodiments, the first left sample index (160) comprises a left universal sample index sequence. In some embodiments, the left sample index (160) comprises a second random sequence (e.g., NNN) and a left universal sample index sequence. In some embodiments, sequencing the right sample index region (170), including the first random sequence (e.g., NNN) and right universal sample index sequence, may provide enough nucleotide diversity so that sequencing the left sample index (160) can be omitted.

In some embodiments of the methods for sequencing the template molecules immobilized to a support, individual template molecules are covalently linked to an immobilized capture primer that lacks uracil bases, and individual template molecules comprise randomly-distributed uracil bases, and individual template molecules comprise: (i) a first left universal adaptor sequence comprising a universal binding sequence for a first surface primer (120), (ii) a first left sample index sequence (160) having a left universal sample index sequence (iii) a second left universal adaptor sequence comprising a universal binding sequence for a forward sequencing primer (140), (iv) a sequence of interest (110), (v) a second right universal adaptor sequence comprising a universal binding sequence for a reverse sequencing primer (150), (vi) a first right sample index sequence having a short random sequence (e.g., NNN) linked directly to a right universal sample index sequence (170), and (vii) a first right universal adaptor sequence comprising a universal binding sequence for a second surface primer (130) (e.g., see FIGS. 5 and 6), wherein the method comprises step (a): hybridizing the template molecules with a first plurality of soluble sequencing primers (e.g., forward sequencing primers) that hybridize to the universal binding sequence for a forward sequencing primer (140) and sequencing the first 3-5 bases of the sequence of interest region (110) thereby generating a plurality of insert extension products that are hybridized to the immobilized template molecules, wherein the plurality of insert extension products are complementary to the sequence of interest (110).

In some embodiments, the methods for sequencing comprise step (b): removing the plurality of insert extension products and retaining the immobilized template molecules.

In some embodiments, the methods for sequencing comprise step (c): hybridizing the template molecules with a second plurality of soluble sequencing primers that hybridize to the universal binding sequence for a reverse sequencing primer (150) and sequencing the right sample index sequence (170) including sequencing the short random sequence (e.g., NNN) and the right universal sample index sequence thereby generating a first plurality of sample index extension products that are hybridized to the immobilized template molecules, wherein the first plurality of sample index extension products are complementary to the right sample index sequence having a short random sequence (e.g., NNN) linked directly to a right universal sample index sequence (170).

In some embodiments, the methods for sequencing comprise step (d): removing the first plurality of sample index extension products and retaining the immobilized template molecules.

In some embodiments, the methods for sequencing comprise step (e): hybridizing the retained immobilized template molecules with a third plurality of soluble sequencing primers that hybridize to the universal binding sequence for a first surface primer (120) and sequencing the left sample index sequence (160) thereby generating a second plurality of sample index extension products that are hybridized to the immobilized template molecules, wherein the second plurality of sample index extension products are complementary to the left sample index sequence (160) having a left universal sample index sequence.

In some embodiments, the methods for sequencing comprise step (f): replacing the second plurality of sample index extension products that are hybridized to the immobilized template molecules by conducting a primer extension reaction using strand-displacing polymerases and a plurality of nucleotides to generate an extension product that is hybridized to the immobilized template molecules including the immobilized capture primer.

In some embodiments, the methods for sequencing comprise step (g): removing the immobilized template molecules by generating abasic sites in the immobilized template molecules at the uracil sites and generating gaps at the abasic sites thereby generating gap-containing template molecules while retaining the extension products that was generated in step (f) wherein individual extension products are retained by being hybridized to an immobilized capture primer. In some embodiments, pairwise turn is achieved by conducting steps (g) and (h).

In some embodiments, the methods for sequencing comprise step (h): hybridizing the retained extension products with a fourth plurality of soluble sequencing primers (e.g., reverse sequencing primers) that hybridize to universal binding sequence for a reverse sequencing primer (150) and sequencing the sequence of interest region (110) (e.g., sequencing at least a portion or the full length of the sequence of interest region (110)).

In some embodiments, the methods for sequencing comprise step (i1): assigning the sequence of (i) the sequence of interest region (110) to (ii) the right sample index sequence having a short random sequence (e.g., NNN) linked directly to a right universal sample index sequence (170), thereby identifying the insert region as being obtained from a first source.

In some embodiments, the methods for sequencing comprise step (i2): assigning the sequence of (i) the sequence of interest region (110) to (ii) the right sample index sequence having a short random sequence (e.g., NNN) linked directly to a right universal sample index sequence (170), and (iii) the left sample index sequence (160), thereby identifying the insert region as being obtained from a first source.

In some embodiments, the removing of the plurality of sequencing extension products of steps (b) and (d) can be conducted using a denaturation reagent comprising SSC (e.g., saline-sodium citrate) buffer with or without formamide, at a temperature that promotes nucleic acid denaturation such as for example 50-90° C.

In some embodiments, the sequencing of steps (a), (c), (e) and (h) include conducting any of the sequencing methods described herein that employ sequencing polymerases and detectably labeled nucleotide analogs. In some embodiments, the sequencing of steps (a), (c), (e) and (h) include conducting any of the two-stage sequencing methods described herein that employ sequencing polymerases, detectably labeled multivalent molecules, and nucleotide analogs. In some embodiments, the sequencing of steps (a), (c), (e) and (h) include conducting any of the sequencing-by-binding methods described herein.

In some embodiments, the density of the plurality of template molecules immobilized to the support is about $10^2$-$10^{15}$ per mm$^2$. In some embodiments, the plurality of template molecules are immobilized at random locations on the support. In some embodiments, the plurality of template molecules are immobilized on the support in a predetermined pattern.

Sequencing 3-Mer Random Sequences to Generate a Polony Map The present disclosure provides methods for sequencing nucleic acids comprising: (a) providing a plurality of nucleic acid template molecules immobilized on a support (e.g., immobilized at random or pre-determined locations), wherein individual immobilized template molecules comprise an sequence of interest region and at least one sample index, wherein the at least one sample index comprises a 3-mer random sequence joined to a universal sample index sequence which identifies the sample source of the insert sequence, wherein different immobilized template molecules have a different 3-mer random sequence and the same universal sample index sequence, and wherein the immobilized template molecules have different insert sequences; (b) conducting three cycles of polymerase-mediated sequencing reactions of the 3-mer random sequence of the plurality of immobilized template molecules using a plurality of detectably labeled nucleotide reagents comprising a mixture of different types of nucleo-bases A, G, C and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized template molecules thereby determining the sequences of the 3-mer random sequences in individual template molecules of the plurality of immobilized template molecules, and wherein a balanced diversity of nucleo-bases of A, G, C and T/U is detected and imaged in each of the first, second and third sequencing cycles among the plurality of immobilized template molecules; and (c) generating a map of the locations of the plurality of immobilized template molecules using the images obtained in step (b), wherein the sequence of the insert region is not used to generate the map.

In some embodiments of the methods for sequencing nucleic acids, the balanced diversity of step (b) is about 5-85%, or about 5-60%, or about 10-50%, or about 15-55%, or about 25-75% of each of the nucleo-bases A, G, C and T/U that are detected and imaged in each of the first, second and third sequencing cycles.

In some embodiments of the methods for sequencing nucleic acids, the method comprises: (a) sequencing the universal sample index sequence of the plurality of immobilized template molecules; (b) sequencing the sequence of interest region of the plurality of immobilized template molecules; and (c) assigning the sequence of interest of a given template molecule obtained in step (b) to the universal sample index sequence from the same given template molecule obtained in step (a), thereby identifying the sample source of the given insert sequence.

In some embodiments of the methods for sequencing nucleic acids, the plurality of nucleic acid template molecules comprise a second sample index which comprises a second universal sample index sequence which identifies the sample source of the insert sequence and the second sample index lacks a random sequence.

In some embodiments of the methods for sequencing nucleic acids, the methods comprise: (a) sequencing the 3-mer random sequence of the plurality of immobilized template molecules to obtain a balanced diversity of nucleo-bases of A, G, C and T/U that are detected and imaged in each of the first, second and third sequencing cycles to generate a map of the locations of the plurality of immobilized template molecules; (b) sequencing the first universal sample index sequence of the plurality of immobilized template molecules; (c) sequencing the second universal sample index sequence of the plurality of immobilized template molecules; (d) sequencing the sequence of interest region of the plurality of immobilized template molecules; and (e) assigning the sequence of interest of a given template molecule obtained in step (c) to the first and second universal sample index sequences from the same given template molecule obtained in steps (a) and (b), thereby identifying the sample source of the given insert sequence.

The present disclosure provides methods for sequencing nucleic acids comprising: (a) providing a plurality of nucleic acid template molecules immobilized on a support (e.g., immobilized at random or pre-determined locations), wherein individual immobilized template molecules comprise an sequence of interest region and one sample index, wherein the sample index comprises a 3-mer random sequence joined to a universal sample index sequence which identifies the sample source of the insert sequence, wherein the universal sample index sequence comprises 3-20 nucleotides, wherein different immobilized template molecules have a different 3-mer random sequence and the same universal sample index sequence, and wherein the immobilized template molecules have different insert sequences; (b) conducting four cycles of polymerase-mediated sequencing reactions of the 3-mer random sequence and the first base position of the universal sample index sequence of the plurality of immobilized template molecules using a plurality of detectably labeled nucleotide reagents comprising a mixture of different types of nucleo-bases A, G, C and T/U, wherein the nucleotide reagents comprise a different detectable color label that corresponds with each different type of nucleo-base, wherein the four cycles of sequencing include detecting and imaging the optical color signals emitted from the detectably labeled nucleotide reagents that are bound to the immobilized template molecules thereby determining the sequences of the 3-mer random sequences and the first base position of the universal sample index sequences in individual template molecules of the plurality of immobilized template molecules, and wherein a balanced diversity of nucleo-bases of A, G, C and T/U is detected and imaged in each of the first, second, third and fourth sequencing cycles among the plurality of immobilized template molecules; and (c) generating a map of the locations of the plurality of immobilized template molecules using the images of the four cycles of polymerase-mediated sequencing reactions obtained in step (b), wherein the sequence of the insert region is not used to generate the map.

In some embodiments of the methods for sequencing nucleic acids, the balanced diversity of step (b) is about 5-85%, or about 5-60%, or about 10-50%, or about 15-55%, or about 25-75% of each of the nucleo-bases A, G, C and T/U that are detected and imaged in each of the first, second, third and fourth sequencing cycles.

In some embodiments of the methods for sequencing nucleic acids, the methods comprise: (a) sequencing the remaining base positions of the universal sample index sequence of the plurality of immobilized template molecules; (b) sequencing the sequence of interest region of the plurality of immobilized template molecules; and (c) assigning the sequence of interest of a given template molecule obtained in step (b) with the universal sample index sequence from the same given template molecule obtained in step (a), thereby identifying the sample source of the given sequence of interest.

In some embodiments, in the methods for sequencing nucleic acids, the plurality of nucleic acid template molecules comprise: a second sample index which comprises a second universal sample index sequence which identifies the sample source of the insert sequence and the second sample index lacks a random sequence.

In some embodiments, in the methods for sequencing nucleic acids, the methods comprise: (a) sequencing the 3-mer random sequence and the first base position of the universal sample index sequence of the plurality of immobilized template molecules to obtain a balanced diversity of nucleo-bases of A, G, C and T/U that are detected and imaged in each of the first, second, third and fourth sequencing cycles to generate a map of the locations of the plurality of immobilized template molecules; (b) sequencing the remaining base positions of the first universal sample index sequence of the plurality of immobilized template molecules; (c) sequencing the second universal sample index sequence of the plurality of immobilized template molecules; (d) sequencing the sequence of interest region of the plurality of immobilized template molecules; and (e) assigning the sequence of interest of a given template molecule obtained in step (c) with the first and second universal sample index sequences from the same given template molecule obtained in steps (a) and (b), thereby identifying the sample source of the given sequence of interest.

In some embodiments, in any of the methods for sequencing nucleic acids, the support comprises a glass or plastic substrate. In some embodiments, the support is configured on a flowcell channel, a flow cell, or a capillary lumen. In some embodiments, the support is passivated with at least one hydrophilic polymer coating having a water contact angle of not more than 45 degrees. In some embodiments, the at least one hydrophilic polymer coating comprises a molecule selected from a group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the at least one hydrophilic polymer coating comprises branched hydrophilic polymer molecules having at least four branches. In some embodiments, the at least one hydrophilic polymer coating comprises polymer molecules having a molecular weight of at least 1000 Daltons.

In some embodiments of the methods for sequencing nucleic acids, the immobilized template molecules comprise a plurality of immobilized concatemer molecules having tandem repeat sequences of the sequence of interest and the one sample index. In some embodiments, the immobilized template molecules comprise a plurality of different clustered template molecules having one copy of the sequence of interest and one copy of the one sample index, wherein the clustered template molecules are generated via bridge amplification. In some embodiments, the density of the immobilized nucleic acid template molecules positioned at random or pre-determined locations on the support is $10^4$-$10^8$ per $mm^2$. In some embodiments, the sample source of the sequences of interest is genomic DNA, double-stranded cDNA or cell free circulating DNA.

In some embodiments of the methods for sequencing nucleic acids, the detectably labeled nucleotide reagents comprise nucleotides comprise an aromatic nucleo-base, a five carbon sugar moiety, 1-10 phosphate groups, and a fluorophore. In some embodiments, the detectably labeled nucleotide reagents comprise nucleotides comprising an aromatic nucleo-base, a five carbon sugar moiety having a chain terminating group at the 3' carbon sugar position, 1-10 phosphate groups, and a fluorophore. In some embodiments, the detectably labeled nucleotide reagents comprise multivalent molecules comprising (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments of the methods for sequencing nucleic acids, the detectably labeled nucleotide reagents that are bound to the immobilized template molecules in step (b) comprise individual immobilized template molecules hybridized to a sequencing primer to form a duplex, and the duplex is bound to a polymerase to form a complexed polymerase, and the complexed polymerase is bound to a detectably labeled nucleotide reagent. In some embodiments, the complexed polymerase is bound to a detectably labeled nucleotide reagent under conditions suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety, 1-10 phosphate groups, and a fluorophore. In some embodiments, the complexed polymerase is bound to a detectably labeled nucleotide reagent under conditions suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety having a chain terminating group at the 3' carbon sugar position, 1-10 phosphate groups, and a fluorophore. In some embodiments, the complexed polymerase is bound to a detectably labeled nucleotide reagent under conditions suitable for binding the detectably labeled nucleotide reagent to the complexed polymerase and the condition is suitable for inhibiting nucleotide incorporation, wherein the detectably labeled nucleotide reagent comprises a multivalent molecule which includes (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments of the methods for sequencing nucleic acids, the immobilized template molecule comprises an immobilized concatemer molecule which is hybridized to a plurality of sequencing primers to form at least a first and second duplex on the same concatemer molecule, wherein the first and duplex is bound to a first polymerase and the second duplex is bound to a second polymerase to form first and second complexed polymerases, and wherein the method comprises: (a) contacting a plurality of multivalent molecules to the first and second complexed polymerases on the same concatemer template molecule, wherein individual multivalent molecules include (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, and the spacer is attached to the linker, and the linker is attached to the nucleotide unit, wherein the contacting is conducted under conditions suitable to bind a single multivalent molecule from the plurality to the first and second complexed polymerases, wherein a first nucleotide unit of the single multivalent molecule is bound to the first complexed polymerase which includes the first sequencing primer hybridized to a first portion of the concatemer template molecule thereby forming a first binding complex, and wherein a second nucleotide unit of the single multivalent molecule is bound to the second complexed polymerase which includes the second sequencing primer hybridized to a second portion of the concatemer template molecule thereby forming a second binding complex, wherein the first and second binding complexes which are bound to the same multivalent molecule forms an avidity complex, and wherein the contacting is conducted under a condition suitable to inhibit polymerase-catalyzed incorporation of the bound first and second nucleotide units in the first and second binding complexes; (b) detecting the first and second binding complexes on the same concatemer template molecule; (c) imaging the optical color signals emitted from the detectably labeled multivalent molecule which forms the first and second binding complexes on the same concatemer template molecule; and (d) identifying the first nucleotide unit in the first binding complex thereby determining the sequence of the first portion of the concatemer template molecule, and identifying the second nucleotide unit in the second binding complex thereby determining the sequence of the second portion of the concatemer template molecule.

Multiplex Sequencing 3-Mer Random Sequences to Generate a Polony Map

The present disclosure provides methods for multiplex sequencing nucleic acids comprising: (a) providing a first plurality of library molecules, wherein individual molecules in the plurality comprise (i) a sequence of interest region derived from a first sample source, (ii) a first sample index having a 3-mer random sequence joined to a first universal sample index sequence, and (iii) a second sample index having a second universal sample index sequence which lacks a random sequence, wherein the combination of the first and second universal sample index sequences uniquely identifies a first sample source of the sequence of interest, wherein different first library molecules have a different 3-mer random sequence and have a different insert sequence; (b) providing a second plurality of library molecules, wherein individual molecules in the plurality comprising (i) a sequence of interest region derived from a second sample source, (ii) a third sample index having a 3-mer random sequence joined to a third universal sample index sequence, and (iii) a fourth sample index having a fourth universal sample index sequence which lacks a random sequence, wherein the combination of the third and fourth universal sample index sequences uniquely identifies a second sample source of the sequence of interest, wherein different second library molecules have a different 3-mer random sequence and have a different sequence of interest; (c) pooling the first and second plurality of library molecules; (d) distributing the pooled library molecules onto a support and conducting an amplification reaction to generate a plurality of clonally amplified template molecules immobilized to the support (e.g., immobilized at random or pre-determined locations); (e) conducting three cycles of polymerase-mediated sequencing reactions of the 3-mer random sequence of the first and third sample indexes using a plurality of detectably labeled nucleotide reagents comprising a mixture of different types of nucleo-bases A, G, C and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized amplified template molecules thereby determining the sequences of the 3-mer random sequences in individual template molecules of the plurality of immobilized template molecules, and wherein a balanced diversity of nucleo-bases of A, G, C and T/U is detected and imaged in each of the first, second and third sequencing cycles among the plurality of immobilized amplified template molecules; and (f) generating a map of the locations of the plurality of immobilized template molecules using the images obtained in step (e), wherein the sequences of the sequence of interest regions are not used to generate the map.

In some embodiments of the methods for multiplex sequencing nucleic acids, the balanced diversity of step (e) is about 5-85%, or about 5-60%, or about 10-50%, or about 15-55%, or about 25-75% of each of the nucleo-bases A, G, C and T/U that are detected and imaged in each of the first, second and third sequencing cycles.

In some embodiments of the methods for multiplex sequencing nucleic acids, the methods further comprises: (a) sequencing the first universal sample index sequences of the plurality of immobilized template molecules; (b) sequencing the second universal sample index sequences of the plurality of immobilized template molecules; (c) sequencing the sequence of interest regions of the plurality of immobilized template molecules derived from the first library molecules; and (d) assigning the sequence of interest of a given template molecule obtained in step (c) with the first and second universal sample index sequences from the same given template molecule thereby identifying the first sample source of the given sequence of interest.

In some embodiments, in the methods for multiplex sequencing nucleic acids, the method comprises: (a) sequencing the third universal sample index sequences of the plurality of immobilized template molecules; (b) sequencing the fourth universal sample index sequences of the plurality of immobilized template molecules; (c) sequencing the sequence of interest regions of the plurality of immobilized template molecules derived from the second library molecules; and (d) assigning the sequence of interest of a given template molecule obtained in step (c) with the third and fourth universal sample index sequences from the same given template molecule thereby identifying the second sample source of the given sequence of interest.

The present disclosure provides methods for multiplex sequencing nucleic acids comprising: (a) providing a first plurality of library molecules wherein individual molecules in the plurality comprised (i) a sequence of interest region derived from a first sample source, (ii) a first sample index having a 3-mer random sequence joined to a first universal sample index sequence, and (iii) a second sample index having a second universal sample index sequence which lacks a random sequence, wherein the combination of the first and second universal sample index sequences uniquely identifies a first sample source of the sequence of interest, wherein the first universal sample index sequence comprises 3-20 nucleotides, wherein different first library molecules have a different 3-mer random sequence and have a different sequence of interest; (b) providing a second plurality of library molecules each molecule in the plurality comprising (i sequence of interest region derived from a second sample source, (ii) a third sample index having a 3-mer random sequence joined to a third universal sample index sequence, and (iii) a fourth sample index having a fourth universal sample index sequence which lacks a random sequence, wherein the combination of the third and fourth universal sample index sequences uniquely identifies a second sample source of the sequence of interest, wherein the third universal sample index sequence comprises 3-20 nucleotides, wherein different second library molecules have a different 3-mer random sequence and have a different insert sequence; (c) pooling the first and second plurality of library molecules; (d) distributing the pooled library molecules onto a support and conducting an amplification reaction to generate a plurality of clonally amplified template molecules immobilized to the support (e.g., immobilized at random or pre-determined locations); (e) conducting four cycles of polymerase-mediated sequencing reactions of the 3-mer random sequence of the first and third sample indexes and sequencing the first base position of the first and third universal sample index sequences using a plurality of detectably labeled nucleotide reagents comprising a mixture of different types of nucleo-bases A, G, C and T/U, wherein the nucleotide reagents comprise a different detectable color label that corresponds with each different type of nucleo-base, wherein the three cycles of sequencing include detecting and imaging the optical color signals emitted from the detectably labeled nucleotide reagents that are bound to the immobilized amplified template molecules thereby determining the sequences of the 3-mer random sequences in individual template molecules of the plurality of immobilized template molecules, and wherein a balanced diversity of nucleo-bases of A, G, C and T/U is detected and imaged in each of the first, second, third and fourth sequencing cycles among the plurality of immobilized amplified template molecules; and (f) generating a map of the locations of the plurality of immobilized template molecules using the images obtained in step (e), wherein the sequence of the sequence of interest regions are not used to generate the map.

In some embodiments, in the methods for multiplex sequencing nucleic acids, the balanced diversity of step (e) is about 5-85%, or about 5-60%, or about 10-50%, or about 15-55%, or about 25-75% of each of the nucleo-bases A, G, C and T/U that are detected and imaged in each of the first, second, third and fourth sequencing cycles.

In some embodiments of the methods for multiplex sequencing nucleic acids, the methods further comprise: (a) sequencing the remaining base positions of the first universal sample index sequences of the plurality of immobilized template molecules; (b) sequencing the second universal sample index sequences of the plurality of immobilized template molecules; (c) sequencing the sequence of interest regions of the plurality of immobilized template molecules derived from the first library molecules; and (d) assigning the sequence of interest of a given template molecule obtained in step (c) with the first and second universal sample index sequences from the same given template molecule thereby identifying the first sample source of the given sequence of interest.

In some embodiments of the methods for multiplex sequencing nucleic acids, the methods comprise: (a) sequencing the remaining base positions of the third universal sample index sequences of the plurality of immobilized template molecules; (b) sequencing the fourth universal sample index sequences of the plurality of immobilized template molecules; (c) sequencing the sequence of interest regions of the plurality of immobilized template molecules derived from the second library molecules; and (d) assigning the sequence of interest of a given template molecule obtained in step (c) with the third and fourth universal sample index sequences from the same given template molecule thereby identifying the second sample source of the given sequence of interest.

In some embodiments, in any of the methods for multiplex sequencing nucleic acids, the support comprises a glass or plastic substrate. In some embodiments, the support is configured on a flowcell channel, a flow cell, or a capillary lumen. In some embodiments, the support is passivated with at least one hydrophilic polymer coating having a water contact angle of not more than 45 degrees. In some embodiments, the at least one hydrophilic polymer coating comprises a molecule selected from a group consisting of polyethylene glycol (PEG), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the at least one hydrophilic polymer coating comprises branched hydrophilic polymer molecules having at least four branches. In some embodiments, the at least one hydrophilic polymer coating comprises polymer molecules having a molecular weight of at least 1000 Daltons.

In some embodiments, in any of the methods for multiplex sequencing nucleic acids, the immobilized template molecules comprise a plurality of immobilized concatemer molecules having tandem repeat sequences of the sequence of interest and the one sample index. In some embodiments, the immobilized template molecules comprise a plurality of different clustered template molecules having one copy of the sequence of interest and one copy of the one sample index, wherein the clustered template molecules are generated via bridge amplification. In some embodiments, the density of the immobilized nucleic acid template molecules (e.g., immobilized at random or pre-determined locations) on the support is $10^4$-$10^8$ per $mm^2$. In some embodiments, the sample source of the sequences of interest is genomic DNA, double-stranded cDNA or cell free circulating DNA.

In some embodiments, in any of the methods for multiplex sequencing nucleic acids, the detectably labeled nucleotide reagents comprise nucleotides each comprising an aromatic nucleo-base, a five carbon sugar moiety, 1-10 phosphate groups, and a fluorophore. In some embodiments, the detectably labeled nucleotide reagents comprise nucleotides each comprising an aromatic nucleo-base, a five carbon sugar moiety having a chain terminating group at the 3' carbon sugar position, 1-10 phosphate groups, and a fluorophore. In some embodiments, the detectably labeled nucleotide reagents comprise multivalent molecules each comprising (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments of the methods for multiplex sequencing nucleic acids, the detectably labeled nucleotide reagents that are bound to the immobilized template molecules in step (e) comprise individual immobilized template molecules hybridized to a sequencing primer to form a duplex, and the duplex is bound to a polymerase to form a complexed polymerase, and the complexed polymerase is bound to a detectably labeled nucleotide reagent. In some embodiments, the complexed polymerase is bound to a detectably labeled nucleotide reagent under conditions suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety, 1-10 phosphate groups, and a fluorophore. In some embodiments, the complexed polymerase is bound to a detectably labeled nucleotide reagent under conditions suitable for binding the detectably labeled nucleotide reagent to the complexed polymerase and incorporating the detectably labeled nucleotide into the hybridized sequencing primer, wherein the detectably labeled nucleotide reagent comprises an aromatic nucleo-base, a five carbon sugar moiety having a chain terminating group at the 3' carbon sugar position, 1-10 phosphate groups, and a fluorophore. In some embodiments, the complexed polymerase is bound to a detectably labeled nucleotide reagent under conditions suitable for binding the detectably labeled nucleotide reagent to the complexed polymerase and the conditions are suitable for inhibiting nucleotide incorporation, wherein the detectably labeled nucleotide reagent comprises a multivalent molecule which includes (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit.

In some embodiments of the methods for multiplex sequencing nucleic acids, the immobilized template molecule comprises an immobilized concatemer molecule which is hybridized to a plurality of sequencing primers to form at least a first and second duplex on the same concatemer molecule, wherein the first and duplex is bound to a first polymerase and the second duplex is bound to a second polymerase to form first and second complexed polymerases, and the method comprises: (a) contacting a plurality of multivalent molecules to the first and second complexed polymerases on the same concatemer template molecule, wherein individual multivalent molecules include (1) a core, (2) a plurality of nucleotide arms, and (3) at least one fluorophore, wherein individual nucleotide arms comprise (i) a core attachment moiety, (ii) a spacer comprising a PEG moiety, (iii) a linker, and (iv) a nucleotide unit, wherein the core is attached to the plurality of nucleotide arms, and the spacer is attached to the linker, and the linker is attached to the nucleotide unit, wherein the contacting is conducted under conditions suitable to bind a single multivalent molecule from the plurality to the first and second complexed polymerases, wherein a first nucleotide unit of the single multivalent molecule is bound to the first complexed polymerase which includes the first sequencing primer hybridized to a first portion of the concatemer template molecule thereby forming a first binding complex, and wherein a second nucleotide unit of the single multivalent molecule is bound to the second complexed polymerase which includes the second sequencing primer hybridized to a second portion of the concatemer template molecule thereby forming a second binding complex, wherein the first and second binding complexes which are bound to the same multivalent molecule forms an avidity complex, and wherein the contacting is conducted under conditions suitable to inhibit polymerase-catalyzed incorporation of the bound first and second nucleotide units in the first and second binding complexes; (b) detecting the first and second binding complexes on the same concatemer template molecule; (c) imaging the optical color signals emitted from the detectably labeled multivalent molecule which forms the first and second binding complexes on the same concatemer template molecule; and (d) identifying the first nucleotide unit in the first binding complex thereby determining the sequence of the first portion of the concatemer template molecule, and identifying the second nucleotide unit in the second binding complex thereby determining the sequence of the second portion of the concatemer template molecule.

Library Molecules

The present disclosure provides nucleic acid library molecules (100) and methods for preparing library-splint complexes (500) and covalently closed circular library molecules (600). The nucleic acid library molecules comprise DNA, RNA, cDNA or chimeric DNA/RNA. The nucleic acid library molecule can be single-stranded or double-stranded, or can include single-stranded or double-stranded portions. The nucleic acid library molecule can be linear, concatemeric, covalently closed circular, dumbbell, hairpin or other forms.

The term nucleic acid "library molecules" as used herein typically refers to a population of nucleic acid molecules each comprising a sequence of interest (e.g., insert (100)) covalently joined to at least one universal adaptor sequence (e.g., (120) and (130). Individual library molecules in the population can include additional universal adaptor sequences, and can further comprise at least one index sequence or unique identification sequence. Individual library molecules in the population can have a sequence of interest that is the same or different as other library molecules in the population.

The sequence of interest region (sometimes also termed "insert region") of a nucleic acid library molecule comprises a sequence of interest extracted from any source including a biological sample (e.g., fresh or live sample) such as a single cell, a plurality of cells or tissue. The sequence of interest region can be isolated from healthy or diseases cells or tissues. The sequence of interest region can be obtained from an archived sample such as a fresh frozen paraffin embedded (FFPE) sample, or from needle biopsies, circulating tumor cells, cell free circulating DNA (e.g., from tumor cells or a fetus). Cells or tissues are typically treated with a lysis buffer to release their DNA and RNA, and the desired nucleic acid is separated from non-desired macromolecules such as proteins.

The sequence of interest of a nucleic acid library molecule can be isolated in any form, including chromosomal, genomic (e.g., whole genomic), organellar (e.g., mitochondrial, chloroplast or ribosomal), recombinant molecules, cloned or amplified. The insert region of a nucleic acid library molecule can be methylated or non-methylated.

The sequence of interest can be isolated from any organism including viruses, fungi, prokaryotes or eukaryotes. The sequence of interest can be isolated from any organism including human, simian, ape, canine, feline, bovine, equine, murine, porcine, caprine, lupine, ranine, piscine, plant, insect or bacteria. The sequence of interest can be isolated from organisms borne in air, water, soil or food.

The sequence of interest can be isolated from any biological fluid, including blood, urine, serum, lymph, tumor, saliva, anal secretions, vaginal secretions, amniotic samples, perspiration, semen, environmental samples or culture samples. The insert region can be isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

The sequence of interest can be prepared using recombinant nucleic acid technology including but not limited to any combination of vector cloning, transgenic host cell preparation, host cell culturing and/or PCR amplification.

The sequence of interest can be appended on one or both ends to at least one universal adaptor sequence to form a recombinant nucleic acid library molecule. The universal adaptor sequences can be prepared using chemical synthesis procedures using native nucleotides with or without nucleotide analogs or modified nucleotide linkages that confer certain properties, including resistance to enzymatic digestion, or increased thermal stability. Examples of nucleotide analogs and modified nucleotide linkages that inhibit nuclease digestion include phosphorothioate, 2'-O-methyl RNA, inverted dT, and 2' 3' dideoxy-dT. Insert regions that include locked nucleic acids (LNA) have increased thermal stability.

The sequence of interest can be in fragmented or unfragmented form. Fragmented insert regions can be obtained by mechanical force, enzymatic or chemical fragmentation methods. The fragmented sequences of interest can be generated using procedures that yield a population of fragments having overlapping sequences or non-overlapping sequences.

Mechanical fragmentation typically generates randomly fragmented nucleic acid molecules. Mechanical fragmentation methods include mechanical shearing such as fluid shear, constant shear and pulsatile shear. Mechanical fragmentation methods also include mechanical stress including sonication, nebulization and acoustic cavitation.

Enzymatic fragmentation procedures can be conducted under conditions suitable to generate randomly or non-randomly fragmented nucleic acid molecules. For example, restriction endonuclease enzyme digestion can be conducted to completion to generate non-randomly fragmented nucleic acid molecule. Alternatively, partial or incomplete restriction enzyme digestion can be conducted to generate randomly-fragmented nucleic acid molecules. Enzymatic fragmentation using restriction endonuclease enzymes includes any one or any combination of two or more restriction enzymes selected from a group consisting of type I, type II, type IIs, type IIB, type III, or type IV restriction enzymes. Enzymatic fragmentation includes digestion of the nucleic acid with a rare-cutting restriction enzyme, comprising NotI, AscI, BaeI, AspCI, PacI, FseI, SapI, SfiI or PsrI. Enzymatic fragmentation include use of any combination of a nicking restriction endonuclease, endonuclease and/or exonuclease. Enzymatic fragmentation can be achieved by conducting a nick translation reaction.

Fragments of the target sequences used to generate the sequence(s) of interest can be generated with PCR using sequence-specific primers that hybridize to target regions in genomic DNA samples to generate insert regions having known fragment lengths and sequences.

Targeted genome fragmentation methods using CRISPR/Cas9 can be used to generate fragmented sequences of interest.

Fragments of a target sequence, i.e. the sequences of interest, can also be generated using a transposase-based tagmentation method using NEXTERA (from Epicentre).

The sequence of interest can be single-stranded or double-stranded. The ends of the double-stranded sequence of interest can be blunt-ended, or have a 5' overhang or a 3' overhang end, or any combination thereof. One or both ends of the sequence of interest can be subjected to an enzymatic tailing reaction to generate a non-template poly-A tail by employing a terminal transferase reaction. The ends of the sequence of interest can be compatible for joining to at least one universal adaptor sequence.

The sequence of interest can be any length, for example the insert region can be about 50-250, or about 250-500, or about 500-750, or about 750-1000 bases or base pairs in length.

The fragments containing the sequence(s) of interest can be subjected to a size selection process, or the fragments are not size selected. For example, the fragments can be size selected by gel electrophoresis and gel slice extraction. The fragments can be size selected using a solid phase adherence/immobilization method which typically employs micro paramagnetic beads coated with a chemical functional group that interacts with nucleic acids under certain ionic strength conditions with or without polyethylene glycol or polyalkylene glycol. Commercially-available solid phase adherence beads include SPRI (Solid Phase Reversible Immobilization) beads from Beckman Coulter (AMPUR XP paramagnetic beads, catalog No. B23318), MAGNA PURE magnetic glass particles (Roche Diagnostics, catalog No. 03003990001), MAGNASIL paramagnetic beads from Promega (catalog No. MD1360), MAGTRATION paramagnetic beads and system from Precision System Science (catalog Nos. A1120 and A1060), MAG-BIND from Omega Bio-Tek (catalog No. M1378-01), MAGPREP silica from Millapore (catalog No. 101193), SNARE DNA purification systems from Bangs Laboratories (catalog Nos. BP691, BP692 and BP693), and CHEMAGEN M-PVA beads from Perkin Elmer (catalog No. CMG-200).

The sequence of interest can be joined at one or both ends to at least one universal adaptor sequence using a ligase enzyme and/or primer extension reaction. Covalent linkage between sequence of interest and the universal adaptor(s) can be achieved with a DNA or RNA ligase. Exemplary DNA ligases that can ligate double-stranded DNA molecules include T4 DNA ligase and T7 DNA ligase. A universal adaptor sequence can be appended to a sequence of interest by primer extension or PCR using a tailed primer having 5' region carrying a universal adaptor sequence and a 3' region that is complementary to a portion of the sequence of interest. A universal adaptor sequence can be appended to a sequence of interest which is flanked on one side or both sides with first and second universal adaptor sequences by primer extension or PCR using a tailed primer having a 5' region carrying a third universal adaptor sequence and a 3' region that is complementary to a portion of the first or second universal adaptor sequence.

In some embodiments, a library molecule (100) can be generated by employing a ligation reaction and at least one primer extension reaction. The library molecule can be generated by (a) providing a double-stranded nucleic acid fragment comprising a sequence of interest (e.g., a double-stranded sequence of interest (110)), (b) joining the first end of the double-stranded sequence of interest (110) to a first double-stranded adaptor having a second left universal adaptor sequence (140), and joining the second end of the double-stranded sequence of interest (110) to a second double-stranded adaptor having a second right universal adaptor sequence (150), wherein the joining is conducted using a DNA ligase enzyme to generate a double-stranded recombinant molecule. In some embodiments, the first and second double-stranded adaptors of step (b) comprise Y-shaped adaptors. In some embodiments, the Y-shaped adaptor comprises first and second oligonucleotide strands having partially complementary regions that hybridize together to form a double-stranded duplex region and a mismatched single-stranded region. In some embodiments, at least a portion of the first oligonucleotide strand comprises a second left universal adaptor sequence (140) or a complementary sequence thereof. In some embodiments, at least a portion of the second oligonucleotide strand comprises a second right universal adaptor sequence (150) or a complementary sequence thereof. The method for generating the library molecule comprises (c) denaturing the double-stranded recombinant molecule of step (b) to generate single-stranded recombinant molecules, and (d) hybridizing the single-stranded recombinant molecules with a first tailed primer having a 5' region carrying a first left universal adaptor sequence (120) and a 3' region that is complementary to at least a portion of the second left universal adaptor sequence (140), and conducting a primer extension reaction thereby generating a double-stranded tailed molecule. In some embodiments, the first tailed primer of step (d) includes a first left index sequence (160). The method for generating a library molecule further comprises (e) hybridizing the double-stranded tailed molecule with a second tailed primer having a 5' region carrying a first right universal adaptor sequence (130) and a 3' region that is complementary to at least a portion of the second right universal adaptor sequence (150), and conducting a primer extension reaction thereby generating a library molecule comprising a first left universal adaptor sequence (120), a second left universal adaptor sequence (140), an insert region (110), a second right universal adaptor sequence (150), and a first right universal adaptor sequence (130). In some embodiments, the second tailed primer of step (e) includes a first right index sequence (170). In some embodiments, a library molecule can be generated using ligation and primer extension reactions and conducting steps (a)-(e), with PCR reaction. In some embodiments, a library molecule can be generated using ligation and primer extension reactions and conducting steps (a)-(e), with no PCR reaction, which reduces amplification bias. In some embodiments, in the method for generating a library molecule, the first left universal adaptor sequence (120) comprises a universal binding sequence for a first surface primer (or a complementary sequence thereof). In some embodiments, the first left universal adaptor sequence (120) in the library molecule can bind the first region of the first splint strand (320). In some embodiments, in the method for generating a library molecule, the first right universal adaptor sequence (130) comprises a universal binding sequence for a second surface primer (or a complementary sequence thereof). In some embodiments, the first right universal adaptor sequence (130) in the library molecule can bind the second region of the first splint strand (330). In some embodiments, in the method for generating a library molecule, the second left universal adaptor sequence (140) comprises a universal binding sequence for a first sequencing primer (or a complementary sequence thereof). In some embodiments, in the method for generating a library molecule, the second right universal adaptor sequence (150) comprises a universal binding sequence for a second sequencing primer (or a complementary sequence thereof).

In some embodiments, the method for generating a library molecule comprises appending additional universal adaptor sequences to the library molecule (100) (e.g., FIGS. 4-8) by conducting at least one primer extension reaction or PCR using additional tailed primers. In some embodiments, the appending methods that employ the additional tailed primers can be used to append additional universal adaptor sequences to the library molecule, or to replace at least a portion of a universal adaptor sequence in a library molecule. In some embodiments, the additional tailed primers comprise a 5' region carrying a first additional universal adaptor sequence and a 3' region that is complementary to at least a portion of the first left universal adaptor sequence (120), wherein the first additional universal adaptor sequence in the additional tailed primers comprise a universal binding sequence for a forward or reverse sequencing primer, a universal binding sequence for a first or second surface primer, a universal binding sequence for a forward or reverse amplification primer and/or a universal binding sequence for a compaction oligonucleotide. In some embodiments, the additional tailed primers comprise a 5' region carrying a second additional universal adaptor sequence and a 3' region that is complementary to at least a portion of the first right universal adaptor sequence (130), wherein the second additional universal adaptor sequence in the additional tailed primers comprise a universal binding sequence for a forward or reverse sequencing primer, a universal binding sequence for a first or second surface primer, a universal binding sequence for a forward or reverse amplification primer and/or a universal binding sequence for a compaction oligonucleotide.

In some embodiments, methods for appending additional universal adaptor sequences to nucleic acid library molecules comprise: step (a) providing a plurality of nucleic acid library molecules (100) each comprising sequences arranged in a 5' to 3' order: (i) a first left universal adaptor sequence (120), (ii) a second left universal adaptor sequence (140), (iii) a sequence of interest (110), (iv) a second right universal adaptor sequence (150), and (v) a first right universal adaptor sequence (130), wherein the plurality of nucleic acid library molecules (100) can be double stranded molecules; step (b) hybridizing individual library molecules of step (a) with a first tailed primer and conducting a first primer extension reaction (or first PCR), wherein the first tailed primers comprise a 5' region carrying a third left universal adaptor sequence and a 3' region that is complementary to at least a portion of the first left universal adaptor sequence (120) of the library molecule (100), wherein the first primer extension reaction (or first PCR) generates a plurality of first modified library molecules each appended at one end with the third left universal adaptor sequence, wherein the third left universal adaptor sequence of the first tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide; and step (c) hybridizing individual first modified library molecules of step (a) with a second tailed primer and conducting a second primer extension reaction (or second PCR), wherein the second tailed primers comprise a 5' region carrying a third right universal adaptor sequence and a 3' region that is complementary to at least a portion of the first right universal adaptor sequence (130) of the first modified library molecule, wherein the second primer extension reaction (or second PCR) generates a plurality of second modified library molecules each appended at one end with the third right universal adaptor sequence, wherein the third right universal adaptor sequence of the second tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide.

In some embodiments, the first primer extension reaction (or first PCR) of step (b) appends a full-length or a portion of the third left universal adaptor sequence to one end of the first modified library molecules. In some embodiments, the second primer extension reaction (or second PCR) of step (c) appends a full-length or a portion of the third right universal adaptor sequence to one end of the second modified library molecules. In some embodiments, the third left universal adaptor sequence comprises a sequence modification of 1-20 nucleotides where the modification comprises an insertion, deletion, truncation and/or base substitution. In some embodiments, the third right universal adaptor sequence comprises a sequence modification of 1-20 nucleotides where the modification comprises an insertion, deletion, truncation and/or base substitution.

In some embodiments, individual nucleic acid library molecules of step (a) comprise sequences arranged in a 5' to 3' order: (i) a first left universal adaptor sequence (120) having a binding sequence for a first surface primer, (ii) a second left universal adaptor sequence (140) having a binding sequence for a first sequencing primer, (iii) a sequence of interest (110), (iv) a second right universal adaptor sequence (150) having a binding sequence for a second sequencing primer, and (v) a first right universal adaptor sequence (130) having a binding sequence for a second surface primer.

In some embodiments, methods for appending more additional universal adaptor sequences to nucleic acid library molecules comprise: step (d) hybridizing individual second modified library molecules of step (c) with a third tailed primer and conducting a third primer extension reaction (or third PCR), wherein the third tailed primers comprise a 5' region carrying a fourth left universal adaptor sequence and a 3' region that is complementary to at least a portion of the third left universal adaptor sequence of the second modified library molecule, wherein the third primer extension reaction (or third PCR) generates a plurality of third modified library molecules each appended at one end with the fourth left universal adaptor sequence, wherein the fourth left universal adaptor sequence of the third tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide; and step (e) hybridizing individual third modified library molecules of step (d) with a fourth tailed primer and conducting a fourth primer extension reaction (or fourth PCR), wherein the fourth tailed primers comprise a 5' region carrying a fourth right universal adaptor sequence and a 3' region that is complementary to at least a portion of the third right universal adaptor sequence of the third modified library molecule, wherein the fourth primer extension reaction (or fourth PCR) generates a plurality of fourth modified library molecules each appended at one end with the fourth right universal adaptor sequence, wherein the fourth right universal adaptor sequence of the fourth tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide.

In some embodiments, the third primer extension reaction (or third PCR) of step (d) appends a full-length or a portion of the fourth left universal adaptor sequence to one end of the third modified library molecules. In some embodiments, the fourth primer extension reaction (or fourth PCR) of step (e) appends a full-length or a portion of the fourth right universal adaptor sequence to one end of the fourth modified library molecules. In some embodiments, the fourth left universal adaptor sequence comprises a sequence modification of 1-20 nucleotides where the modification comprises an insertion, deletion, truncation and/or base substitution. In some embodiments, the fourth right universal adaptor sequence comprises a sequence modification of 1-20 nucleotides where the modification comprises an insertion, deletion, truncation and/or base substitution.

In some embodiments, methods for appending even more additional universal adaptor sequences to nucleic acid library molecules comprise: step (f) hybridizing individual fourth modified library molecules of step (e) with a fifth tailed primer and conducting a fifth primer extension reaction (or fifth PCR), wherein the fifth tailed primers comprise a 5' region carrying a fifth left universal adaptor sequence and a 3' region that is complementary to at least a portion of the fourth left universal adaptor sequence of the fourth modified library molecule, wherein the fifth primer extension reaction (or fifth PCR) generates a plurality of fifth modified library molecules each appended at one end with the fifth left universal adaptor sequence, wherein the fifth left universal adaptor sequence of the fifth tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide; and step (g) hybridizing individual fifth modified library molecules of step (f) with a sixth tailed primer and conducting a sixth primer extension reaction (or sixth PCR), wherein the sixth tailed primers comprise a 5' region carrying a fifth right universal adaptor sequence and a 3' region that is complementary to at least a portion of the fourth right universal adaptor sequence of the fifth modified library molecule, wherein the sixth primer extension reaction (or sixth PCR) generates a plurality of sixth modified library molecules each appended at one end with the fifth right universal adaptor sequence, wherein the fifth right universal adaptor sequence of the sixth tailed primers comprise (i) a universal binding sequence for a forward or reverse sequencing primer, (ii) a universal binding sequence for a first or second surface primer, (iii) a universal binding sequence for a forward or reverse amplification primer and/or (iv) a universal binding sequence for a compaction oligonucleotide.

In some embodiments, the fifth primer extension reaction (or fifth PCR) of step (f) appends a full-length or a portion of the fifth left universal adaptor sequence to one end of the fifth modified library molecules. In some embodiments, the sixth primer extension reaction (or sixth PCR) of step (g) appends a full-length or a portion of the fifth right universal adaptor sequence to one end of the sixth modified library molecules. In some embodiments, the fifth left universal adaptor sequence comprises a sequence modification of 1-20 nucleotides where the modification comprises an insertion, deletion, truncation and/or base substitution. In some embodiments, the fifth right universal adaptor sequence comprises a sequence modification of 1-20 nucleotides where the modification comprises an insertion, deletion, truncation and/or base substitution.

In some embodiments, the first tailed primer of step (b), the third tailed primer of step (d) and/or the fifth tailed primer of step (f) further comprise a left index sequence and/or a random sequence (e.g., NN) comprising 2-10 nucleotides. In some embodiments, the random sequence and at least a portion of a juxtaposed universal adaptor sequence can be sequenced and the sequence information can be used for polony mapping and/or template registration.

In some embodiments, the first tailed primer of step (b), the third tailed primer of step (d) and/or the fifth tailed primer of step (f) further comprise a left unique identification sequence.

In some embodiments, the second tailed primer of step (c), the fourth tailed primer of step (e) and/or the sixth tailed primer of step (g) further comprises a right index sequence and/or a random sequence (e.g., NN) comprising 2-10 nucleotides. In some embodiments, the random sequence and at least a portion of a juxtaposed universal adaptor sequence can be sequenced and the sequence information can be used for polony mapping and/or template registration.

In some embodiments, the second tailed primer of step (c), the fourth tailed primer of step (e) and/or the sixth tailed primer of step (g) further comprises a right unique identification sequence.

In some embodiments, the appended third left universal adaptor sequence of step (b) can bind a first region (320) of a first splint strand.

In some embodiments, the appended third right universal adaptor sequence of step (c) can bind a second region (330) of a first splint strand.

In some embodiments, the appended fourth left universal adaptor sequence of step (d) can bind a first region (320) of a first splint strand.

In some embodiments, the appended fourth right universal adaptor sequence of step (e) can bind a second region (330) of a first splint strand.

In some embodiments, the appended fifth left universal adaptor sequence of step (f) can bind a first region (320) of a first splint strand.

In some embodiments, the appended fifth right universal adaptor sequence of step (g) can bind a second region (330) of a first splint strand.

The skilled artisan will appreciate that additional universal adaptor sequences can be appended to the library molecule by repeating the primer extension reactions or PCR. In some embodiments, the library molecule can be appended with ten or more additional universal adaptor sequences on one or both sides of the library molecule.

Reducing Sequencing Errors Using Alkaline Conditions

In a pairwise sequencing workflow, we have observed low quality base calls for T bases when sequencing the first strand (e.g., R1 reads), and low quality base calls for A bases when sequencing corresponding positions on the complementary second strand (e.g., R2 reads). Many of the low quality T base calls on the first strand sequence align with C bases in a known reference sequence. Without wishing to be bound by theory, we postulated that some of the bases in the library molecules were deaminated which lead to the base substitutions including C:G to T:A transitions.

Deamination is generally the removal of an amino group from a molecule. With respect to nucleotide bases, cytosine (C) can be deaminated to generate uracil (U) where uracil can base pair with adenine (A), guanine (G) can be deaminated to generate xanthine where xanthine can base pair with cytosine (C), and adenine (A) can be deaminate to generate hypoxanthine where hypoxanthine can base pair with cytosine (C).

Workflows for preparing nucleic acid library molecules involve numerous steps that include conditions that can cause deamination of nucleotide bases. For example, deamination can be caused by the presence of deaminase enzymes at any stage in the library prep workflow. As another example, any of the library prep buffers having a low pH can cause base deamination. In another example, high temperatures employed for nucleic acid denaturation, enzyme deactivation (e.g., enzyme heat-kill) and PCR can cause base deamination. In another example, mechanical shearing forces that are used to fragment input nucleic acids can generate damaging free radicals which leads to deamination. Exemplary mechanical forces includes sonication force, acoustic force, nebulizing force, shearing force and cavitation force. In another example, certain chemical such as bisulfites can cause deamination. The skilled artisan will recognize that nucleotide base deamination can be generated by many other conditions.

In a sequencing run, nucleic acid molecules that carry fewer deaminated nucleotide bases can generate higher quality base calls compared to nucleic acid molecules carrying numerous deaminated nucleotide bases. Thus, reducing base deamination during nucleic acid library preparation can improve base calling accuracy and quality leading to higher quality sequencing scores (e.g., Q-scores).

The present disclosure provides compositions and methods for preparing nucleic acid library molecules having reduced deaminated nucleotide bases by replacing heat with an alkaline reagent. In some embodiments, nucleic acid denaturation can be conducted using an alkaline reagent instead of heat. In some embodiments, enzyme deactivation can be conducted using an alkaline reagent instead of heat-kill conditions (i.e., denaturing nucleic acids or enzymes by heating the reaction mixture to temperatures sufficient to cause nucleic acid or enzyme denaturation). The compositions and methods described herein can be applied to any type of nucleic acid library molecules, including for example linear and/or circularized library molecules, and can be applied at any step in a nucleic acid library preparation workflow.

In some embodiments, methods for preparing nucleic acid library molecules having reduced deaminated nucleotide bases comprises step (a): preparing a plurality of linear nucleic acid library molecules (e.g., single-stranded or double-stranded library molecules); and contacting the plurality of linear library molecules with a first alkaline reagent thereby generating a plurality of denatured linear library molecules while reducing the formation of deaminated nucleotide bases in the linear library molecules compared to library molecules that are denatured with heat. In some embodiments, the first alkaline reagent comprises NaOH and/or KOH. In some embodiments, the denatured linear library molecules comprise single-stranded library molecules (100) comprising: a first left universal adaptor sequence (120); an optional first left unique identification sequence (180); a first left index sequence (160); a second left universal adaptor sequence (140); a sequence of interest (110); a second right universal adaptor sequence (150); a first right index sequence (170); and a first right universal adaptor sequence (130) (e.g., FIG. 5). In some embodiments, the plurality of linear library molecules can be denatured with a first alkaline reagent (e.g., NaOH and/or KOH) at a concentration of about 0.01-0.05 M, or about 0.05-0.1 M, or about 0.1-0.5 M, or about 0.5-1 M, or about 1-1.5 M, or about 1.5-2 M.

In some embodiments, the methods for preparing nucleic acid library molecules having reduced deaminated nucleotide bases comprises step (b): hybridizing the single-stranded library molecules (100) with a double-stranded splint molecule (200) thereby circularizing the library molecule to form a library-splint complex (500) with two nicks. In some embodiments, the double-stranded splint molecule (200) comprises a first splint strand (long strand (300)) hybridized to a second splint strand (short strand (400)). The first splint strand comprises a first region (320) that hybridizes with a sequence on one end of the linear single stranded library molecule, and a second region (330) that hybridizes with a sequence on the other end of the linear single stranded library molecule. The internal region (310) of the first splint strand hybridizes to the second splint strand (400). In some embodiments, the double-stranded splint molecule (200) comprises any of the structures shown in FIGS. 1-5.

In some embodiments, the methods for preparing nucleic acid library molecules having reduced deaminated nucleotide bases comprises step (c): conducting a ligation reaction to close the nicks to form a covalently closed circular library molecule (600) which is hybridized to a first splint strand (300). In some embodiments, the ligation reaction can be conducted with a ligase enzyme. In some embodiments, the ligase enzyme comprises T7 DNA ligase, T3 ligase, T4 ligase, or Taq ligase.

In some embodiments, the methods for preparing nucleic acid library molecules having reduced deaminated nucleotide bases comprises step (d): deactivating the ligase enzyme by contacting the ligase enzyme with a second alkaline reagent. In some embodiments, the second alkaline reagent comprises NaOH and/or KOH. In some embodiments, the plurality of covalently closed circular library molecules (600) is retained. In some embodiments, deactivating the ligase enzyme with the second alkaline reagent can reduce the formation of deaminated nucleotide bases in the plurality of covalently closed circular library molecule (600) compared to covalently closed circular library molecules that are subjected to ligase heat deactivation. In some embodiments, the ligase enzyme can be deactivated with a second alkaline reagent (e.g., NaOH and/or KOH) at a concentration of about 0.01-0.05 M, or about 0.05-0.1 M, or about 0.1-0.5 M, or about 0.5-1 M, or about 1-1.5 M, or about 1.5-2 M.

In some embodiments, the methods for preparing nucleic acid library molecules having reduced deaminated nucleotide bases comprises optional step (e1): removing the first splint strands (300) while retaining the covalently closed circular library molecules (600) by contacting the first splint strands (300) with an exonuclease enzyme. In some embodiments, the exonuclease enzyme comprises any one or any combination of two or more of exonuclease I, thermolabile exonuclease I and/or T7 exonuclease.

In some embodiments, the methods for preparing nucleic acid library molecules having reduced deaminated nucleotide bases comprises step (e2): deactivating the exonuclease enzyme by contacting the exonuclease enzyme with a third alkaline reagent. In some embodiments, the plurality of covalently closed circular library molecules (600) is retained. In some embodiments, the third alkaline reagent comprises NaOH and/or KOH. In some embodiments, deactivating the exonuclease enzyme with the third alkaline reagent can reduce the formation of deaminated nucleotide bases in the plurality of covalently closed circular library molecule (600) compared to covalently closed circular library molecules that are subjected to exonuclease heat deactivation. In some embodiments, the exonuclease enzyme can be deactivated with a third alkaline reagent (e.g., NaOH and/or KOH) at a concentration of about 0.01-0.05 M, or about 0.05-0.1 M, or about 0.1-0.5 M, or about 0.5-1 M, or about 1-1.5 M, or about 1.5-2 M.

In some embodiments, the methods for preparing nucleic acid library molecules having reduced deaminated nucleotide bases comprises step (f): distributing the plurality of covalently closed circular library molecules (600) onto a support having a plurality of surface primers (e.g., third surface primers, capture primers) immobilized on the support, under a condition suitable for hybridizing individual covalently closed circular library molecules (600) to individual immobilized third surface primers thereby immobilizing the plurality of covalently closed circular library molecules (600).

In some embodiments, the methods for preparing nucleic acid library molecules having reduced deaminated nucleotide bases comprises step (g): contacting the plurality of immobilized covalently closed circular library molecules (600) with a plurality of strand-displacing polymerases and a plurality of nucleotides, under a condition suitable to conduct a rolling circle amplification reaction on the support using the plurality of third surface primers as immobilized amplification primers and the plurality of covalently closed circular library molecules (600) as template molecules, thereby generating a plurality of nucleic acid concatemer molecules immobilized to the third surface primers. In some embodiments, the plurality of nucleotides comprises any combination of two or more of dATP, dGTP, dCTP, dTTP and/or dUTP.

In some embodiments, the methods for preparing nucleic acid library molecules having reduced deaminated nucleotide bases comprises step (h): sequencing the plurality of immobilized nucleic acid concatemers. In some embodiments, the sequencing of step (h) can be conducted using any of the sequencing methods described herein. In some embodiments, the plurality of immobilized nucleic acid concatemers can be sequenced using a two-stage sequencing reaction comprising binding detectably labeled multivalent molecules, and incorporating nucleotide analogs. In some embodiments, the plurality of immobilized nucleic acid concatemers carry fewer C:G to T:A base transitions bases which can generate higher quality base calls during sequencing and higher quality sequencing scores (e.g., Q-scores of Q40 or higher). For example, see FIGS. 15A-15D, 16A-16D, 17 and 18.

In some embodiments, the base calling from sequencing data can assessed for accuracy and quality. Q-score is a measure of data quality. The Q-score can be defined as a Phred quality score. The Q-score is based on a logarithmic scale. It is defined as $Q=-10 \log(P)$ where P is the error probability. For example, Q10 represents 10% error, Q20 represents 1% error, Q30 represents 0.1% error and Q40 represent 0.01% error. In another example, Q10 is one error in 10, Q20 is one error in 100, Q30 is one error in 1000, Q40 is one error in 10,000, and Q50 is one error in 100,000.

Supports with Low Non-Specific Binding Coatings

The present disclosure provides compositions and methods for sequencing which employ a support having a plurality of surface primers immobilized thereon. In some embodiments, the support is passivated with a low non-specific binding coating. The surface coatings described herein exhibit very low non-specific binding to reagents typically used for nucleic acid capture, amplification and sequencing workflows, such as dyes, nucleotides, enzymes, and nucleic acid primers. The surface coatings exhibit low background fluorescence signals or high contrast-to-noise (CNR) ratios compared to conventional surface coatings.

In general, the supports comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded target nucleic acid(s) to the support surface. In some embodiments, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

The substrate or support structure that comprises the one or more chemically-modified layers, e.g., layers of a low non-specific binding polymer, may be independent or integrated into another structure or assembly. For example, in some embodiments, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The attachment chemistry used to graft a first chemically-modified layer to a surface will generally be dependent on both the material from which the surface is fabricated and the chemical nature of the layer. In some embodiments, the first layer may be covalently attached to the surface. In some embodiments, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the surface. For example, glass or silicon surfaces may be acid-washed using a Piranha solution (a mixture of sulfuric acid ($H_2SO_4$) and hydrogen peroxide ($H_2O_2$)), base treatment in KOH and NaOH, and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the surface, where the choice of components used may be varied to alter one or more properties of the surface, e.g., the surface density of functional groups and/or tethered oligonucleotide primers, the hydrophilicity/hydrophobicity of the surface, or the three three-dimensional nature (i.e., "thickness") of the surface. Examples of preferred polymers that may be used to create one or more layers of low non-specific binding material in any of the disclosed surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

The low non-specific binding surface coating may be applied uniformly across the substrate. Alternately, the surface coating may be patterned, such that the chemical modification layers are confined to one or more discrete regions of the substrate. For example, the surface may be patterned using photolithographic techniques to create an ordered array or random pattern of chemically-modified regions on the surface. Alternately or in combination, the substrate surface may be patterned using, e.g., contact printing and/or ink-jet printing techniques. In some embodiments, an ordered array or random patter of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In order to achieve low nonspecific binding surfaces, hydrophilic polymers may be nonspecifically adsorbed or covalently grafted to the surface. Typically, passivation is performed utilizing poly(ethylene glycol) (PEG, also known as polyethylene oxide (PEO) or polyoxyethylene) or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some embodiments, two or more layers of a hydrophilic polymer, e.g., a linear polymer, branched polymer, or multi-branched polymer, may be deposited on the surface. In some embodiments, two or more layers may be covalently coupled to each other or internally cross-linked to improve the stability of the resulting surface. In some embodiments, oligonucleotide primers with different base sequences and base modifications (or other biomolecules, e.g., enzymes or antibodies) may be tethered to the resulting surface layer at various surface densities. In some embodiments, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In order to scale primer surface density and add additional dimensionality to hydrophilic or amphoteric surfaces, surfaces comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some embodiments, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some embodiments, high primer density materials may be constructed in solution and subsequently layered onto the surface in multiple steps.

As noted, the low non-specific binding coatings of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some embodiments, exposure of the surface to fluorescent dyes (e.g., cyanine dyes such as Cy3, or Cy5, etc., fluoresceins, coumarins, rhodamines, etc. or other dyes disclosed herein), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some embodiments, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under a condition where fluorescence signal is linearly related (or related in a predictable manner) to the number of fluorophores on the support surface (e.g., under a condition where signal saturation and/or self-quenching of the fluorophore is not an issue) and suitable calibration standards are used. In some embodiments, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some embodiments, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some embodiments, the label may comprise a fluorescent label. In some embodiments, the label may comprise a radioisotope. In some embodiments, the label may comprise any other detectable label known to one of skill in the art. In some embodiments, the degree of non-specific binding exhibited by a given support surface formulation may thus be assessed in terms of the number of non-specifically bound protein molecules (or other molecules) per unit area. In some embodiments, the low-binding supports of the present disclosure may exhibit non-specific protein binding (or non-specific binding of other specified molecules, (e.g., cyanine dyes such as Cy3, or Cy5, etc., fluoresceins, coumarins, rhodamines, etc. or other dyes disclosed herein)) of less than 0.001 molecule per µm2, less than 0.01 molecule per $\mu m^2$, less than 0.1 molecule per $\mu m^2$, less than 0.25 molecule per $\mu m^2$, less than 0.5 molecule per $\mu m^2$, less than 1 molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/$\mu m^2$ following contact with a 1 µM solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per $\mu m^2$. In independent nonspecific binding assays, 1 µM labeled Cy3 SA (ThermoFisher), 1 µM Cy5 SA dye (ThermoFisher), 10 µM Aminoallyl-dUTP-ATTO-647N (Jena Biosciences), 10 µM Aminoallyl-dUTP-ATTO-Rho11 (Jena Biosciences), 10 µM Aminoallyl-dUTP-ATTO-Rho11 (Jena Biosciences), 10 µM 7-Propargylamino-7-deaza-dGTP-Cy5 (Jena Biosciences, and 10 µM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, PA) with a total internal reflectance fluorescence (TIRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75 W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some embodiments, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some embodiments, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some embodiments, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some embodiments, a static contact angle may be determined. In some embodiments, an advancing or receding contact angle may be determined. In some embodiments, the water contact angle for the hydrophilic, low-binding support surfaced disclosed herein may range from about 0 degrees to about 30 degrees. In some embodiments, the water contact angle for the hydrophilic, low-binding support surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding support surface of the present disclosure may exhibit a water contact angle having a value of anywhere within this range.

In some embodiments, the hydrophilic surfaces disclosed herein facilitate reduced wash times for bioassays, often due to reduced nonspecific binding of biomolecules to the low-binding surfaces. In some embodiments, adequate wash steps may be performed in less than 60, 50, 40, 30, 20, 15, 10, or less than 10 seconds. For example, in some embodiments adequate wash steps may be performed in less than 30 seconds.

The low-binding surfaces of the present disclosure exhibit significant improvement in stability or durability to prolonged exposure to solvents and elevated temperatures, or to repeated cycles of solvent exposure or changes in temperature. For example, in some embodiments, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some embodiments, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some embodiments, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some embodiments, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

In some embodiments, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

One or more types of primer (e.g., capture oligonucleotides and/or circularization oligonucleotides) may be attached or tethered to the support surface. In some embodiments, the one or more types of adapters or primers may comprise spacer sequences, adapter sequences for hybridization to adapter-ligated target library nucleic acid sequences, forward amplification primers, reverse amplification primers, sequencing primers, and/or molecular barcoding sequences, or any combination thereof. In some embodiments, 1 primer or adapter sequence may be tethered to at least one layer of the surface. In some embodiments, at least 2, 3, 4, 5, 6, 7, 8, 9, 10, or more than 10 different primer or adapter sequences may be tethered to at least one layer of the surface.

In some embodiments, the tethered adapter and/or primer sequences may range in length from about 10 nucleotides to about 100 nucleotides. In some embodiments, the tethered adapter and/or primer sequences may be at least 10, at least 20, at least 30, at least 40, at least 50, at least 60, at least 70, at least 80, at least 90, or at least 100 nucleotides in length. In some embodiments, the tethered adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some embodiments the length of the tethered adapter and/or primer sequences may range from about 20 nucleotides to about 80 nucleotides. Those of skill in the art will recognize that the length of the tethered adapter and/or primer sequences may have any value within this range, e.g., about 24 nucleotides.

In some embodiments, the resultant surface density of primers on the low binding support surfaces of the present disclosure may range from about 100 primer molecules per $\mu m^2$ to about 100,000 primer molecules per $\mu m^2$. In some embodiments, the resultant surface density of primers on the low binding support surfaces of the present disclosure may range from about 100,000 primer molecules per $\mu m^2$ to about $10^{15}$ primer molecules per $\mu m^2$. In some embodiments, the surface density of primers may be at least 1,000, at least 10,000, at least 100,000, or at least $10^{15}$ primer molecules per $\mu m^2$. In some embodiments, the surface density of primers may be at most 10,000, at most 100,000, at most 1,000,000, or at most $10^{15}$ primer molecules per $\mu m^2$. Any of the lower and upper values described in this paragraph may be combined to form a range included within the present disclosure, for example, in some embodiments the surface density of primers may range from about 10,000 molecules per $\mu m^2$ to about $10^{15}$ molecules per $\mu m^2$. Those of skill in the art will recognize that the surface density of primer molecules may have any value within this range, e.g., about 455,000 molecules per $\mu m^2$. In some embodiments, the surface density of target library nucleic acid sequences initially hybridized to adapter or primer sequences on the support surface may be less than or equal to that indicated for the surface density of tethered primers. In some embodiments, the surface density of clonally-amplified target library nucleic acid sequences hybridized to adapter or primer sequences on the support surface may span the same range as that indicated for the surface density of tethered primers.

Local densities as listed above do not preclude variation in density across a surface, such that a surface may comprise a region having an oligo density of, for example, 500,000 per $\mu m^2$, while also comprising at least a second region having a substantially different local density.

The low non-specific binding coating comprise one or more layers of a multi-layered surface coating may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some embodiments, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branched.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some embodiments, e.g., wherein at least one layer of a multi-layered surface comprises a branched polymer, the number of covalent bonds between a branched polymer molecule of the layer being deposited and molecules of the previous layer may range from about one covalent linkage per molecule to about 32 covalent linkages per molecule. In some embodiments, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some embodiments, the number of layers is at least 1, at least 2, at least 3, at least 4, at least 5, at least 6, at least 7, at least 8, at least 9, or at least 10. In some embodiments, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some embodiments the number of layers may range from about 2 to about 4. In some embodiments, all of the layers may comprise the same material. In some embodiments, each layer may comprise a different material. In some embodiments, the plurality of layers may comprise a plurality of materials. In some embodiments at least one layer may comprise a branched polymer. In some embodiment, all of the layers may comprise a branched polymer.

One or more layers of low non-specific binding material may in some cases be deposited on and/or conjugated to the substrate surface using a polar protic solvent, a polar or polar aprotic solvent, a nonpolar solvent, or any combination thereof. In some embodiments the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some embodiments, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some embodiments, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than pH 9.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, fluorescence microscopy imaging, fluorescence confocal imaging, two-photon fluorescence, and the like. Examples of fluorescence imaging instruments that may be used include, but are not limited to, fluorescence microscopes equipped with an image sensor or camera, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified colonies (polonies) of template nucleic acid sequences hybridized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

In some instances, the performance of nucleic acid hybridization and/or amplification reactions using the disclosed reaction formulations and low non-specific binding supports may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. The surfaces of the instant disclosure are also provided in co-pending International Application Serial No. PCT/US2019/061556, which is hereby incorporated by reference in its entirety.

In most ensemble-based sequencing approaches, the background term is typically measured as the signal associated with 'interstitial' regions. In addition to "interstitial" background ($B_{inter}$), "intrastitial" background ($B_{intra}$) exists within the region occupied by an amplified DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)−$B_{inter}$ in the FOV) yields a discernable feature that can be classified. In some instances, the intrastitial background ($B_{intra}$) can contribute a confounding fluorescence signal that is not specific to the target of interest, but is present in the same ROI thus making it far more difficult to average and subtract.

The implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization buffer formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the read-out or detection mode, the same principles apply to the use of the disclosed low non-specific binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit: (i) negligible non-specific binding of protein and other reaction components (thus minimizing substrate background), (ii) negligible non-specific nucleic acid amplification product, and (iii) provide tunable nucleic acid amplification reactions.

In some embodiments, fluorescence images of the disclosed low background surfaces when used in nucleic acid hybridization or amplification applications to create polonies of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

In some embodiments, a fluorescence image of the surface exhibits a contrast-to-noise ratio (CNR) of at least 20 when a sample nucleic acid molecule or complementary sequences thereof are labeled with a Cyanine dye-3 (Cy3) fluorophore, and when the fluorescence image is acquired using an inverted fluorescence microscope (e.g., Olympus IX83) with a 20×0.75 NA objective, a 532 nm light source, a bandpass and dichroic mirror filter set optimized for 532 nm excitation and Cy3 fluorescence emission, and a camera (e.g., Andor sCMOS, Zyla 4.2) under non-signal saturating conditions while the surface is immersed in a buffer (e.g., 25 mM ACES, pH 7.4 buffer).

Sequencing Polymerases

The present disclosure provides methods for sequencing nucleic acid molecules, where any of the sequencing methods described herein employ at least one type of sequencing polymerase and a plurality of nucleotides, or employ at least one type of sequencing polymerase and a plurality of nucleotides and a plurality of multivalent molecules. In some embodiments, the sequencing polymerase(s) is/are capable of incorporating a complementary nucleotide opposite a nucleotide in a concatemer template molecule. In some embodiments, the sequencing polymerase(s) is/are capable of binding a complementary nucleotide unit of a multivalent molecule opposite a nucleotide in a concatemer template molecule. In some embodiments, the plurality of sequencing polymerases comprise recombinant mutant polymerases.

Examples of suitable polymerases for use in sequencing with nucleotides and/or multivalent molecules include but are not limited to: Klenow DNA polymerase; *Thermus aquaticus* DNA polymerase I (Taq polymerase); KlenTaq polymerase; Candidatus altiarchaeales archaeon; Candidatus Hadarchaeum Yellowstonense; Hadesarchaea archaeon; Euryarchaeota archaeon; Thermoplasmata archaeon; *Thermococcus* polymerases such as *Thermococcus litoralis*, bacteriophage T7 DNA polymerase; human alpha, delta and epsilon DNA polymerases; bacteriophage polymerases such as T4, RB69 and phi29 bacteriophage DNA polymerases; *Pyrococcus furiosus* DNA polymerase (Pfu polymerase); *Bacillus subtilis* DNA polymerase III; *E. coli* DNA polymerase III alpha and epsilon; 9 degree N polymerase; reverse transcriptases such as HIV type M or O reverse transcriptases; avian myeloblastosis virus reverse transcriptase; Moloney Murine Leukemia Virus (MMLV) reverse transcriptase; or telomerase. Further non-limiting examples of DNA polymerases include those from various Archaea genera, such as, *Aeropyrum, Archaeglobus, Desulfurococcus, Pyrobaculum, Pyrococcus, Pyrolobus, Pyrodictium, Staphylothermus, Stetteria, Sulfolobus, Thermococcus*, and *Vulcanisaeta* and the like or variants thereof, including such polymerases as are known in the art such as 9 degrees N, VENT®, DEEP VENT®, THERMINATOR™, Pfu, KOD, Pfx, Tgo and RB69 polymerases.

Nucleotides

The present disclosure provides methods for sequencing nucleic acid molecules using nucleotides, wherein at least one nucleotide in the plurality of nucleotides comprise a base, sugar and at least one phosphate group. In some embodiments, at least one nucleotide in the plurality comprises an aromatic base, a five carbon sugar (e.g., ribose or deoxyribose), and one or more phosphate groups (e.g., 1-10 phosphate groups). The plurality of nucleotides can comprise at least one type of nucleotide selected from a group consisting of dATP, dGTP, dCTP, dTTP and dUTP. The plurality of nucleotides can comprise at a mixture of any combination of two or more types of nucleotides selected from a group consisting of dATP, dGTP, dCTP, dTTP and/or dUTP. In some embodiments, at least one nucleotide in the plurality is not a nucleotide analog. In some embodiments, at least one nucleotide in the plurality comprises a nucleotide analog.

In some embodiments, in any of the methods for sequencing nucleic acid molecules described herein, at least one nucleotide in the plurality of nucleotides comprise a chain of one, two or three phosphorus atoms where the chain is typically attached to the 5' carbon of the sugar moiety via an ester or phosphoramide linkage. In some embodiments, at least one nucleotide in the plurality is an analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide, for example by reacting the chain terminating moiety with a chemical agent, pH change, light or heat. In some embodiments, the chain terminating moieties alkyl, alkenyl, alkynyl and allyl are cleavable with tetrakis(triphenylphosphine)palladium(0) ($Pd(PPh_3)_4$) with piperidine, or with 2,3-Dichloro-5,6-dicyano-1,4-benzo-quinone (DDQ). In some embodiments, the chain terminating moieties aryl and benzyl are cleavable with H2 Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate ($K_2CO_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, at least one nucleotide in the plurality of nucleotides comprises a terminator nucleotide analog having a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, in any of the methods for sequencing nucleic acid molecules described herein, the nucleotide comprises a chain terminating moiety which is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, in any of the methods for sequencing nucleic acid molecules described herein, the plurality of nucleotides comprises a plurality of nucleotides labeled with detectable reporter moiety. The detectable reporter moiety comprises a fluorophore. In some embodiments, the fluorophore is attached to the nucleotide base. In some embodiments, the fluorophore is attached to the nucleotide base with a linker which is cleavable/removable from the base. In some embodiments, at least one of the nucleotides in the plurality is not labeled with a detectable reporter moiety. In some embodiments, a particular detectable reporter moiety (e.g., fluorophore) that is attached to the nucleotide can correspond to the nucleotide base (e.g., dATP, dGTP, dCTP, dTTP or dUTP) to permit detection and identification of the nucleotide base.

In some embodiments, in any of the methods for sequencing nucleic acid molecules described herein, the cleavable linker on the nucleotide base comprises a cleavable moiety comprising an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the cleavable linker on the base is cleavable/removable from the base by reacting the cleavable moiety with a chemical agent, pH change, light or heat. In some embodiments, the cleavable moieties alkyl, alkenyl, alkynyl and allyl are cleavable with tetrakis(triphenylphosphine)palladium(0) ($Pd(PPh_3)_4$) with piperidine, or with 2,3-Dichloro-5,6-dicyano-1,4-benzo-quinone (DDQ). In some embodiments, the cleavable moieties aryl and benzyl are cleavable with $H_2$ Pd/C. In some embodiments, the cleavable moieties amine, amide, keto, isocyanate, phosphate, thio, disulfide are cleavable with phosphine or with a thiol group including beta-mercaptoethanol or dithiothritol (DTT). In some embodiments, the cleavable moiety carbonate is cleavable with potassium carbonate ($K_2CO_3$) in MeOH, with triethylamine in pyridine, or with Zn in acetic acid (AcOH). In some embodiments, the cleavable moieties urea and silyl are cleavable with tetrabutylammonium fluoride, pyridine-HF, with ammonium fluoride, or with triethylamine trihydrofluoride.

In some embodiments, in any of the methods for sequencing nucleic acid molecules described herein, the cleavable linker on the nucleotide base comprises cleavable moiety including an azide, azido or azidomethyl group. In some embodiments, the cleavable moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, in any of the methods for sequencing nucleic acid molecules described herein, the chain terminating moiety (e.g., at the sugar 2' and/or sugar 3' position) and the cleavable linker on the nucleotide base have the same or different cleavable moieties. In some embodiments, the chain terminating moiety (e.g., at the sugar 2' and/or sugar 3' position) and the detectable reporter moiety linked to the base are chemically cleavable/removable with the same chemical agent. In some embodiments, the chain terminating moiety (e.g., at the sugar 2' and/or sugar 3' position) and the detectable reporter moiety linked to the base are chemically cleavable/removable with different chemical agents.

Multivalent Molecules

Figure 24:
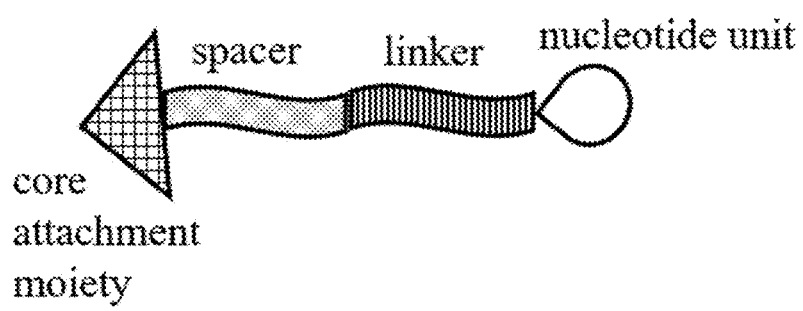
FIG. 24 is a schematic of an exemplary nucleotide-arm comprising a core attachment moiety, spacer, linker and nucleotide unit.
Figure 26:
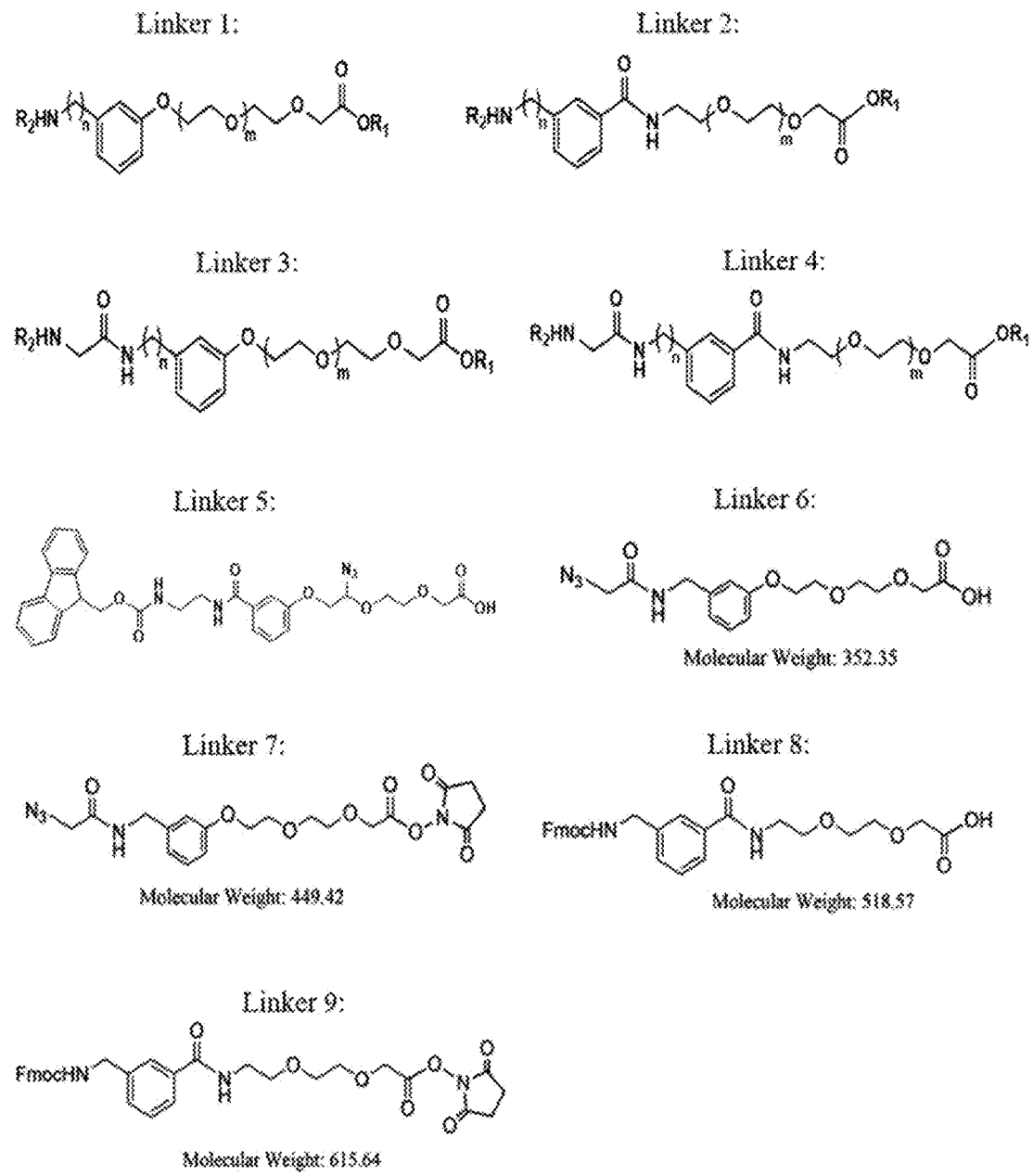
FIG. 26 shows the chemical structures of various exemplary linkers, including Linkers 1-9.
Figure 30:
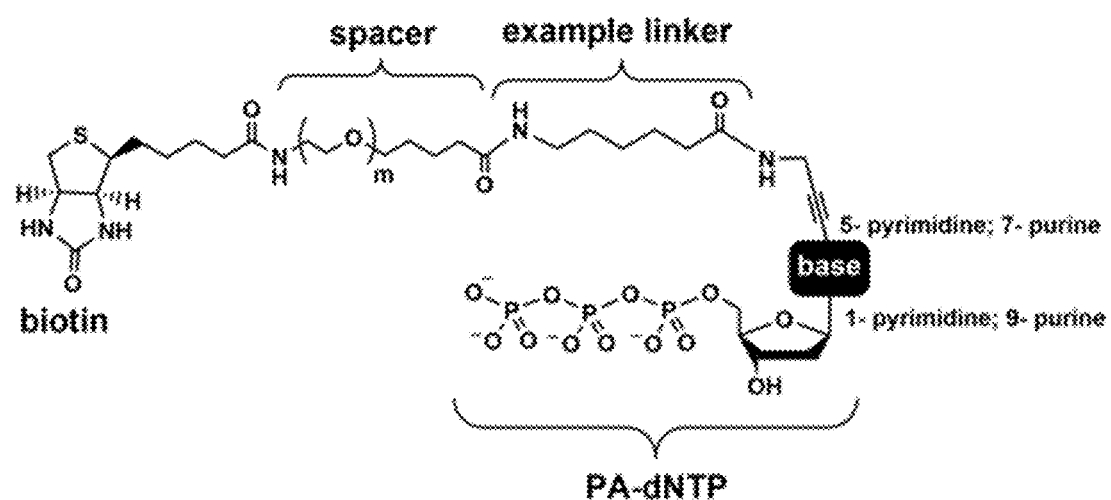
FIG. 30 shows the chemical structure of an exemplary biotinylated nucleotide-arm. In this example, the nucleotide unit is connected to the linker via a propargyl amine attachment at the 5 position of a pyrimidine base or the 7 position of a purine base.

The present disclosure provides methods for sequencing nucleic acid molecules which employ multivalent molecules. In some embodiments, the multivalent molecule comprises a plurality of nucleotide arms attached to a core and having any configuration including a starburst, helter skelter, or bottle brush configuration (e.g., FIGS. 20-24). The multivalent molecule comprises: (1) a core; and (2) a plurality of nucleotide arms which comprise (i) a core attachment moiety, (ii) a spacer comprising a PEG moiety, (iii) a linker, and (iv) a nucleotide unit, wherein the core is attached to the plurality of nucleotide arms, wherein the spacer is attached to the linker, wherein the linker is attached to the nucleotide unit. In some embodiments, the nucleotide unit comprises a base, sugar and at least one phosphate group, and the linker is attached to the nucleotide unit through the base. In some embodiments, the linker comprises an aliphatic chain or an oligo ethylene glycol chain where both linker chains having 2-6 subunits. In some embodiments, the linker also includes an aromatic moiety. An exemplary nucleotide arm is shown in FIG. 24. Exemplary multivalent molecules are shown in FIGS. 20-23. An exemplary spacer is shown in FIG. 25 (top) and exemplary linkers are shown in FIG. 25 (bottom) and FIG. 26. Exemplary nucleotides attached to a linker are shown in FIGS. 27-29. An exemplary biotinylated nucleotide arm is shown in FIG. 30.

In some embodiments, a multivalent molecule comprises a core attached to multiple nucleotide arms, and wherein the multiple nucleotide arms have the same type of nucleotide unit which is selected from a group consisting of dATP, dGTP, dCTP, dTTP and dUTP.

In some embodiments, a multivalent molecule comprises a core attached to multiple nucleotide arms, where each arm includes a nucleotide unit. The nucleotide unit comprises an aromatic base, a five carbon sugar (e.g., ribose or deoxyribose), and one or more phosphate groups (e.g., 1-10 phosphate groups). The plurality of multivalent molecules can comprise one type multivalent molecule having one type of nucleotide unit selected from a group consisting of dATP, dGTP, dCTP, dTTP and dUTP. The plurality of multivalent molecules can comprise at a mixture of any combination of two or more types of multivalent molecules, where individual multivalent molecules in the mixture comprise nucleotide units selected from a group consisting of dATP, dGTP, dCTP, dTTP and/or dUTP.

In some embodiments, the nucleotide unit comprises a chain of one, two or three phosphorus atoms where the chain is typically attached to the 5' carbon of the sugar moiety via an ester or phosphoramide linkage. In some embodiments, at least one nucleotide unit is a nucleotide analog having a phosphorus chain in which the phosphorus atoms are linked together with intervening O, S, NH, methylene or ethylene. In some embodiments, the phosphorus atoms in the chain include substituted side groups including O, S or $BH_3$. In some embodiments, the chain includes phosphate groups substituted with analogs including phosphoramidate, phosphorothioate, phosphordithioate, and O-methylphosphoroamidite groups.

In some embodiments, the multivalent molecule comprises a core attached to multiple nucleotide arms, and wherein individual nucleotide arms comprise a nucleotide unit which is a nucleotide analog having a chain terminating moiety (e.g., blocking moiety) at the sugar 2' position, at the sugar 3' position, or at the sugar 2' and 3' position. In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety can inhibit polymerase-catalyzed incorporation of a subsequent nucleotide unit or free nucleotide in a nascent strand during a primer extension reaction. In some embodiments, the chain terminating moiety is attached to the 3' sugar hydroxyl position where the sugar comprises a ribose or deoxyribose sugar moiety. In some embodiments, the chain terminating moiety is removable/cleavable from the 3' sugar hydroxyl position to generate a nucleotide having a 3'OH sugar group which is extendible with a subsequent nucleotide in a polymerase-catalyzed nucleotide incorporation reaction. In some embodiments, the chain terminating moiety comprises an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the chain terminating moiety is cleavable/removable from the nucleotide unit, for example by reacting the chain terminating moiety with a chemical agent, pH change, light or heat. In some embodiments, the chain terminating moieties alkyl, alkenyl, alkynyl and allyl are cleavable with tetrakis(triphenylphosphine) palladium(0) (Pd(PPh$_3$)$_4$) with piperidine, or with 2,3-Dichloro-5,6-dicyano-1,4-benzo-quinone (DDQ). In some embodiments, the chain terminating moieties aryl and benzyl are cleavable with H$_2$ Pd/C. In some embodiments, the chain terminating moieties amine, amide, keto, isocyanate, phosphate, thio, disulfide are cleavable with phosphine or with a thiol group including beta-mercaptoethanol or dithiothritol (DTT). In some embodiments, the chain terminating moiety carbonate is cleavable with potassium carbonate ($K_2CO_3$) in MeOH, with triethylamine in pyridine, or with Zn in acetic acid (AcOH). In some embodiments, the chain terminating moieties urea and silyl are cleavable with tetrabutylammonium fluoride, pyridine-HF, with ammonium fluoride, or with triethylamine trihydrofluoride.

In some embodiments, the nucleotide unit comprises a chain terminating moiety (e.g., blocking moiety) at the sugar 2' position, at the sugar 3' position, or at the sugar 2' and 3' position. In some embodiments, the chain terminating moiety comprises an azide, azido or azidomethyl group. In some embodiments, the chain terminating moiety comprises a 3'-O-azido or 3'-O-azidomethyl group. In some embodiments, the chain terminating moieties azide, azido and azidomethyl group are cleavable/removable with a phosphine compound. In some embodiments, the phosphine compound comprises a derivatized tri-alkyl phosphine moiety or a derivatized tri-aryl phosphine moiety. In some embodiments, the phosphine compound comprises Tris(2-carboxyethyl)phosphine (TCEP) or bis-sulfo triphenyl phosphine (BS-TPP) or Tri(hydroxyproyl)phosphine (THPP). In some embodiments, the cleaving agent comprises 4-dimethylaminopyridine (4-DMAP).

In some embodiments, the nucleotide unit comprising a chain terminating moiety which is selected from a group consisting of 3'-deoxy nucleotides, 2',3'-dideoxynucleotides, 3'-methyl, 3'-azido, 3'-azidomethyl, 3'-O-azidoalkyl, 3'-O-ethynyl, 3'-O-aminoalkyl, 3'-O-fluoroalkyl, 3'-fluoromethyl, 3'-difluoromethyl, 3'-trifluoromethyl, 3'-sulfonyl, 3'-malonyl, 3'-amino, 3'-O-amino, 3'-sulfhydral, 3'-aminomethyl, 3'-ethyl, 3'butyl, 3'-tert butyl, 3'-Fluorenylmethyloxycarbonyl, 3' tert-Butyloxycarbonyl, 3'-O-alkyl hydroxylamino group, 3'-phosphorothioate, and 3-O-benzyl, or derivatives thereof.

In some embodiments, the multivalent molecule comprises a core attached to multiple nucleotide arms, wherein the nucleotide arms comprise a spacer, linker and nucleotide unit, and wherein the core, linker and/or nucleotide unit is labeled with detectable reporter moiety. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP or dUTP) of the nucleotide unit to permit detection and identification of the nucleotide base.

In some embodiments, at least one nucleotide arm of a multivalent molecule has a nucleotide unit that is attached to a detectable reporter moiety. In some embodiments, the detectable reporter moiety is attached to the nucleotide base. In some embodiments, the detectable reporter moiety comprises a fluorophore. In some embodiments, a particular detectable reporter moiety (e.g., fluorophore) that is attached to the multivalent molecule can correspond to the base (e.g., dATP, dGTP, dCTP, dTTP or dUTP) of the nucleotide unit to permit detection and identification of the nucleotide base.

In some embodiments, the core of a multivalent molecule comprises an avidin-like or streptavidin-like moiety and the core attachment moiety comprises biotin. In some embodiments, the core comprises an streptavidin-type or avidin-type moiety which includes an avidin protein, as well as any derivatives, analogs and other non-native forms of avidin that can bind to at least one biotin moiety. Other forms of avidin moieties include native and recombinant avidin and streptavidin as well as derivatized molecules, e.g. non-glycosylated avidin and truncated streptavidins. For example, avidin moiety includes de-glycosylated forms of avidin, bacterial streptavidin produced by Streptomyces (e.g., Streptomyces avidinii), as well as derivatized forms, for example, N-acyl avidins, e.g., N-acetyl, N-phthalyl and N-succinyl avidin, and the commercially-available products EXTRAVIDIN®, CAPTAVIDIN™, NEUTRAVIDIN™ and NEUTRALITE AVIDIN™.

In some embodiments, any of the methods for sequencing nucleic acid molecules described herein can include forming a binding complex, where the binding complex comprises (i) a polymerase, a nucleic acid concatemer molecule duplexed with a primer, and a nucleotide, or the binding complex comprises (ii) a polymerase, a nucleic acid concatemer molecule duplexed with a primer, and a nucleotide unit of a multivalent molecule. In some embodiments, the binding complex has a persistence time of greater than about 0.1, 0.2, 0.3, 0.4, 0.5, 0.6, 0.7, 0.8, 0.9 or 1 second. The binding complex has a persistence time of greater than about 0.1-0.25 seconds, or about 0.25-0.5 seconds, or about 0.5-0.75 seconds, or about 0.75-1 second, or about 1-2 seconds, or about 2-3 seconds, or about 3-4 second, or about 4-5 seconds, and/or wherein the method is or may be carried out at a temperature of at or above 15° C., at or above 20° C., at or above 25° C., at or above 35° C., at or above 37° C., at or above 42° C. at or above 55° C. at or above 60° C., or at or above 72° C., or at or above 80° C., or within a range defined by any of the foregoing. The binding complex (e.g., ternary complex) remains stable until subjected to a condition that causes dissociation of interactions between any of the polymerase, template molecule, primer and/or the nucleotide unit or the nucleotide. For example, a dissociating condition comprises contacting the binding complex with any one or any combination of a detergent, EDTA and/or water. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the contacting is performed under a condition that stabilizes the binding complex when the nucleotide or nucleotide unit is complementary to a next base of the template nucleic acid, and destabilizes the binding complex when the nucleotide or nucleotide unit is not complementary to the next base of the template nucleic acid.

EXAMPLES

The following examples are meant to be illustrative and can be used to further understand embodiments of the present disclosure and should not be construed as limiting the scope of the present teachings in any way.

Example 1: Linear Nucleic Acid Libraries

Commercially-available kits were used to prepare linear nucleic acid libraries having a sequence of interest (insert) appended to at least one universal sequencing primer, and universal binding sequences P5 (e.g., first surface primer) and P7 (e.g., second surface primer) at their terminal ends. The commercially-available kits are intended for preparing library molecules for a next gen sequencing platform such as Illumina. Input nucleic acids containing the sequences of interest included DNA and RNA from various organisms. The input nucleic acids were sheared using Covaris to achieve insert sizes of about 200, 250, 350 and 400 bp. The amount of input fragmented nucleic acids used to prepare the linear library molecules included 50 ng, 100 ng, 500 ng and 1 ug.

The input nucleic acids were obtained from Haemophilus influenzae (38% GC); E. coli (51% GC); Rhodopseudomonas palustris (65% GC); PhiX; Human; Human exome; and Human mRNA. A metagenomic DNA sample was also used to prepare linear library molecules. The metagenomic sample contained approximately 10% DNA of each of the following: Bacillus cereus (ATCC 10987); Bifidobacterium adolescentis (ATCC 15703); Clostridium beijerinckii (ATCC 35702); Deinococcus radiodurans (ATCC BAA-816); Enterococcus faecalis (ATCC 47077); Escherichia coli (ATCC 700926); Lactobacillus gasseri (ATCC 33323); Rhodobacter sphaeroides (ATCC 17029); Staphylococcus epidermidis (ATCC 12228); and Streptococcus mutans (ATCC 700610).

Example 2: Preparing Library-Splint Complexes

Fragmented input DNA (e.g., 0.25, 0.5 or 1 pmol) was annealed to the double-stranded splint adaptors (200) in an annealing buffer containing 100 mM potassium acetate and 30 mM HEPES (pH 7.5), in a thermal cycler apparatus. The annealing program was programmed to run: 5 minutes at 95 degrees C., 5 minutes at 37 degrees C., and hold at 37 degrees C.

Alternatively, the fragmented input DNA and double-stranded splint adaptors (200) were denatured for 5 minutes with 0.1 M NaOH, with a Tris and HEPES buffer, and without 95 degree heat. Denaturation using an alkali condition (e.g., using NaOH and/or KOH) instead of high heat was postulated to reduce deamination of cytosines, adenines and/or guanines. For every decrease of 10 degrees C. it was postulated to decrease the cytosine deamination rate by approximately 10-fold (Lindahl and Nyberg 1974 Biochemistry 13(16):3405-3410, "Heat-Induced Deamination of Cytosine Residues in Deoxyribonucleic Acid"; and Wang, et al., 1982 Biochimica et Biophisica Acta 697:371-377, "Heat- and Alkali-Induced Deamination of 5-methylcytosine and Cytosine Residues in DNA"). It was also postulated that denaturation with NaOH and/or KOH instead of heat would reduce secondary structures formed in library molecules. For example, NaOH or KOH could reduce intramolecular secondary structures formed between an insert region (110) and sample index regions (160) and/or (170). See FIGS. 5, 6, 7A and 7B for exemplary library molecules. A reduction in formation of intramolecular secondary structures could improve/reduce the index coefficient of variation (index CV).

The double-stranded splint adaptors comprised: first splint strands (300) hybridized to second splint strands (400). Exemplary double-stranded splint adaptor is shown in FIGS. 2 and 3.

The second splint strands (400) comprised: a first sub-region that hybridizes with a third surface primer and a second sub-region that hybridizes with a fourth surface primer (or a complementary sequence thereof). The 5' ends of the second splint strands (400) carried a phosphorylated end. The second splint strands (400) are designed to carry universal sequences that are not found in a commercially-available library preparation kit.

The first splint strands (300) comprised: a first region (320) that hybridizes with a P5 sequence at one end of the linear library molecule; an internal region (310) which hybridized with the second splint strands (400); and a second region (330) that hybridizes with a P7 sequence at the other end of the linear library molecule.

Example 3: Preparing Covalently Closed Circular Library Molecules

The annealing mixture from Example 2 was subjected to an enzymatic ligation and phosphorylation reaction by adding to the annealing mixture T7 DNA ligase and T4 polynucleotide kinase with a T4 DNA ligase reaction buffer. The enzymatic mixture was incubated in a thermal cycling apparatus with a heated lid set to 75 degrees C. The thermal cycling apparatus program included: 10 minutes at 37 degrees C., 10 minutes at 65 degrees, and hold at 4 degrees. The ligation and phosphorylation reactions generated covalently closed circular library molecules (600) that were hybridized to first splint strands (300).

An enzymatic exonuclease digestion was conducted by adding to the ligation/phosphorylation reaction mixture T7 exonuclease and Thermolabile exonuclease. The exonuclease reaction mixture was incubated in a thermal cycling apparatus which was programed: 10 minutes at 37 degrees C., 2 minutes at 80 degrees C., and hold at 4 degrees C.

The exonuclease reaction mixture was subjected to multiple cycles of clean-up using SPRI SELECT beads (from Beckman Coulter).

Alternatively, the ligation and phosphorylation reaction were conducted using a heated lid set to 75 degrees C., and the thermal cycling apparatus program was set to run: 10 minutes at 37 degrees C. Single-stranded molecules were degraded using exonuclease I for 10 minutes at 37 degrees, without high heat for an extended time (e.g., without 65 degrees C. for 10 minutes). The exonuclease I was heat-inactivated at 80 degrees C. for 2 minutes, followed by EDTA addition. The SPRI SELECT bead clean-step was not conducted.

Alternatively, the ligation heat-kill step was replaced with enzyme deactivation using NaOH.

Figure 34:
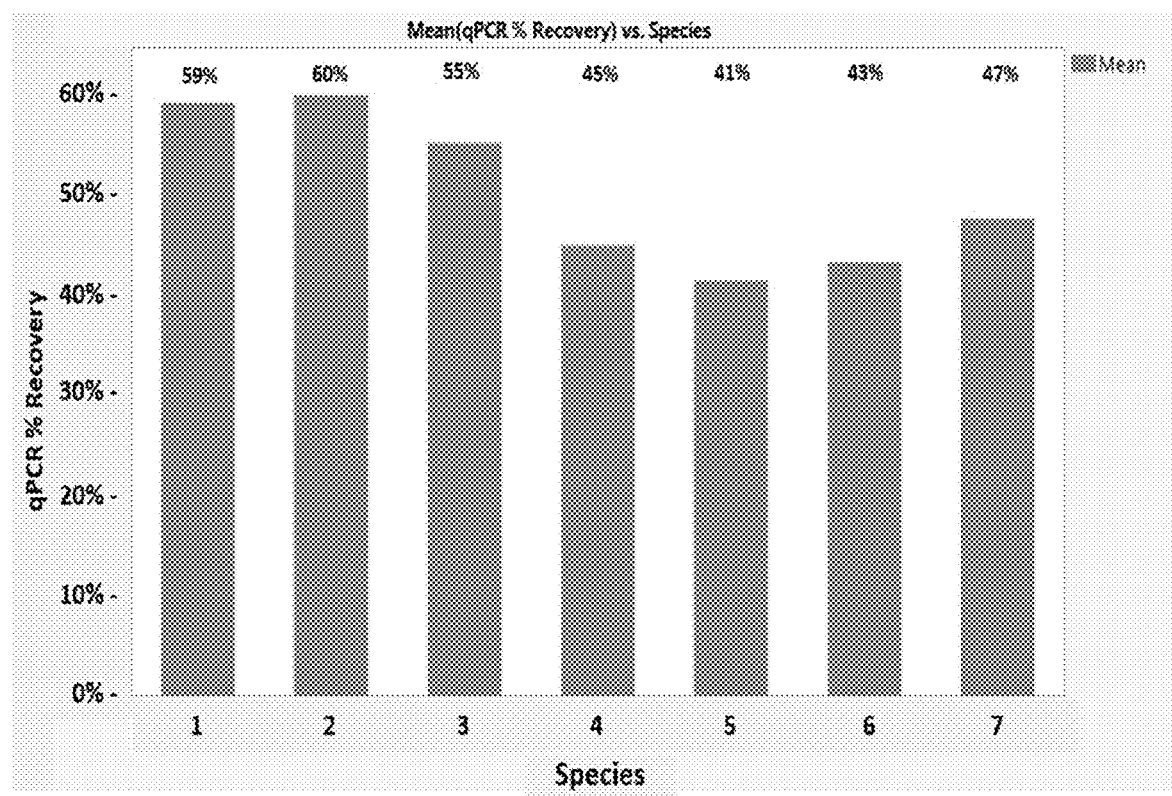
FIG. 34 is a bar graph showing the mean percent recovery of covalently closed circular library molecules using input DNA from various species as determined by qPCR. Lane 1: *Haemophilus influenzae* (38% GC); Lane 2: *E. coli* (51% GC); Lane 3: *Rhodopseudomonas palustris* (65% GC); Lane 4: PhiX; Lane 5: Human; Lane 6: Human exome; Lane 7: Human mRNA. See Examples 1-3.

The yield of the cleaned preparation of covalently closed circular library molecules (e.g., single stranded molecules) were quantified using Qubit or qPCR. The mean percent circularization recovery are shown in FIG. 34 Lane 1: *Haemophilus influenzae* (38% GC); Lane 2: *E. coli* (51% GC); Lane 3: *Rhodopseudomonas palustris* (65% GC); Lane 4: PhiX; Lane 5: Human; Lane 6: Human exome; Lane 7: Human mRNA.

Example 4: Quantifying Covalently Closed Circular Library Molecules

The covalently closed circular library molecules (600) were prepared using double-stranded splint adaptors (200) comprising variant long splint strands (first splint strands (300)) to reduce carry-over of the long splint strands during and after qPCR. The long splint carry-over over-inflates the quantization of the covalently closed circular library molecules. Exemplary variant long splint strands included truncated long splint strands (FIG. 11B), long splint strands having mis-match sequences (FIG. 11C), long splint strands having abasic sites (FIG. 11D, top) and long splint strands having uracil (FIG. 11D, bottom). In some cases, the long splint strands were modified at their 5' ends to include one or more phosphorothioate bond substitutes to inhibit exonuclease degradation.

The covalently closed circular library molecules from Example 3 were quantified using qPCR. The qPCR primers were designed to have complete complementarity to a universal adaptor sequence of the covalently closed circular library molecules. The qPCR primers hybridized to either the first right universal adaptor sequence (120) which comprises a primer binding site for a surface pinning primer, or the first left universal adaptor sequence (130) which comprises a primers binding site for a surface capture primer. The qPCR reaction was catalyzed by Taq DNA polymerase.

The 5' truncated ends of the various truncated long splint strands (FIG. 11B) carried enough sequence in the first region (320) to permit circularization and formation of covalently closed circular library molecules with good circularization yields and reduced long splint carry-over.

The mis-match sequences of the various mis-match long splint strand (FIG. 11C) permitted circularization and formation of covalently closed circular library molecules with good circularization yields and reduced long splint carry-over.

The abasic sites of the abasic-containing long splint strand (FIG. 11D; top) permitted circularization and formation of covalently closed circular library molecules with good circularization yields and reduced long splint carry-over.

The uracil-containing sequence of the long splint strand (FIG. 11D, bottom) permitted circularization and formation of covalently closed circular library molecules with good circularization yields and reduced long splint carry-over. The qPCR workflow included treatment with uracil DNA glycosylase (UDG) in the qPCR mix.

Example 5: Rolling Circle Amplification and Sequencing

Figure 35:
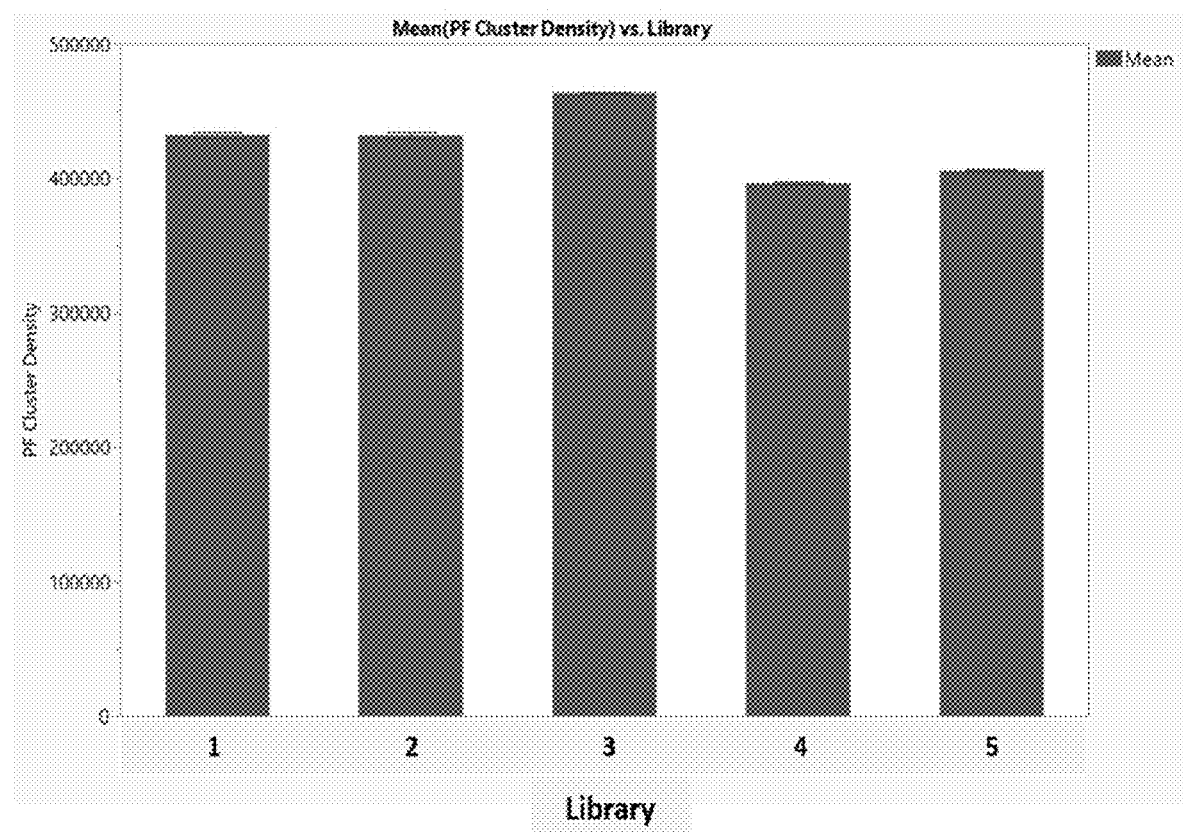
FIG. 35 is a bar graph showing the mean polony density obtained by distributing covalently closed circular library molecules onto a support, and performing on-support rolling circle amplification. The covalently closed circular library molecules were prepared from input DNA from various species. Lane 1: cell free DNA; Lane 2: *E. coli*; Lane 3: Human; Lane 4: metagenomic DNA; and Lane 5: PhiX. See Example 4.

The covalently closed circular library molecules from Example 3 were distributed onto a support that was passivated with a low non-specific binding coating in the presence of a high efficiency hybridization buffer, and subjected to on-support rolling circle amplification to generate immobilized concatemers. The mean polony density of the immobilized concatemers is shown in FIG. 35. Lane 1: cell free DNA; Lane 2: *E. coli*; Lane 3: Human; Lane 4: metagenomic DNA; and Lane 5: PhiX.

Example 6: Sequencing Using Multivalent Molecules and Nucleotides

The concatemers were subjected to multiple cycles of two-stage sequencing reactions using fluorescently-labeled multivalent molecules in the first stage and un-labeled nucleotide analogs (e.g., 3' chain terminator blocking group) in the second stage.

The two-stage sequencing reaction was conducted on a flow cell having a plurality of concatemer template molecules immobilized thereon (e.g., immobilized polonies).

The first-stage sequencing reaction was conducted by hybridizing a plurality of a soluble sequencing primers to concatemer template molecules that were immobilized to a flow cells to form immobilized primer-concatemer duplexes. A plurality of a first sequencing polymerase was flowed onto the flow cell (e.g., contacting the immobilized primer-concatemer duplexes) and incubated under a condition suitable to bind the sequencing polymerase to the duplexes to form complexed polymerases. A mixture of fluorescently labeled multivalent molecules (e.g., at different concentrations of about 20-100 nM) was flowed onto the flow cell in the presence of a buffer that included a non-catalytic cation (e.g., strontium, barium and/or calcium) and incubated under conditions suitable to bind complementary nucleotide units of the multivalent molecules to the complexed polymerases to form avidity complexes without polymerase-catalyzed incorporation of the nucleotide units. The fluorescently labeled multivalent molecules were labeled at their cores. The complexed polymerases were washed. An image was obtained of the fluorescently labeled multivalent molecules that remained bound to the complexed polymerases. The first sequencing polymerases and multivalent molecules were removed, while retaining the sequencing primers hybridized to the immobilized concatemers (retained duplexes), by washing with a buffer comprising a detergent.

The first stage sequencing reaction was suitable for forming a plurality of avidity complexes on the concatemer template molecules (e.g., polonies). For example, the first stage sequencing reaction comprised: (a) binding a first nucleic acid primer, a first polymerase, and a first multivalent molecule to a first portion of a concatemer template molecule thereby forming a first binding complex, wherein a first nucleotide unit of the first multivalent molecule was bound to the first polymerase; and (b) binding a second nucleic acid primer, a second polymerase, and the first multivalent molecule to a second portion of the same concatemer template molecule thereby forming a second binding complex, wherein a second nucleotide unit of the first multivalent molecule was bound to the second polymerase, wherein the first and second binding complexes which included the same multivalent molecule formed a first avidity complex.

The second-stage sequencing reaction was conducted by contacting the retained duplexes with a plurality of second sequencing polymerases to form complexed polymerases. A mixture of non-labeled nucleotide analogs (e.g., 3'O-methylazido nucleotides) (e.g., at different concentrations of about 1-5 uM) was added to the complexed polymerases in the presence of a buffer that included a catalytic cation (e.g., magnesium and/or manganese) and incubated under conditions suitable to bind complementary nucleotides to the complexed polymerases and promote polymerase-catalyzed incorporation of the nucleotides to generate a nascent extended sequencing primer (e.g., extended forward sequencing primer). The complexed polymerases were washed. No image was obtained. The incorporated non-labeled nucleotide analogs were reacted with a cleaving reagent that removes the 3' O-methylazido group and generates an extendible 3'OH group.

In an alternative second stage sequencing reaction, a mixture of fluorescently labeled nucleotide analogs (e.g., 3'O-methylazido nucleotides) (e.g., about 1-5 uM) was added to the complexed polymerases in the presence of a buffer that included a catalytic cation (e.g., magnesium and/or manganese) and incubated under conditions suitable to bind complementary nucleotides to the complexed polymerases and promote polymerase-catalyzed incorporation of the nucleotides to generate a nascent extended sequencing primer. The complexed polymerases were washed. An image was obtained of the incorporated fluorescently labeled nucleotide analogs as a part of the complexed polymerases. The incorporated fluorescently labeled nucleotide analogs were reacted with a cleaving reagent that removes the 3' O-methylazido group and generates an extendible 3'OH group.

The second sequencing polymerases were removed, while retaining the nascent extended sequencing primers hybridized to the concatemers (retained duplexes), by washing with a buffer comprising a detergent. Recurring sequencing reactions were conducted by performing multiple cycles of first-stage and second-stage sequencing reactions to generate extended forward sequencing primer strands.

The first strand sequencing was performed using the two-stage sequencing reactions described above. In some cases, a pairwise turn was conducted to obtain sequencing information from the first template strand (R1 sequencing reads) and second template strand (R2 sequencing reads). For pairwise sequencing, the immobilized template molecules included one or more uracils. After sequencing of the first template strands was completed (R1 sequencing reads), the extended forward sequencing primers were removed from the first template strands, and replaced by conducting a primer extension reaction on the first template strands to generate forward extension strands which were immobilized to the flowcell and hybridized to the first template strands. The first template strands were removed by subjecting the first template strands (which included uracil) to a mixture of enzymes that generated abasic sites and gaps at the abasic sites, while retaining the forward extension strands which were immobilized to the flowcell. The forward extension strands were hybridized to a plurality of reverse sequencing primers and multiple cycles of two-stage sequencing reactions were conducted to generate R2 sequencing reads.

A comparison of sequencing quality scores was conducted, comparing libraries that were prepared using either (1) high heat for denaturation and heat inactivation of ligase, (2) NaOH denaturation and no heat inactivation of ligase and exonuclease I digestion, (3) HEPES buffer, and (4) a cocktail mixture of enzymes that can generate abasic sites and remove the abasic sites. For example, DNA glycosylase (UDG) can generate abasic sites at uracil bases. In some embodiments, the reagent that removes deaminated bases comprises a compound that generates a gap at abasic sites in a nucleic acid strand. For example, the gaps can be generated with an enzyme or a mixture of enzymes having lyase activity that breaks the phosphodiester backbone at the 5' and 3' sides of the abasic site to release the base-free deoxyribose and generate a gap. The abasic sites can be removed using AP lyase, Endo IV endonuclease, FPG glycosylase/AP lyase and/or Endo VIII glycosylase/AP lyase. In some embodiments, generating the abasic sites and removal of the abasic sites to generate gaps can be achieved using a mixture of uracil DNA glycosylase and DNA glycosylase-lyase endonuclease VIII, for example USER™ (Uracil-Specific Excision Reagent Enzyme from New England Biolabs) or thermolabile USER (also from New England Biolabs).

In a series of sequencing runs conducted with 50-plus first strand sequencing cycles (R1 sequencing reads), the results showed that the quality scores of T-base calls increased from about Q39 (for high heat treatment) to about Q45 (for NaOH treatment) (e.g., FIGS. 15A-D).

In a series of sequencing runs conducted with 50-plus second strand sequencing cycles conducted after a paired end turn (R2 sequencing reads), the results showed that the quality scores of A-base calls increased from about Q38 (for high heat treatment) to about Q42 (for NaOH treatment) (e.g., FIGS. 16A-D).

Figure 17:
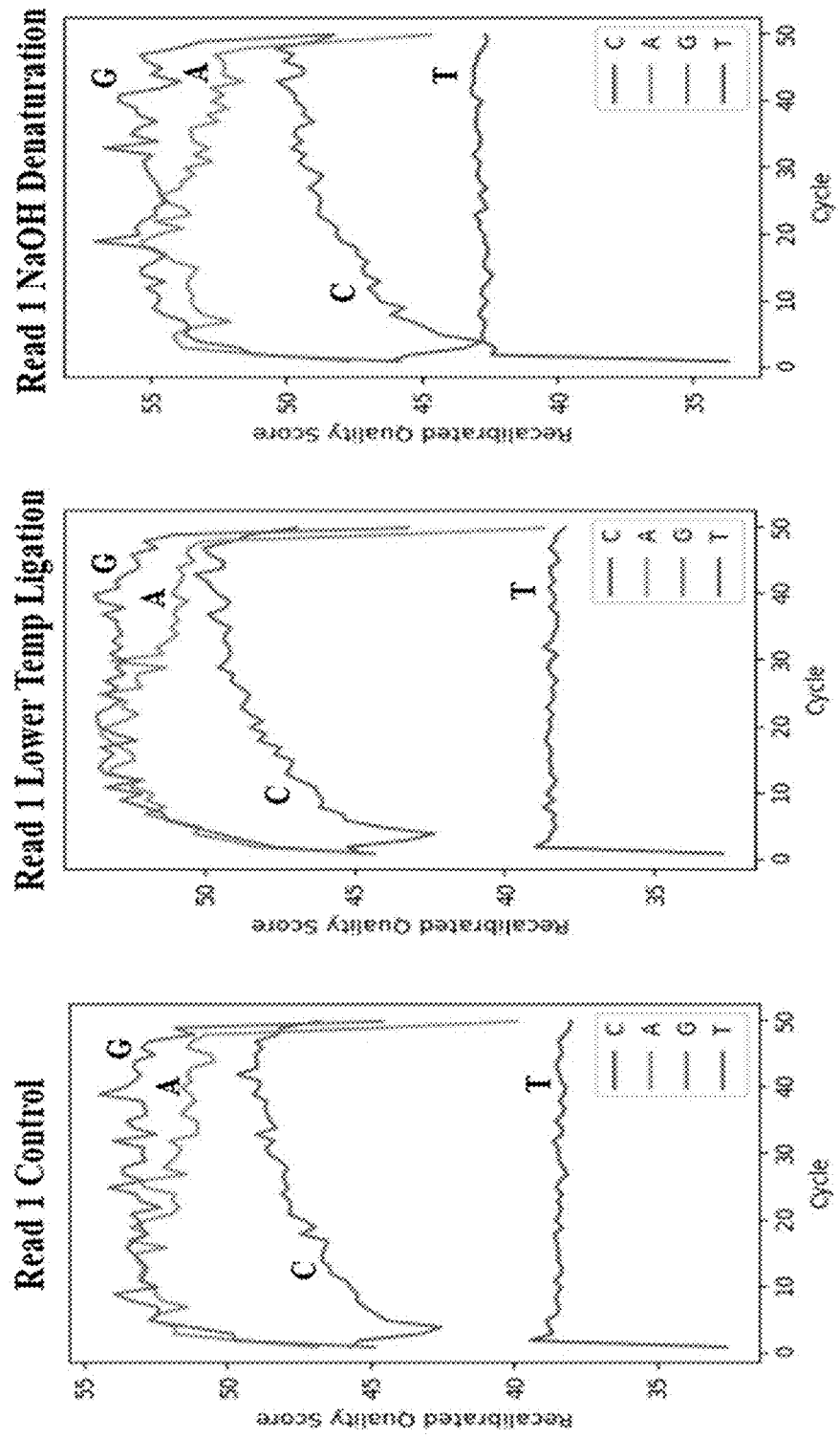
FIG. 17 is a series of 3 graphs showing sequencing quality scores of A, G, C and T base calls of first strand concatemer template molecules (read 1) that were generated by a workflow that included circularizing linear library molecules using double-stranded splint adaptors (e.g., see FIG. 5 or 6, but without unique identification sequences (180) and (190)), with ligase enzyme deactivation, and conducting on-support rolling circle amplification to generate concatemer template molecules immobilized to a coated support. The library preparation workflow compared the effect of ligase high heat-kill control (left panel), ligase lower heat-kill (middle panel) and ligase NaOH deactivation (right panel). The X-axis is the number of sequencing cycles. The Y-axis is the quality scores.
Figure 18:
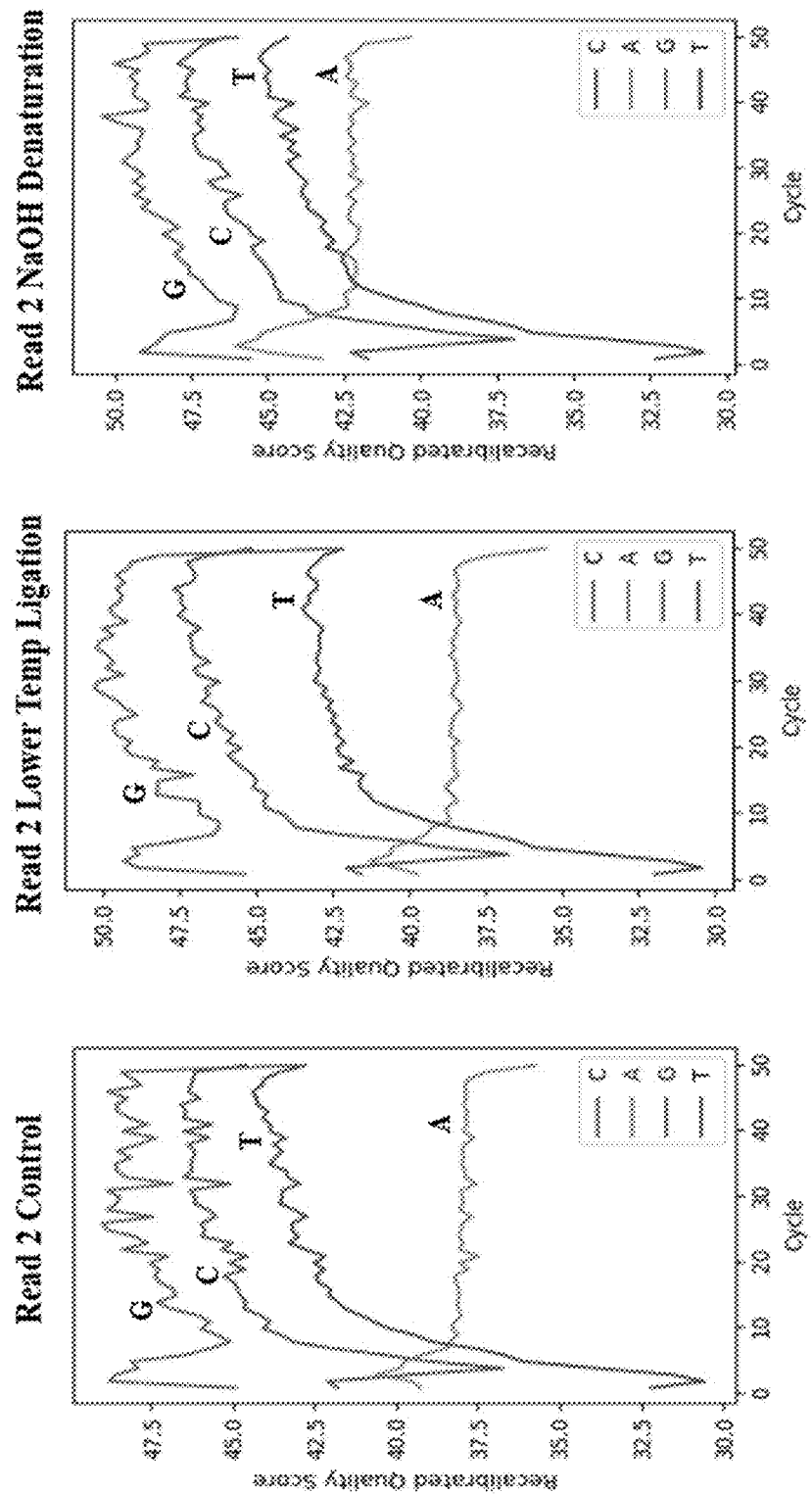
FIG. 18 is a series of 3 graphs showing sequencing quality scores of A, G, C and T base calls of second strand concatemer template molecules (read 2) that were generated by a workflow that included circularizing linear library molecules using double-stranded splint adaptors (e.g., see FIG. 5 or 6, but without unique identification sequences (180) and (190)), with ligase enzyme deactivation, and conducting on-support rolling circle amplification to generate concatemer template molecules immobilized to a coated support. The library preparation workflow compared the effect of ligase high heat-kill control (left panel), ligase lower heat-kill (middle panel) and ligase NaOH deactivation (right panel). The X-axis is the number of sequencing cycles. The Y-axis is the quality scores.

In a series of sequencing runs conducted with 50 first strand (R1 sequencing reads) and 50 second strand (R2 sequencing reads) sequencing cycles, where the workflow included a comparison deactivating ligase enzyme using either high heat (control), lower heat or NaOH deactivation, the results show that the quality scores of T-base call for R1 was below Q40 for high heat kill (e.g., FIG. 17, left) and lower heat kill (e.g., FIG. 17, middle), but improved to over Q42 for NaOH deactivation (e.g., FIG. 17, right). The results also show that the quality scores of A-base call for R2 was below Q40 for high heat kill (e.g., FIG. 18, left) and lower heat kill (e.g., FIG. 18, middle), but improved to over Q42 for NaOH deactivation (e.g., FIG. 18, right).

In a series of sequencing runs conducted with 50 first strand (R1 sequencing reads) and 50 second strand (R2 sequencing reads) sequencing cycles, the index CV improved from 10.9% for workflows that included heat denaturation to 10.79% for workflows that included NaOH denaturation (data not shown).

What is claimed:

1. A library-splint complex (500) comprising:
   (i) a single-stranded nucleic acid library molecule (100) comprising a sequence of interest (110) flanked on one side by at least a first left universal adaptor sequence (120), and flanked on the other side by at least a first right universal adaptor sequence (130); and
   (ii) a double-stranded splint adaptor (200) comprising a first splint strand (300) and a second splint strand (400), wherein the double-stranded splint adaptor (200) comprises a double-stranded region and two single-stranded regions, one on either side of the double-stranded region, wherein the first splint strand (300) comprises a first region (320), an internal region (310), and a second region (330), and wherein the first splint strand comprises at least one abasic site or uracil;
   wherein the internal region (310) of the first splint strand (300) is hybridized to the second splint strand (400), wherein the first region (320) of the first splint strand (300) is hybridized to the at least first left universal adaptor sequence (120) of the single-stranded nucleic acid library molecule, and wherein the second region (330) of the first splint strand (300) is hybridized to the at least first right universal sequence (130) of the single-stranded nucleic acid library molecule, thereby circularizing the single-stranded nucleic acid library molecule to generate a library-splint complex (500).

2. The library-splint complex (500) of claim 1, wherein the single-stranded nucleic acid library molecule (100) comprises: a second left universal adaptor sequence (140).

3. The library-splint complex (500) of claim 1, wherein the single-stranded nucleic acid library molecule (100) comprises: a second right universal adaptor sequence (150).

4. The library-splint complex (500) of claim 1, wherein the single-stranded nucleic acid library molecule (100) comprises: a first left index sequence (160).

5. The library-splint complex (500) of claim 1, wherein the single-stranded nucleic acid library molecule (100) comprises: a first right index sequence (170).

6. The library-splint complex (500) of claim 1, wherein the single-stranded nucleic acid library molecule (100) comprises: a first left unique identification sequence (180).

7. The library-splint complex (500) of claim 1, wherein the single-stranded nucleic acid library molecule (100) comprises: a first right unique identification sequence (190).

8. The library-splint complex (500) of claim 1, wherein the single-stranded nucleic acid library molecule (100) comprises any combination of two or more of:
   (i) a second left universal adaptor sequence (140);
   (ii) a second right universal adaptor sequence (150);
   (iii) a first left index sequence (160);
   (iv) a first right index sequence (170);
   (v) a first left unique identification sequence (180); and/or
   (vi) a first right unique identification sequence (190).

9. The library-splint complex (500) of claim 2, wherein the at least first left universal adaptor sequence (120) and/or the second left universal adaptor sequence (140) comprises:
   (i) a universal binding sequence for a forward sequencing primer;
   (ii) a universal binding sequence for a reverse sequencing primer;

(iii) a universal binding sequence for a first surface primer;
(iv) a universal binding sequence for a second surface primer;
(v) a universal binding sequence for a forward amplification primer;
(vi) a universal binding sequence for a reverse amplification primer; and/or
(vii) a universal binding sequence for a compaction oligonucleotide.

10. The library-splint complex (500) of claim 9, wherein the second splint strand (400) includes at least a first sub-region and a second sub-region, wherein the first sub-region comprises a universal binding sequence for a third surface primer and the second sub-region comprises a universal binding sequence for a fourth surface primer, and wherein the first and second sub-regions do not hybridize or exhibit very little hybridization to the first surface primer and second surface primer.

11. The library-splint complex (500) of claim 10, wherein the second splint strand (400) comprises third sub-region, wherein the third sub-region comprises a sample index sequence having 5-20 bases and/or a unique identification sequence having 2-10 or more bases.

12. The library-sprint complex (500) of claim 11, wherein the unique identification sequence comprises a random sequence.

13. The library-splint complex (500) of claim 10, wherein the internal region (310) of the first splint strand (300) comprises at least a fourth sub-region and a fifth sub-region, wherein the fourth sub-region hybridizes to the first sub-region of the second splint strand (400), wherein the fifth sub-region hybridizes to the second sub-region of the second splint strand (400), and wherein the fourth and fifth sub-regions do not hybridize or exhibit very little hybridization to the first and second surface primers.

14. The library-splint complex (500) of claim 11, wherein the internal region (310) of the first splint strand (300) comprises a sixth sub-region comprising a sample index sequence having 5-20 bases and/or a unique identification sequence having 2-10 or more bases, and wherein the sixth sub-region hybridizes to the third sub-region of the second splint strand (400).

15. The library-splint complex (500) of claim 14, wherein the unique identification sequence comprises a random sequence.

16. The library-splint complex (500) of claim 1, wherein the first right universal adaptor sequence (130) and/or the second right universal adaptor sequence (150) comprises:
(i) a universal binding sequence for a forward sequencing primer;
(ii) a universal binding sequence for a reverse sequencing primer;
(iii) a universal binding sequence for a first surface primer;
(iv) a universal binding sequence for a second surface primer;
(v) a universal binding sequence for a forward amplification primer;
(vi) a universal binding sequence for a reverse amplification primer; and/or
(vii) a universal binding sequence for a compaction oligonucleotide.

17. The library-splint complex (500) of claim 16, wherein the second splint strand (400) includes at least a first sub-region and a second sub-region, wherein the first sub-region comprises a universal binding sequence for a third surface primer and the second sub-region comprises a universal binding sequence for a fourth surface primer, and wherein the first and second sub-regions do not hybridize or exhibit very little hybridization to the first and second surface primers.

18. The library-splint complex (500) of claim 17, wherein the second splint strand (400) comprises a third sub-region, wherein the third sub-region comprises a sample index sequence having 5-20 bases and/or a unique identification sequence having 2-10 or more bases.

19. The library-sprint complex (500) of claim 18, wherein the unique identification sequence comprises a random sequence.

20. The library-splint complex (500) of claim 17, wherein the internal region (310) of the first splint strand (300) comprises at least a fourth sub-region and a fifth sub-region, wherein the fourth sub-region hybridizes to the first sub-region of the second splint strand (400), and the fifth sub-region hybridizes to the second sub-region of the second splint strand (400), and wherein the fourth and fifth sub-regions do not hybridize or exhibit very little hybridization to the first and second surface primers.

21. The library-splint complex (500) of claim 18, wherein the internal region (310) of the first splint strand (300) comprises a sixth sub-region which comprises a sample index sequence having 5-20 bases and/or a unique identification sequence having 2-10 or more bases, and wherein the sixth sub-region hybridizes to the third sub-region of the second splint strand (400).

22. The library-splint complex (500) of claim 21, wherein the unique identification sequence comprises a random sequence.

23. A library-splint complex (500) comprising:
a) a single-stranded nucleic acid library molecule (100) comprising from 5' to 3': (i) a first left universal adaptor sequence (120) having a binding sequence for a first surface primer; (ii) a second left universal adaptor sequence (140) having a binding sequence for a first sequencing primer; (iii) a sequence of interest (110); (iv) a second right universal adaptor sequence (150) having a binding sequence for a second sequencing primer; and (v) a first right universal adaptor sequence (130) having a binding sequence for a second surface primer;
b) a first splint strand (300) comprising from 5' to 3': a first region (320); an internal region (310); and a second region (330), wherein the first splint strand comprises at least one abasic site or uracil; and
c) a second splint strand (400) comprising from 3' to 5': a first sub-region having a universal binding sequence for a third surface primer; and a second sub-region having a universal binding sequence for a fourth surface primer; wherein the first splint strand (300) is hybridized to portions of the single-stranded nucleic acid library molecule (100) thereby circularizing the single-stranded nucleic acid library molecule to generate a library-splint complex (500), wherein the first region (320) of the first splint strand (300) is hybridized to the binding sequence for the first surface primer, and the third region (330) of the first splint strand (300) is hybridized to the binding sequence for the second surface primer, wherein the second splint strand (400) is hybridized to the internal region (310) of the first splint strand (300), wherein the library-splint complex (500) comprises a first nick between a 5' end of the single-stranded nucleic acid library molecule and a 3' end of the second splint strand (400), wherein the library-splint complex (500) comprises a second nick between a 5' end of the second splint strand (400) and a 3' end of the single-stranded nucleic acid library molecule.

24. The library splint complex (500) of claim 23, wherein the first and second nicks are enzymatically ligatable.

25. A plurality of library-splint complexes comprising the library-splint complex (500) of claim 1, wherein the sequence of interest (110) of individual library-splint complexes in the plurality comprises the same sequence of interest or different sequences of interest.

26. A kit comprising reagents for generating the library splint complex of claim 1, comprising a plurality of double-stranded splint adaptors.

* * * * *

```
                              SEQUENCE LISTING

Sequence total quantity: 243
SEQ ID NO: 1            moltype =    length =
SEQUENCE: 1
000

SEQ ID NO: 2            moltype =    length =
SEQUENCE: 2
000

SEQ ID NO: 3            moltype =    length =
SEQUENCE: 3
000

SEQ ID NO: 4            moltype =    length =
SEQUENCE: 4
000

SEQ ID NO: 5            moltype =    length =
SEQUENCE: 5
000

SEQ ID NO: 6            moltype =    length =
SEQUENCE: 6
000

SEQ ID NO: 7            moltype =    length =
SEQUENCE: 7
000

SEQ ID NO: 8            moltype =    length =
SEQUENCE: 8
000

SEQ ID NO: 9            moltype =    length =
SEQUENCE: 9
000

SEQ ID NO: 10           moltype =    length =
SEQUENCE: 10
000

SEQ ID NO: 11           moltype =    length =
SEQUENCE: 11
000

SEQ ID NO: 12           moltype =    length =
SEQUENCE: 12
000

SEQ ID NO: 13           moltype =    length =
SEQUENCE: 13
000

SEQ ID NO: 14           moltype =    length =
SEQUENCE: 14
000

SEQ ID NO: 15           moltype =    length =
SEQUENCE: 15
000

SEQ ID NO: 16           moltype =    length =
SEQUENCE: 16
000

SEQ ID NO: 17           moltype =    length =
SEQUENCE: 17
000
```

| | | |
|---|---|---|
| SEQ ID NO: 18 SEQUENCE: 18 000 | moltype = | length = |
| SEQ ID NO: 19 SEQUENCE: 19 000 | moltype = | length = |
| SEQ ID NO: 20 SEQUENCE: 20 000 | moltype = | length = |
| SEQ ID NO: 21 SEQUENCE: 21 000 | moltype = | length = |
| SEQ ID NO: 22 SEQUENCE: 22 000 | moltype = | length = |
| SEQ ID NO: 23 SEQUENCE: 23 000 | moltype = | length = |
| SEQ ID NO: 24 SEQUENCE: 24 000 | moltype = | length = |
| SEQ ID NO: 25 SEQUENCE: 25 000 | moltype = | length = |
| SEQ ID NO: 26 SEQUENCE: 26 000 | moltype = | length = |
| SEQ ID NO: 27 SEQUENCE: 27 000 | moltype = | length = |
| SEQ ID NO: 28 SEQUENCE: 28 000 | moltype = | length = |
| SEQ ID NO: 29 SEQUENCE: 29 000 | moltype = | length = |
| SEQ ID NO: 30 SEQUENCE: 30 000 | moltype = | length = |
| SEQ ID NO: 31 SEQUENCE: 31 000 | moltype = | length = |
| SEQ ID NO: 32 SEQUENCE: 32 000 | moltype = | length = |
| SEQ ID NO: 33 SEQUENCE: 33 000 | moltype = | length = |
| SEQ ID NO: 34 SEQUENCE: 34 000 | moltype = | length = |
| SEQ ID NO: 35 SEQUENCE: 35 000 | moltype = | length = |
| SEQ ID NO: 36 SEQUENCE: 36 000 | moltype = | length = |
| SEQ ID NO: 37 SEQUENCE: 37 | moltype = | length = |

| | | |
|---|---|---|
| SEQ ID NO: 38 SEQUENCE: 38 000 | moltype = | length = |
| SEQ ID NO: 39 SEQUENCE: 39 000 | moltype = | length = |
| SEQ ID NO: 40 SEQUENCE: 40 000 | moltype = | length = |
| SEQ ID NO: 41 SEQUENCE: 41 000 | moltype = | length = |
| SEQ ID NO: 42 SEQUENCE: 42 000 | moltype = | length = |
| SEQ ID NO: 43 SEQUENCE: 43 000 | moltype = | length = |
| SEQ ID NO: 44 SEQUENCE: 44 000 | moltype = | length = |
| SEQ ID NO: 45 SEQUENCE: 45 000 | moltype = | length = |
| SEQ ID NO: 46 SEQUENCE: 46 000 | moltype = | length = |
| SEQ ID NO: 47 SEQUENCE: 47 000 | moltype = | length = |
| SEQ ID NO: 48 SEQUENCE: 48 000 | moltype = | length = |
| SEQ ID NO: 49 SEQUENCE: 49 000 | moltype = | length = |
| SEQ ID NO: 50 SEQUENCE: 50 000 | moltype = | length = |
| SEQ ID NO: 51 SEQUENCE: 51 000 | moltype = | length = |
| SEQ ID NO: 52 SEQUENCE: 52 000 | moltype = | length = |
| SEQ ID NO: 53 SEQUENCE: 53 000 | moltype = | length = |
| SEQ ID NO: 54 SEQUENCE: 54 000 | moltype = | length = |
| SEQ ID NO: 55 SEQUENCE: 55 000 | moltype = | length = |
| SEQ ID NO: 56 SEQUENCE: 56 000 | moltype = | length = |
| SEQ ID NO: 57 | moltype = | length = |

| | | |
|---|---|---|
| SEQUENCE: 57 000 | | |
| SEQ ID NO: 58 SEQUENCE: 58 000 | moltype = | length = |
| SEQ ID NO: 59 SEQUENCE: 59 000 | moltype = | length = |
| SEQ ID NO: 60 SEQUENCE: 60 000 | moltype = | length = |
| SEQ ID NO: 61 SEQUENCE: 61 000 | moltype = | length = |
| SEQ ID NO: 62 SEQUENCE: 62 000 | moltype = | length = |
| SEQ ID NO: 63 SEQUENCE: 63 000 | moltype = | length = |
| SEQ ID NO: 64 SEQUENCE: 64 000 | moltype = | length = |
| SEQ ID NO: 65 SEQUENCE: 65 000 | moltype = | length = |
| SEQ ID NO: 66 SEQUENCE: 66 000 | moltype = | length = |
| SEQ ID NO: 67 SEQUENCE: 67 000 | moltype = | length = |
| SEQ ID NO: 68 SEQUENCE: 68 000 | moltype = | length = |
| SEQ ID NO: 69 SEQUENCE: 69 000 | moltype = | length = |
| SEQ ID NO: 70 SEQUENCE: 70 000 | moltype = | length = |
| SEQ ID NO: 71 SEQUENCE: 71 000 | moltype = | length = |
| SEQ ID NO: 72 SEQUENCE: 72 000 | moltype = | length = |
| SEQ ID NO: 73 SEQUENCE: 73 000 | moltype = | length = |
| SEQ ID NO: 74 SEQUENCE: 74 000 | moltype = | length = |
| SEQ ID NO: 75 SEQUENCE: 75 000 | moltype = | length = |
| SEQ ID NO: 76 SEQUENCE: 76 000 | moltype = | length = |

| | | |
|---|---|---|
| SEQ ID NO: 77
SEQUENCE: 77
000 | moltype = | length = |
| SEQ ID NO: 78
SEQUENCE: 78
000 | moltype = | length = |
| SEQ ID NO: 79
SEQUENCE: 79
000 | moltype = | length = |
| SEQ ID NO: 80
SEQUENCE: 80
000 | moltype = | length = |
| SEQ ID NO: 81
SEQUENCE: 81
000 | moltype = | length = |
| SEQ ID NO: 82
SEQUENCE: 82
000 | moltype = | length = |
| SEQ ID NO: 83
SEQUENCE: 83
000 | moltype = | length = |
| SEQ ID NO: 84
SEQUENCE: 84
000 | moltype = | length = |
| SEQ ID NO: 85
SEQUENCE: 85
000 | moltype = | length = |
| SEQ ID NO: 86
SEQUENCE: 86
000 | moltype = | length = |
| SEQ ID NO: 87
SEQUENCE: 87
000 | moltype = | length = |
| SEQ ID NO: 88
SEQUENCE: 88
000 | moltype = | length = |
| SEQ ID NO: 89
SEQUENCE: 89
000 | moltype = | length = |
| SEQ ID NO: 90
SEQUENCE: 90
000 | moltype = | length = |
| SEQ ID NO: 91
SEQUENCE: 91
000 | moltype = | length = |
| SEQ ID NO: 92
SEQUENCE: 92
000 | moltype = | length = |
| SEQ ID NO: 93
SEQUENCE: 93
000 | moltype = | length = |
| SEQ ID NO: 94
SEQUENCE: 94
000 | moltype = | length = |
| SEQ ID NO: 95
SEQUENCE: 95
000 | moltype = | length = |
| SEQ ID NO: 96
SEQUENCE: 96
000 | moltype = | length = |

| | | |
|---|---|---|
| SEQ ID NO: 97<br>SEQUENCE: 97<br>000 | moltype = | length = |
| SEQ ID NO: 98<br>SEQUENCE: 98<br>000 | moltype = | length = |
| SEQ ID NO: 99<br>SEQUENCE: 99<br>000 | moltype = | length = |
| SEQ ID NO: 100<br>SEQUENCE: 100<br>000 | moltype = | length = |
| SEQ ID NO: 101<br>SEQUENCE: 101<br>000 | moltype = | length = |
| SEQ ID NO: 102<br>SEQUENCE: 102<br>000 | moltype = | length = |
| SEQ ID NO: 103<br>SEQUENCE: 103<br>000 | moltype = | length = |
| SEQ ID NO: 104<br>SEQUENCE: 104<br>000 | moltype = | length = |
| SEQ ID NO: 105<br>SEQUENCE: 105<br>000 | moltype = | length = |
| SEQ ID NO: 106<br>SEQUENCE: 106<br>000 | moltype = | length = |
| SEQ ID NO: 107<br>SEQUENCE: 107<br>000 | moltype = | length = |
| SEQ ID NO: 108<br>SEQUENCE: 108<br>000 | moltype = | length = |
| SEQ ID NO: 109<br>SEQUENCE: 109<br>000 | moltype = | length = |
| SEQ ID NO: 110<br>SEQUENCE: 110<br>000 | moltype = | length = |
| SEQ ID NO: 111<br>SEQUENCE: 111<br>000 | moltype = | length = |
| SEQ ID NO: 112<br>SEQUENCE: 112<br>000 | moltype = | length = |
| SEQ ID NO: 113<br>SEQUENCE: 113<br>000 | moltype = | length = |
| SEQ ID NO: 114<br>SEQUENCE: 114<br>000 | moltype = | length = |
| SEQ ID NO: 115<br>SEQUENCE: 115<br>000 | moltype = | length = |
| SEQ ID NO: 116<br>SEQUENCE: 116 | moltype = | length = |

000

SEQ ID NO: 117         moltype =    length =
SEQUENCE: 117
000

SEQ ID NO: 118         moltype =    length =
SEQUENCE: 118
000

SEQ ID NO: 119         moltype =    length =
SEQUENCE: 119
000

SEQ ID NO: 120         moltype =    length =
SEQUENCE: 120
000

SEQ ID NO: 121         moltype =    length =
SEQUENCE: 121
000

SEQ ID NO: 122         moltype =    length =
SEQUENCE: 122
000

SEQ ID NO: 123         moltype =    length =
SEQUENCE: 123
000

SEQ ID NO: 124         moltype =    length =
SEQUENCE: 124
000

SEQ ID NO: 125         moltype =    length =
SEQUENCE: 125
000

SEQ ID NO: 126         moltype =    length =
SEQUENCE: 126
000

SEQ ID NO: 127         moltype =    length =
SEQUENCE: 127
000

SEQ ID NO: 128         moltype =    length =
SEQUENCE: 128
000

SEQ ID NO: 129         moltype =    length =
SEQUENCE: 129
000

SEQ ID NO: 130         moltype =    length =
SEQUENCE: 130
000

SEQ ID NO: 131         moltype =    length =
SEQUENCE: 131
000

SEQ ID NO: 132         moltype =    length =
SEQUENCE: 132
000

SEQ ID NO: 133         moltype =    length =
SEQUENCE: 133
000

SEQ ID NO: 134         moltype =    length =
SEQUENCE: 134
000

SEQ ID NO: 135         moltype =    length =
SEQUENCE: 135
000

SEQ ID NO: 136         moltype =    length =

```
SEQUENCE: 136
000

SEQ ID NO: 137          moltype =    length =
SEQUENCE: 137
000

SEQ ID NO: 138          moltype =    length =
SEQUENCE: 138
000

SEQ ID NO: 139          moltype =    length =
SEQUENCE: 139
000

SEQ ID NO: 140          moltype =    length =
SEQUENCE: 140
000

SEQ ID NO: 141          moltype =    length =
SEQUENCE: 141
000

SEQ ID NO: 142          moltype =    length =
SEQUENCE: 142
000

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype =    length =
SEQUENCE: 154
000

SEQ ID NO: 155          moltype =    length =
SEQUENCE: 155
000
```

| | | |
|---|---|---|
| SEQ ID NO: 156<br>SEQUENCE: 156<br>000 | moltype = | length = |
| SEQ ID NO: 157<br>SEQUENCE: 157<br>000 | moltype = | length = |
| SEQ ID NO: 158<br>SEQUENCE: 158<br>000 | moltype = | length = |
| SEQ ID NO: 159<br>SEQUENCE: 159<br>000 | moltype = | length = |
| SEQ ID NO: 160<br>SEQUENCE: 160<br>000 | moltype = | length = |
| SEQ ID NO: 161<br>SEQUENCE: 161<br>000 | moltype = | length = |
| SEQ ID NO: 162<br>SEQUENCE: 162<br>000 | moltype = | length = |
| SEQ ID NO: 163<br>SEQUENCE: 163<br>000 | moltype = | length = |
| SEQ ID NO: 164<br>SEQUENCE: 164<br>000 | moltype = | length = |
| SEQ ID NO: 165<br>SEQUENCE: 165<br>000 | moltype = | length = |
| SEQ ID NO: 166<br>SEQUENCE: 166<br>000 | moltype = | length = |
| SEQ ID NO: 167<br>SEQUENCE: 167<br>000 | moltype = | length = |
| SEQ ID NO: 168<br>SEQUENCE: 168<br>000 | moltype = | length = |
| SEQ ID NO: 169<br>SEQUENCE: 169<br>000 | moltype = | length = |
| SEQ ID NO: 170<br>SEQUENCE: 170<br>000 | moltype = | length = |
| SEQ ID NO: 171<br>SEQUENCE: 171<br>000 | moltype = | length = |
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |

| | | |
|---|---|---|
| SEQ ID NO: 176<br>SEQUENCE: 176<br>000 | moltype = | length = |
| SEQ ID NO: 177<br>SEQUENCE: 177<br>000 | moltype = | length = |
| SEQ ID NO: 178<br>SEQUENCE: 178<br>000 | moltype = | length = |
| SEQ ID NO: 179<br>SEQUENCE: 179<br>000 | moltype = | length = |
| SEQ ID NO: 180<br>SEQUENCE: 180<br>000 | moltype = | length = |
| SEQ ID NO: 181<br>SEQUENCE: 181<br>000 | moltype = | length = |
| SEQ ID NO: 182<br>SEQUENCE: 182<br>000 | moltype = | length = |
| SEQ ID NO: 183<br>SEQUENCE: 183<br>000 | moltype = | length = |
| SEQ ID NO: 184<br>SEQUENCE: 184<br>000 | moltype = | length = |
| SEQ ID NO: 185<br>SEQUENCE: 185<br>000 | moltype = | length = |
| SEQ ID NO: 186<br>SEQUENCE: 186<br>000 | moltype = | length = |
| SEQ ID NO: 187<br>SEQUENCE: 187<br>000 | moltype = | length = |
| SEQ ID NO: 188<br>SEQUENCE: 188<br>000 | moltype = | length = |
| SEQ ID NO: 189<br>SEQUENCE: 189<br>000 | moltype = | length = |
| SEQ ID NO: 190<br>SEQUENCE: 190<br>000 | moltype = | length = |
| SEQ ID NO: 191<br>SEQUENCE: 191<br>000 | moltype = | length = |
| SEQ ID NO: 192<br>SEQUENCE: 192<br>000 | moltype = | length = |
| SEQ ID NO: 193<br>FEATURE<br>source<br><br>SEQUENCE: 193<br>tcggtggtcg ccgtatcatt | moltype = DNA  length = 20<br>Location/Qualifiers<br>1..20<br>mol_type = other DNA<br>organism = synthetic construct<br><br> | <br><br><br><br><br>20 |
| SEQ ID NO: 194<br>FEATURE | moltype = DNA  length = 24<br>Location/Qualifiers | |

```
source                  1..24
                        mol_type = other DNA
                        organism = synthetic construct
SEQUENCE: 194
aatgatacgg cgaccaccga gatc                                              24

SEQ ID NO: 195          moltype = DNA   length = 21
FEATURE                 Location/Qualifiers
source                  1..21
                        mol_type = other DNA
                        organism = synthetic construct
SEQUENCE: 195
caagcagaag acggcatacg a                                                 21

SEQ ID NO: 196          moltype = DNA   length = 24
FEATURE                 Location/Qualifiers
source                  1..24
                        mol_type = other DNA
                        organism = synthetic construct
SEQUENCE: 196
caagcagaag acggcatacg agat                                              24

SEQ ID NO: 197          moltype = DNA   length = 25
FEATURE                 Location/Qualifiers
source                  1..25
                        mol_type = other DNA
                        organism = synthetic construct
SEQUENCE: 197
accctgaaag tacgtgcatt acatg                                             25

SEQ ID NO: 198          moltype = DNA   length = 23
FEATURE                 Location/Qualifiers
source                  1..23
                        mol_type = other DNA
                        organism = synthetic construct
SEQUENCE: 198
gatcaggtga ggctgcgacg act                                               23

SEQ ID NO: 199          moltype = DNA   length = 89
FEATURE                 Location/Qualifiers
source                  1..89
                        mol_type = other DNA
                        organism = synthetic construct
SEQUENCE: 199
tcggtggtcg ccgtatcatt accctgaaag tacgtgcatt acatgatca ggtgaggctg        60
cgacgactca agcagaagac ggcatacga                                         89

SEQ ID NO: 200          moltype = DNA   length = 25
FEATURE                 Location/Qualifiers
source                  1..25
                        mol_type = other DNA
                        organism = synthetic construct
SEQUENCE: 200
catgtaatgc acgtactttc agggt                                             25

SEQ ID NO: 201          moltype = DNA   length = 23
FEATURE                 Location/Qualifiers
source                  1..23
                        mol_type = other DNA
                        organism = synthetic construct
SEQUENCE: 201
agtcgtcgca gcctcacctg atc                                               23

SEQ ID NO: 202          moltype = DNA   length = 48
FEATURE                 Location/Qualifiers
source                  1..48
                        mol_type = other DNA
                        organism = synthetic construct
SEQUENCE: 202
agtcgtcgca gcctcacctg atccatgtaa tgcacgtact ttcagggt                    48

SEQ ID NO: 203          moltype = DNA   length = 20
FEATURE                 Location/Qualifiers
source                  1..20
                        mol_type = other DNA
                        organism = synthetic construct
SEQUENCE: 203
aatgatacgg cgaccaccga                                                   20
```

-continued

```
SEQ ID NO: 204          moltype = DNA   length = 33
FEATURE                 Location/Qualifiers
source                  1..33
                        mol_type = other DNA
                        organism = synthetic construct
SEQUENCE: 204
acactctttc cctacacgac gctcttccga tct                                33

SEQ ID NO: 205          moltype = DNA   length = 34
FEATURE                 Location/Qualifiers
source                  1..34
                        mol_type = other DNA
                        organism = synthetic construct
SEQUENCE: 205
agatcggaag agcacacgtc tgaactccag tcac                               34

SEQ ID NO: 206          moltype = DNA   length = 21
FEATURE                 Location/Qualifiers
source                  1..21
                        mol_type = other DNA
                        organism = synthetic construct
SEQUENCE: 206
tcgtatgccg tcttctgctt g                                             21

SEQ ID NO: 207          moltype = DNA   length = 33
FEATURE                 Location/Qualifiers
source                  1..33
                        mol_type = other DNA
                        organism = synthetic construct
SEQUENCE: 207
tcgtcggcag cgtcagatgt gtataagaga cag                                33

SEQ ID NO: 208          moltype = DNA   length = 35
FEATURE                 Location/Qualifiers
source                  1..35
                        mol_type = other DNA
                        organism = synthetic construct
SEQUENCE: 208
cgtgctggat tggctcacca gacaccttcc gacat                              35

SEQ ID NO: 209          moltype = DNA   length = 34
FEATURE                 Location/Qualifiers
source                  1..34
                        mol_type = other DNA
                        organism = synthetic construct
SEQUENCE: 209
ctgtctctta tacacatctc cgagcccacg agac                               34

SEQ ID NO: 210          moltype = DNA   length = 35
FEATURE                 Location/Qualifiers
source                  1..35
                        mol_type = other DNA
                        organism = synthetic construct
SEQUENCE: 210
atgtcggaag gtgtgcaggc taccgcttgt caact                              35

SEQ ID NO: 211          moltype = DNA   length = 19
FEATURE                 Location/Qualifiers
source                  1..19
                        mol_type = other DNA
                        organism = synthetic construct
SEQUENCE: 211
agatgtgtat aagagacag                                                19

SEQ ID NO: 212          moltype = DNA   length = 19
FEATURE                 Location/Qualifiers
source                  1..19
                        mol_type = other DNA
                        organism = synthetic construct
SEQUENCE: 212
ctgtctctta tacacatct                                                19

SEQ ID NO: 213          moltype = DNA   length = 25
FEATURE                 Location/Qualifiers
source                  1..25
                        mol_type = other DNA
                        organism = synthetic construct
SEQUENCE: 213
catgtaatgc acgtactttc aggt                                          25
```

```
SEQ ID NO: 214          moltype = DNA  length = 23
FEATURE                 Location/Qualifiers
source                  1..23
                        mol_type = other DNA
                        organism = synthetic construct
SEQUENCE: 214
agtcgtcgca gcctcacctg atc                                              23

SEQ ID NO: 215          moltype = DNA  length = 25
FEATURE                 Location/Qualifiers
source                  1..25
                        mol_type = other DNA
                        organism = synthetic construct
SEQUENCE: 215
accctgaaag tacgtgcatt acatg                                            25

SEQ ID NO: 216          moltype = DNA  length = 23
FEATURE                 Location/Qualifiers
source                  1..23
                        mol_type = other DNA
                        organism = synthetic construct
SEQUENCE: 216
gatcaggtga ggctgcgacg act                                              23

SEQ ID NO: 217          moltype = DNA  length = 78
FEATURE                 Location/Qualifiers
source                  1..78
                        mol_type = other DNA
                        organism = synthetic construct
SEQUENCE: 217
ccgtatcatt accctgaaag tacgtgcatt acatggatca ggtgaggctg cgacgactca      60
agcagaagac ggcatacg                                                    78

SEQ ID NO: 218          moltype = DNA  length = 79
FEATURE                 Location/Qualifiers
source                  1..79
                        mol_type = other DNA
                        organism = synthetic construct
SEQUENCE: 218
gccgtatcat taccctgaaa gtacgtgcat tacatggatc aggtgaggct gcgacgactc      60
aagcagaaga cggcatacg                                                   79

SEQ ID NO: 219          moltype = DNA  length = 80
FEATURE                 Location/Qualifiers
source                  1..80
                        mol_type = other DNA
                        organism = synthetic construct
SEQUENCE: 219
cgccgtatca ttaccctgaa agtacgtgca ttacatggat caggtgaggc tgcgacgact      60
caagcagaag acggcatacg                                                  80

SEQ ID NO: 220          moltype = DNA  length = 81
FEATURE                 Location/Qualifiers
source                  1..81
                        mol_type = other DNA
                        organism = synthetic construct
SEQUENCE: 220
tcgccgtatc attaccctga aagtacgtgc attacatgga tcaggtgagg ctgcgacgac      60
tcaagcagaa gacggcatac g                                                81

SEQ ID NO: 221          moltype = DNA  length = 82
FEATURE                 Location/Qualifiers
source                  1..82
                        mol_type = other DNA
                        organism = synthetic construct
SEQUENCE: 221
gtcgccgtat cattaccctg aaagtacgtg cattacatgg atcaggtgag gctgcgacga      60
ctcaagcaga agacggcata cg                                               82

SEQ ID NO: 222          moltype = DNA  length = 88
FEATURE                 Location/Qualifiers
source                  1..88
                        mol_type = other DNA
                        organism = synthetic construct
SEQUENCE: 222
tcggtggtct gagtatcatt accctgaaag tacgtgcatt acatggatca ggtgaggctg      60
cgacgactca agcagaagac ggcatacg                                         88
```

```
SEQ ID NO: 223          moltype = DNA  length = 88
FEATURE                 Location/Qualifiers
source                  1..88
                        mol_type = other DNA
                        organism = synthetic construct
SEQUENCE: 223
tcggtggtct gggtatcatt accctgaaag tacgtgcatt acatggatca ggtgaggctg    60
cgacgactca agcagaagac ggcatacg                                      88

SEQ ID NO: 224          moltype = DNA  length = 88
FEATURE                 Location/Qualifiers
source                  1..88
                        mol_type = other DNA
                        organism = synthetic construct
SEQUENCE: 224
tcggtggtct gtgtatcatt accctgaaag tacgtgcatt acatggatca ggtgaggctg    60
cgacgactca agcagaagac ggcatacg                                      88

SEQ ID NO: 225          moltype = DNA  length = 88
FEATURE                 Location/Qualifiers
source                  1..88
                        mol_type = other DNA
                        organism = synthetic construct
SEQUENCE: 225
tcggtggtca gggtatcatt accctgaaag tacgtgcatt acatggatca ggtgaggctg    60
cgacgactca agcagaagac ggcatacg                                      88

SEQ ID NO: 226          moltype = DNA  length = 88
FEATURE                 Location/Qualifiers
source                  1..88
                        mol_type = other DNA
                        organism = synthetic construct
SEQUENCE: 226
tcggtggtca gagtatcatt accctgaaag tacgtgcatt acatggatca ggtgaggctg    60
cgacgactca agcagaagac ggcatacg                                      88

SEQ ID NO: 227          moltype = DNA  length = 88
FEATURE                 Location/Qualifiers
source                  1..88
                        mol_type = other DNA
                        organism = synthetic construct
SEQUENCE: 227
tcggtggtca gtgtatcatt accctgaaag tacgtgcatt acatggatca ggtgaggctg    60
cgacgactca agcagaagac ggcatacg                                      88

SEQ ID NO: 228          moltype = DNA  length = 30
FEATURE                 Location/Qualifiers
source                  1..30
                        mol_type = other DNA
                        organism = synthetic construct
SEQUENCE: 228
tcggtggtcg ccgtatcatt accctgaaag                                    30

SEQ ID NO: 229          moltype = DNA  length = 26
FEATURE                 Location/Qualifiers
source                  1..26
                        mol_type = other DNA
                        organism = synthetic construct
SEQUENCE: 229
acgtgcatta catggatcag gtgagg                                        26

SEQ ID NO: 230          moltype = DNA  length = 30
FEATURE                 Location/Qualifiers
source                  1..30
                        mol_type = other DNA
                        organism = synthetic construct
SEQUENCE: 230
tgcgacgact caagcagaag acggcatacg                                    30

SEQ ID NO: 231          moltype = DNA  length = 88
FEATURE                 Location/Qualifiers
source                  1..88
                        mol_type = other DNA
                        organism = synthetic construct
modified_base           8
                        mod_base = OTHER
                        note = uracil
modified_base           31
                        mod_base = OTHER
```

```
                        note = uracil
modified_base           39
                        mod_base = OTHER
                        note = uracil
modified_base           44
                        mod_base = OTHER
                        note = uracil
modified_base           53
                        mod_base = OTHER
                        note = uracil
modified_base           85
                        mod_base = OTHER
                        note = uracil
SEQUENCE: 231
tcggtggtcg ccgtatcatt accctgaaag tacgtgcatt acatggatca ggtgaggctg    60
cgacgactca agcagaagac ggcatacg                                       88

SEQ ID NO: 232          moltype = DNA  length = 51
FEATURE                 Location/Qualifiers
source                  1..51
                        mol_type = other DNA
                        organism = synthetic construct
SEQUENCE: 232
agtcgtcgca gcctcacctg atccatgtaa tnnngcacgt actttcaggg t             51

SEQ ID NO: 233          moltype = DNA  length = 91
FEATURE                 Location/Qualifiers
source                  1..91
                        mol_type = other DNA
                        organism = synthetic construct
SEQUENCE: 233
tcggtggtcg ccgtatcatt accctgaaag tacgtgcgcg attacatgga tcaggtgagg    60
ctgcgacgac tcaagcagaa gacggcatac g                                   91

SEQ ID NO: 234          moltype = DNA  length = 51
FEATURE                 Location/Qualifiers
source                  1..51
                        mol_type = other DNA
                        organism = synthetic construct
SEQUENCE: 234
gtcgtcgcag cctcacctga tccatgtaat nnnngcacgt actttcaggg t             51

SEQ ID NO: 235          moltype = DNA  length = 92
FEATURE                 Location/Qualifiers
source                  1..92
                        mol_type = other DNA
                        organism = synthetic construct
SEQUENCE: 235
tcggtggtcg ccgtatcatt accctgaaag tacgtgcgtc gattacatgg atcaggtgag    60
gctgcgacga ctcaagcaga agacggcata cg                                  92

SEQ ID NO: 236          moltype = DNA  length = 47
FEATURE                 Location/Qualifiers
source                  1..47
                        mol_type = other DNA
                        organism = synthetic construct
SEQUENCE: 236
gtcgtcgcag cctcacctga tccatgtaat nnncgtactt tcagggt                  47

SEQ ID NO: 237          moltype = DNA  length = 89
FEATURE                 Location/Qualifiers
source                  1..89
                        mol_type = other DNA
                        organism = synthetic construct
SEQUENCE: 237
tcggtggtcg ccgtatcatt accctgaaag tacgtgcatt acatggatca ggtgaggctg    60
cgacgactca agcagaagac ggcatacga                                      89

SEQ ID NO: 238          moltype = DNA  length = 48
FEATURE                 Location/Qualifiers
source                  1..48
                        mol_type = other DNA
                        organism = synthetic construct
SEQUENCE: 238
agtcgtcgca gcctcacctg atccatgtaa tnnnngtact ttcagggt                 48

SEQ ID NO: 239          moltype = DNA  length = 89
FEATURE                 Location/Qualifiers
source                  1..89
```

```
                      mol_type = other DNA
                      organism = synthetic construct
SEQUENCE: 239
tcggtggtcg ccgtatcatt accctgaaag tacgtgcatt acatggatca ggtgaggctg    60
cgacgactca agcagaagac ggcatacga                                      89

SEQ ID NO: 240        moltype = DNA  length = 60
FEATURE               Location/Qualifiers
source                1..60
                      mol_type = other DNA
                      organism = synthetic construct
SEQUENCE: 240
agtcgtcgca gcctcacctg atccatgtaa tgcacgtact ttcagggtnn ncactattcc    60

SEQ ID NO: 241        moltype = DNA  length = 100
FEATURE               Location/Qualifiers
source                1..100
                      mol_type = other DNA
                      organism = synthetic construct
SEQUENCE: 241
tcggtggtcg ccgtatcatt ggaatagtga caaccctgaa agtacgtgca ttacatggat    60
caggtgaggc tgcgacgact caagcagaag acggcatacg                         100

SEQ ID NO: 242        moltype = DNA  length = 61
FEATURE               Location/Qualifiers
source                1..61
                      mol_type = other DNA
                      organism = synthetic construct
SEQUENCE: 242
agtcgtcgca gcctcacctg atccatgtaa tgcacgtact ttcagggtnn nncactattc    60
c                                                                    61

SEQ ID NO: 243        moltype = DNA  length = 100
FEATURE               Location/Qualifiers
source                1..100
                      mol_type = other DNA
                      organism = synthetic construct
SEQUENCE: 243
cggtggtcgc cgtatcattg gaatagtgac agaccctgaa agtacgtgca ttacatggat    60
caggtgaggc tgcgacgact caagcagaag acggcatacg                         100
```